United States Patent [19]
Bauer et al.

[11] Patent Number: 6,057,133
[45] Date of Patent: *May 2, 2000

[54] MULTIVARIANT HUMAN IL-3 FUSION PROTEINS AND THEIR RECOMBINANT PRODUCTION

[75] Inventors: S. Christopher Bauer, New Haven; Mark Allen Abrams; Sarah Ruth Braford-Goldberg, both of St. Louis; Maire Helena Caparon, Chesterfield; Alan Michael Easton, Maryland Heights; Barbara Kure Klein, St. Louis; John Patrick McKearn; Peter O. Olins, both of Glencoe; Kumnan Paik, Ballwin; John Warren Thomas, Town & Country, all of Mo.

[73] Assignee: G. D. Searle, Chicago, Ill.

[*] Notice: This patent is subject to a terminal disclaimer.

[21] Appl. No.: 08/192,325
[22] Filed: Feb. 4, 1994

Related U.S. Application Data

[63] Continuation-in-part of application No. PCT/US93/11197, Nov. 22, 1993, which is a continuation-in-part of application No. 07/981,044, Nov. 24, 1992, abandoned.

[51] Int. Cl.[7] .......................... C12N 15/62; A61K 38/20; C07K 14/54
[52] U.S. Cl. .................... 435/69.7; 435/69.5; 435/69.52; 536/23.4; 536/23.5; 536/23.51; 530/351; 424/85.1; 424/85.2
[58] Field of Search .............................. 435/69.5, 69.52, 435/69.7; 530/351; 424/85.1, 85.2; 536/23.5, 23.4, 23.51

[56] References Cited

U.S. PATENT DOCUMENTS

| | | |
|---|---|---|
| 4,438,032 | 3/1984 | Golde et al. . |
| 4,810,643 | 3/1989 | Souza . |
| 4,877,729 | 10/1989 | Clark et al. . |
| 4,959,455 | 9/1990 | Clark et al. . |
| 4,999,291 | 3/1991 | Souza . |
| 5,032,395 | 7/1991 | Clark et al. . |
| 5,073,627 | 12/1991 | Curtis et al. . |
| 5,108,910 | 4/1992 | Curtis et al. . |
| 5,218,092 | 6/1993 | Sasaki et al. . |
| 5,376,367 | 12/1994 | Williams . |
| 5,501,962 | 3/1996 | Bradford-Goldberg et al. .... 435/69.52 |
| 5,591,427 | 1/1997 | Vadas et al. ........................... 424/85.2 |

FOREIGN PATENT DOCUMENTS

| | | |
|---|---|---|
| 0 183 350 | 6/1986 | European Pat. Off. . |
| 275598 A1 | 7/1988 | European Pat. Off. . |
| 0 337 359 | 10/1989 | European Pat. Off. . |
| WO88/05469 | 7/1988 | WIPO . |
| WO90/01039 | 2/1990 | WIPO . |
| WO90/12877 | 11/1990 | WIPO . |
| WO91/02754 | 3/1991 | WIPO . |
| WO 92/04455 | 3/1992 | WIPO . |
| WO 92/04455 | 4/1992 | WIPO . |
| WO92/06166 | 4/1992 | WIPO . |
| 93/07171 | 4/1993 | WIPO . |
| 94/12639 | 6/1994 | WIPO . |

OTHER PUBLICATIONS

Kaushansky, K., et al. (Nov. 1992) J. Clin. Invest. 90: 1879–88.
Dorssers, L. C. J., et al. (Nov. 1991) J. Biol. Chem. 266: 21310–17.
Fojo et al., Biochem., vol. 17., No. 15, 3109 (1978).
Pack et al., Biotech., vol. 11, (1993).
Curtis et al., Proc. Nat'l. Acad. Sci. USA, 88, 5809 (1991).
Williams et al., Cancer, 67, 2705–2702 (1991).
Welch et al., *Exp. Hem* 21:647–655 (1993).

*Primary Examiner*—David L. Fitzgerald
*Attorney, Agent, or Firm*—Dennis A. Bennett

[57] ABSTRACT

The present invention relates to fusion molecules composed of human interleukin-3 (hIL-3) variant or mutant proteins (muteins) functionally joined to a second colony stimulating factor (CSF), cytokine, lymphokine, interleukin, hematopoietic growth factor or IL-3 variant. The invention also relates to pharmaceutical compositions containing the fusion molecules and methods for using them.

70 Claims, 1 Drawing Sheet

FIG. 1

```
      1                           5                              10
ATG   GCT   CCA   ATG   ACT   CAG   ACT   ACT   TCT   CTT   AAG   ACT   TCT
Met   Ala   Pro   Met   Thr   Gln   Thr   Thr   Ser   Leu   Lys   Thr   Ser
                  15                        20                          25
TGG   GTT   AAC   TGC   TCT   AAC   ATG   ATC   GAT   GAA   ATT   ATA   ACA
Trp   Val   Asn   Cys   Ser   Asn   Met   Ile   Asp   Glu   Ile   Ile   Thr
                        30                        35
CAC   TTA   AAG   CAG   CCA   CCT   TTG   CCT   TTG   CTG   GAC   TTC   AAC
His   Leu   Lys   Gln   Pro   Pro   Leu   Pro   Leu   Leu   Asp   Phe   Asn
      40                        45                        50
AAC   CTC   AAT   GGG   GAA   GAC   CAA   GAC   ATT   CTG   ATG   GAA   AAT
Asn   Leu   Asn   Gly   Glu   Asp   Gln   Asp   Ile   Leu   Met   Glu   Asn
                        55                        60
AAC   CTT   CGA   AGG   CCA   AAC   CTG   GAG   GCA   TTC   AAC   AGG   GCT
Asn   Leu   Arg   Arg   Pro   Asn   Leu   Glu   Ala   Phe   Asn   Arg   Ala
65                              70                        75
GTC   AAG   AGT   TTA   CAG   AAT   GCA   TCA   GCA   ATT   GAG   AGC   ATT
Val   Lys   Ser   Leu   Gln   Asn   Ala   Ser   Ala   Ile   Glu   Ser   Ile
                  80                        85                          90
CTT   AAA   AAT   CTC   CTG   CCA   TGT   CTG   CCC   CTG   GCC   ACG   GCC
Leu   Lys   Asn   Leu   Leu   Pro   Cys   Leu   Pro   Leu   Ala   Thr   Ala
                        95                        100
GCA   CCC   ACG   CGA   CAT   CCA   ATC   CAT   ATC   AAG   GAC   GGT   GAC
Ala   Pro   Thr   Arg   His   Pro   Ile   His   Ile   Lys   Asp   Gly   Asp
      105                       110                       115
TGG   AAT   GAA   TTC   CGT   CGT   AAA   CTG   ACC   TTC   TAT   CTG   AAA
Trp   Asn   Glu   Phe   Arg   Arg   Lys   Leu   Thr   Phe   Tyr   Leu   Lys
                        120                       125
ACC   TTG   GAG   AAC   GCG   CAG   GCT   CAA   CAG   ACC   ACT   CTG   TCG
Thr   Leu   Glu   Asn   Ala   Gln   Ala   Gln   Gln   Thr   Thr   Leu   Ser
130
CTA   GCG   ATC   TTT   TAA   TAA          (SEQ ID NO: 53)
Leu   Ala   Ile   Phe                      (SEQ ID NO: 49)
```

MULTIVARIANT HUMAN IL-3 FUSION PROTEINS AND THEIR RECOMBINANT PRODUCTION

This is a continuation-in-part of international application PCT/US93/11197, which was filed on Nov. 22, 1993 and which entered the U.S. national stage under 35 U.S.C. § as Ser. No. 08/411,795 (now U.S. Pat. No. 5,604,116) on Apr. 6, 1995 and which is in turn a continuation-in-part of U.S. Ser. No. 07/981,044, filed Nov. 24, 1992 (now abandoned).

FIELD OF THE INVENTION

The present invention relates to fusion molecules composed of mutants or variants of human interleukin-3 (hIL-3) fused to a second colony stimulating factor (CSF), cytokine, lymphokine, interleukin, hematopoietic growth factor or IL-3 variant, with or without a linker.

BACKGROUND OF THE INVENTION

Colony stimulating factors (CSFS) which stimulate the differentiation and/or proliferation of bone marrow cells have generated much interest because of their therapeutic potential for restoring depressed levels of hematopoietic stem cell-derived cells. CSFs in both human and murine systems have been identified and distinguished according to their activities. For example, granulocyte-CSF (G-CSF) and macrophage-CSF (M-CSF) stimulate the in vitro formation of neutrophilic granulocyte and macrophage colonies, respectively while GM-CSF and interleukin-3 (IL-3) have broader activities and stimulate the formation of both macrophage, neutrophilic and eosinophilic granulocyte colonies. IL-3 also stimulates the formation of mast, megakaryocyte and pure and mixed erythroid colonies.

Because of its ability to stimulate the proliferation of a number of different cell types and to support the growth and proliferation of progenitor cells, IL-3 has potential for therapeutic use in restoring hematopoietic cells to normal amounts in those cases where the number of cells has been reduced due to diseases or to therapeutic treatments such as radiation and/or chemotherapy.

Interleukin-3 (IL-3) is a hematopoietic growth factor which has the property of being able to promote the survival, growth and differentiation of hematopoietic cells. Among the biological properties of IL-3 are the ability (a) to support the growth and differentiation of progenitor cells committed to all, or virtually all, blood cell lineages; (b) to interact with early multipotential stem cells; (c) to sustain the growth of pluripotent precursor cells; (d) to stimulate proliferation of chronic myelogenous leukemia (CML) cells; (e) to stimulate proliferation of mast cells, eosinophils and basophils; (f) to stimulate DNA synthesis by human acute myelogenous leukemia (AML) cells; (g) to prime cells for production of leukotrienes and histamines; (h) to induce leukocyte chemotaxis; and (i) to induce cell surface molecules needed for leukocyte adhesion.

Mature human interleukin-3 (hIL-3) consists of 133 amino acids. It has one disulfide bridge and two potential glycosylation sites (Yang, et al., CELL 47:3 (1986)).

Murine IL-3 (mIL-3) was first identified by Ihle, et al., J. IMMUNOL. 126:2184 (1981) as a factor which induced expression of a T cell associated enzyme, 20-hydroxysteroid dehydrogenase. The factor was purified to homogeneity and shown to regulate the growth and differentiation of numerous subclasses of early hematopoietic and lymphoid progenitor cells.

In 1984, cDNA clones coding for murine IL-3 were isolated (Fung, et al., NATURE 307:233 (1984) and Yokota, et al., PROC. NATL. ACAD. SCI. USA 81:1070 (1984)). The murine DNA sequence coded for a polypeptide of 166 amino acids including a putative signal peptide.

The gibbon IL-3 sequence was obtained using a gibbon cDNA expression library. The gibbon IL-3 sequence was then used as a probe against a human genomic library to obtain a human IL-3 sequence.

Gibbon and human genomic DNA homologues of the murine IL-3 sequence were disclosed by Yang, et al., CELL 47:3 (1986). The human sequence reported by Yang, et al. included a serine residue at position 8 of the mature protein sequence. Following this finding, others reported isolation of $Pro^8$ hIL-3 cDNAs having proline at position 8 of the protein sequence. Thus it appears that there may be two allelic forms of hIL-3.

Dorssers, et al., GENE 55:115 (1987), found a clone from a human cDNA library which hybridized with mIL-3. This hybridization was the result of the high degree of homology between the 3' noncoding regions of mIL-3 and hIL-3. This cDNA coded for an hIL-3 ($Pro^8$) sequence.

U.S. Pat. No. 4,877,729 and U.S. Pat. No. 4,959,454 disclose human IL-3 and gibbon IL-3 cDNAs and the protein sequences for which they code. The hIL-3 disclosed has serine rather than proline at position 8 in the protein sequence.

Clark-Lewis, et al., SCIENCE 231:134 (1986) performed a functional analysis of murine IL-3 analogues synthesized with an automated peptide synthesizer. The authors concluded that the stable tertiary structure of the complete molecule was required for full activity. A study on the role of the disulfide bridges showed that replacement of all four cysteines by alanine gave a molecule with 1/500th the activity as the native molecule. Replacement of two of the four Cys residues by Ala($Cys^{79}$, $Cys^{140}$—>$Ala^{79}$, $Ala^{140}$) resulted in an increased activity. The authors concluded that in murine IL-3 a single disulfide bridge is required between cysteines 17 and 80 to get biological activity that approximates physiological levels and that this structure probably stabilizes the tertiary structure of the protein to give a conformation that is optimal for function. (Clark-Lewis, et al., PROC. NATL. ACAD. SCI. USA 85:7897 (1988)).

International Patent Application (PCT) WO 88/00598 discloses gibbon- and human-like IL-3. The hIL-3 contains a $Ser^8$—>$Pro^8$ replacement. Suggestions are made to replace Cys by Ser, thereby breaking the disulfide bridge, and to replace one or more amino acids at the glycosylation sites.

EP-A-0275598 (WO 88/04691) illustrates that $Ala^1$ can be deleted while retaining biological activity. Some mutant hIL-3 sequences are provided, e.g., two double mutants, $Ala^1$—>$Asp^1$, $Trp^{13}$—>$Arg^{13}$ (pGB/IL-302) and $Ala^1$—>$Asp^1$, $Met^3$—>$Thr^3$ (pGB/IL-304) and one triple mutant $Ala^1$—>$Asp^1$, $Leu^9$—>$Pro^9$, $Trp^{13}$—>$Arg^{13}$ (pGB/IL-303).

WO 88/05469 describes how deglycosylation mutants can be obtained and suggests mutants of $Arg^{54}Arg^{55}$ and $Arg^{108}Arg^{109}Lys^{110}$ might avoid proteolysis upon expression in Saccharomyces cerevisiae by KEX2 protease. No mutated proteins are disclosed. Glycosylation and the KEX2 protease activity are only important, in this context, upon expression in yeast.

WO 88/06161 mentions various mutants which theoretically may be conformationally and antigenically neutral. The only actually performed mutations are $Met^2$—>$Ile^2$ and $Ile^{131}$—>$Leu^{131}$. It is not disclosed whether the contemplated neutralities were obtained for these two mutations.

WO 91/00350 discloses nonglycosylated hIL-3 analog proteins, for example, hIL-3 ($Pro^8Asp^{15}Asp^{70}$), $Met^3$ rhuI-3

(Pro⁸Asp¹⁵Asp⁷⁰); Thr⁴ rhuL-3 (Pro⁸Asp¹⁵Asp⁷⁰)and Thr⁶ rhuIL-3 (Pro⁸Asp¹⁵Asp⁷⁰). It is said that these protein compositions do not exhibit certain adverse side effects associated with native hIL-3 such as urticaria resulting from infiltration of mast cells and lymphocytes into the dermis. The disclosed analog hIL-3 proteins may have N termini at Met³, Thr⁴, or Thr⁶.

WO 90/12874 discloses cysteine added variants (CAVs) of IL-3 which have at least one Cys residue substituted for a naturally occurring amino acid residue.

U.S. Pat. No. 4,810,643 discloses the DNA sequence encoding human G-CSF.

WO 91/02754 discloses a fusion protein composed of GM-CSF and IL-3 which has increased biological activity compared to GM-CSF or IL-3 alone. Also disclosed are nonglycosylated IL-3 and GM-CSF analog proteins as components of the fusion.

WO 92/04455 discloses fusion proteins composed of IL-3 fused to a lymphokine selected from the group consisting of IL-3, IL-6, IL-7, IL-9, IL-11, EPO and G-CSF.

SUMMARY OF THE INVENTION

The present invention encompasses recombinant human interleukin-3 (hIL-3) variant or mutant proteins (muteins) fused to a second colony stimulating factor (CSF), cytokine, lymphokine, interleukin, hematopoietic growth factor (herein collectively referred to as "colony stimulating factors") or IL-3 variant with or without a linker. These hIL-3 muteins contain amino acid substitutions and may also have amino acid deletions at either/or both the N- and C- termini. This invention encompasses mixed function colony stimulating factors formed from covalently linked polypeptides, each of which may act through a different and specific cell receptor to initiate complementary biological activities.

Novel compounds of this invention are represented by the formulas

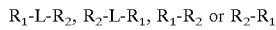

where $R_1$ is a hIL-3 variant which contains multiple amino acid substitutions and which may have portions of the hIL-3 molecule deleted, R2 is a CSF with a different but complementary activity. The R1 polypeptide is fused either directly or through a linker segment to the R2 polypeptide. Thus L represents a chemical bond or polypeptide segment to which both R1 and R2 are fused. Preferably, these mutant IL-3 polypeptides of the present invention contain four or more amino acids which differ from the amino acids found at the corresponding positions in the native hIL-3 polypeptide. The invention also relates to pharmaceutical compositions containing the fusion molecules, DNA coding for the fusion molecules, and methods for using the fusion molecules. Additionally, the present invention relates to recombinant expression vectors comprising nucleotide sequences encoding the hIL-3 fusion molecules, related microbial expression systems, and processes for making the fusion molecules using the microbial expression systems.

These fusion molecules may be characterized by having the usual activity of both of the peptides forming the fusion molecule or it may be further characterized by having a biological or physiological activity greater than simply the additive function of the presence of IL-3 or the second colony stimulating factor alone. The fusion molecule may also unexpectedly provide an enhanced effect on the activity or an activity different from that expected by the presence of IL-3 or the second colony stimulating factor or IL-3 variant. The fusion molecule may also have an improved activity profile which may include reduction of undesirable biological activities associated with native hIL-3.

The present invention also includes mutants of hIL-3 in which from 1 to 14 amino acids have been deleted from the N-terminus and/or from 1 to 15 amino acids have been deleted from the C-terminus, containing multiple amino acid substitutions, to which a second colony stimulating factor or IL-3 variant has been fused. Preferred fusion molecules of the present invention are composed of hIL-3 variants in which amino acids 1 to 14 have been deleted from the N-terminus, amino acids 126 to 133 have been deleted from the C-terminus, and contains from about four to about twenty-six amino acid substitutions in the polypeptide sequence fused to second colony stimulating factor or IL-3 variant.

The present invention also provides fusion molecules which may function as IL-3 antagonists or as discrete antigenic fragments for the production of antibodies useful in immunoassay and immunotherapy protocols. Antagonists of hIL-3 would be particularly useful in blocking the growth of certain cancer cells like AML, CML and certain types of B lymphoid cancers. Other conditions where antagonists would be useful include those in which certain blood cells are produced at abnormally high numbers or are being activated by endogenous ligands. Antagonists would effectively compete for ligands, presumably naturally occurring hemopoietins including and not limited to IL-3, GM-CSF and IL-5, which might trigger or augment the growth of cancer cells by virtue of their ability to bind to the IL-3 receptor complex while intrinsic activation properties of the ligand are diminished. IL-3, GM-CSF and/or IL-5 also play a role in certain asthmatic responses. An antagonist of the IL-3 receptor may have the utility in this disease by blocking receptor-mediated activation and recruitment of inflammatory cells.

In addition to the use of the fusion molecules of the present invention in vivo, it is envisioned that in vitro uses would include the ability to stimulate bone marrow and blood cell activation and growth before infusion into patients.

BRIEF DESCRIPTION OF THE DRAWINGS

FIG. 1 is the human IL-3 gene for *E. coli* expression (pMON5873), encoding the polypeptide sequence of natural (wild type) human IL-3 [SEQ ID NO:49], plus an initiator methionine, as expressed in *E. coli*, with the amino acids numbered from the N-terminus of the natural hIL-3.

DETAILED DESCRIPTION OF THE INVENTION

The present invention encompasses recombinant human interleukin-3 (hIL-3) variant or mutant proteins (muteins) fused to a second colony stimulating factor (CSF), cytokine, lymphokine, interleukin, hematopoietic growth factor or IL-3 variant with or without a linker. This invention encompasses mixed function colony stimulating factors formed from covalently linked polypeptides, each of which may act through a different and specific cell receptor to initiate complementary biological activities. Hematopoiesis requires a complex series of cellular events in which stem cells generate continuously into large populations of maturing cells in all major lineages. There are currently at least 20 known regulators with hematopoietic proliferative activity.

Most of these proliferative regulators can stimulate one or another type of colony formation in vitro, the precise pattern of colony formation stimulated by each regulator is quite distinctive. No two regulators stimulate exactly the same pattern of colony formation, as evaluated by colony numbers or, more importantly, by the lineage and maturation pattern of the cells making up the developing colonies. Proliferative responses can most readily be analyzed in simplified in vitro culture systems. Three quite different parameters can be distinguished: alteration in colony size, alteration in colony numbers and cell lineage. Two or more factors may act on the progenitor cell, inducing the formation of larger number of progeny thereby increasing the colony size. Two or more factors may allow increased number of progenitor cells to proliferate either because distinct subsets of progenitors cells exist that respond exclusively to one factor or because some progenitors require stimulation by two or more factors before being able to respond. Activation of additional receptors on a cell by the use of two or more factors is likely to enhance the mitotic signal because of coalescence of initially differing signal pathways into a common final pathway reaching the nucleus (Metcalf, 1989). Other mechanisms could explain synergy. For example, if one signalling pathway is limited by an intermediate activation of an additional signalling pathway by a second factor may result in a superadditive response. In some cases, activation of one receptor type can induce a enhanced expression of other receptors (Metcalf, 1993). Two or more factors may result in a different pattern of cell lineages then from a single factor. The use of fusion molecules may have the potential clinical advantage resulting from a proliferative response that is not possible by any single factor.

Hematopoietic and other growth factors can be grouped in to two distinct families of related receptors: (1) tyrosine kinase receptors, including those for epidermal growth factor, M-CSF (Sherr, 1990) and SCF (Yarden et al., 1987): and (2) hematopoietic receptors, not containing a tyrosine kinase domain, but exhibiting obvious homology in their extracellular domain (Bazan, 1990). Included in this later group are erythropoietin (EPO) (D'Andrea et al., 1989), GM-CSF (Gearing et al., 1989), IL-3 (Kitamura et al., 1991), G-CSF (Fukunaga et al., 1990), IL-4 (Harada et al., 1990), IL-5 ((Takaki et al., 1990), IL-6 (Yamasaki et al., 1988), IL-7 (Goodwin et al., 1990), LIF (Gearing et al., 1991) and IL-2 (Cosman et al., 1987). Most of the later group of receptors exists in high-affinity form as a heterodimers. After ligand binding, the specific α-chains become associated with at least one other receptor chain (β-chain, γ-chain). Many of these factors share a common receptor subunit. The α-chains for GM-CSF, IL-3 and IL-5 share the same β-chain (Miyajima et al., 1992) and receptor complexes for IL-6, LIF and IL-11 share a common β-chain (gp130) (Taga et al., 1989; Taga et al., 1992; Gearing et al., 1992). The receptor complexs of IL-2, IL-4 and IL-7 share a common γ-chain (Motonari et al., 1993; Russell et al., 1993; Masayuki et al., 1993).

The use of multiple factors may also have potential advantage by lowering the demands placed on factor-producing cells and their induction systems. If there are limitations in the ability of a cell to produce a factor then by lowering the required concentrations of each of the factors by using them in combination may usefully reduce demands on the factor-producing cells. The use of multiple factors may lower the amount of the factors that would be needed, probably reducing the likelihood of adverse responses.

Novel compounds of this invention are represented by a formula selected from the group consisting of $R_1$-L-$R_2$, $R_2$-L-$R_1$, $R_1$-$R_2$ or $R_2$-$R_1$ where R1 is a hIL-3 variant which contains multiple amino acid substitutions and which may have portions of the hIL-3 molecule deleted as is disclosed in co-pending International patent Application Serial No. PCT/US93/11197, the U.S. National State of which is now U.S. Pat. No. 5,608,116, R2 is a colony stimulating factor with a different but complementary activity. By complementary activity is meant activity which enhances or changes the response to another cell modulator. The R1 polypeptide is fused either directly or through a linker segment to the R2 polypeptide. The term "directly" defines fusions in which the polypeptides are joined without a peptide linker. Thus L represents a chemical bound or polypeptide segment to which both R1 and R2 are fused in frame, most commonly L is a linear peptide to which R1 and R2 are bound by amide bonds linking the carboxy terminus of R1 to the amino terminus of L and carboxy terminus of L to the amino terminus of R2. By "fused in frame" is meant that there is no translation termination or disruption between the reading frames of R1 and R2. A non-exclusive list of other growth factors, colony stimulating factors (CSFs), cytokine, lymphokine, interleukin, hematopoietic growth factor within the definition of R2, which can be fused to a hIL-3 variant of the present invention include GM-CSF, CSF-1, G-CSF, Meg-CSF, M-CSF, erythropoietin (EPO), IL-1, IL-4, IL-2, IL-5, IL-6, IL-7, IL-8, IL-9, IL-10, IL-11, IL-12, IL-13, LIF, flt3/flk2, human growth hormone, B-cell growth factor, B-cell differentiation factor, eosinophil differentiation factor and stem cell factor (SCF) also known as steel factor or c-kit ligand. Additionally, this invention encompasses the use of modified R2 molecules or mutated or modified DNA sequences encoding these R2 molecules. The present invention also includes fusion molecules in which R2 is a hIL-3 variant which contains multiple amino acid substitutions and which may have portions of the hIL-3 molecule deleted.

The linking group (L) is generally a polypeptide of between 1 and 500 amino acids in length. The linkers joining the two molecules are preferably designed to (1) allow the two molecules to fold and act independently of each other, (2) not have a propensity for developing an ordered secondary structure which could interfere with the functional domains of the two proteins, (3) have minimal hydrophobic or charged characteristic which could interact with the functional protein domains and (4) provide steric separation of R1 and R2 such that R1 and R2 could interact simultaneously with their corresponding receptors on a single cell. Typically surface amino acids in flexible protein regions include Gly, Asn and Ser. Virtually any permutation of amino acid sequences containing Gly, Asn and Ser would be expected to satisfy the above criteria for a linker sequence. Other neutral amino acids, such as Thr and Ala, may also be used in the linker sequence. Additional amino acids may also be included in the linkers due to the addition of unique restriction sites in the linker sequence to facilitate construction of the fusions.

Preferred linkers of the present invention include sequences selected from the group of formulas:

$(Gly_3Ser)_n$, $(Gly_4Ser)_n$, $(Gly_5Ser)_n$, $(Gly_nSer)_n$ or $(AlaGlySer)_n$

One example of a highly-flexible linker is the (GlySer)-rich spacer region present within the pIII protein of the filamentous bacteriophages, e.g. bacteriophages M13 or fd (Schaller et al., 1975). This region provides a long, flexible spacer region between two domains of the pIII surface protein. The spacer region consists of the amino acid sequence:

GlyGlyGlySerGlyGlyGlySerGlyGlyGlySerGluGlyGlyGlySerGlu
GlyGlyGlySerGluGlyGlyGlySer-
GluGlyGlyGlySerGlyGlyGlySer [SEQ ID NO:50]

The present invention also includes linkers in which an endopeptidase recognition sequence is included. Such a cleavage site may be valuable to separate the individual components of the fusion to determine if they are properly folded and active in vitro. Examples of various endopeptidases include, but are not limited to, Plasmin, Enterokinase, Kallikerin, Urokinase, Tissue Plasminogen activator, clostripain, Chymosin, Collagenase, Russell's Viper Venom Protease, Postproline cleavage enzyme, V8 protease, Thrombin and factor Xa.

Peptide linker segments from the hinge region of heavy chain immunoglobulins IgG, IgA, IgM, IgD or IgE provide an angular relationship between the attached polypeptides. Especially useful are those hinge regions where the cysteines are replaced with serines. Preferred linkers of the present invention include sequences derived from murine IgG gamma 2b hinge region in which the cysteins have been changed to serines. These linkers may also include an endopeptidase cleavage site. Examples of such linkers include the following sequences selected from the group of sequences IleSerGluProSerGlyProIleSerThrIleAsnProSerProProSerLys
GluSerHisLysSerPro [SEQ ID NO:51]

IleGluGlyArgIleSerGluProSerGlyProIleSerThrIleAsnProSer Pro-
ProSerLysGluSerHisLysSerPro [SEQ ID NO:52]

The present invention is, however, not limited by the form, size or number of linker sequences employed and the only requirement of the linker is that functionally it does not interfere adversely with the folding and function of the individual molecules of the fusion.

An alternative method for connecting two hematopoietic growth factors is by means of a non-covalent interaction. Such complexed proteins can be described by one the formulae:

R1-C1+R2-C2; or C1-R1+C2-R2; C1-R1+R2-C2; or C1-R1+R2-C2.

where R1 is a hIL-3 variant which contains multiple amino acid substitutions and which may have portions of the hIL-3 molecule deleted, R2 is a colony stimulating factor with a different but complementary activity. A non-exclusive list of other growth hormones, colony stimulating factors (CSFs), cytokine, lymphokine, interleukin, hematopoietic growth factor within the definition of R2, which can be fused to a hIL-3 variant of the present invention include GM-CSF, CSF-1, G-CSF, Meg-CSF, M-CSF, erythropoietin (EPO), IL-1, IL-4, IL-2, IL-5, IL-6, IL-7, IL-8, IL-9, IL-10, IL-11, IL-12, IL-13, LIF, flt3/flk2, human growth hormone, B-cell growth factor, B-cell differentiation factor, eosinophil differentiation factor and stem cell factor (SCF) also known as steel factor or c-kit ligand. Domains C1 and C2 are either identical or non-identical chemical structures, typically proteinaceous, which can form a non-covalent, specific association. Complexes between C1 and C2 result in a one-to-one stoichiometric relationship between R1 and R2 for each complex. Examples of domains which associate are "leucine zipper" domains of transcription factors, dimerization domains of bacterial transcription repressors and immunoglobulin constant domains. Covalent bonds link R1 and C1, and R2 and C2, respectively. As indicated in the formulae, the domains C1 and C2 can be present either at the N-terminus or C-terminus of their corresponding hematopoietic growth factor (R). These multimerization domains (C1 and C2) include those derived from the bZIP family of protiens (Abel et al., 1989; Landshulz et al., 1988; Pu et al., 1993; Korarides et al., 1988) as well as multimerization domains of the helix-loop-helix family of proteins (Abel et al., 1989; Murre et al., 1989; Tapscott et al., 1988; Fisher et al., 1991). Preferred fusions of the present invention include colony stimulating factors dimerized by virtue of their incorporation as translational fusions the leucine zipper dimerization domains of the bZIP family proteins Fos and Jun. The leucine zipper domain of Jun is capable of interacting with identical domains. On the other hand, the leucine zipper domain of Fos interacts with the Jun leucine zipper domain, but does not interact with other Fos leucine zipper domains. Mixtures of Fos and Jun predominantly result in formation of Fos-Jun heterodimers. Consequently, when fused to colony stimulating factors, the Jun domain can be used to direct the formation of either homo or heterodimers. Preferential formation of heterodimers can be achieved if one of the colony stimulating factor partner is engineered to possess the Jun leucine zipper domain while the other is engineered to possess the Fos zipper.

Peptides may also be added to facilitate purification or identification of fusion proteins (e.g., poly-His). A highly antigenic peptide may also be added that would enable rapid assay and facile purification of the fusion protein by a specific monoclonal antibody.

The present invention relates to novel fusion molecules composed of novel variants of human interleukin-3 (hIL-3) in which amino acid substitutions have been made at four or more positions in amino acid sequence of the polypeptide fused to second colony stimulating factor or IL-3 variant. Preferred fusion molecules of the present invention are (15–125) hIL-3 deletion mutants which have deletions of amino acids 1 to 14 at the N-terminus and 126 to 133 at the C-terminus and which also have four or more amino acid substitutions in the polypeptide fused to second colony stimulating factor or IL-3 variant. The present invention includes mutant polypeptides comprising minimally amino acids residues 15 to 118 of hIL-3 with or without additional amino acid extensions to the N-terminus and/or C-terminus which further contain four or more amino acid substitutions in the amino acid sequence of the polypeptide fused to another colony stimulating factor or IL-3 variant.

As used herein human interleukin-3 corresponds to the amino acid sequence (1–133) as depicted in FIG. 1 and (15–125) hIL-3 corresponds to the 15 to 125 amino acid sequence of the hIL-3 polypeptide. Naturally occurring variants of hIL-3 polypeptide amino acids are also included in the present invention (for example, the allele in which proline rather than serine is at position 8 in the hIL-3 polypeptide sequence) as are variant hIL-3 molecules which are modified post-translationally (e.g. glycosylation).

"Mutant amino acid sequence," "mutant protein" or "mutant polypeptide" refers to a polypeptide having an amino acid sequence which varies from a native sequence or is encoded by a nucleotide sequence intentionally made variant from a native sequence. "Mutant protein," "variant protein" or "mutein" means a protein comprising a mutant amino acid sequence and includes polypeptides which differ from the amino acid sequence of native hIL-3 due to amino acid deletions, substitutions, or both. "Native sequence" refers to an amino acid or nucleic acid sequence which is identical to a wild-type or native form of a gene or protein.

Human IL-3 can be characterized by its ability to stimulate colony formation by human hematopoietic progenitor cells. The colonies formed include erythroid, granulocyte, megakaryocyte, granulocytic macrophages and mixtures thereof. Human IL-3 has demonstrated an ability to restore bone marrow function and peripheral blood cell populations to therapeutically beneficial levels in studies performed initially in primates and subsequently in humans (Gillio, A. P., et al. (1990); Ganser, A, et al. (1990); Falk, S., et al. (1991). Additional activities of hIL-3 include the ability to stimulate leukocyte migration and chemotaxis; the ability to prime human leukocytes to produce high levels of inflammatory mediators like leukotrienes and histamine; the ability to induce cell surface expression of molecules needed for leukocyte adhesion; and the ability to trigger dermal inflammatory responses and fever. Many or all of these biological activities of hIL-3 involve signal transduction and high affinity receptor binding. Fusion molecules of the present invention may exhibit useful properties such as having similar or greater biological activity when compared to native hIL-3 or by having improved half-life or decreased adverse side effects, or a combination of these properties. They may also be useful as antagonists. Fusion molecules which have little or no activity when compared to native hIL-3 may still be useful as antagonists, as antigens for the production of antibodies for use in immunology or immunotherapy, as genetic probes or as intermediates used to construct other useful hIL-3 muteins.

The novel fusion molecules of the present invention will preferably have at least one biological property of human IL-3 and the other colony stimulating factor or IL-3 variant to which it is fused and may have more than one IL-3-like biological property, or an improved property, or a reduction in an undesirable biological property of human IL-3. Some mutant polypeptides of the present invention may also exhibit an improved side effect profile. For example, they may exhibit a decrease in leukotriene release or histamine release when compared to native hIL-3 or (15–125) hIL-3. Such hIL-3 or hIL-3-like biological properties may include one or more of the following biological characteristics and in vivo and in vitro activities.

One such property is the support of the growth and differentiation of progenitor cells committed to erythroid, lymphoid, and myeloid lineages. For example, in a standard human bone marrow assay, an IL-3-like biological property is the stimulation of granulocytic type colonies, megakaryocytic type colonies, monocyte/macrophage type colonies, and erythroid bursts. Other IL-3-like properties are the interaction with early multipotential stem cells, the sustaining of the growth of pluripotent precursor cells, the ability to stimulate chronic myelogenous leukemia (CML) cell proliferation, the stimulation of proliferation of mast cells, the ability to support the growth of various factor-dependent cell lines, and the ability to trigger immature bone marrow cell progenitors. Other biological properties of IL-3 have been disclosed in the art. Human IL-3 also has some biological activities which may in some cases be undesirable, for example the ability to stimulate leukotriene release and the ability to stimulate increased histamine synthesis in spleen and bone marrow cultures and in vivo.

Biological activity of hIL-3 and hIL-3 fusion proteins of the present invention is determined by DNA synthesis by human acute myelogenous leukemia cells (AML). The factor-dependent cell line AML 193 was adapted for use in testing biological activity. The biological activity of hIL-3 and hIL-3 fusion proteins of the present invention is also determined by counting the colony forming units in a bone marrow assay.

Other in vitro cell based assays may also be useful to determine the activity of the fusion molecules depending on the colony stimulating factors that comprise the fusion. The following are examples of other useful assays.

TF-1 proliferation assay: The TF-1 cell line was derived from bone marrow of a patient with erythroleukemia (Kitamura et al., 1989). TF-1 cells respond to IL-3, GM-CSF, EPO and IL-5.

32D proliferation assay: 32D is a murine IL-3 dependent cell line which does not respond to human IL-3 but does respond to human G-CSF which is not species restricted.

T1165 proliferation assay: T1165 cells are a IL-6 dependent murine cell line (Nordan et al., 1986) which respond to IL-6 and IL-11.

Human Plasma Clot meg-CSF Assay: Used to assay megakaryocyte colony formation activity (Mazur et al., 1981).

One object of the present invention is to provide hIL-3 variant with four or more amino acid substitutions in the polypeptide sequence fused to a second colony stimulating factor or IL-3 variant, which have similar or improved biological activity in relation to native hIL-3 or the second colony stimulating factor or IL-3 variant.

The hIL-3 variant fusion molecules of the present invention may have hIL-3 or hIL-3-like activity. For example, they may possess one or more of the biological activities of native hIL-3 and may be useful in stimulating the production of hematopoietic cells by human or primate progenitor cells. The fusion molecules of the present invention and pharmaceutical compositions containing them may be useful in the treatment of conditions in which hematopoietic cell populations have been reduced or destroyed due to disease or to treatments such as radiation or chemotherapy. Pharmaceutical compositions containing fusion molecules of the present invention can be administered parenterally, intravenously, or subcutaneously.

Native hIL-3 possesses considerable inflammatory activity and has been shown to stimulate synthesis of the arachidonic acid metabolites $LTC_4$, $LTD_4$, and $LTE_4$; histamine synthesis and histamine release. Human clinical trials with native hIL-3 have documented inflammatory responses (Biesma, et al., BLOOD, 80:1141–1148 (1992) and Postmus, et al., J. CLIN. ONCOL., 10:1131–1140 (1992)). A recent study indicates that leukotrienes are involved in IL-3 actions in vivo and may contribute significantly to the biological effects of IL-3 treatment (Denzlinger, C., et al., BLOOD, 81:2466–2470 (1993))

Some fusion molecules of the present invention may have an improved therapeutic profile as compared to native hIL-3. For example, some fusion molecules of the present invention may have a similar or more potent growth factor activity relative to native hIL-3 without having a similar or corresponding increase in the stimulation of leukotriene or histamine. These fusion molecules would be expected to have a more favorable therapeutic profile since the amount of polypeptide which needs to be given to achieve the desired growth factor activity (e. g. cell proliferation) would have a lesser leukotriene or histamine stimulating effect. In studies with native hIL-3, the stimulation of inflammatory factors has been an undesirable side effect of the treatment. Reduction or elimination of the stimulation of mediators of inflammation would provide an advantage over the use of native hIL-3.

Novel fusion molecules of the present invention may also be useful as antagonists which block the hIL-3 receptor by binding specifically to it and preventing binding of the agonist.

One potential advantage of the novel fusion molecules of the present invention, particularly those which retain activity similar to or better than that of native hIL-3, is that it may be possible to use a smaller amount of the biologically active mutein to produce the desired therapeutic effect. This may make it possible to reduce the number of treatments necessary to produce the desired therapeutic effect. The use of smaller amounts may also reduce the possibility of any potential antigenic effects or other possible undesirable side effects. For example, if a desired therapeutic effect can be achieved with a smaller amount of polypeptide it may be possible to reduce or eliminate side effects associated with the administration of native IL-3 such as the stimulation of leukotriene and/or histamine release. The novel fusion molecules of the present invention may also be useful in the activation of stem cells or progenitors which have low receptor numbers.

The present invention also includes the DNA sequences which code for the fusion proteins, DNA sequences which are substantially similar and perform substantially the same function, and DNA sequences which differ from the DNAs encoding the fusion molecules of the invention only due to the degeneracy of the genetic code. Also included in the present invention are; the oligonucleotide intermediates used to construct the mutant DNAs; and the polypeptides coded for by these oligonucleotides. These polypeptides may be useful as antagonists or as antigenic fragments for the production of antibodies useful in immunoassay and immunotherapy protocols.

Compounds of this invention are preferably made by genetic engineering techniques now standard in the art U.S. Pat. No. 4,935,233 and Sambrook et al., "Molecular Cloning. A Laboratory Manual", Cold Spring Harbor Laboratory (1989)]. One method of creating the preferred hIL-3 (15–125) mutant genes is cassette mutagenesis [Wells, et al. (1985)] in which a portion of the coding sequence of hIL-3 in a plasmid is replaced with synthetic oligonucleotides that encode the desired amino acid substitutions in a portion of the gene between two restriction sites. In a similar manner amino acid substitutions could be made in the full-length hIL-3 gene, or genes encoding variants of hIL-3 in which from 1 to 14 amino acids have been deleted from the N-terminus and/or from 1 to 15 amino acids have been deleted from the C-terminus. When properly assembled these oligonucleotides would encode hIL-3 variants with the desired amino acid substitutions and/or deletions from the N-terminus and/or C-terminus. These and other mutations could be created by those skilled in the art by other mutagenesis methods including; oligonucleotide-directed mutagenesis [Zoller and Smith (1982, 1983, 1984), Smith (1985), Kunkel (1985), Taylor, et al. (1985), Deng and Nickoloff (1992)] or polymerase chain reaction (PCR) techniques [Saiki, (1985)].

Pairs of complementary synthetic oligonucleotides encoding the desired gene can be made and annealed to each other. The DNA sequence of the oligonucleotide would encode sequence for amino acids of desired gene with the exception of those substituted and/or deleted from the sequence.

Plasmid DNA can be treated with the chosen restriction endonucleases then ligated to the annealed oligonucleotides. The ligated mixtures can be used to transform competent JM101 cells to resistance to an appropriate antibiotic. Single colonies can be picked and the plasmid DNA examined by restriction analysis and/or DNA sequencing to identify plasmids with the desired genes.

Fusing of the DNA sequences of the hIL-3 variant with the DNA sequence of the other colony stimulating factor or IL-3 variant may be accomplished by the use of intermediate vectors. Alternatively one gene can be cloned directly into a vector containing the other gene. Linkers and adapters can be used for joining the DNA sequences, as well as replacing lost sequences, where a restriction site was internal to the region of interest. Thus genetic material (DNA) encoding one polypeptide, peptide linker, and the other polypeptide is inserted into a suitable expression vector which is used to transform bacteria, yeast, insect cell or mammalian cells. The transformed organism is grown and the protein isolated by standard techniques. The resulting product is therefore a new protein which has a hIL-3 variant joined by a linker region to a second colony stimulating factor or IL-3 variant.

Another aspect of the present invention provides plasmid DNA vectors for use in the expression of these novel fusion molecules. These vectors contain the novel DNA sequences described above which code for the novel polypeptides of the invention. Appropriate vectors which can transform microorganisms capable of expressing the fusion molecules include expression vectors comprising nucleotide sequences coding for the fusion molecules joined to transcriptional and translational regulatory sequences which are selected according to the host cells used.

Vectors incorporating modified sequences as described above are included in the present invention and are useful in the production of the fusion polypeptides. The vector employed in the method also contains selected regulatory sequences in operative association with the DNA coding sequences of the invention and capable of directing the replication and expression thereof in selected host cells.

As another aspect of the present invention, there is provided a method for producing the novel fusion molecules. The method of the present invention involves culturing a suitable cell or cell line, which has been transformed with a vector containing a DNA sequence coding for expression of a novel hIL-3 variant fusion molecule. Suitable cells or cell lines may be bacterial cells. For example, the various strains of *E. coli* are well-known as host cells in the field of biotechnology. Examples of such strains include *E. coli* strains JM101 [Yanish-Perron, et al. (1985)] and MON105 [Obukowicz, et al. (1992)]. Also included in the present invention is the expression of the fusion protein utilizing a chromosomal expression vector for *E. coli* based on the bacteriophage Mu (Weinberg et al., 1993). Various strains of *B. subtilis* may also be employed in this method. Many strains of yeast cells known to those skilled in the art are also available as host cells for expression of the polypeptides of the present invention. When expressed in the *E. coli* cytoplasm, the above-mentioned mutant hIL-3 variant fusion molecules of the present invention may also be constructed with Met-Ala- at the N-terminus so that upon expression the Met is cleaved off leaving Ala at the N-terminus. The fusion molecules of the present invention may include fusion polypeptides having Met-, Ala- or Met-Ala- attached to the N-terminus. When the fusion molecules are expressed in the cytoplasm of *E. coli*, polypeptides with and without Met attached to the N-terminus are obtained. The N-termini of proteins made in the cytoplasm of *E. coli* are affected by posttranslational processing by methionine aminopeptidase (Ben-Bassat et al., 1987) and possibly by other peptidases. These mutant fusion molecules may also be expressed in E. coli by fusing a signal peptide to the N-terminus. This signal peptide is cleaved from the polypeptide as part of the secretion process. Secretion in E. coli can be used to obtain the correct amino acid at the N-terminus (e.g., $Asn^{15}$ in the (15–125) hIL-3 polypeptide) due to the precise nature of the signal peptidase. This is in contrast to the heterogeneity often observed at the N-terminus of proteins expressed in the cytoplasm in E. coli.

Also suitable for use in the present invention are mammalian cells, such as Chinese hamster ovary cells (CHO). General methods for expression of foreign genes in mammalian cells are reviewed in: Kaufman, R. J. (1987) High level production of proteins in mammalian cells, in Genetic Engineering, Principles and Methods, Vol. 9, J. K. Setlow, editor, Plenum Press, New York. An expression vector is constructed in which a strong promoter capable of functioning in mammalian cells drives transcription of a eukaryotic secretion signal peptide coding region, which is translationally fused to the coding region for the fusion molecule. For example, plasmids such as pcDNA I/Neo, pRc/RSV, and pRc/CMV (obtained from Invitrogen Corp., San Diego, Calif.) can be used. The eukaryotic secretion signal peptide coding region can be from the hIL-3 gene itself or it can be from another secreted mammalian protein (Bayne, M. L. et al. (1987) Proc. Natl. Acad. Sci. USA 84, 2638–2642). After construction of the vector containing the hIL-3 variant gene, the vector DNA is transfected into mammalian cells. Such cells can be, for example, the COS7, HeLa, BHK, CHO, or mouse L lines. The cells can be cultured, for example, in DMEM media (JRH Scientific). The hIL-3 variant secreted into the media can be recovered by standard biochemical approaches following transient expression 24–72 hours after transfection of the cells or after establishment of stable cell lines following selection for neomycin resistance. The selection of suitable mammalian host cells and methods for transformation, culture, amplification, screening and product production and purification are known in the art. See, e.g., Gething and Sambrook, Nature, 293:620–625 (1981), or alternatively, Kaufman et al, Mol. Cell. Biol., 5(7) :1750–1759 (1985) or Howley et al., U.S. Pat. No. 4,419, 446. Another suitable mammalian cell line is the monkey COS-1 cell line. A similarly useful mammalian cell line is the CV-1 cell line.

Where desired, insect cells may be utilized as host cells in the method of the present invention. See, e.g. Miller et al, Genetic Engineering, 8:277–298 (Plenum Press 1986) and references cited therein. In addition, general methods for expression of foreign genes in insect cells using Baculovirus vectors are described in: Summers, M. D. and Smith, G. E. (1987)—A manual of methods for Baculovirus vectors and insect cell culture procedures, Texas Agricultural Experiment Station Bulletin No. 1555. An expression vector is constructed comprising a Baculovirus transfer vector, in which a strong Baculovirus promoter (such as the polyhedron promoter) drives transcription of a eukaryotic secretion signal peptide coding region, which is translationally fused to the coding region for the fusion polypeptide. For example, the plasmid pVL1392 (obtained from Invitrogen Corp., San Diego, Calif.) can be used. After construction of the vector carrying the gene encoding the fusion polypeptide, two micrograms of this DNA is cotransfected with one microgram of Baculovirus DNA (see Summers & Smith, 1987) into insect cells, strain SF9. Pure recombinant Baculovirus carrying the fusion molecule is used to infect cells cultured, for example, in Excell 401 serum-free medium (JRH Biosciences, Lenexa, Kans.). The fusion molecule secreted into the medium can be recovered by standard biochemical approaches. Supernatants from mammalian or insect cells expressing the fusion protein can be first concentrated using any of an number of commercial concentration units.

The fusion molecules of the present invention may be useful in the treatment of diseases characterized by a decreased levels of either myeloid, erythroid, lymphoid, or megakaryocyte cells of the hematopoietic system or combinations thereof. In addition, they may be used to activate mature myeloid and/or lymphoid cells. Among conditions susceptible to treatment with the polypeptides of the present invention is leukopenia, a reduction in the number of circulating leukocytes (white cells) in the peripheral blood. Leukopenia may be induced by exposure to certain viruses or to radiation. It is often a side effect of various forms of cancer therapy, e.g., exposure to chemotherapeutic drugs, radiation and of infection or hemorrhage. Therapeutic treatment of leukopenia with these fusion molecules of the present invention may avoid undesirable side effects caused by treatment with presently available drugs.

The fusion molecules of the present invention may be useful in the treatment of neutropenia and, for example, in the treatment of such conditions as aplastic anemia, cyclic neutropenia, idiopathic neutropenia, Chediak-Higashi syndrome, systemic lupus erythematosus (SLE), leukemia, myelodysplastic syndrome and myelofibrosis.

The fusion molecule of the present invention may be useful in the treatment or prevention of thrombocytopenia. Currently the only therapy for thrombocytopenia is platelet transfusions which are costly and carry the significant risks of infection (HIV, HBV) and alloimunization. The fusion molecule may alleviate or diminish the need for platelet transfusions. Severe thrombocytopenia may result from genetic defects such as Fanconi's Anemia, Wiscott-Aldrich, or May-Hegglin syndromes. Acquired thrombocytopenia may result from auto- or allo-antibodies as in Immune Thrombocytopenia Purpura, Systemic Lupus Erythromatosis, hemolytic anemia, or fetal maternal incompatibility. In addition, splenomegaly, disseminated intravascular coagulation, thrombotic thrombocytopenic purpura, infection or prosthetic heart valves may result in thrombocytopenia. Severe thrombocytopenia may also result from chemotherapy and/or radiation therapy or cancer. Thrombocytopenia may also result from marrow invasion by carcinoma, lymphoma, leukemia or fibrosis.

The fusion molecules of the present invention may be useful in the mobilization of hematopoietic progenitors and stem cells into peripheral blood. Peripheral blood derived progenitors have been shown to be effective in reconstituting patients in the setting of autologous marrow transplantation. Hematopoietic growth factors including G-CSF and GM-CSF have been shown to enhance the number of circulating progenitors and stem cells in the peripheral blood. This has simplified the procedure for peripheral stem cell collection and dramatically decreased the cost of the procedure by decreasing the number of pheresis required. The fusion molecule may be useful in mobilization of stem cells and further enhance the efficacy of peripheral stem cell transplantation.

Another projected clinical use of growth factors has been in the in vitro activation of hematopoietic progenitors and stem cells for gene therapy. In order to have the gene of interest incorporated into the genome of the hematopoietic progenitor or stem cell one needs to stimulate cell division and DNA replication. Hematopoietic stem cells cycle at a very low frequency which means that growth factors may be useful to promote gene transduction and thereby enhance the clinical prospects for gene therapy.

Many drugs may cause bone marrow suppression or hematopoietic deficiencies. Examples of such drugs are AZT, DDI, alkylating agents and anti-metabolites used in chemotherapy, antibiotics such as chloramphenicol, penicillin, gancyclovir, daunomycin and sulfa drugs, phenothiazones, tranquilizers such as meprobamate, analgesics such as aminopyrine and dipyrone, anti convulsants such as phenytoin or carbamazepine, antithyroids such as propylthiouracil and methimazole and diuretics. The fusion molecules of the present invention may be useful in preventing or treating the bone marrow suppression or hematopoietic deficiencies which often occur in patients treated with these drugs.

Hematopoietic deficiencies may also occur as a result of viral, microbial or parasitic infections and as a result of treatment for renal disease or renal failure, e.g., dialysis. The fusion molecules of the present invention may be useful in treating such hematopoietic deficiency.

The treatment of hematopoietic deficiency may include administration of a pharmaceutical composition containing the fusion molecules to a patient. The fusion molecules of the present invention may also be useful for the activation and amplification of hematopoietic precursor cells by treating these cells in vitro with the fusion proteins of the present invention prior to injecting the cells into a patient.

Various immunodeficiencies e.g., in T and/or B lymphocytes, or immune disorders, e.g., rheumatoid arthritis, may also be beneficially affected by treatment with the fusion molecules of the present invention. Immunodeficiencies may be the result of viral infections e.g. HTLVI, HTLVII, HTLVIII, severe exposure to radiation, cancer therapy or the result of other medical treatment. The fusion molecules of the present invention may also be employed, alone or in combination with other hematopoietins, in the treatment of other blood cell deficiencies, including thrombocytopenia (platelet deficiency), or anemia. Other uses for these novel polypeptides are in the treatment of patients recovering from bone marrow transplants in vivo and ex vivo, and in the development of monoclonal and polyclonal antibodies generated by standard methods for diagnostic or therapeutic use.

Other aspects of the present invention are methods and therapeutic compositions for treating the conditions referred to above. Such compositions comprise a therapeutically effective amount of one or more of the fusion molecules of the present invention in a mixture with a pharmaceutically acceptable carrier. This composition can be administered either parenterally, intravenously or subcutaneously. When administered, the therapeutic composition for use in this invention is preferably in the form of a pyrogen-free, parenterally acceptable aqueous solution. The preparation of such a parenterally acceptable protein solution, having due regard to pH, isotonicity, stability and the like, is within the skill of the art.

The dosage regimen involved in a method for treating the above-described conditions will be determined by the attending physician considering various factors which modify the action of drugs, e.g. the condition, body weight, sex and diet of the patient, the severity of any infection, time of administration and other clinical factors. Generally, a daily regimen may be in the range of 0.2–150 μg/kg of fusion protein per kilogram of body weight. This dosage regimen is referenced to a standard level of biological activity which recognizes that native IL-3 generally possesses an $EC_{50}$ at or about 10 picoMolar to 100 picoMolar in the AML proliferation assay described herein. Therefore, dosages would be adjusted relative to the activity of a given fusion protein vs. the activity of native (reference) IL-3 and it would not be unreasonable to note that dosage regimens may include doses as low as 0.1 microgram and as high as 1 milligram per kilogram of body weight per day. In addition, there may exist specific circumstances where dosages of fusion molecule would be adjusted higher or lower than the range of 10–200 micrograms per kilogram of body weight. These include co-administration with other colony stimulating factor or IL-3 variant or growth factors; co-administration with chemotherapeutic drugs and/or radiation; the use of glycosylated fusion protein; and various patient-related issues mentioned earlier in this section. As indicated above, the therapeutic method and compositions may also include co-administration with other human factors. A non-exclusive list of other appropriate hematopoietins, CSFs, cytokines, lymphokines, hematopoietic growth factors and interleukins for simultaneous or serial co-administration with the polypeptides of the present invention includes GM-CSF, CSF-1, G-CSF, Meg-CSF, M-CSF, erythropoietin (EPO), IL-1, IL-4, IL-2, IL-5, IL-6, IL-7, IL-8, IL-9, IL-10, IL-11, IL-12, IL-13, LIF, flt3/flk2, B-cell growth factor, B-cell differentiation factor and eosinophil differentiation factor, stem cell factor (SCF) also known as steel factor or c-kit ligand, or combinations thereof. The dosage recited above would be adjusted to compensate for such additional components in the therapeutic composition. Progress of the treated patient can be monitored by periodic assessment of the hematological profile, e.g., differential cell count and the like.

The present invention is also directed to the following;

1. A fusion protein having the formula selected from the group consisting of $R_1$-L-$R_2$, $R_2$-L-$R_1$, $R_1$-$R_2$ or $R_2$-$R_1$ wherein R1 is a human interleukin-3 mutant polypeptide of the Formula:

```
Ala Pro Met Thr Gln Thr Thr Ser Leu Lys Thr Ser Trp Val Asn  [SEQ ID NO:1]
 1           5                   10                      15

Cys Xaa Xaa Xaa Xaa Xaa Xaa Xaa Xaa Xaa Xaa Xaa Xaa Xaa Xaa
                 20                  25                  30

Xaa Xaa Xaa Xaa Xaa Xaa Xaa Xaa Xaa Xaa Xaa Xaa Xaa Xaa Xaa
                 35                  40                  45

Xaa Xaa Xaa Xaa Xaa Xaa Xaa Xaa Xaa Xaa Xaa Xaa Xaa Xaa Xaa
                 50                  55                  60

Xaa Xaa Xaa Xaa Xaa Xaa Xaa Xaa Xaa Xaa Xaa Xaa Xaa Xaa Xaa
```

-continued

```
                    65                    70                    75
Xaa Xaa Xaa Xaa Xaa Xaa Xaa Xaa Xaa Xaa Xaa Xaa Xaa Xaa Xaa
                        80                    85                    90

Xaa Xaa Xaa Xaa Xaa Xaa Xaa Xaa Xaa Xaa Xaa Xaa Xaa Xaa Xaa
                        95                   100                   105

Xaa Xaa Xaa Xaa Xaa Xaa Xaa Xaa Xaa Xaa Xaa Xaa Xaa Xaa Xaa
                       110                   115                   120

Xaa Xaa Xaa Gln Gln Thr Thr Leu Ser Leu Ala Ile Phe
                125                 130
``` wherein
Xaa at position 17 is Ser, Lys, Gly, Asp, Met, Gln, or Arg;
Xaa at position 18 is Asn, His, Leu, Ile, Phe, Arg, or Gln;
Xaa at position 19 is Met, Phe, Ile, Arg, Gly, Ala, or Cys;
Xaa at position 20 is Ile, Cys, Gln, Glu, Arg, Pro, or Ala;
Xaa at position 21 is Asp, Phe, Lys, Arg, Ala, Gly, Glu, Gln, Asn, Thr, Ser or Val;
Xaa at position 22 is Glu, Trp, Pro, Ser, Ala, His, Asp, Asn, Gln, Leu, Val or Gly;
Xaa at position 23 is Ile, Val, Ala, Leu, Gly, Trp, Lys, Phe, Ser, or Arg;
Xaa at position 24 is Ile, Gly, Val, Arg, Ser, Phe, or Leu;
Xaa at position 25 is Thr, His, Gly, Gln, Arg, Pro, or Ala;
Xaa at position 26 is His, Thr, Phe, Gly, Arg, Ala, or Trp;
Xaa at position 27 is Leu, Gly, Arg, Thr, Ser, or Ala;
Xaa at position 28 is Lys, Arg, Leu, Gln, Gly, Pro, Val or Trp;
Xaa at position 29 is Gln, Asn, Leu, Pro, Arg, or Val;
Xaa at position 30 is Pro, His, Thr, Gly, Asp, Gln, Ser, Leu, or Lys;
Xaa at position 31 is Pro, Asp, Gly, Ala, Arg, Leu, or Gln;
Xaa at position 32 is Leu, Val, Arg, Gln, Asn, Gly, Ala, or Glu;
Xaa at position 33 is Pro, Leu, Gln, Ala, Thr, or Glu;
Xaa at position 34 is Leu, Val, Gly, Ser, Lys, Glu, Gln, Thr, Arg, Ala, Phe, Ile or Met;
Xaa at position 35 is Leu, Ala, Gly, Asn, Pro, Gln, or Val;
Xaa at position 36 is Asp, Leu, or Val;
Xaa at position 37 is Phe, Ser, Pro, Trp, or Ile;
Xaa at position 38 is Asn, or Ala;
Xaa at position 40 is Leu, Trp, or Arg;
Xaa at position 41 is Asn, Cys, Arg, Leu, His, Met, or Pro;
Xaa at position 42 is Gly, Asp, Ser, Cys, Asn, Lys, Thr, Leu, Val, Glu, Phe, Tyr, Ile, Met or Ala;
Xaa at position 43 is Glu, Asn, Tyr, Leu, Phe, Asp, Ala, Cys, Gln, Arg, Thr, Gly or Ser;
Xaa at position 44 is Asp, Ser, Leu, Arg, Lys, Thr, Met, Trp, Glu, Asn, Gln, Ala or Pro;
Xaa at position 45 is Gln, Pro, Phe, Val, Met, Leu, Thr, Lys, Trp, Asp, Asn, Arg, Ser, Ala, Ile, Glu or His;
Xaa at position 46 is Asp, Phe, Ser, Thr, Cys, Glu, Asn, Gln, Lys, His, Ala, Tyr, Ile, Val or Gly;
Xaa at position 47 is Ile, Gly, Val, Ser, Arg, Pro, or His;
Xaa at position 48 is Leu, Ser, Cys, Arg, Ile, His, Phe, Glu, Lys, Thr, Ala, Met, Val or Asn;
Xaa at position 49 is Met, Arg, Ala, Gly, Pro, Asn, His, or Asp;
Xaa at position 50 is Glu, Leu, Thr, Asp, Tyr, Lys, Asn, Ser, Ala, Ile, Val, His, Phe, Met or Gln;
Xaa at position 51 is Asn, Arg, Met, Pro, Ser, Thr, or His;
Xaa at position 52 is Asn, His, Arg, Leu, Gly, Ser, or Thr;
Xaa at position 53 is Leu, Thr, Ala, Gly, Glu, Pro, Lys, Ser, or Met;
Xaa at position 54 is Arg, Asp, Ile, Ser, Val, Thr, Gln, Asn, Lys, His, Ala or Leu;

Xaa at position 55 is Arg, Thr, Val, Ser, Leu, or Gly;
Xaa at position 56 is Pro, Gly, Cys, Ser, Gln, Glu, Arg, His, Thr, Ala, Tyr, Phe, Leu, Val or Lys;
Xaa at position 57 is Asn or Gly;
Xaa at position 58 is Leu, Ser, Asp, Arg, Gln, Val, or Cys;
Xaa at position 59 is Glu Tyr, His, Leu, Pro, or Arg;
Xaa at position 60 is Ala, Ser, Pro, Tyr, Asn, or Thr;
Xaa at position 61 is Phe, Asn, Glu, Pro, Lys, Arg, or Ser;
Xaa at position 62 is Asn His, Val, Arg, Pro, Thr, Asp, or Ile;
Xaa at position 63 is Arg, Tyr, Trp, Lys, Ser, His, Pro, or Val;
Xaa at position 64 is Ala, Asn, Pro, Ser, or Lys;
Xaa at position 65 is Val, Thr, Pro, His, Leu, Phe, or Ser;
Xaa at position 66 is Lys, Ile, Arg, Val, Asn, Glu, or Ser;
Xaa at position 67 is Ser, Ala, Phe, Val, Gly, Asn, Ile, Pro, or His;
Xaa at position 68 is Leu, Val, Trp, Ser, Ile, Phe, Thr, or His;
Xaa at position 69 is Gln, Ala, Pro, Thr, Glu, Arg, Trp, Gly, or Leu;
Xaa at position 70 is Asn, Leu, Val, Trp, Pro, or Ala;
Xaa at position 71 is Ala, Met, Leu, Pro, Arg, Glu, Thr, Gln, Trp, or Asn;
Xaa at position 72 is Ser, Glu, Met, Ala, His, Asn, Arg, or Asp;
Xaa at position 73 is Ala, Glu, Asp, Leu, Ser, Gly, Thr, or Arg;
Xaa at position 74 is Ile, Met, Thr, Pro, Arg, Gly, Ala;
Xaa at position 75 is Glu, Lys, Gly, Asp, Pro, Trp, Arg, Ser, Gln, or Leu;
Xaa at position 76 is Ser, Val, Ala, Asn, Trp, Glu, Pro, Gly, or Asp;
Xaa at position 77 is Ile, Ser, Arg, Thr, or Leu;
Xaa at position 78 is Leu, Ala, Ser, Glu, Phe, Gly, or Arg;
Xaa at position 79 is Lys, Thr, Asn, Met, Arg, Ile, Gly, or Asp;
Xaa at position 80 is Asn, Trp, Val, Gly, Thr, Leu, Glu, or Arg;
Xaa at position 81 is Leu, Gln, Gly, Ala, Trp, Arg, Val, or Lys;
Xaa at position 82 is Leu, Gln, Lys, Trp, Arg, Asp, Glu, Asn, His, Thr, Ser, Ala, Tyr, Phe, Ile, Met or Val;
Xaa at position 83 is Pro, Ala, Thr, Trp, Arg, or Met;
Xaa at position 84 is Cys, Glu, Gly, Arg, Met, or Val;
Xaa at position 85 is Leu, Asn, Val, or Gln;
Xaa at position 86 is Pro, Cys, Arg, Ala, or Lys;
Xaa at position 87 is Leu, Ser, Trp, or Gly;
Xaa at position 88 is Ala, Lys, Arg, Val, or Trp;
Xaa at position 89 is Thr, Asp, Cys, Leu, Val, Glu, His, Asn, or Ser;
Xaa at position 90 is Ala, Pro, Ser, Thr, Gly, Asp, Ile, or Met;
Xaa at position 91 is Ala, Pro, Ser, Thr, Phe, Leu, Asp, or His;
Xaa at position 92 is Pro, Phe, Arg, Ser, Lys, His, Ala, Gly, Ile or Leu;
Xaa at position 93 is Thr, Asp, Ser, Asn, Pro, Ala, Leu, or Arg;

Xaa at position 94 is Arg, Ile, Ser, Glu, Leu, Val, Gln, Lys, His, Ala, or Pro;

Xaa at position 95 is His, Gln, Pro, Arg, Val, Leu, Gly, Thr, Asn, Lys, Ser, Ala, Trp, Phe, Ile, or Tyr;

Xaa at position 96 is Pro, Lys, Tyr, Gly, Ile, or Thr;

Xaa at position 97 is Ile, Val, Lys, Ala, or Asn;

Xaa at position 98 is His, Ile, Asn, Leu, Asp, Ala, Thr, Glu, Gln, Ser, Phe, Met, Val, Lys, Arg, Tyr or Pro;

Xaa at position 99 is Ile, Leu, Arg, Asp, Val, Pro, Gln, Gly, Ser, Phe, or His;

Xaa at position 100 is Lys, Tyr, Leu, His, Arg, Ile, Ser, Gln, or Pro;

Xaa at position 101 is Asp, Pro, Met, Lys, His, Thr, Val, Tyr, Glu, Asn, Ser, Ala, Gly, Ile, Leu, or Gln;

Xaa at position 102 is Gly, Leu, Glu, Lys, Ser, Tyr, or Pro;

Xaa at position 103 is Asp, or Ser;

Xaa at position 104 is Trp, Val, Cys, Tyr, Thr, Met, Pro, Leu, Gln, Lys, Ala, Phe, or Gly;

Xaa at position 105 is Asn, Pro, Ala, Phe, Ser, Trp, Gln, Tyr, Leu, Lys, Ile, Asp, or His;

Xaa at position 106 is Glu, Ser, Ala, Lys, Thr, Ile, Gly, or Pro;

Xaa at position 108 is Arg, Lys, Asp, Leu, Thr, Ile, Gln, His, Ser, Ala or Pro;

Xaa at position 109 is Arg, Thr, Pro, Glu, Tyr, Leu, Ser, or Gly;

Xaa at position 110 is Lys, Ala, Asn, Thr, Leu, Arg, Gln, His, Glu, Ser, Ala, or Trp;

Xaa at position 111 is Leu, Ile, Arg, Asp, or Met;

Xaa at position 112 is Thr, Val, Gln, Tyr, Glu, His, Ser, or Phe;

Xaa at position 113 is Phe, Ser, Cys, His, Gly, Trp, Tyr, Asp, Lys, Leu, Ile, Val or Asn;

Xaa at position 114 is Tyr, Cys, His, Ser, Trp, Arg, or Leu;

Xaa at position 115 is Leu, Asn, Val, Pro, Arg, Ala, His, Thr, Trp, or Met;

Xaa at position 116 is Lys, Leu, Pro, Thr, Met, Asp, Val, Glu, Arg, Trp, Ser, Asn, His, Ala, Tyr, Phe, Gln, or Ile;

Xaa at position 117 is Thr, Ser, Asn, Ile, Trp, Lys, or Pro;

Xaa at position 118 is Leu, Ser, Pro, Ala, Glu, Cys, Asp, or Tyr;

Xaa at position 119 is Glu, Ser, Lys, Pro, Leu, Thr, Tyr, or Arg;

Xaa at position 120 is Asn, Ala, Pro, Leu, His, Val, or Gln;

Xaa at position 121 is Ala, Ser, Ile, Asn, Pro, Lys, Asp, or Gly;

Xaa at position 122 is Gln, Ser, Met, Trp, Arg, Phe, Pro, His, Ile, Tyr, or Cys;

Xaa at position 123 is Ala, Met, Glu, His, Ser, Pro, Tyr, or Leu;

and which can additionally have Met- preceding the amino acid in position 1; and wherein from 1 to 14 amino acids can be deleted from the N-terminus and/or from 1 to 15 amino acids can be deleted from the C-terminus; and wherein from 4 to 44 of the amino acids designated by Xaa are different from the corresponding amino acids of native (1–133) human interleukin-3;

$R_2$ is a colony stimulating factor selected from the group cons

Xaa at position 38 is Asn or Ala;
Xaa at position 42 is Gly, Asp, Ser, Cys, Ala, Asn, Ile, Leu, Met, Tyr or Arg;
Xaa at position 44 is Asp or Glu;
Xaa at position 45 is Gln, Val, Met, Leu, Thr, Ala, Asn, Glu, Ser or Lys;
Xaa at position 46 is Asp, Phe, Ser, Thr, Ala, Asn Gln, Glu, His, Ile, Lys, Tyr, Val or Cys;
Xaa at position 50 is Glu, Ala, Asn, Ser or Asp;
Xaa at position 51 is Asn, Arg, Met, Pro, Ser, Thr, or His;
Xaa at position 54 is Arg or Ala;
Xaa at position 55 is Arg, Thr, Val, Leu, or Gly;
Xaa at position 56 is Pro, Gly, Ser, Gln, Ala, Arg, Asn, Glu, Leu, Thr, Val or Lys;
Xaa at position 60 is Ala or Ser;
Xaa at position 62 is Asn, Pro, Thr, or Ile;
Xaa at position 63 is Arg or Lys;
Xaa at position 64 is Ala or Asn;
Xaa at position 65 is Val or Thr;
Xaa at position 66 is Lys or Arg;
Xaa at position 67 is Ser, Phe, or His;
Xaa at position 68 is Leu, Ile, Phe, or His;
Xaa at position 69 is Gln, Ala, Pro, Thr, Glu, Arg, or Gly;
Xaa at position 71 is Ala, Pro, or Arg;
Xaa at position 72 is Ser, Glu, Arg, or Asp;
Xaa at position 73 is Ala or Leu;
Xaa at position 76 is Ser, Val, Ala, Asn, Glu, Pro, or Gly;
Xaa at position 77 is Ile or Leu;
Xaa at position 79 is Lys, Thr, Gly, Asn, Met, Arg, Ile, or Asp;
Xaa at position 80 is Asn, Gly, Glu, or Arg;
Xaa at position 82 is Leu, Gln, Trp, Arg, Asp, Ala, Asn, Glu, His, Ile, Met, Phe, Ser, Thr, Tyr or Val;
Xaa at position 83 is Pro or Thr;
Xaa at position 85 is Leu or Val;

Xaa at position 98 is His, Ile, Asn, Leu, Ala, Thr, Arg, Gln, Lys, Met, Ser, Tyr, Val or Pro;
Xaa at position 99 is Ile, Leu, or Val;
Xaa at position 100 is Lys, Arg, Ile, Gln, Pro, or Ser;
Xaa at position 101 is Asp, Pro, Met, Lys, His, Thr, Pro, Asn, Ile, Leu or Tyr;
Xaa at position 104 is Trp or Leu;
Xaa at position 105 is Asn, Pro, Ala, Ser, Trp, Gln, Tyr, Leu, Lys, Ile, Asp, or His;
Xaa at position 106 is Glu or Gly;
Xaa at position 108 is Arg, Ala, or Ser;
Xaa at position 109 is Arg, Thr, Glu, Leu, or Ser;
Xaa at position 112 is Thr, Val, or Gln;
Xaa at position 114 is Tyr or Trp;
Xaa at position 115 is Leu or Ala;
Xaa at position 116 is Lys, Thr, Val, Trp, Ser, Ala, His, Met, Phe, Tyr or Ile;
Xaa at position 117 is Thr or Ser;
Xaa at position 120 is Asn, Pro, Leu, His, Val, or Gln;
Xaa at position 121 is Ala, Ser, Ile, Asn, Pro, Asp, or Gly;
Xaa at position 122 is Gln, Ser, Met, Trp, Arg, Phe, Pro, His, Ile, Tyr, or Cys;
Xaa at position 123 is Ala, Met, Glu, His, Ser, Pro, Tyr, or Leu;
and which can additionally have Met- preceding the amino acid in position 1; and wherein from 1 to 14 amino acids can be deleted from the N-terminus and/or from 1 to 15 amino acids can be deleted from the C-terminus; and wherein from 4 to 35 of the amino acids designated by Xaa are different from the corresponding amino acids of native (1–133)human interleukin-3.

3. The fusion protein of claim 2 wherein said human interleukin-3 mutant polypeptide is of the Formula:

```
Ala Pro Met Thr Gln Thr Thr Ser Leu Lys Thr Ser Trp Val Asn  [SEQ ID NO:3]
 1               5                  10                  15

Cys Xaa Xaa Met Ile Asp Glu Xaa Ile Xaa Xaa Leu Lys Xaa Xaa
                 20                  25                  30

Pro Xaa Pro Xaa Xaa Asp Phe Xaa Asn Leu Asn Xaa Glu Asp Xaa
                 35                  40                  45

Xaa Ile Leu Met Xaa Xaa Asn Leu Arg Xaa Xaa Asn Leu Glu Ala
                 50                  55                  60

Phe Xaa Arg Xaa Xaa Lys Xaa Xaa Xaa Asn Ala Ser Ala Ile Glu
                 65                  70                  75

Xaa Xaa Leu Xaa Xaa Leu Xaa Pro Cys Leu Pro Xaa Xaa Thr Ala
                 80                  85                  90

Xaa Pro Xaa Arg Xaa Pro Ile Xaa Xaa Xaa Xaa Gly Asp Trp Xaa
                 95                 100                 105

Glu Phe Xaa Xaa Lys Leu Xaa Phe Tyr Leu Xaa Xaa Leu Glu Xaa
                110                 115                 120

Xaa Xaa Xaa Gln Gln Thr Thr Leu Ser Leu Ala Ile Phe
                125                 130
```

Xaa at position 87 is Leu or Ser;
Xaa at position 88 is Ala or Trp;
Xaa at position 91 is Ala or Pro;
Xaa at position 93 is Thr, Asp, Ser, Pro, Ala, Leu, or Arg;
Xaa at position 95 is His, Pro, Arg, Val, Leu, Gly, Asn, Phe, Ser or Thr;
Xaa at position 96 is Pro or Tyr;
Xaa at position 97 is Ile or Val;

wherein
Xaa at position 17 is Ser, Gly, Asp, or Gln;
Xaa at position 18 is Asn, His, or Ile;
Xaa at position 23 is Ile, Ala, Leu, or Gly;
Xaa at position 25 is Thr, His, or Gln;
Xaa at position 26 is His or Ala;
Xaa at position 29 is Gln or Asn;
Xaa at position 30 is Pro or Gly;

Xaa at position 32 is Leu, Arg, Asn, or Ala;
Xaa at position 34 is Leu, Val, Ser, Ala, Arg, Gln, Glu, Ile, Phe, Thr, or Met;
Xaa at position 35 is Leu, Ala, Asn, or Pro;
Xaa at position 38 is Asn or Ala;
Xaa at position 42 is Gly, Asp, Ser, Ala, Asn, Ile, Leu, Met, Tyr or Arg;
Xaa at position 45 is Gln, Val, Met, Leu, Ala, Asn, Glu, or Lys;
Xaa at position 46 is Asp, Phe, Ser, Gln, Glu, His, Val or Thr;
Xaa at position 50 is Glu Asn, Ser or Asp;
Xaa at position 51 is Asn, Arg, Pro, Thr, or His;
Xaa at position 55 is Arg, Leu, or Gly;
Xaa at position 56 is Pro, Gly, Ser, Ala, Asn, Val, Leu or Gln;
Xaa at position 62 is Asn, Pro, or Thr;
Xaa at position 64 is Ala or Asn;
Xaa at position 65 is Val or Thr;
Xaa at position 67 is Ser or Phe;
Xaa at position 68 is Leu or Phe;
Xaa at position 69 is Gln, Ala, Glu, or Arg;
Xaa at position 76 is Ser, Val, Asn, Pro, or Gly;
Xaa at position 77 is Ile or Leu;
Xaa at position 79 is Lys, Asn, Met, Arg, Ile, or Gly;
Xaa at position 80 is Asn, Gly, Glu, or Arg;
Xaa at position 82 is Leu, Gln, Trp, Arg, Asp, Asn, Glu, His, Met, Phe, Ser, Thr, Tyr or Val;
Xaa at position 87 is Leu or Ser;
Xaa at position 88 is Ala or Trp;
Xaa at position 91 is Ala or Pro;
Xaa at position 93 is Thr, Asp, or Ala;
Xaa at position 95 is His, Pro, Arg, Val, Gly, Asn, Ser or Thr;
Xaa at position 98 is His, Ile, Asn, Ala, Thr, Gln, Glu, Lys, Met, Ser, Tyr, Val or Leu;
Xaa at position 99 is Ile or Leu;
Xaa at position 100 is Lys or Arg;
Xaa at position 101 is Asp, Pro, Met, Lys, Thr, His, Pro, Asn, Ile, Leu or Tyr;
Xaa at position 105 is Asn, Pro, Ser, Ile or Asp;
Xaa at position 108 is Arg, Ala, or Ser;
Xaa at position 109 is Arg, Thr, Glu, Leu, or Ser;
Xaa at position 112 is Thr or Gln;

Xaa at position 122 is Gln, Met, Trp, Phe, Pro, His, Ile, or Tyr;
Xaa at position 123 is Ala, Met, Glu, Ser, or Leu;
and which can additionally have Met- preceding the amino acid in position 1; and wherein from 1 to 14 amino acids can be deleted from the N-terminus and/or from 1 to 15 amino acids can be deleted from the C-terminus; and wherein from 4 to 44 of the amino acids designated by Xaa are different from the corresponding amino acids of native (1–133)human interleukin-3

Xaa at position 6 is Ile, Cys, Gln, Glu, Arg, Pro, or Ala;
Xaa at position 7 is Asp, Phe, Lys, Arg, Ala, Gly, Glu, Gln, Asn, Thr, Ser or Val;
Xaa at position 8 is Glu, Trp, Pro, Ser, Ala, His, Asp, Asn, Gln, Leu, Val, or Gly;
Xaa at position 9 is Ile, Val, Ala, Leu, Gly, Trp, Lys, Phe, Ser, or Arg;
Xaa at position 10 is Ile, Gly, Val, Arg, Ser, Phe, or Leu;
Xaa at position 11 is Thr, His, Gly, Gln, Arg, Pro, or Ala;
Xaa at position 12 is His, Thr, Phe, Gly, Arg, Ala, or Trp;
Xaa at position 13 is Leu, Gly, Arg, Thr, Ser, or Ala;
Xaa at position 14 is Lys, Arg, Leu, Gln, Gly, Pro, Val or Trp;
Xaa at position 15 is Gln, Asn, Leu, Pro, Arg, or Val;
Xaa at position 16 is Pro, His, Thr, Gly, Asp, Gln, Ser, Leu, or Lys;
Xaa at position 17 is Pro, Asp, Gly, Ala, Arg, Leu, or Gln;
Xaa at position 18 is Leu, Val, Arg, Gln, Asn, Gly, Ala, or Glu;
Xaa at position 19 is Pro, Leu, Gln, Ala, Thr, or Glu;
Xaa at position 20 is Leu, Val, Gly, Ser, Lys, Glu, Gln, Thr, Arg, Ala, Phe, Ile or Met;
Xaa at position 21 is Leu, Ala, Gly, Asn, Pro, Gln, or Val;
Xaa at position 22 is Asp, Leu, or Val;
Xaa at position 23 is Phe, Ser, Pro, Trp, or Ile;
Xaa at position 24 is Asn, or Ala;
Xaa at position 26 is Leu, Trp, or Arg;
Xaa at position 27 is Asn, Cys, Arg, Leu, His, Met, Pro;
Xaa at position 28 is Gly, Asp, Ser, Cys, Ala, Lys, Asn, Thr, Leu, Val, Glu, Phe, Tyr, Ile or Met;
Xaa at position 29 is Glu, Asn, Tyr, Leu, Phe, Asp, Ala, Cys, Gln, Arg, Thr, Gly or Ser;
Xaa at position 30 is Asp, Ser, Leu, Arg, Lys, Thr, Met, Trp, Glu, Asn, Gln, Ala or Pro;
Xaa at position 31 is Gln, Pro, Phe, Val, Met, Leu, Thr, Lys, Asp, Asn, Arg, Ser, Ala, Ile, Glu, His or Trp;
Xaa at position 32 is Asp, Phe, Ser, Thr, Cys, Glu, Asn, Gln, Lys, His, Ala, Tyr, Ile, Val or Gly;
Xaa at position 33 is Ile, Gly, Val, Ser, Arg, Pro, or His;
Xaa at position 34 is Leu, Ser, Cys, Arg, Ile, His, Phe, Glu, Lys, Thr, Ala, Met, Val or Asn;
Xaa at position 35 is Met, Arg, Ala, Gly, Pro, Asn, His, or Asp;
Xaa at position 36 is Glu, Leu, Thr, Asp, Tyr, Lys, Asn, Ser, Ala, Ile, Val, His, Phe, Met or Gln;
Xaa at position 37 is Asn, Arg, Met, Pro, Ser, Thr, or His;
Xaa at position 38 is Asn, His, Arg, Leu, Gly, Ser, or Thr;
Xaa at position 39 is Leu, Thr, Ala, Gly, Glu, Pro, Lys, Ser, Met, or;
Xaa at position 40 is Arg, Asp, Ile, Ser, Val, Thr, Gln, Asn, Lys, His, Ala or Leu;
Xaa at position 41 is Arg, Thr, Val, Ser, Leu, or Gly;
Xaa at position 42 is Pro, Gly, Cys, Ser, Gln, Glu, Arg, His, Thr, Ala, Tyr, Phe, Leu, Val or Lys;
Xaa at position 43 is Asn or Gly;
Xaa at position 44 is Leu, Ser, Asp, Arg, Gln, Val, or Cys;
Xaa at position 45 is Glu Tyr, His, Leu, Pro, or Arg;
Xaa at position 46 is Ala, Ser, Pro, Tyr, Asn, or Thr;
Xaa at position 47 is Phe, Asn, Glu, Pro, Lys, Arg, or Ser;
Xaa at position 48 is Asn, His, Val, Arg, Pro, Thr, Asp, or Ile;
Xaa at position 49 is Arg, Tyr, Trp, Lys, Ser, His, Pro, or Val;
Xaa at position 50 is Ala, Asn, Pro, Ser, or Lys;
Xaa at position 51 is Val, Thr, Pro, His, Leu, Phe, or Ser;
Xaa at position 52 is Lys, Ile, Arg, Val, Asn, Glu, or Ser;
Xaa at position 53 is Ser, Ala, Phe, Val, Gly, Asn, Ile, Pro, or His;
Xaa at position 54 is Leu, Val, Trp, Ser, Ile, Phe, Thr, or His;
Xaa at position 55 is Gln, Ala, Pro, Thr, Glu, Arg, Trp, Gly, or Leu;
Xaa at position 56 is Asn, Leu, Val, Trp, Pro, or Ala;
Xaa at position 57 is Ala, Met, Leu, Pro, Arg, Glu, Thr, Gln, Trp, or Asn;
Xaa at position 58 is Ser, Glu, Met, Ala, His, Asn, Arg, or Asp;
Xaa at position 59 is Ala, Glu, Asp, Leu, Ser, Gly, Thr, or Arg;
Xaa at position 60 is Ile, Met, Thr, Pro, Arg, Gly, Ala;
Xaa at position 61 is Glu, Lys, Gly, Asp, Pro, Trp, Arg, Ser, Gln, or Leu;
Xaa at position 62 is Ser, Val, Ala, Asn, Trp, Glu, Pro, Gly, or Asp;
Xaa at position 63 is Ile, Ser, Arg, Thr, or Leu;
Xaa at position 64 is Leu, Ala, Ser, Glu, Phe, Gly, or Arg;
Xaa at position 65 is Lys, Thr, Gly, Asn, Met, Arg, Ile, or Asp;
Xaa at position 66 is Asn, Trp, Val, Gly, Thr, Leu, Glu, or Arg;
Xaa at position 67 is Leu, Gln, Gly, Ala, Trp, Arg, Val, or Lys;
Xaa at position 68 is Leu, Gln, Lys, Trp, Arg, Asp, Glu, Asn, His, Thr, Ser, Ala, Tyr, Phe, Ile, Met or Val;
Xaa at position 69 is Pro, Ala, Thr, Trp, Arg, or Met;
Xaa at position 70 is Cys, Glu, Gly, Arg, Met, or Val;
Xaa at position 71 is Leu, Asn, Val, or Gln;
Xaa at position 72 is Pro, Cys, Arg, Ala, or Lys;
Xaa at position 73 is Leu, Ser, Trp, or Gly;
Xaa at position 74 is Ala, Lys, Arg, Val, or Trp;
Xaa at position 75 is Thr, Asp, Cys, Leu, Val, Glu, His, Asn, or Ser;
Xaa at position 76 is Ala, Pro, Ser, Thr, Gly, Asp, Ile, or Met;
Xaa at position 77 is Ala, Pro, Ser, Thr, Phe, Leu, Asp, or His;
Xaa at position 78 is Pro, Phe, Arg, Ser, Lys, His, Ala, Gly, Ile or Leu;
Xaa at position 79 is Thr, Asp, Ser, Asn, Pro, Ala, Leu, or Arg;
Xaa at position 80 is Arg, Ile, Ser, Glu, Leu, Val, Gln, Lys, His, Ala or Pro;
Xaa at position 81 is His, Gln, Pro, Arg, Val, Leu, Gly, Thr, Asn, Lys, Ser, Ala, Trp, Phe, Ile or Tyr;
Xaa at position 82 is Pro, Lys, Tyr, Gly, Ile, or Thr;
Xaa at position 83 is Ile, Val, Lys, Ala, or Asn;
Xaa at position 84 is His, Ile, Asn, Leu, Asp, Ala, Thr, Glu, Gln, Ser, Phe, Met, Val, Lys, Arg, Tyr or Pro;
Xaa at position 85 is Ile, Leu, Arg, Asp, Val, Pro, Gln, Gly, Ser, Phe, or His;
Xaa at position 86 is Lys, Tyr, Leu, His, Arg, Ile, Ser, Gln, Pro;
Xaa at position 87 is Asp, Pro, Met, Lys, His, Thr, Val, Tyr, Glu, Asn, Ser, Ala, Gly, Ile, Leu or Gln;
Xaa at position 88 is Gly, Leu, Glu, Lys, Ser, Tyr, or Pro;
Xaa at position 89 is Asp, or Ser;
Xaa at position 90 is Trp, Val, Cys, Tyr, Thr, Met, Pro, Leu, Gln, Lys, Ala, Phe, or Gly;
Xaa at position 91 is Asn, Pro, Ala, Phe, Ser, Trp, Gln, Tyr, Leu, Lys, Ile, Asp, or His;
Xaa at position 92 is Glu, Ser, Ala, Lys, Thr, Ile, Gly, or Pro;
Xaa at position 94 is Arg, Lys, Asp, Leu, Thr, Ile, Gln, His, Ser, Ala, or Pro;
Xaa at position 95 is Arg, Thr, Pro, Glu, Tyr, Leu, Ser, or Gly;
Xaa at position 96 is Lys, Asn, Thr, Leu, Gln, Arg, His, Glu, Ser, Ala or Trp;
Xaa at position 97 is Leu, Ile, Arg, Asp, or Met;
Xaa at position 98 is Thr, Val, Gln, Tyr, Glu, His, Ser, or Phe;
Xaa at position 99 is Phe, Ser, Cys, His, Gly, Trp, Tyr, Asp, Lys, Leu, Ile, Val or Asn;

Xaa at position 100 is Tyr, Cys, His, Ser, Trp, Arg, or Leu;
Xaa at position 101 is Leu, Asn, Val, Pro, Arg, Ala, His, Thr, Trp, or Met;
Xaa at position 102 is Lys, Leu, Pro, Thr, Met, Asp, Val, Glu, Arg, Trp, Ser, Asn, His, Ala, Tyr, Phe, Gln, or Ile;
Xaa at position 103 is Thr, Ser, Asn, Ile, Trp, Lys, or Pro;
Xaa at position 104 is Leu, Ser, Pro, Ala, Glu, Cys, Asp, or Tyr;
Xaa at position 105 is Glu, Ser, Lys, Pro, Leu, Thr, Tyr, or Arg;
Xaa at position 106 is Asn, Ala, Pro, Leu, His, Val, or Gln;
Xaa at position 107 is Ala, Ser, Ile, Asn, Pro, Lys, Asp, or Gly;
Xaa at position 108 is Gln, Ser, Met, Trp, Arg, Phe, Pro, His, Ile, Tyr, or Cys;
Xaa at position 109 is Ala, Met, Glu, His, Ser, Pro, Tyr, or Leu;
and which can additionally have Met- or Met-Ala-preceding the amino acid in position 1; and
wherein from 4 to 44 of the amino acids designated by Xaa are different from the corresponding native amino acids of (1–133) human interleukin-3;
$R_2$ is a colony stimulating factor; and
L is a linker capable of Linking $R_1$ to $R_2$.

6. The fusion protein of claim 5 wherein said human interleukin-3 mutant polypeptide is of the Formula:

Xaa at position 28 is Gly, Asp, Ser, Cys, Ala, Asn, Ile, Leu, Met Tyr or Arg;
Xaa at position 30 is Asp or Glu;
Xaa at position 31 is Gln, Val, Met, Leu, Thr, Ala, Asn, Glu, Ser or Lys;
Xaa at position 32 is Asp, Phe, Ser, Thr, Ala, Asn, Gln, Glu, His, Ile, Lys, Tyr, Val or Cys;
Xaa at position 36 is Glu, Ala, Asn, Ser or Asp;
Xaa at position 37 is Asn, Arg, Met, Pro, Ser, Thr, or His;
Xaa at position 40 is Arg or Ala;
Xaa at position 41 is Arg, Thr, Val, Leu, or Gly;
Xaa at position 42 is Pro, Gly, Ser, Gln, Ala, Arg, Asn, Glu, Leu, Thr, Val Or Lys;
Xaa at position 46 is Ala or Ser;
Xaa at position 48 is Asn, Pro, Thr, or Ile;
Xaa at position 49 is Arg or Lys;
Xaa at position 50 is Ala or Asn;
Xaa at position 51 is Val or Thr;
Xaa at position 52 is Lys or Arg;
Xaa at position 53 is Ser, Phe, or His;
Xaa at position 54 is Leu, Ile, Phe, or His;
Xaa at position 55 is Gln, Ala, Pro, Thr, Glu, Arg, or Gly;
Xaa at position 57 is Ala, Pro, or Arg;
Xaa at position 58 is Ser, Glu, Arg, or Asp;
Xaa at position 59 is Ala or Leu;
Xaa at position 62 is Ser, Val, Ala, Asn, Glu, Pro, or Gly;

```
Asn Cys Xaa Xaa Xaa Ile Xaa Glu Xaa Xaa Xaa Xaa Leu Lys Xaa [SEQ ID NO:5]
1               5                   10                  15

Xaa Xaa Xaa Xaa Xaa Xaa Asp Xaa Xaa Asn Leu Asn Xaa Glu Xaa
                20                  25                  30

Xaa Xaa Ile Leu Met Xaa Xaa Asn Leu Xaa Xaa Xaa Ans Leu Glu
                35                  40                  45

Xaa Phe Xaa Xaa Xaa Xaa Xaa Xaa Xaa Xaa Asn Xaa Xaa Xaa Ile
                50                  55                  60

Glu Xaa Xaa Leu Xaa Xaa Leu Xaa Xaa Cys Xaa Pro Xaa Xaa Thr
                65                  70                  75

Ala Xaa Pro Xaa Arg Xaa Xaa Xaa Xaa Xaa Xaa Xaa Gly Asp Xaa
                80                  85                  90

Xaa Xaa Phe Xaa Xaa Lys Leu Xaa Phe Xaa Xaa Xaa Xaa Leu Glu
                95                  100                 105

Xaa Xaa Xaa Xaa Gln Gln
                110
``` wherein
Xaa at position 3 is Ser, Gly, Asp, Met, or Gln;
Xaa at position 4 is Asn, His, or Ile;
Xaa at position 5 is Met or Ile;
Xaa at position 7 is Asp or Glu;
Xaa at position 9 is Ile, Ala, Leu, or Gly;
Xaa at position 10 is Ile, Val, or Leu;
Xaa at position 11 is Thr, His, Gln, or Ala;
Xaa at position 12 is His or Ala;
Xaa at position 15 is Gln, Asn, or Val;
Xaa at position 16 is Pro, Gly, or Gln;
Xaa at position 17 is Pro, Asp, Gly, or Gln;
Xaa at position 18 is Leu, Arg, Gln, Asn, Gly, Ala, or Glu;
Xaa at position 19 is Pro or Glu;
Xaa at position 20 is Leu, Val, Gly, Ser, Lys, Ala, Arg, Gln, Glu, Ile, Phe, Thr or Met;
Xaa at position 21 is Leu, Ala, Asn, Pro, Gln, or Val;
Xaa at position 23 is Phe, Ser, Pro, or Trp;
Xaa at position 24 is Asn or Ala;

Xaa at position 63 is Ile or Leu;
Xaa at position 65 is Lys, Thr, Gly, Asn, Met, Arg, Ile, or Asp;
Xaa at position 66 is Asn, Gly, Glu, or Arg;
Xaa at position 68 is Leu, Gln, Trp, Arg, Asp, Ala, Asn, Glu, His, Ile, Met, Phe, Ser, Thr, Tyr or Val;
Xaa at position 69 is Pro or Thr;
Xaa at position 71 is Leu or Val;
Xaa at position 73 is Leu or Ser;
Xaa at position 74 is Ala or Trp;
Xaa at position 77 is Ala or Pro;
Xaa at position 79 is Thr, Asp, Ser, Pro, Ala, Leu, or Arg;
Xaa at position 81 is His, Pro, Arg, Val, Leu, Gly, Asn, Phe, Ser or Thr;
Xaa at position 82 is Pro or Tyr;
Xaa at position 83 is Ile or Val;
Xaa at position 84 is His, Ile, Asn, Leu, Ala, Thr, Arg, Gln, Lys, Met, Ser, Tyr, Val or Pro;
Xaa at position 85 is Ile, Leu, or Val;

Xaa at position 86 is Lys, Arg, Ile, Gln, Pro, or Ser;
Xaa at position 87 is Asp, Pro, Met, Lys, His, Thr, Asn, Ile, Leu or Tyr;
Xaa at position 90 is Trp or Leu;
Xaa at position 91 is Asn, Pro, Ala, Ser, Trp, Gln, Tyr, Leu, Lys, Ile, Asp, or His;
Xaa at position 92 is Glu, or Gly;
Xaa at position 94 is Arg, Ala, or Ser;
Xaa at position 95 is Arg, Thr, Glu, Leu, or Ser;
Xaa at position 98 is Thr, Val, or Gln;
Xaa at position 100 is Tyr or Trp;
Xaa at position 101 is Leu or Ala;
Xaa at position 102 is Lys, Thr, Val, Trp, Ser, Ala, His, Met, Phe, Tyr or Ile;
Xaa at position 103 is Thr or Ser;
Xaa at position 106 is Asn, Pro, Leu, His, Val, or Gln;
Xaa at position 107 is Ala, Ser, Ile, Asn, Pro, Asp, or Gly;
Xaa at position 108 is Gln, Ser, Met, Trp, Arg, Phe, Pro, His, Ile, Tyr, or Cys;
Xaa at position 109 is Ala, Met, Glu, His, Ser, Pro, Tyr, or Leu;
which can additionally have Met- or Met-Ala-preceding the amino acid in position 1; and wherein from 4 to 35 of the amino acids designated by Xaa are different from the corresponding amino acids of native human interleukin-3.

7. The fusion protein of claim 6 wherein said human interleukin-3 mutant polypeptide is of the Formula:

Xaa at position 36 is Glu, Asn, Ser or Asp;
Xaa at position 37 is Asn, Arg, Pro, Thr, or His;
Xaa at position 41 is Arg, Leu, or Gly;
Xaa at position 42 is Pro, Gly, Ser, Ala, Asn, Val, Leu or Gln;
Xaa at position 48 is Asn, Pro, or Thr;
Xaa at position 50 is Ala or Asn;
Xaa at position 51 is Val or Thr;
Xaa at position 53 is Ser or Phe;
Xaa at position 54 is Leu or Phe;
Xaa at position 55 is Gln, Ala, Glu, or Arg;
Xaa at position 62 is Ser, Val, Asn, Pro, or Gly;
Xaa at position 63 is Ile or Leu;
Xaa at position 65 is Lys, Asn, Met, Arg, Ile, or Gly;
Xaa at position 66 is Asn, Gly, Glu, or Arg;
Xaa at position 68 is Leu, Gln, Trp, Arg, Asp, Asn, Glu, His, Met, Phe, Ser, Thr, Tyr or Val;
Xaa at position 73 is Leu or Ser;
Xaa at position 74 is Ala or Trp;
Xaa at position 77 is Ala or Pro;
Xaa at position 79 is Thr, Asp, or Ala;
Xaa at position 81 is His, Pro, Arg, Val, Gly, Asn, Ser or Thr;
Xaa at position 84 is His, Ile, Asn, Ala, Thr, Arg, Gln, Glu, Lys, Met, Ser, Tyr, Val or Leu;
Xaa at position 85 is Ile or Leu;
Xaa at position 86 is Lys or Arg;
Xaa at position 87 is Asp, Pro, Met, Lys, His, Pro, Asn, Ile, Leu or Tyr;

```
Asn Cys Xaa Xaa Met Ile Asp Glu Xaa Ile Xaa Xaa Leu Lys Xaa [SEQ ID NO:6]
 1               5                  10                  15

Xaa Pro Xaa Pro Xaa Xaa Asp Phe Xaa Asn Leu Asn Xaa Glu Asp
                20                  25                  30

Xaa Xaa Ile Leu Met Xaa Xaa Asn Leu Arg Xaa Xaa Asn Leu Glu
                35                  40                  45

Ala Phe Xaa Arg Xaa Xaa Lys Xaa Xaa Xaa Asn Ala Ser Ala Ile
                50                  55                  60

Glu Xaa Xaa Leu Xaa Xaa Leu Xaa Pro Cys Leu Pro Xaa Xaa Thr
                65                  70                  75

Ala Xaa Pro Xaa Arg Xaa Pro Ile Xaa Xaa Xaa Xaa Gly Asp Trp
                80                  85                  90

Xaa Glu Phe Xaa Xaa Lys Leu Xaa Phe Tyr Leu Xaa Xaa Leu Glu
                95                  100                 105

Xaa Xaa Xaa Xaa Gln Gln
                110
``` wherein
Xaa at position 3 is Ser, Gly, Asp, or Gln;
Xaa at position 4 is Asn, His, or Ile;
Xaa at position 9 is Ile, Ala, Leu, or Gly;
Xaa at position 11 is Thr, His, or Gln;
Xaa at position 12 is His or Ala;
Xaa at position 15 is Gln or Asn;
Xaa at position 16 is Pro or Gly;
Xaa at position 18 is Leu, Arg, Asn, or Ala;
Xaa at position 20 is Leu, Val, Ser, Ala, Arg, Gln, Glu, Ile, Phe, Thr or Met;
Xaa at position 21 is Leu, Ala, Asn, or Pro;
Xaa at position 24 is Asn or Ala;
Xaa at position 28 is Gly, Asp, Ser, Ala, Asn, Ile, Leu, Met, Tyr or Arg;
Xaa at position 31 is Gln, Val, Met, Leu, Ala, Asn, Glu or Lys;
Xaa at position 32 is Asp, Phe, Ser, Ala, Gln, Glu, His, Val or Thr;

Xaa at position 91 is Asn, Pro, Ser, Ile or Asp;
Xaa at position 94 is Arg, Ala, or Ser;
Xaa at position 95 is Arg, Thr, Glu, Leu, or Ser;
Xaa at position 98 is Thr or Gln;
Xaa at position 102 is Lys, Val, Trp, or Ile;
Xaa at position 103 is Thr, Ala, His, Phe, Tyr or Ser;
Xaa at position 106 is Asn, Pro, Leu, His, Val, or Gln;
Xaa at position 107 is Ala, Ser, Ile, Pro, or Asp;
Xaa at position 108 is Gln, Met, Trp, Phe, Pro, His, Ile, or Tyr;
Xaa at position 109 is Ala, Met, Glu, Ser, or Leu;

and which can additionally have Met- or Met-Ala-preceding the amino acid in position 1; and wherein from 4 to 26 of the amino acids designated by Xaa are different from the corresponding amino acids of native (1–133)human interleukin-3.

8. The fusion protein of claim 7 wherein said human interleukin-3 mutant polypeptide is of the Formula:

Xaa at position 17 is Ser, Lys, Asp, Met, Gln, or Arg;
Xaa at position 18 is Asn, His, Leu, Ile, Phe, Arg, or Gln;
Xaa at position 19 is Met, Arg, Gly, Ala, or Cys;
Xaa at position 20 is Ile, Cys, Gln, Glu, Arg, Pro, or Ala;
Xaa at position 21 is Asp, Phe, Lys, Arg, Ala, Gly, or Val;
Xaa at position 22 is Glu, Trp, Pro, Ser, Ala, His, or Gly;
Xaa at position 23 is Ile, Ala, Gly, Trp, Lys, Leu, Ser, or Arg;
Xaa at position 24 is Ile, Gly, Arg, or Ser;
Xaa at position 25 is Thr, His, Gly, Gln, Arg, Pro, or Ala;
Xaa at position 26 is His, Thr, Phe, Gly, Ala, or Trp;
Xaa at position 27 is Leu, Gly, Arg, Thr, Ser, or Ala;
Xaa at position 28 is Lys, Leu, Gln, Gly, Pro, Val or Trp;
Xaa at position 29 is Gln, Asn, Pro, Arg, or Val;
Xaa at position 30 is Pro, His, Thr, Gly, Asp, Gln, Ser, Leu, or Lys;
Xaa at position 31 is Pro, Asp, Gly, Arg, Leu, or Gln;
Xaa at position 32 is Leu, Arg, Gln, Asn, Gly, Ala, or Glu;
Xaa at position 33 is Pro, Leu, Gln, Thr, or Glu;
Xaa at position 34 is Leu, Gly, Ser, or Lys;
Xaa at position 35 is Leu, Ala, Gly, Asn, Pro, or Gln;
Xaa at position 36 is Asp, Leu, or Val;
Xaa at position 37 is Phe, Ser, or Pro;
Xaa at position 38 is Asn, or Ala;
Xaa at position 40 is Leu, Trp, or Arg;
Xaa at position 41 is Asn, Cys, Arg, Leu, His, Met, Pro;
Xaa at position 42 is Gly, Asp, Ser, Cys, or Ala;
Xaa at position 42 is Glu, Asn, Tyr, Leu, Phe, Asp, Ala, Cys, or Ser;
Xaa at position 44 is Asp, Ser, Leu, Arg, Lys, Thr, Met, Trp, or Pro;
Xaa at position 45 is Gln, Pro, Phe, Val, Met, Leu, Thr, Lys, or Trp;
Xaa at position 46 is Asp, Phe, Ser, Thr, Cys, or Gly;
Xaa at position 47 is Ile, Gly, Ser, Arg, Pro, or His;
Xaa at position 48 is Leu, Ser, Cys, Arg, His, Phe, or Asn;
Xaa at position 49 is Met, Arg, Ala, Gly, Pro, Asn, His, or Asp;
Xaa at position 50 is Glu, Leu, Thr, Asp, or Tyr;
Xaa at position 51 is Asn, Arg, Met, Pro, Ser, Thr, or His;
Xaa at position 52 is Asn, His, Arg, Leu, Gly, Ser, or Thr;
Xaa at position 53 is Leu, Thr, Ala, Gly, Glu, Pro, Lys, Ser, or;
Xaa at position 54 is Arg, Asp, Ile, Ser, Val, Thr, Gln, or Leu;
Xaa at position 55 is Arg, Thr, Val, Ser, Leu, or Gly;
Xaa at position 56 is Pro, Gly, Cys, Ser, Gln, or Lys;
Xaa at position 57 is Asn or Gly;
Xaa at position 58 is Leu, Ser, Asp, Arg, Gln, Val, or Cys;
Xaa at position 59 is Glu Tyr, His, Leu, Pro, or Arg;
Xaa at position 60 is Ala, Ser, Tyr, Asn, or Thr;
Xaa at position 61 is Phe, Asn, Glu, Pro, Lys, Arg, or Ser;
Xaa at position 62 is Asn His, Val, Arg, Pro, Thr, or Ile;
Xaa at position 63 is Arg, Tyr, Trp, Ser, Pro, or Val;
Xaa at position 64 is Ala, Asn, Ser, or Lys;
Xaa at position 65 is Val, Thr, Pro, His, Leu, Phe, or Ser;
Xaa at position 66 is Lys, Ile, Val, Asn, Glu, or Ser;
Xaa at position 67 is Ser, Ala, Phe, Val, Gly, Asn, Ile, Pro, or His;
Xaa at position 68 is Leu, Val, Trp, Ser, Thr, or His;
Xaa at position 69 is Gln, Ala, Pro, Thr, Arg, Trp, Gly, or Leu;
Xaa at position 70 is Asn, Leu, Val, Trp, Pro, or Ala;
Xaa at position 71 is Ala, Met, Leu, Arg, Glu, Thr, Gln, Trp, or Asn;
Xaa at position 72 is Ser, Glu, Met, Ala, His, Asn, Arg, or Asp;
Xaa at position 73 is Ala, Glu, Asp, Leu, Ser, Gly, Thr, or Arg;
Xaa at position 74 is Ile, Thr, Pro, Arg, Gly, Ala;
Xaa at position 75 is Glu, Lys, Gly, Asp, Pro, Trp, Arg, Ser, or Leu;
Xaa at position 76 is Ser, Val, Ala, Asn, Trp, Glu, Pro, Gly, or Asp;
Xaa at position 77 is Ile, Ser, Arg, or Thr;
Xaa at position 78 is Leu, Ala, Ser, Glu, Gly, or Arg;
Xaa at position 79 is Lys, Thr, Gly, Asn, Met, Ile, or Asp;
Xaa at position 80 is Asn, Trp, Val, Gly, Thr, Leu, or Arg;
Xaa at position 81 is Leu, Gln, Gly, Ala, Trp, Arg, or Lys;
Xaa at position 82 is Leu, Gln, Lys, Trp, Arg, or Asp;
Xaa at position 83 is Pro, Thr, Trp, Arg, or Met;
Xaa at position 84 is Cys, Glu, Gly, Arg, Met, or Val;
Xaa at position 85 is Leu, Asn, or Gln;
Xaa at position 86 is Pro, Cys, Arg, Ala, or Lys;
Xaa at position 87 is Leu, Ser, Trp, or Gly;
Xaa at position 88 is Ala, Lys, Arg, Val, or Trp;
Xaa at position 89 is Thr, Asp, Cys, Leu, Val, Glu, His, or Asn;
Xaa at position 90 is Ala, Ser, Asp, Ile, or Met;
Xaa at position 91 is Ala, Ser, Thr, Phe, Leu, Asp, or His;
Xaa at position 92 is Pro, Phe, Arg, Ser, Lys, His, or Leu;
Xaa at position 93 is Thr, Asp, Ser, Asn, Pro, Ala, Leu, or Arg;
Xaa at position 94 is Arg, Ile, Ser, Glu, Leu, Val, or Pro;
Xaa at position 95 is His, Gln, Pro, Val, Leu, Thr or Tyr;
Xaa at position 96 is Pro, Lys, Tyr, Gly, Ile, or Thr;
Xaa at position 97 is Ile, Lys, Ala, or Asn;
Xaa at position 98 is His, Ile, Asn, Leu, Asp, Ala, Thr, or Pro;
Xaa at position 99 is Ile, Arg, Asp, Pro, Gln, Gly, Phe, or His;
Xaa at position 100 is Lys, Tyr, Leu, His, Ile, Ser, Gln, or Pro;
Xaa at position 101 is Asp, Pro, Met, Lys, His, Thr, Val, Tyr, or Gln;
Xaa at position 102 is Gly, Leu, Glu, Lys, Ser, Tyr, or Pro;
Xaa at position 103 is Asp, or Ser;
Xaa at position 104 is Trp, Val, Cys, Tyr, Thr, Met, Pro, Leu, Gln, Lys, Ala, Phe, or Gly;
Xaa at position 105 is Asn, Pro, Ala, Phe, Ser, Trp, Gln, Tyr, Leu, Lys, Ile, or His;
Xaa at position 106 is Glu, Ser, Ala, Lys, Thr, Ile, Gly, or Pro;
Xaa at position 108 is Arg, Asp, Leu, Thr, Ile, or Pro;
Xaa at position 109 is Arg, Thr, Pro, Glu, Tyr, Leu, Ser, or Gly.

9. The fusion protein of claim 8 wherein said human interleukin-3 mutant polypeptide is of the Formula:

```
              1                    5                    10
(Met)$_m$-Ala Pro Met Thr Gln Thr Thr Ser Leu Lys Thr   [SEQ ID NO:7]

15                   20
Ser Trp Val Asn Cys Ser Xaa Xaa Xaa Asp Glu Xaa Ile 25              30              35
```

```
                                      -continued
Xaa His Leu Lys Xaa Pro Pro Xaa Pro Xaa Leu Asp Xaa 40                  45                  50
Xaa Asn Leu Asn Xaa Glu Asp Xaa Xaa Ile Leu Xaa Xaa 55                  60
Xaa Asn Leu Arg Xaa Xaa Asn Leu Xaa Xaa Phe Xaa Xaa 65                  70                  75
Ala Xaa Lys Xaa Leu Xaa Asn Ala Ser Xaa Ile Glu Xaa 80                  85
Ile Leu Xaa Asn Leu Xaa Pro Cys Xaa Pro Xaa Xaa Thr 90                  95                  100
Ala Xaa Pro Xaa Arg Xaa Pro Ile Xaa Ile Xaa Xaa Gly 105                 110                 115
Asp Trp Xaa Glu Phe Arg Xaa Lys Leu Xaa Phe Tyr Leu 120                 125
Xaa Xaa Leu Glu Xaa Ala Gln Xaa Gln Gln Th wherein m is 0 or 1; n is 0 or 1; p is 0 or 1; Xaa at position 4 is Asn or Ile; Xaa at position 5 is Met, Ala or Ile: Xaa at position 6 is Ile, Pro or Leu; Xaa at position 9 is Ile, Ala or Leu; Xaa at position 11 is Thr or His; Xaa at position 15 is Gln, Arg, Val or Leu; Xaa at position 18 is Leu, Ala, Asn or Arg; Xaa at position 20 is Leu or Ser; Xaa at position 23 is Phe, Pro, or Ser; Xaa at position 24 is Asn or Ala; Xaa at position 28 is Gly, Ala, Ser, Asp or Asn; Xaa at position 31 is Gln, Val, or Met; Xaa at position 32 is Asp or Ser; Xaa at position 35 is Met, Leu or Asp; Xaa at position 36 is Glu or Asp; Xaa at position 37 is Asn, Arg or Ser; Xaa at position 41 is Arg, Leu, or Thr; Xaa at position 42 is Pro or Ser; Xaa at position 45 is Glu or Leu; Xaa at position 46 is Ala or Ser; Xaa at position 48 is Asn, Val or Pro; Xaa at position 49 is Arg or His; Xaa at position 51 is Val or Ser; Xaa at position 53 is Ser, Asn, His or Gly; Xaa at position 55 is Gln or Glu; Xaa at position 59 is Ala or Gly; Xaa at position 62 is Ser, Ala or Pro; Xaa at position 65 is Lys, Arg or Ser; Xaa at position 67 is Leu, Glu, or Val; Xaa at position 68 is Leu, Glu, Val or Trp; Xaa at position 71 is Leu or Val; Xaa at position 73 is Leu, Ser or Trp; Xaa at position 74 is Ala or Trp; Xaa at position 77 is Ala or Pro; Xaa at position 79 is Pro or Ser; Xaa at position 81 is His or Thr; Xaa at position 84 is His, Ile, or Thr; Xaa at position 86 is Lys or Arg; Xaa at position 87 is Asp, Ala or Met; Xaa at position 91 is Asn or Glu; Xaa at position 95 is Arg, Glu, Leu; Xaa at position 98 Thr or Gln; Xaa at position 102 is Lys, Val, Trp or Ser; Xaa at position 103 is Thr or Ser; Xaa at position 106 is Asn, Gln, or His; Xaa at position 109 is Ala or Glu; with the proviso that from four to forty-four of the amino acids designated by Xaa are different from the corresponding amino acids of native (15–125) human interleukin-3.

11. The fusion protein of claim 10 wherein said human interleukin-3 mutant polypeptide is of the Formula:

```
     Asn Cys Ser Ile Met Ile Asp Glu Ile Ile His          [SEQ ID NO.:9];
His Leu Lys Arg Pro Pro Ala Pro Leu Leu Asp Pro
Asn Asn Leu Asn Ala Glu Asp Val Asp Ile Leu Met
Glu Asn Asn Leu Arg Arg Pro Asn Leu Glu Ala Phe
Asn Arg Ala Val Lys Ser Leu Gln Asn Ala Ser Ala
Ile Glu Ser Ile Leu Lys Asn Leu Leu Pro Cys Leu
Pro Leu Ala Thr Ala Ala Pro Thr Arg His Pro Ile
His Ile Lys Asp Gly Asp Trp Asn Glu Phe Arg Arg
Lys Leu Thr Phe Tyr Leu Lys Thr
Leu Glu Asn Ala Gln Ala Gln Gln
     Asn Cys Ser Ile Met Ile Asp Glu Ile Ile His          [SEQ ID NO.:10];
His Leu Lys Arg Pro Pro Asn Pro Leu Leu Asp Pro
Asn Asn Leu Asn Ser Glu Asp Met Asp Ile Leu Met
Glu Asn Asn Leu Arg Arg Pro Asn Leu Glu Ala Phe
Asn Arg Ala Val Lys Ser Leu Gln Asn Ala Ser Ala
Ile Glu Ser Ile Leu Lys Asn Leu Leu Pro Cys Leu
Pro Leu Ala Thr Ala Ala Pro Thr Arg His Pro Ile
His Ile Lys Asp Gly Asp Trp Asn Glu Phe Arg Arg
Lys Leu Thr Phe Tyr Leu Lys Thr Leu Glu Asn Ala
Gln Ala Gln Gln
     Asn Cys Ser Ile Met Ile Asp Glu Ile Ile His          [SEQ ID NO.:11];
His Leu Lys Val Pro Pro Ala Pro Leu Leu Asp Ser
Asn Asn Leu Asn Ser Glu Asp Met Asp Ile Leu Met
Glu Asn Asn Leu Arg Arg Pro Asn Leu Glu Ala Phe
Asn Arg Ala Val Lys Ser Leu Gln Asn Ala Ser Ala
Ile Glu Ser Ile Leu Lys Asn Leu Leu Pro Cys Leu
Pro Leu Ala Thr Ala Ala Pro Thr Arg His Pro Ile
His Ile Lys Asp Gly Asp Trp Asn Glu Phe Arg Arg
Lys Leu Thr Phe Tyr Leu Lys Thr Leu Glu Asn Ala
```

Gln Ala Gln Gln

Asn Cys Ser Asn Met Ile Asp Glu Ile Ile Thr          [SEQ ID NO.:12];
His Leu Lys Gln Pro Pro Leu Pro Leu Leu Asp Phe
Asn Asn Leu Asn Gly Glu Asp Gln Asp Ile Leu Met
Glu Arg Asn Leu Arg Leu Pro Asn Leu Leu Ala Phe
Val Arg Ala Val Lys Asn Leu Glu Asn Ala Ser Ala
Ile Glu Ser Ile Leu Lys Asn Leu Leu Pro Cys Leu
Pro Leu Ala Thr Ala Ala Pro Thr Arg His Pro Ile
His Ile Lys Asp Gly Asp Trp Asn Glu Phe Arg Arg
Lys Leu Thr Phe Tyr Leu Lys Thr Leu Glu Asn Ala
Gln Ala Gln Gln

Asn Cys Ser Asn Met Ile Asp Glu Ile Ile Thr          [SEQ ID NO.:13];
His Leu Lys Gln Pro Pro Leu Pro Leu Leu Asp Phe
Asn Asn Leu Asn Gly Glu Asp Gln Asp Ile Leu Met
Glu Arg Asn Leu Arg Leu Pro Asn Leu Glu Ser Phe
Val Arg Ala Val Lys Asn Leu Glu Asn Ala Ser Ala
Ile Glu Ser Ile Leu Lys Asn Leu Leu Pro Cys Leu
Pro Ala Leu Thr Ala Ala Pro Thr Arg His Pro Ile
His Ile Lys Asp Gly Asp Trp Asn Glu Phe Arg Arg
Lys Leu Thr Phe Tyr Leu Lys Thr Leu Glu Asn Ala
Gln Ala Gln Gln

Asn Cys Ser Asn Met Ile Asp Glu Ile Ile Thr          [SEQ ID NO.:14];
His Leu Lys Gln Pro Pro Leu Pro Leu Leu Asp Phe
Asn Asn Leu Asn Gly Glu Asp Gln Asp Ile Leu Met
Glu Arg Asn Leu Arg Thr Pro Asn Leu Leu Ala Phe
Val Arg Ala Val Lys His Leu Glu Asn Ala Ser Ala
Ile Glu Ser Ile Leu Lys Asn Leu Leu Pro Cys Leu
Pro Leu Ala Thr Ala Ala Pro Thr Arg His Pro Ile
His Ile Lys Asp Gly Asp Trp Asn Glu Phe Arg Arg
Lys Leu Thr Phe Tyr Leu Lys Thr Leu Glu Asn Ala
Gln Ala Gln Gln

Asn Cys Ser Asn Met Ile Asp Glu Ile Ile Thr          [SEQ ID NO.:15];
His Leu Lys Gln Pro Pro Leu Pro Leu Leu Asp Phe
Asn Asn Leu Asn Gly Glu Asp Gln Asp Ile Leu Met
Glu Asn Asn Leu Arg Arg Pro Asn Leu Glu Ala Phe
Asn Arg Ala Val Lys Ser Leu Gln Asn Ala Ser Gly
Ile Glu Ala Ile Leu Arg Asn Leu Gln Pro Cys Leu
Pro Ser Ala Thr Ala Ala Pro Ser Arg His Pro Ile
Ile Ile Lys Ala Gly Asp Trp Gln Glu Phe Arg Arg
Lys Leu Thr Phe Tyr Leu Lys Thr Leu Glu Asn Ala

-continued

Gln Ala Gln Gln

Asn Cys Ser Asn Met Ile Asp Glu Ile Ile Thr     [SEQ ID NO.:16];
His Leu Lys Gln Pro Pro Leu Pro Leu Leu Asp Phe
Asn Asn Leu Asn Gly Glu Asp Gln Asp Ile Leu Met
Glu Asn Asn Leu Arg Arg Pro Asn Leu Glu Ala Phe
Asn Arg Ala Val Lys Ser Leu Gln Asn Ala Ser Gly
Ile Glu Ala Ile Leu Arg Asn Leu Val Pro Cys Leu
Pro Ser Ala Thr Ala Ala Pro Ser Arg His Pro Ile
Thr Ile Lys Ala Gly Asp Trp Gln Glu Phe Arg Arg
Lys Leu Thr Phe Tyr Leu Lys Thr Leu Glu Asn Ala
Gln Ala Gln Gln

Asn Cys Ser Asn Met Ile Asp Glu Ile Ile Thr     [SEQ ID NO.:17];
His Leu Lys Gln Pro Pro Leu Pro Leu Leu Asp Phe
Asn Asn Leu Asn Gly Glu Asp Gln Asp Ile Leu Met
Glu Asn Asn Leu Arg Arg Pro Asn Leu Glu Ala Phe
Asn Arg Ala Val Lys Ser Leu Gln Asn Ala Ser Ala
Ile Glu Ser Ile Leu Lys Asn Leu Leu Pro Cys Leu
Pro Leu Ala Thr Ala Ala Pro Thr Arg His Pro Ile
His Ile Lys Asp Gly Asp Trp Asn Glu Phe Arg Glu
Lys Leu Thr Phe Tyr Leu Val Thr Leu Glu Gln Ala
Gln Glu Gln Gln

Asn Cys Ser Asn Met Ile Asp Glu Ile Ile Thr     [SEQ ID NO.:18];
His Leu Lys Gln Pro Pro Leu Pro Leu Leu Asp Phe
Asn Asn Leu Asn Gly Glu Asp Gln Asp Ile Leu Met
Glu Asn Asn Leu Arg Arg Pro Asn Leu Glu Ala Phe
Asn Arg Ala Val Lys Ser Leu Gln Asn Ala Ser Ala
Ile Glu Ser Ile Leu Lys Asn Leu Leu Pro Cys Leu
Pro Leu Ala Thr Ala Ala Pro Thr Arg His Pro Ile
His Ile Lys Asp Gly Asp Trp Asn Glu Phe Arg Glu
Lys Leu Thr Phe Tyr Leu Val Ser Leu Glu His Ala
Gln Glu Gln Gln

Asn Cys Ser Asn Met Ile Asp Glu Ile Ile Thr     [SEQ ID NO.:19];
His Leu Lys Gln Pro Pro Leu Pro Leu Leu Asp Phe
Asn Asn Leu Asn Gly Glu Asp Gln Asp Ile Leu Met
Glu Asn Asn Leu Arg Arg Pro Asn Leu Glu Ala Phe
Asn Arg Ala Val Lys Ser Leu Gln Asn Ala Ser Gly
Ile Glu Ala Ile Leu Arg Asn Leu Gln Pro Cys Leu
Pro Ser Ala Thr Ala Ala Pro Ser Arg His Pro Ile
Ile Ile Lys Ala Gly Asp Trp Gln Glu Phe Arg Glu
Lys Leu Thr Phe Tyr Leu Val Thr Leu Glu Gln Ala

-continued

Gln Glu Gln Gln

Asn Cys Ser Asn Met Ile Asp Glu Ile Ile Thr    [SEQ ID NO.:20];
His Leu Lys Gln Pro Pro Leu Pro Leu Leu Asp Phe
Asn Asn Leu Asn Gly Glu Asp Gln Asp Ile Leu Met
Glu Asn Asn Leu Arg Arg Pro Asn Leu Glu Ala Phe
Asn Arg Ala Val Lys Ser Leu Gln Asn Ala Ser Gly
Ile Glu Ala Ile Leu Arg Asn Leu Val Pro Cys Leu
Pro Ser Ala Thr Ala Ala Pro Ser Arg His Pro Ile
Thr Ile Lys Ala Gly Asp Trp Gln Glu Phe Arg Glu
Lys Leu Thr Phe Tyr Leu Val Thr Leu Glu Gln Ala
Gln Glu Gln Gln

Asn Cys Ser Asn Met Ile Asp Glu Ile Ile Thr    [SEQ ID NO.:21];
His Leu Lys Gln Pro Pro Leu Pro Leu Leu Asp Phe
Asn Asn Leu Asn Gly Glu Asp Gln Asp Ile Leu Met
Glu Asn Asn Leu Arg Arg Pro Asn Leu Glu Ala Phe
Asn Arg Ala Val Lys Ser Leu Gln Asn Ala Ser Gly
Ile Glu Ala Ile Leu Arg Asn Leu Val Pro Cys Leu
Pro Ser Ala Thr Ala Ala Pro Ser Arg His Pro Ile
Thr Ile Lys Ala Gly Asp Trp Gln Glu Phe Arg Glu
Lys Leu Thr Phe Tyr Leu Val Ser Leu Glu His Ala
Gln Glu Gln Gln

Asn Cys Ser Ile Met Ile Asp Glu Ile Ile His    [SEQ ID NO.:22];
His Leu Lys Arg Pro Pro Ala Pro Leu Leu Asp Pro
Asn Asn Leu Asn Ala Glu Asp Val Asp Ile Leu Met
Glu Arg Asn Leu Arg Leu Pro Asn Leu Glu Ser Phe
Val Arg Ala Val Lys Asn Leu Glu Asn Ala Ser Ala
Ile Glu Ser Ile Leu Lys Asn Leu Leu Pro Cys Leu
Pro Leu Ala Thr Ala Ala Pro Thr Arg His Pro Ile
His Ile Lys Asp Gly Asp Trp Asn Glu Phe Arg Arg
Lys Leu Thr Phe Tyr Leu Lys Thr Leu Glu Asn Ala
Gln Ala Gln Gln

Asn Cys Ser Ile Met Ile Asp Glu Ile Ile His    [SEQ ID NO.:23];
His Leu Lys Arg Pro Pro Asn Pro Leu Leu Asp Pro
Asn Asn Leu Asn Ser Glu Asp Met Asp Ile Leu Met
Glu Arg Asn Leu Arg Thr Pro Asn Leu Leu Ala Phe
Val Arg Ala Val Lys His Leu Glu Asn Ala Ser Ala
Ile Glu Ser Ile Leu Lys Asn Leu Leu Pro Cys Leu
Pro Leu Ala Thr Ala Ala Pro Thr Arg His Pro Ile
His Ile Lys Asp Gly Asp Trp Asn Glu Phe Arg Arg
Lys Leu Thr Phe Tyr Leu Lys Thr Leu Glu Asn Ala

-continued

Gln Ala Gln Gln

Asn Cys Ser Ile Met Ile Asp Glu Ile Ile His     [SEQ ID NO.:24];
His Leu Lys Val Pro Pro Ala Pro Leu Leu Asp Ser
Asn Asn Leu Asn Ser Glu Asp Met Asp Ile Leu Met
Glu Arg Asn Leu Arg Leu Pro Asn Leu Leu Ala Phe
Val Arg Ala Val Lys Asn Leu Glu Asn Ala Ser Ala
Ile Glu Ser Ile Leu Lys Asn Leu Leu Pro Cys Leu
Pro Leu Ala Thr Ala Ala Pro Thr Arg His Pro Ile
His Ile Lys Asp Gly Asp Trp Asn Glu Phe Arg Arg
Lys Leu Thr Phe Tyr Leu Lys Thr Leu Glu Asn Ala
Gln Ala Gln Gln

Met Ala Asn Cys Ser Asn Met Ile Asp Glu Ile Ile     [SEQ ID NO.:25];
Thr His Leu Lys Gln Pro Pro Leu Pro Leu Leu Asp
Phe Asn Asn Leu Asn Gly Glu Asp Gln Asp Ile Leu
Met Glu Asn Asn Leu Arg Arg Pro Asn Leu Glu Ala
Phe Asn Arg Ala Val Lys Ser Leu Gln Asn Ala Ser
Gly Ile Glu Ala Ile Leu Arg Asn Leu Gln Pro Cys
Leu Pro Ser Ala Thr Ala Ala Pro Ser Arg His Pro
Ile Ile Ile Lys Ala Gly Asp Trp Gln Glu Phe Arg
Glu Lys Leu Thr Phe Tyr Leu Val Thr Leu Glu Gln
Ala Gln Glu Gln Gln

Met Ala Asn Cys Ser Asn Met Ile Asp Glu Ile Ile     [SEQ ID NO.:26];
Thr His Leu Lys Gln Pro Pro Leu Pro Leu Leu Asp
Phe Asn Asn Leu Asn Gly Glu Asp Gln Asp Ile Leu
Met Glu Asn Asn Leu Arg Arg Pro Asn
Leu Glu Ala Phe Asn Arg Ala Val Lys Ser Leu Gln
Asn Ala Ser Gly Ile Glu Ala Ile Leu Arg Asn Leu
Val Pro Cys Leu Pro Ser Ala Thr Ala Ala Pro Ser
Arg His Pro Ile Thr Ile Lys Ala Gly Asp Trp Gln
Glu Phe Arg Glu Lys Leu Thr Phe Tyr Leu Val Thr
Leu Glu Gln Ala Gln Glu Gln Gln

Met Ala Asn Cys Ser Asn Met Ile Asp Glu Ile Ile     [SEQ ID NO.:27];
Thr His Leu Lys Gln Pro Pro Leu Pro Leu Leu Asp
Phe Asn Asn Leu Asn Gly Glu Asp Gln Asp Ile Leu
Met Glu Asn Asn Leu Arg Arg Pro Asn Leu Glu Ala
Phe Asn Arg Ala Val Lys Ser Leu Gln Asn Ala Ser
Gly Ile Glu Ala Ile Leu Arg Asn Leu Val Pro Cys
Leu Pro Ser Ala Thr Ala Ala Pro Ser Arg His Pro
Ile Thr Ile Lys Ala Gly Asp Trp Gln Glu Phe Arg
Glu Lys Leu Thr Phe Tyr Leu Val Ser Leu Glu His

-continued

```
Ala Gln Glu Gln Gln

Met Ala Asn Cys Ser Ile Met Ile Asp Glu Ile Ile        [SEQ ID NO.:28];
His His Leu Lys Arg Pro Pro Ala Pro Leu Leu Asp
Pro Asn Asn Leu Asn Ala Glu Asp Val Asp Ile Leu
Met Glu Arg Asn Leu Arg Leu Pro Asn Leu Glu Ser
Phe Val Arg Ala Val Lys Asn Leu Glu Asn Ala Ser
Ala Ile Glu Ser Ile Leu Lys Asn Leu Leu Pro Cys
Leu Pro Leu Ala Thr Ala Ala Pro Thr Arg His Pro
Ile His Ile Lys Asp Gly Asp Trp Asn Glu Phe Arg
Arg Lys Leu Thr Phe Tyr Leu Lys Thr Leu Glu Asn
Ala Gln Ala Gln Gln

Met Ala Asn Cys Ser Ile Met Ile Asp Glu Ile Ile        [SEQ ID NO.:29];
His His Leu Lys Arg Pro Pro Asn Pro Leu Leu Asp
Pro Asn Asn Leu Asn Ser Glu Asp Met Asp Ile Leu
Met Glu Arg Asn Leu Arg Thr Pro Asn Leu Leu Ala
Phe Val Arg Ala Val Lys His Leu Glu Asn Ala Ser
Ala Ile Glu Ser Ile Leu Lys Asn Leu Leu Pro Cys
Leu Pro Leu Ala Thr Ala Ala Pro Thr Arg His Pro
Ile His Ile Lys Asp Gly Asp Trp Asn Glu Phe Arg
Arg Lys Leu Thr Phe Tyr Leu Lys Thr Leu Glu Asn
Ala Gln Ala Gln Gln

Met Ala Asn Cys Ser Ile Met Ile Asp Glu Ile Ile        [SEQ ID NO.:30];
His His Leu Lys Val Pro Pro Ala Pro Leu Leu Asp
Ser Asn Asn Leu Asn Ser Glu Asp Met Asp Ile Leu
Met Glu Arg Asn Leu Arg Leu Pro Asn Leu Leu Ala
Phe Val Arg Ala Val Lys Asn Leu Glu Asn Ala Ser
Ala Ile Glu Ser Ile Leu Lys Asn Leu Leu Pro Cys
Leu Pro Leu Ala Thr Ala Ala Pro Thr Arg His Pro
Ile His Ile Lys Asp Gly Asp Trp Asn Glu Phe Arg
Arg Lys Leu Thr Phe Tyr Leu Lys Thr Leu Glu Asn
Ala Gln Ala Gln Gln

Met Ala Asn Cys Ser Ile Met Ile Asp Glu Ile Ile        [SEQ ID NO.:31];
His His Leu Lys Arg Pro Pro Ala Pro Leu Leu Asp
Pro Asn Asn Leu Asn Ala Glu Asp Val Asp Ile Leu
Met Glu Arg Asn Leu Arg Leu Pro Asn Leu Glu Ser
Phe Val Arg Ala Val Lys Asn Leu Glu Asn Ala Ser
Gly Ile Glu Ala Ile Leu Arg Asn Leu Gln Pro Cys
Leu Pro Ser Ala Thr Ala Ala Pro Ser Arg His Pro
Ile Ile Ile Lys Ala Gly Asp Trp Gln Glu Phe Arg
Glu Lys Leu Thr Phe Tyr Leu Val Thr Leu Glu Gln
```

```
Ala Gln Glu Gln Gln

Met Ala Asn Cys Ser Ile Met Ile Asp Glu Ile Ile        [SEQ ID NO.:32];
His His Leu Lys Arg Pro Pro Asn Pro Leu Leu Asp
Pro Asn Asn Leu Asn Ser Glu Asp Met Asp Ile Leu
Met Glu Arg Asn Leu Arg Thr Pro Asn Leu Leu Ala
Phe Val Arg Ala Val Lys His Leu Glu Asn Ala Ser
Gly Ile Glu Ala Ile Leu Arg Asn Leu Gln Pro Cys
Leu Pro Ser Ala Thr Ala Ala Pro Ser Arg His Pro
Ile Ile Ile Lys Ala Gly Asp Trp Gln Glu Phe Arg
Glu Lys Leu Thr Phe Tyr Leu Val Thr Leu Glu Gln
Ala Gln Glu Gln Gln

Met Ala Asn Cys Ser Ile Met Ile Asp Glu Ile Ile        [SEQ ID NO.:33];
His His Leu Lys Val Pro Pro Ala Pro Leu Leu Asp
Ser Asn Asn Leu Asn Ser Glu Asp Met Asp Ile Leu
Met Glu Arg Asn Leu Arg Leu Pro Asn Leu Leu Ala
Phe Val Arg Ala Val Lys Asn Leu Glu Asn Ala Ser
Gly Ile Glu Ala Ile Leu Arg Asn Leu Gln Pro Cys
Leu Pro Ser Ala Thr Ala Ala Pro Ser Arg His Pro
Ile Ile Ile Lys Ala Gly Asp Trp Gln Glu Phe Arg
Glu Lys Leu Thr Phe Tyr Leu Val Thr Leu Glu Gln
Ala Gln Glu Gln Gln

Met Ala Asn Cys Ser Ile Met Ile Asp Glu Ile Ile        [SEQ ID NO.:34];
His His Leu Lys Arg Pro Pro Ala Pro Leu Leu Asp
Pro Asn Asn Leu Asn Ala Glu Asp Val Asp Ile Leu
Met Glu Arg Asn Leu Arg Leu Pro Asn Leu Glu Ser
Phe Val Arg Ala Val Lys Asn Leu Glu Asn Ala Ser
Gly Ile Glu Ala Ile Leu Arg Asn Leu Val Pro Cys
Leu Pro Ser Ala Thr Ala Ala Pro Ser Arg His Pro
Ile Thr Ile Lys Ala Gly Asp Trp Gln Glu Phe Arg
Glu Lys Leu Thr Phr Tyr Leu Val Thr Leu Glu Gln
Ala Gln Glu Gln Gln

Met Ala Asn Cys Ser Ile Met Ile Asp Glu Ile Ile        [SEQ ID NO.:35];
His His Leu Lys Val Pro Pro Ala Pro Leu Leu Asp
Ser Asn Asn Leu Asn Ser Glu Asp Met Asp Ile Leu
Met Glu Arg Asn Leu Arg Leu Pro Asn Leu Leu Ala
Phe Val Arg Ala Val Lys Asn Leu Glu Asn Ala Ser
Gly Ile Glu Ala Ile Leu Arg Asn Leu Val Pro Cys
Leu Pro Ser Ala Thr Ala Ala Pro Ser Arg His Pro
Ile Thr Ile Lys Ala Gly Asp Trp Gln Glu Phe Arg
Glu Lys Leu Thr Phe Tyr Leu Val Thr Leu Glu Gln
```

```
Ala Gln Glu Gln Gln

Met Ala Asn Cys Ser Ile Met Ile Asp Glu Ile Ile        [SEQ ID NO.:36];
His His Leu Lys Arg Pro Pro Asn Pro Leu Leu Asp
Pro Asn Asn Leu Asn Ser Glu Asp Met Asp Ile Leu
Met Glu Arg Asn Leu Arg Thr Pro Asn Leu Leu Ala
Phe Val Arg Ala Val Lys His Leu Glu Asn Ala Ser
Gly Ile Glu Ala Ile Leu Arg Asn Leu Val Pro Cys
Leu Pro Ser Ala Thr Ala Ala Pro Ser Arg His Pro
Ile Thr Ile Lys Ala Gly Asp Trp Gln Glu Phe Arg
Glu Lys Leu Thr Phe Tyr Leu Val Ser Leu Glu His
Ala Gln Glu Gln Gln

Met Ala Asn Cys Ser Ile Met Ile Asp Glu Ile Ile        [SEQ ID NO.:37];
His His Leu Lys Val Pro Pro Ala Pro Leu Leu Asp
Ser Asn Asn Leu Asn Ser Glu Asp Met Asp Ile Leu
Met Glu Arg Asn Leu Arg Leu Pro Asn Leu Leu Ala
Phe Val Arg Ala Val Lys Asn Leu Glu Asn Ala Ser
Gly Ile Glu Ala Ile Leu Arg Asn Leu Val Pro Cys
Leu Pro Ser Ala Thr Ala Ala Pro Ser Arg His Pro
Ile Thr Ile Lys Ala Gly Asp Trp Gln Glu Phe Arg
Glu Lys Leu Thr Phe Tyr Leu Val Ser Leu Glu His
Ala Gln Glu Gln Gln

Met Ala Asn Cys Ser Ile Met Ile Asp Glu Ile Ile        [SEQ ID NO.:38];
His His Leu Lys Arg Pro Pro Asn Pro Leu Leu Asp
Pro Asn Asn Leu Asn Ser Glu Asp Met Asp Ile Leu
Met Glu Arg Asn Leu Arg Thr Pro Asn Leu Leu Ala
Phe Val Arg Ala Val Lys His Leu Glu Asn Ala Ser
Gly Ile Glu Ala Ile Leu Arg Asn Leu Val Pro Cys
Leu Pro Ser Ala Thr Ala Ala Pro Ser Arg His Pro
Ile Thr Ile Lys Ala Gly Asp Trp Gln Glu Phe Arg
Glu Lys Leu Thr Phe Tyr Leu Val Thr Leu Glu Gln
Ala Gln Glu Gln Gln and Met Ala Asn Cys Ser Ile Met Ile Asp Glu Ile Ile        [SEQ ID NO.:39];
His His Leu Lys Arg Pro Pro Ala Pro Leu Leu Asp
Pro Asn Asn Leu Asn Ala Glu Asp Val Asp Ile Leu
Met Glu Arg Asn Leu Arg Leu Pro Asn Leu Glu Ser
Phe Val Arg Ala Val Lys Asn Leu Glu Asn Ala Ser
Gly Ile Glu Ala Ile Leu Arg Asn Leu Val Pro Cys
Leu Pro Ser Ala Thr Ala Ala Pro Ser Arg His Pro
Ile Thr Ile Lys Ala Gly Asp Trp Gln Glu Phe Arg
Glu Lys Leu Thr Phe Tyr Leu Val Ser Leu Glu His
```

```
Ala Gln Glu Gln Gln

Met Ala Asn Cys Ser Ile Met Ile Asp Glu Ile Ile     [SEQ ID NO.:40];
His His Leu Lys Arg Pro Pro Ala Pro Leu Leu Asp
Pro Asn Asn Leu Asn Ala Glu Asp Val Asp Ile Leu
Met Asp Arg Asn Leu Arg Leu Ser Asn Leu Glu Ser
Phe Val Arg Ala Val Lys Asn Leu Glu Asn Ala Ser
Gly Ile Glu Ala Ile Leu Arg Asn Leu Gln Pro Cys
Leu Pro Ser Ala Thr Ala Ala Pro Ser Arg His Pro
Ile Ile Ile Lys Ala Gly Asp Trp Gln Glu Phe Arg
Glu Lys Leu Thr Phe Tyr Leu Val Thr Leu Glu Gln
Ala Gln Glu Gln Gln

Met Ala Asn Cys Ser Ile Met Ile Asp Glu Ala Ile     [SEQ ID NO.:41];
His His Leu Lys Arg Pro Pro Ala Pro Ser Leu Asp
Pro Asn Asn Leu Asn Asp Glu Asp Met Ser Ile Leu
Met Glu Arg Asn Leu Arg Leu Pro Asn Leu Glu Ser
Phe Val Arg Ala Val Lys Asn Leu Glu Asn Ala Ser
Gly Ile Glu Ala Ile Leu Arg Asn Leu Gln Pro Cys
Leu Pro Ser Ala Thr Ala Ala Pro Ser Arg His Pro
Ile Ile Ile Lys Ala Gly Asp Trp Gln Glu Phe Arg
Glu Lys Leu Thr Phe Tyr Leu Val Thr Leu Glu Gln
Ala Gln Glu Gln Gln

Met Ala Asn Cys Ser Ile Met Ile Asp Glu Ile Ile     [SEQ ID NO.:42];
His His Leu Lys Arg Pro Pro Ala Pro Leu Leu Asp
Pro Asn Asn Leu Asn Asp Glu Asp Met Ser Ile Leu
Met Glu Arg Asn Leu Arg Leu Pro Asn Leu Glu Ser
Phe Val Arg Ala Val Lys Asn Leu Glu Asn Ala Ser
Gly Ile Glu Ala Ile Leu Arg Asn Leu Gln Pro Cys
Leu Pro Ser Ala Thr Ala Ala Pro Ser Arg His Pro
Ile Ile Ile Lys Ala Gly Asp Trp Gln Glu Phe Arg
Glu Lys Leu Thr Phe Tyr Leu Val Thr Leu Glu Gln
Ala Gln Glu Gln Gln

Met Ala Asn Cys Ser Ile Met Ile Asp Glu Ile Ile     [SEQ ID NO.:308];
His His Leu Lys Arg Pro Pro Ala Pro Leu Leu Asp
Pro Asn Asn Leu Asn Ala Glu Asp Val Asp Ile Leu
Met Asp Arg Asn Leu Arg Leu Pro Asn Leu Glu Ser
Phe Val Arg Ala Val Lys Asn Leu Glu Asn Ala Ser
Gly Ile Glu Ala Ile Leu Arg Asn Leu Gln Pro Cys
Leu Pro Ser Ala Thr Ala Ala Pro Ser Arg His Pro
Ile Ile Ile Lys Ala Gly Asp Trp Gln Glu Phe Arg
Glu Lys Leu Thr Phe Tyr Leu Val Thr Leu Glu Gln
```

-continued

```
Ala Gln Glu Gln Gln

Met Ala Asn Cys Ser Ile Met Ile Asp Glu Ile Ile        [SEQ ID NO.:44];

His His Leu Lys Arg Pro Pro Ala Pro Leu Leu Asp

Pro Asn Asn Leu Asn Asp Glu Asp Val Ser Ile Leu

Met Glu Arg Asn Leu Arg Leu Pro Asn Leu Glu Ser

Phe Val Arg Ala Val Lys Asn Leu Glu Asn Ala Ser

Gly Ile Glu Ala Ile Leu Arg Asn Leu Gln Pro Cys

Leu Pro Ser Ala Thr Ala Ala Pro Ser Arg His Pro

Ile Ile Ile Lys Ala Gly Asp Trp Gln Glu Phe Arg

Glu Lys Leu Thr Phe Tyr Leu Val Thr Leu Glu Gln

Ala Gln Glu Gln Gln

Met Ala Asn Cys Ser Ile Met Ile Asp Glu Ile Ile        [SEQ ID NO.:45];

His His Leu Lys Arg Pro Pro Ala Pro Leu Leu Asp

Pro Asn Asn Leu Asn Asp Glu Asp Met Ser Ile Leu

Met Glu Arg Asn Leu Arg Leu Pro Asn Leu Glu Ser

Phe Val Arg Ala Val Lys Asn Leu Glu Asn Ala Ser

Gly Ile Glu Ala Ile Leu Arg Asn Leu Gln Pro Cys

Leu Pro Ser Ala Thr Ala Ala Pro Ser Arg His Pro

Ile Ile Ile Lys Ala Gly Asp Trp Gln Glu Phe Arg

Glu Lys Leu Thr Phe Tyr Leu Val Thr Leu Glu Gln

Ala Gln Glu Gln Gln

Met Ala Tyr Pro Glu Thr Asp Tyr Lys Asp Asp Asp        [SEQ ID NO.:46];

Asp Lys Asn Cys Ser Ile Met Ile Asp Glu Ile Ile

His His Leu Lys Arg Pro Pro Ala Pro Leu Leu Asp

Pro Asn Asn Leu Asn Ala Glu Asp Val Asp Ile Leu

Met Glu Arg Asn Leu Arg Leu Pro Asn Leu Glu Ser

Phe Val Arg Ala Val Lys Asn Leu Glu Asn Ala Ser

Gly Ile Glu Ala Ile Leu Arg Asn Leu Gln Pro Cys

Leu Pro Ser Ala Thr Ala Ala Pro Ser Arg His Pro

Ile Ile Ile Lys Ala Gly Asp Trp Gln Glu Phe Arg

Glu Lys Leu Thr Phe Tyr Leu Val Thr Leu Glu Gln

Ala Gln Glu Gln Gln

Met Ala Tyr Pro Glu Thr Asp Tyr Lys Asp Asp Asp        [SEQ ID NO.:47];

Asp Lys Asn Cys Ser Ile Met Ile Asp Glu Ile Ile

His His Leu Lys Arg Pro Pro Asn Pro Leu Leu Asp

Pro Asn Asn Leu Asn Ser Glu Asp Met Asp Ile Leu

Met Glu Arg Asn Leu Arg Thr Pro Asn Leu Leu Ala

Phe Val Arg Ala Val Lys His Leu Glu Asn Ala Ser

Gly Ile Glu Ala Ile Leu Arg Asn Leu Gln Pro Cys

Leu Pro Ser Ala Thr Ala Ala Pro Ser Arg His Pro
```

```
                            -continued
Ile Ile Ile Lys Ala Gly Asp Trp Gln Glu Phe Arg Glu Lys Leu Thr Phe Tyr Leu Val Thr Leu Glu Gln Ala Gln Glu Gln Gln Met Ala Asn Cys Ser Ile Met Ile Asp Glu Leu Ile          [SEQ ID NO.:48];

His His Leu Lys Ile Pro Pro Asn Pro Ser Leu Asp

Ser Ala Asn Leu Asn Ser Glu Asp Val Ser Ile Leu

Met Glu Arg Asn Leu Arg Thr Pro Asn Leu Leu Ala

Phe Val Arg Ala Val Lys His Leu Glu Asn Ala Ser

Gly Ile Glu Ala Ile Leu Arg Asn Leu Gln Pro Cys Leu Pro

Ser Ala Thr Ala Ala Pro Ser Arg His Pro Ile Ile Ile Lys

Ala Gly Asp Trp Gln Glu Phe Arg Glu Lys Leu Thr Phe Tyr

Leu Val Thr Leu Glu Gln Ala Gln Glu Gln Gln
```

Materials and methods for fusion molecule Expression in *E. coli*

Unless noted otherwise, all specialty chemicals are obtained from Sigma Co., (St. Louis, Mo.). Restriction endonucleases, T4 poly-nucleotides kinase, *E. coli* DNA polymerase I large fragment (Klenow) and T4 DNA ligase are obtained from New England Biolabs (Beverly, Mass.).

*Escherichia coli* strains

Strain JM101: delta (pro lac), supE, thi, F'(traD36, rpoAB, lacI-Q, lacZdeltaM15) (Messing, 1979). This strain can be obtained from the American Type Culture Collection (ATCC), 12301 Parklawn Drive, Rockville, Md. 20852, accession number 33876. MON 105 (W3110 rpoH358) is a derivative of W3110 (Bachmann, 1972) and has been assigned ATCC accession number 55204. Strain GM48: dam-3, dcm-6, gal, ara, lac, thr, leu, tonA, tsx (Marinus, 1973) is used to make plasmid DNA that is not methylated at the sequence GATC.

Genes and plasmids

The gene used for hIL-3 production in *E. coli* is obtained from British Biotechnology Incorporated, Cambridge, England, catalogue number BBG14. This gene is carried on a pUC based plasmid designated pP0518. Many other human CSF genes can be obtained from R&D Systems, Inc. (Minn, Minn.) including IL-1 alpha, IL-1 beta, IL-2, IL-4, IL-5, IL-6, IL-7, IL-8, G-CSF, GM-CSF and LIF.

The plasmids used for production of hIL-3 in *E. coli* contain genetic elements whose use has been described (Olins et al., 1988; Olins and Rangwala, 1990). The replicon used is that of pBR327 (Covarrubias, et al., 1981) which is maintained at a copy number of about 100 in the cell (Soberon et al., 1980). A gene encoding the beta-lactamase protein is present on the plasmids. This protein confers ampicillin resistance on the cell. This resistance serves as a selectable phenotype for the presence of the plasmid in the cell.

For cytoplasmic expression vectors the transcription promoter is derived from the recA gene of *E. coli* (Sancar et al., 1980). This promoter, designated precA, includes the RNA polymerase binding site and the lexA repressor binding site (the operator). This segment of DNA provides high level transcription that is regulated even when the recA promoter is on a plasmid with the pBR327 origin of replication (Olins et al., 1988) incorporated herein by reference.

The ribosome binding site used is that from gene 10 of phage T7 (Olins et al., 1988). This is encoded in a 100 base pair (bp) fragment placed adjacent to precA. In the plasmids used herein, the recognition sequence for the enzyme NcoI (CCATGG) follows the g10-L. It is at this NcoI site that the hIL-3 genes are joined to the plasmid. It is expected that the nucleotide sequence at this junction will be recognized in mRNA as a functional start site for translation (Olins et al., 1988). The hIL-3 genes used were engineered to have a HindIII recognition site (AAGCTT) downstream from the coding sequence of the gene. At this HindIII site is a 514 base pair RsaI fragment containing the origin of replication of the single stranded phage f1 (Dente et al., 1983; Olins, et al., 1990) both incorporated herein by reference. A plasmid containing these elements is pMON2341. Another plasmid containing these elements is pMON5847 which has been deposited at the American Type Culture Collection, 12301 Parklawn Drive, Rockville, Md. 20852 under the accession number ATCC 68912.

In secretion expression plasmids the transcription promoter is derived from the ara B, A, and D genes of *E. coli* (Greenfield et al., 1978). This promoter is designated pAra-BAD and is contained on a 323 base pair SacII, BglII restriction fragment. The LamB secretion leader (Wong et al., 1988, Clement et al., 1981) is fused to the N-terminus of the hIL-3 gene at the recognition sequence for the enzyme NcoI (5'CCATGG3'). The hIL-3 genes used were engineered to have a HindIII recognition site (5'AAGCTT3') following the coding sequence of the gene.

Recombinant DNA Methods

Synthetic gene assembly

The hIL-3 variant genes and other CSF genes can be constructed by the assembly of synthetic oligonucleotides. Synthetic oligonucleotides are designed so that they would anneal in complementary pairs, with protruding single stranded ends, and when the pairs are properly assembled would result in a DNA sequence that encoded a portion of the desired gene. Amino acid substitutions in the hIL-3 gene are made by designing the oligonucleotides to encode the desired substitutions. The complementary oligonucleotides are annealed at concentration of 1 picomole per microliter in ligation buffer plus 50 mM NaCl. The samples are heated in a 100 ml beaker of boiling water and permitted to cool slowly to room temperature. One picomole of each of the annealed pairs of oligonucleotides are ligated with approximately 0.2 picomoles of plasmid DNA, digested with the appropriate restriction enzymes, in ligation buffer (25 mM Tris pH 8.0, 10 mM $MgCl_2$, 10 mM dithiothreitol, 1 mM ATP, 2 mM spermidine) with T4 DNA ligase obtained from New England Biolabs (Beverly, Mass.) in a total volume of 20 μl at room temperature overnight.

Polymerase Chain Reaction

Polymerase Chain Reaction (hereafter referred to as PCR) techniques (Saiki, 1985) used the reagent kit and thermal cycler from Perkin-Elmer Cetus (Norwalk, Conn.). PCR is based on a thermostable DNA polymerase from *Thermus aquaticus*. The PCR technique is a DNA amplification method that mimics the natural DNA replication process in that the number of DNA molecules doubles after each cycle, in a way similar to in vivo replication. The DNA polymerase mediated extension is in a 5' to 3' direction. The term "primer" as used herein refers to an oligonucleotide sequence that provides an end to which the DNA polymerase can add nucleotides that are complementary to a nucleotide sequence. The latter nucleotide sequence is referred to as the "template", to which the primers are annealed. The amplified PCR product is defined as the region comprised between the 5' ends of the extension primers. Since the primers have defined sequences, the product will have discrete ends, corresponding to the primer sequences. The primer extension reaction is carried out using 20 picomoles (pmoles) of each of the oligonucleotides and 1 picogram of template plasmid DNA for 35 cycles (1 cycle is defined as 94 degrees C. for one minute, 50 degrees C. for two minutes and 72 degrees for three minutes.). The reaction mixture is extracted with an equal volume of phenol/chloroform (50% phenol and 50% chloroform, volume to volume) to remove proteins. The aqueous phase, containing the amplified DNA, and solvent phase are separated by centrifugation for 5 minutes in a microcentrifuge (Model 5414 Eppendorf Inc, Fremont CA.). To precipitate the amplified DNA the aqueous phase is removed and transferred to a fresh tube to which is added 1/10 volume of 3M NaOAc (pH 5.2) and 2.5 volumes of ethanol (100% stored at minus 20 degrees C.). The solution is mixed and placed on dry ice for 20 minutes. The DNA is pelleted by centrifugation for 10 minutes in a microcentrifuge and the solution is removed from the pellet. The DNA pellet is washed with 70% ethanol, ethanol removed and dried in a speedvac concentrator (Savant, Farmingdale, N.Y.). The pellet is resuspended in 25 microliters of TE (20 mM Tris-HCl pH 7.9, 1 mM EDTA). Alternatively the DNA is precipitated by adding equal volume of 4M $NH_4OAc$ and one volume of isopropanol [Treco et al., (1988)]. The solution is mixed and incubated at room temperature for 10 minutes and centrifuged. These conditions selectively precipitate DNA fragments larger than ~20 bases and are used to remove oligonucleotide primers. One quarter of the reaction is digested with restriction enzymes [Higuchi, (1989)] an on completion heated to 70 degrees C. to inactivate the enzymes.

Recovery of recombinant plasmids from ligation mixes *E. coli* JM101 cells are made competent to take up DNA. Typically, 20 to 100 ml of cells are grown in LB medium to a density of approximately 150 Klett units and then collected by centrifugation. The cells are resuspended in one half culture volume of 50 mM $CaCl_2$ and held at 4° C. for one hour. The cells are again collected by centrifugation and resuspended in one tenth culture volume of 50 mM $CaCl_2$. DNA is added to a 150 microliter volume of these cells, and the samples are held at 4° C. for 30 minutes. The samples are shifted to 42° C. for one minute, one milliliter of LB is added, and the samples are shaken at 37° C. for one hour. Cells from these samples are spread on plates containing ampicillin to select for transformants. The plates are incubated overnight at 37° C. Single colonies are picked, grown in LB supplemented with ampicillin overnight at 37° C. with shaking. From these cultures DNA is isolated for restriction analysis.

Culture medium

LB medium (Maniatis et al., 1982) is used for growth of cells for DNA isolation. M9 minimal medium supplemented with 1.0% casamino acids, acid hydrolyzed casein, Difco (Detroit, Mich.) is used for cultures in which recombinant fusion molecule is produced. The ingredients in the M9 medium are as follows: 3 g/liter $KH_2PO_4$, 6 g/l $Na_2HPO_4$, 0.5 g/l NaCl, 1 g/l $NH_4Cl$, 1.2 mM $MgSO_4$, 0.025 mM $CaCl_2$, 0.2% glucose (0.2% glycerol with the AraBAD promoter), 1% casamino acids, 0.1 ml/l trace minerals (per liter 108 g $FeCl_3.6H_2O$, 4.0 g $ZnSO_4.7H_2O$, 7.0 g $CoCl_2.2H_2O$, 7.0 g $Na_2MoO_4.2H_2O$, 8.0 g $CuSO_4.5H_2O$, 2.0 g $H_3BO_3$, 5.0 g $MnSO_4.H_2O$, 100 ml concentrated HCl). Bacto agar is used for solid media and ampicillin is added to both liquid and solid LB media at 200 micrograms per milliliter.

Production of fusion molecules in *E. coli* with vectors employing the recA promoter

*E. coli* strains harboring the plasmids of interest are grown at 37° C. in M9 plus casamino acids medium with shaking in a Gyrotory water bath Model G76 from New Brunswick Scientific (Edison, N.J.). Growth is monitored with a Klett Summerson meter (green 54 filter), Klett Mfg. Co. (New York, N.Y.). At a Klett value of approximately 150, an aliquot of the culture (usually one milliliter) is removed for protein analysis. To the remaining culture, nalidixic acid (10 mg/ml) in 0.1 N NaOH is added to a final concentration of 50 μg/ml. The cultures are shaken at 37° C. for three to four hours after addition of nalidixic acid. A high degree of aeration is maintained throughout the bacterial growth in order to achieve maximal production of the desired gene product. The cells are examined under a light microscope for the presence of refractile bodies (RBs). One milliliter aliquots of the culture are removed for analysis of protein content.

Fractionation of *E. coli* cells producing fusion proteins in the cytoplasm

The first step in purification of the fusion molecules is to sonicate the cells. Aliquots of the culture are resuspended from cell pellets in sonication buffer: 10 mM Tris, pH 8.0, 1 mM EDTA, 50 mM NaCl and 0.1 mM PMSF. These resuspended cells are subjected to several repeated sonication bursts using the microtip from a Sonicator cell disrupter, Model W-375 obtained from Heat Systems-Ultrasonics Inc. (Farmingdale, N.Y.). The extent of sonication is monitored by examining the homogenates under a light microscope. When nearly all of the cells are broken, the homogenates are fractionated by centrifugation. The pellets, which contain most of the refractile bodies, are highly enriched for fusion proteins.

Methods: Extraction. Refolding and Purification of Fusion Molecules Expressed as Refractile Bodies in *E. coli*.

These fusion proteins can be purified by a variety of standard methods. Some of these methods are described in detail in Methods in Enzymology, Volume 182 'Guide to Protein Purification' edited by Murray Deutscher, Academic Press, San Diego, Calif. (1990).

Fusion proteins which are produced as insoluble inclusion bodies in *E. coli* can be solubilized in high concentrations of denaturant, such as Guanidine HCl or Urea including dithiothreitol or beta mercaptoethanol as a reducing agent. Folding of the protein to an active conformation may be accomplished via sequential dialysis to lower concentrations of denaturant without reducing agent.

In some cases the folded proteins can be affinity purified using affinity reagents such as mAbs or receptor subunits attached to a suitable matrix. Alternatively, (or in addition) purification can be accomplished using any of a variety of chromatographic methods such as: ion exchange, gel filtration or hydrophobic chromatography or reversed phase HPLC.

hIL-3 SANDWICH ELISA

The fusion protein concentrations can be determined using a sandwich ELISA based on an appropriate affinity purified antibody. Microtiter plates (Dynatech Immulon II) are coated with 150 μl goat-anti-rhIL-3 at a concentration of approximately 1 μg/ml in 100 mM NaHCO3, pH 8.2. Plates are incubated overnight at room temperature in a chamber maintaining 100% humidity. Wells are emptied and the remaining reactive sites on the plate are blocked with 200 μl of solution containing 10 mM PBS, 3% BSA and 0.05% Tween 20, pH 7.4 for 1 hour at 37° C. and 100% humidity. Wells are emptied and washed 4× with 150 mM NaCl containing 0.05% Tween 20 (wash buffer). Each well then receives 150 μl of dilution buffer (10 mM PBS containing 0.1% BSA, 0.01% Tween 20, pH 7.4), containing rhIL-3 standard, control, sample or dilution buffer alone. A standard curve is prepared with concentrations ranging from 0.125 ng/ml to 5 ng/ml using a stock solution of rhIL-3 (concentration determined by amino acid composition analysis). Plates are incubated 2.5 hours at 37° C. and 100% humidity. Wells are emptied and each plate is washed 4× with wash buffer. Each well then received 150 μl of an optimal dilution (as determined in a checkerboard assay format) of goat anti-rhIL-3 conjugated to horseradish peroxidase. Plates are incubated 1.5 hours at 37° C. and 100% humidity. Wells are emptied and each plate is washed 4× with wash buffer. Each well then received 150 ul of ABTS substrate solution (Kirkegaard and Perry). Plates are incubated at room temperature until the color of the standard wells containing 5 ng/ml rhIL-3 had developed enough to yield an absorbance between 0.5–1.0 when read at a test wavelength of 410 nm and a reference wavelength of 570 nm on a Dynatech microtiter plate reader. Concentrations of immunoreactive rhIL-3 in unknown samples are calculated from the standard curve using software supplied with the plate reader.

AML Proliferation Assay for Bioactive Human Interleukin-3

The factor-dependent cell line AML 193 was obtained from the American Type Culture Collection (ATCC, Rockville, Md.). This cell line, established from a patient with acute myelogenous leukemia, is a growth factor dependent cell line which displayed enhanced growth in GM-CSF supplemented medium (Lange, B., et al., (1987); Valtieri, M., et al., (1987). The ability of AML 193 cells to proliferate in the presence of human IL-3 has also been documented. (Santoli, D., et al., (1987)). A cell line variant was used, AML 193 1.3, which was adapted for long term growth in IL-3 by washing out the growth factors and starving the cytokine dependent AML 193 cells for growth factors for 24 hours. The cells are then replated at $1\times10^5$ cells/well in a 24 well plate in media containing 100 U/ml IL-3. It took approximately 2 months for the cells to grow rapidly in IL-3. These cells are maintained as AML 193 1.3 thereafter by supplementing tissue culture medium (see below) with human IL-3.

AML 193 1.3 cells are washed 6 times in cold Hanks balanced salt solution (HBSS, Gibco, Grand Island, N.Y.) by centrifuging cell suspensions at 250×g for 10 minutes followed by decantation of supernatant. Pelleted cells are resuspended in HBSS and the procedure is repeated until six wash cycles are completed. Cells washed six times by this procedure are resuspended in tissue culture medium at a density ranging from $2\times10^5$ to $5\times10^5$ viable cells/ml. This medium is prepared by supplementing Iscove's modified Dulbecco's Medium (IMDM, Hazleton, Lenexa, Kans.) with albumin, transferrin, lipids and 2-mercaptoethanol. Bovine albumin (Boehringer-Mannheim, Indianapolis, Ind.) is added at 500 μg/ml; human transferrin (Boehringer-Mannheim, Indianapolis, Ind.) is added at 100 μg/ml; soybean lipid (Boehringer-Mannheim, Indianapolis, Ind.) is added at 50 μg/ml; and 2-mercaptoethanol (Sigma, St. Louis, Mo.) is added at $5\times10^{-5}$ M.

Serial dilutions of human interleukin-3 or fusion protein (hIL-3 mutein) are made in triplicate series in tissue culture medium supplemented as stated above in 96 well Costar 3596 tissue culture plates. Each well contained 50 μl of medium containing interleukin-3 or fusion protein once serial dilutions are completed. Control wells contained tissue culture medium alone (negative control). AML 193 1.3 cell suspensions prepared as above are added to each well by pipetting 50 μl ($2.5\times10^4$ cells) into each well. Tissue culture plates are incubated at 37° C. with 5% $CO_2$ in humidified air for 3 days. On day 3, 0.5 μCi $^3$H-thymidine (2 Ci/mM, New England Nuclear, Boston, Mass.) is added in 50 μl of tissue culture medium. Cultures are incubated at 37° C. with 5% $CO_2$ in humidified air for 18–24 hours. Cellular DNA is harvested onto glass filter mats (Pharmacia LKB, Gaithersburg, Md.) using a TOMTEC cell harvester (TOMTEC, Orange, Conn.) which utilized a water wash cycle followed by a 70% ethanol wash cycle. Filter mats are allowed to air dry and then placed into sample bags to which scintillation fluid (Scintiverse II, Fisher Scientific, St. Louis, Mo. or BetaPlate Scintillation Fluid, Pharmacia LKB, Gaithersburg, Md.) is added. Beta emissions of samples from individual tissue culture wells are counted in a LKB Betaplate model 1205 scintillation counter (Pharmacia LKB, Gaithersburg, Md.) and data is expressed as counts per minute of $^3$H-thymidine incorporated into cells from each tissue culture well. Activity of each human interleukin-3 preparation or fusion protein preparation is quantitated by measuring cell proliferation ($^3$H-thymidine incorporation) induced by graded concentrations of interleukin-3 or fusion protein. Typically, concentration ranges from 0.05 pM–$10^5$ pM are quantitated in these assays. Activity is determined by measuring the dose of interleukin-3 or fusion molecule which provides 50% of maximal proliferation [$EC_{50}$=0.5× (maximum average counts per minute of $^3$H-thymidine incorporated per well among triplicate cultures of all concentrations of interleukin-3 tested—background proliferation measured by $^3$H-thymidine incorporation observed in triplicate cultures lacking interleukin-3]. This $EC_{50}$ value is also equivalent to 1 unit of bioactivity. Every assay is performed with native interleukin-3 as a reference standard so that relative activity levels could be assigned.

Methylcellulose Assay

This assay provides a reasonable approximation of the growth activity of colony stimulating factors to stimulate normal bone marrow cells to produce different types of hematopoietic colonies in vitro (Bradley et al., 1966, Pluznik et al., 1965).

Methods

Approximately 30 ml of fresh, normal, healthy bone marrow aspirate are obtained from individuals. Under sterile conditions samples are diluted 1:5 with a 1×PBS (#14040.059 Life Technologies, Gaithersburg, Md.) solution in a 50 ml conical tube (#25339-50 Corning, Corningn Md.). Ficoll (Histopaque-1077 Sigma H-8889) is layered under the diluted sample and centrifuged, 300×g for 30 min. The mononuclear cell band is removed and washed two times in 1×PBS and once with 1% BSA PBS (CellPro Co., Bothel, Wash.). Mononuclear cells are counted and CD34+ cells are selected using the Ceprate LC (CD34) Kit (CellPro Co., Bothel, Wash.) column. This fractionation is performed since all stem and progenitor cells within the bone marrow display CD34 surface antigen. Alternatively whole bone marrow or peripheral blood may be used.

Cultures are set up in triplicate wells with a final volume of 0.1 ml in 48 well tissue culture plates (#3548 CoStar, Cambridge, Mass.). Culture medium is purchased from Terry Fox Labs. (HCC-4330 medium (Terry Fox Labs, Vancouver, B.C., Canada)). 600–1000 CD34+ cells are added per well. Native IL-3 and fusion molecule are added to give final concentrations ranging from 0.001 nm–10 nm. G-CSF and GM-CSF and C-Kit ligand are added at a final concentration of 0.1 nm. Native IL-3 and fusion molecules are supplied in house. C-Kit Ligand (#255-CS), G-CSF (#214-CS) and GM-CSF (#215-GM) are purchased from R&D Systems (Minneapolis, Minn.). Cultures are resuspended using an Eppendorf repeater and 0.1 ml is dispensed per well. Control (baseline response) cultures received no colony stimulating factors. Positive control cultures received conditioned media (PHA stimulated human cells:Terry Fox Lab. H2400). Cultures are incubated at 37° C., 5% $CO_2$ in humidified air.

Hematopoietic colonies which are defined as greater than 50 cells are counted on the day of peak response (days 10–11) using a Nikon inverted phase microscope with a 40× objective combination. Groups of cells containing fewer than 50 cells are referred to as clusters. Alternatively colonies can be identified by spreading the colonies on a slide and stained or they can be picked, resuspended and spun onto cytospin slides for staining.

Human Cord Blood Hemopoietic Growth Factor Assays

Bone marrow cells are traditionally used for in vitro assays of hematopoietic colony stimulating factor (CSF) activity. However, human bone marrow is not always available, and there is considerable variability between donors. Umbilical cord blood is comparable to bone marrow as a source of hematopoietic stem cells and progenitors (Broxmeyer et al., 1992; Mayani et al., 1993). In contrast to bone marrow, cord blood is more readily available on a regular basis. There is also a potential to reduce assay variability by pooling cells obtained fresh from several donors, or to create a bank of cryopreserved cells for this purpose. By modifying the culture conditions, and/or analyzing for lineage specific markers, it should be possible to assay specifically for granulocyte/macrophage colonies (CFU-GM), for megakaryocyte CSF activity, or for high proliferative potential colony forming cell (HPP-CFC) activity.

METHODS

Mononuclear cells (MNC) are isolated from cord blood within 24 hrs of collection, using a standard density gradient (1.077 g/ml Histopaque). Cord blood MNC have been further enriched for stem cells and progenitors by several procedures, including immunomagnetic selection for CD14-, CD34+ cells; panning for SBA-, CD34+ fraction using coated flasks from Applied Immune Science (Santa Clara, Calif.); and CD34+ selection using a CellPro (Bothell, Wash.) avidin column. Either freshly isolated or cryopreserved CD34+ cell enriched fractions are used for the assay. Duplicate cultures for each serial dilution of sample (concentration range from 1 pm to 1204 pm) are prepared with 1×104 cells in 1 ml of 0.9% methocellulose containing medium without additional growth factors (Methocult H4230 from Stem Cell Technologies, Vancouver, BC.). In some experiments, Methocult H4330 containing erythropoietin (EPO) was used instead of Methocult H4230, or Stem Cell Factor (SCF), 50 ng/ml (Biosource International, Camarillo, Calif.) was added. After culturing for 7–9 days, colonies containing >30 cells are counted. In order to rule out subjective bias in scoring, assays are scored blind.

IL-3 Mediated Sulfidoleukotriene Release from Human Mononuclear Cells

The following assay is used to measure IL-3 mediated sulfidoleukotriene release from human mononuclear cells.

Heparin-containing human blood is collected and layered onto an equal volume of Ficoll-Paque (Pharmacia # 17-0840-02) ready to use medium (density 1.077 g/ml.). The Ficoll is warmed to room temperature prior to use and clear 50 ml polystyrene tubes are utilized. The Ficoll gradient is spun at 300×g for 30 minutes at room temperature using a H1000B rotor in a Sorvall RT6000B refrigerated centrifuge. The band containing the mononuclear cells is carefully removed, the volume adjusted to 50 mls with Dulbecco's phosphate-buffered saline (Gibco Laboratories cat. # 310-4040PK), spun at 400×g for 10 minutes at 4° C. and the supernatant is carefully removed. The cell pellet is washed twice with HA Buffer [20 nM Hepes (Sigma # H-3375), 125 mM NaCl (Fisher # S271-500), 5 mM KCl (Sigma # P-9541), 0.5 mm glucose (Sigma # G-5000), 0.025% Human Serum Albumin (Calbiochem #126654) and spun at 300×g, 10 min., 4° C. The cells are resuspended in HACM Buffer (HA buffer supplemented with 1 mM $CaCl_2$ (Fisher # C79-500) and 1 mM $MgCl_2$ (Fisher # M-33) at a concentration of 1×106 cells/ml and 180 μl are transferred into each well of 96 well tissue culture plates. The cells are allowed to acclimate at 37° C. for 15 minutes. The cells are primed by adding 10 μls of a 20× stock of various concentrations of cytokine to each well (typically 100000, 20000, 4000, 800, 160, 32, 6.4, 1.28, 0 fM IL3). The cells are incubated for 15 minutes at 37° C. Sulfidoleukotriene release is activated by the addition of 10 μls of 20×(1000 nM) fmet-leu-phe (Calbiochem # 344252) final concentration 50 nM FMLP and incubated for 10 minutes at 37° C. The plates are spun at 350×g at 4° C. for 20 minutes. The supernatants are removed and assayed for sulfidoleukotrienes using Cayman's Leukotriene C4 EIA kit (Cat. #420211) according to manufacturers' directions. Native hIL-3 is run as a standard control in each assay.

Further details known to those skilled in the art may be found in T. Maniatis, et al., *Molecular Cloning, A Laboratory Manual,* Cold Spring Harbor Laboratory (1982) and references cited therein, incorporated herein by reference; and in J. Sambrook, et al., *Molecular Cloning, A Laboratory Manual,* 2nd edition, Cold Spring Harbor Laboratory (1989) and references cited therein, incorporated herein by reference.

Additional details on the IL-3 variants of the present invention may be found in co-pending U.S. Patent Application Serial No. PCT/US93/11197 which is hereby incorporated by reference in its entirety as if written herein.

Additional details on how to make the fusion protein can be found in WO 92/04455 and WO 91/02754.

Additional details about the lymphokine and the variants thereof can be found in U.S. Pat. Nos. 4,810,643, and 5,218,092 E.P. Application 02174004.

All references, patents or applications cited herein are incorporated by reference in their entirety as if written herein.

EXAMPLE 1

Construction of Expression Plasmid for Fusion Molecules

Construction of a plasmid encoding a fusion protein composed of the IL-3 variant protein found in the plasmid, pMON13288 (U.S. Pat. No. 5,604,116), followed by a factor Xa proteolytic cleavage site, followed by murine IgG 2b hinge region, in which the cysteins have replaced with serines, as the polypeptide linker sequence between the two proteins of the fusion and followed by G-CSF. The plasmid, pMON13288, is digested with EcoRI (which is internal in the IL-3 variant gene) and HindIII (which is after the stop codons for the IL-3 variant) and the 3900 base pair EcoRI, HindIII restriction fragment is purified. The genetic elements derived from pMON13288 are the beta-lactamase gene (AMP), pBR327 origin of replication, recA promoter, g10L ribosome binding site, the bases encoding amino acids 15–105 of (15–125)IL-3 variant gene, and phage f1 origin of replication. Pairs of complementary synthetic oligonucleotides are designed to replace the portion of the IL-3 variant gene after the EcoRI site (bases encoding amino acids 106–125), DNA sequence encoding the factor Xa cleavage site, DNA sequence encoding the polypeptide linker and AflIII restriction site to allow for cloning of the second gene in the fusion. When properly assembled the oligonucleotides results in a DNA sequence, encoding the above mentioned components in-frame, with EcoRI and HindIII restriction ends. Within this DNA sequence unique restriction sites are also created to allow for the subsequent replacement of specific regions with a sequence that has similar function (eg. alternative polypeptide linker region). A unique SnaBI restriction site is created at the end of the 13288 gene which allows for the cloning of other genes in the C-terminus position of the fusion. A unique XmaI site is created between sequence encoding the factor Xa cleavage site and the region encoding the polypeptide linker. A unique AflIII site is created after the linker region that allows for the cloning of the N-terminal protein of the fusion. The 3900 base pair fragment from pMON13288 is ligated with the assembled oligonucleotides and transformed into an appropriate E. coli strain. The resulting clones are screened by restriction analysis and DNA sequenced to confirm that the desired DNA sequence are created. The resulting plasmid is used as an intermediate into which other genes can be cloned as a NcoI,HindIII fragment into the AflIII and HindIII sites to create the desired fusion. The overhangs created by NcoI and AflIII are compatible but the flanking sequence of the restriction recognition sites are different. The NcoI and AflIII sites are lost as a result of the cloning. The above mentioned restrictions site are used as examples and are not limited to those described. Other unique restriction site may also be engineered which serve the function of allowing the regions to be replaced. The plasmid encoding the resulting fusion is DNA sequenced to confirm that the desired DNA sequence is obtained. Other IL-3 variant genes or other colony stimulating factor genes can be altered in a similar manner by genetic engineering techniques to create the appropriate restriction sites which would allow for cloning either into the C-terminal or N-terminal position of the fusion construct described above. Likewise alternative peptidase cleavage sites or polypeptide linkers can be engineered into the fusion plasmids.

EXAMPLE 2

Expression, Extraction, Refolding and Purification of Fusion Proteins Expressed as Refractile Bodies in E. coli E. coli strains harboring the plasmids of interest are grown overnight at 37° C. and diluted the following morning, approximately 1/50, in fresh M9 plus casamino acids medium. The culture is grown at 37° C. for three to four hours to mid-log (OD600=~1) with vigorous shaking. Nalidixic acid (10 mg/ml) in 0.1 N NaOH is added to a final concentration of 50 $\mu$g/ml. The cultures are grown at 37° C. for three to four hours after the addition of nalidixic acid. A high degree of aeration is maintained throughout the bacterial growth in order to achieve maximal production of the desired fusion protein. In cases were the fusion proteins are produced as insoluble inclusion bodies in E. coli the cells are examined under a light microscope for the presence of refractile bodies (RBs).

The first step in purification of the fusion molecules is to sonicate the cells. Aliquots of the culture are resuspended from cell pellets in sonication buffer: 10 mM Tris, pH 8.0, 1 mM EDTA, 50 mM NaCl and 0.1 mM PMSF. These resuspended cells are subjected to several repeated sonication bursts using the microtip from a Sonicator cell disrupter, Model W-375 obtained from Heat Systems-Ultrasonics Inc. (Farmingdale, N.Y.). The extent of sonication is monitored by examining the homogenates under a light microscope. When nearly all of the cells are broken, the homogenates are fractionated by centrifugation. The pellets, which contain most of the refractile bodies, are highly enriched for fusion proteins.

Fusion proteins which are produced as insoluble inclusion bodies in E. coli can be solubilized in high concentrations of denaturant, such as Guanidine HCl or Urea including dithiothreitol or beta mercaptoethanol as a reducing agent. Folding of the protein to an active conformation may be accomplished via sequential dialysis to lower concentrations of denaturant without reducing agent.

In some cases the folded proteins can be affinity purified using affinity reagents such as mAbs or receptor subunits attached to a suitable matrix. Alternatively, (or in addition) purification can be accomplished using any of a variety of chromatographic methods such as: ion exchange, gel filtration or hydrophobic chromatography or reversed phase HPLC.

These and other protein purification methods are described in detail in Methods in Enzymology, Volume 182 'Guide to Protein Purification' edited by Murray Deutscher, Academic Press, San Diego, Calif. (1990).

EXAMPLE 3

Determination of the In Vitro Activity of Fusion Proteins

The protein concentration of the fusion protein can be determined using a sandwich ELISA based on an affinity purified polyclonal antibody. Alternatively the protein concentration can be determined by amino acid composition. The bioactivity of the fusion molecule can be determined in a number of in vitro assays compared with native IL-3, the IL-3 variant or G-CSF alone or together. One such assay is the AML-193 cell proliferation assay. AML-193 cells respond to IL-3 and G-CSF which allows for the combined bioactivity of the IL-3 variant/G-CSF fusion to be determined. In addition other factor dependent cell lines, such as 32D which is a murine IL-3 dependent cell line, may be used. The activity of IL-3 is species specific whereas G-CSF is not, therefor the bioactivity of the G-CSF component of the IL-3 variant/G-CSF fusion can be determined independently. The methylcellulose assay can be used to determine the effect of the IL-3 variant/G-CSF fusion protein on the expansion of the hematopoietic progenitor cells and the pattern of the different types of hematopoietic colonies in vitro. The methylcellulose assay can provide an estimate of precursor frequency since one measures the frequency of progenitors per 100,000 input cells. Long term, stromal dependent cultures have been used to delineate primitive hematopoietic progenitors and stem cells. This assay can be used to determine whether the fusion molecule stimulates the expansion of very primitive progenitors and/or stem cells. In addition, limit dilution cultures can be performed which will indicate the frequency of primitive progenitors stimulated by the fusion molecule.

The factor Xa cleavage site is useful to cleave the fusion protein after it is purified and re-folded to separate the IL-3 and G-CSF components of the fusion. After cleavage with factor Xa the IL-3 and G-CSF components of the fusion can be purified to homogeneity and assayed separately to demonstrate that both components are in an active conformation after being expressed, refolded and purified as a fusion.

Various other examples will be apparent to the person skilled in the art after reading the present disclosure without departing from the spirit and scope of the invention. It is intended that all such other examples be included within the scope of the appended claims.

Amino acids are shown herein by standard one letter or three letter abbreviations as follows:

| Abbreviated | Designation | Amino Acid |
|---|---|---|
| A | Ala | Alanine |
| C | Cys | Cysteine |
| D | Asp | Aspartic acid |
| E | Glu | Glutamic acid |
| F | Phe | Phenylalanine |
| G | Gly | Glycine |
| H | His | Histidine |
| I | Ile | Isoleucine |
| K | Lys | Lysine |
| L | Leu | Leucine |
| M | Met | Methionine |
| N | Asn | Asparagine |
| P | Pro | Proline |
| Q | Gln | Glutamine |
| R | Arg | Arginine |
| S | Ser | Serine |
| T | Thr | Threonine |
| V | Val | Valine |
| W | Trp | Tryptophan |
| Y | Tyr | Tyrosine |

References

Abel, T. and T. Maniatis. *Nature* 341:24–25, (1989).

Adams, S. P., Kavka, K. S., Wykes, E. J., Holder, S. B. and Galluppi, G. R. Hindered Dialkyamino Nucleoside Phosphate reagents in the synthesis of two DNA 51-mers. *J. Am. Chem. Soc.*, 105, 661–663 (1983).

Atkinson, T. and Smith, M., in Gait, M. J., Oligonucleotide Sythesis (1984) (IRL Press, Oxford England).

Bachmann, B., Pedigrees of some mutant strains of *Escherichia coli* K-12, *Bacteriological Reviews*, 36:525–557 (1972).

Bayne, M. L., Expression of a synthetic gene encoding human insulin-like growth factor I in cultured mouse fibroblasts. *Proc. Natl. Acad. Sci. USA* 84, 2638–2642 (1987).

Ben-Bassat, A., K. Bauer, S-Y. Chang, K. Myambo, A. Boosman and S. Ching. Processing of the initiating methionine from proteins: properties of the *Escherichia coli* methionine aminopeptidase and its gene structure. *J. Bacteriol.*, 169: 751–757 (1987).

Biesma, B. et al., Effects of interleukin-3 after chemotherapy for advanced ovarian cancer. *Blood*, 80:1141–1148 (1992).

Birnboim, H. C. and J. Doly. A rapid alkaline extraction method for screening recombinant plasmid DNA. *Nucleic Acids Research*, 7(6): 1513–1523 (1979).

Bradford, M. M., A rapid and sensitive method for the quantitation of microgram quantities of protein utilizing the principle of protein-dye binding, *Analytical Biochemistry*, 72: 248–254 (1976).

Bradley, T R and Metcalf, D. The growth of mouse bone marrow cells in vitro. *Aust. Exp. Biol. Med. Sci.* 44:287–300, (1966).

Broxmeyer, H. E. et al, Growth characteristics and expansion of human umbilical cord blood and estimation of its potential for transplantation in adults, *Proc. Natl. Acad. Sci. USA*, 89:4109–4113, (1992).

Clark-Lewis, I., L. E. Hood and S. B. H. Kent. Role of disulfide bridges in determining the biological activity of interleukin 3, *Proc. Natl. Acad. Sci.*, 85: 7897–7901 (1988).

Clement, J. M. and Hofnung, M. Gene sequence of the receptor, an outer membrane protein of *E. coli* K12. *Cell*, 7: 507–514 (1981).

Covarrubias, L., L. Cervantes, A. Covarrubias, X. Soberon, I. Vichido, A. Blanco, Y. M. Kupersztoch-Portnoy and F. Bolivar. Construction and characterization of new cloning vehicles. V. Mobilization and coding properties of pBR322 and several deletion derivates including pBR327 and pBR328. Gene 13: 25–35 (1981).

D'Andrea, A. D., Lodish, H. G., Wong, G. G.:Expression cloning of the murine erythropoietin receptor. Cell 57:277, 1989

Deng, W. P. & Nickoloff, J. A. Site-directed mutagenesis of virtually any plasmid by eliminating a unique site *Anal. Biochem.* 200:81 (1992).

Dente, L., G. Cesareni and R. Cortese, pEMBL: a new family of single stranded plasmids, *Nucleic Acids Research*, 11: 1645–1655 (1983).

Dunn, J. J. and Studier, F. W., Complete nucleotide sequence of bacteriophage T7 DNA and the locations of T7 genetic elements. *J. Mol. Biol.* 166:477–535 (1983).

Falk, S., G. Seipelt, A. Ganser, O. G. Ottmann, D. Hoelzer, H. J. Stutte and K. Hubner. *Hematopathology* 95: 355 (1991).

Fisher, D. E., C. S. Carr, L. A. Parent and P. A. Sharp. *Genes and Development* 5:2342–2352, (1991).

Fling, M. E., et al. Nucleotide sequence of the transposon Tn7 gene encoding an aminoglycoside-modifying enzyme, 3"(9)-O-nucleotidyltransferase. *Nucl. Acids Res.* 13:7095–7106 (1985).

Ganser, A., A. Lindemann, G. Seipelt, O. G. Ottmann, F. Herrmann, M. Eder, J. Frisch, G. Schulz, R. Mertelsmann and D. Hoelzer. Effects of Recombinant Human Interleukin-3 in Patients With Normal Hematopoiesis and in Patients with Bone Marrow Failure, *Blood* 76: 666 (1990).

Gearing, D. P., King, J. A., Gough, N. M., Nicola, N. A.: Expression cloning of a receptor for human granulocyte-macrophage colony-stimulating factor. EMBO J 8:3667, 1989

Gearing, D. P., Thut, C. J., VandenBos, T., Gimpel, S. D., Delaney, P. B., King, J. A., Price V., Cosman, D., Beckmann M P: Leukemia inhibitory factor receptor is structurally related to the IL-6 signal transducer, gp130. EMBO J 10:2839, 1991

Gething and Sambrook, Cell-surface expression of influenza haemagglutinin from a cloned DNA copy of the RNA gene, *Nature* , 29: 620–625 (1981).

Gillio, A. P., C. Gasparetto, J. Laver, M. Abboud, M. A. Bonilla, M. B. Garnick and R. J. O'Reilly. *J. Clin. Invest.* 85: 1560 (1990).

Gouy, M. and G. Gautier, Codon usage in bacteria: Correlation with gene expressivity, *Nucleic Acids Research,* 10: 7055–7074 (1982).

Greenfield, L., T. Boone, and G. Wilcox. DNA sequence of the araBAD promoter in *Escherichia coli* B/r. *Proc. Natl. Acad. Sci. USA,* 75: 4724–4728 (1978).

Harada, N., Castle, B. E., Gorman, D. M., Itoh, N., Schreurs, J., Barrett R. L., Howard, M., Miyajima, A.: Expression cloning of a cDNA encoding the murine interleukin 4 receptor based on ligand binding. Proc Natl Acad Sci USA 87:857, 1990

Higuchi, R, (1989) in *PCR Technology,* H. A. Erlich ed., Stockton Press, N.Y. chapter 2–6.

Hunkapiller, M. W., R. W. Hewick, R. J. Dreyer and L. E. Hood. High sensitivity sequencing with a gas-phase sequenator. *Methods in Enzymology* 153: 399–413 (1983).

Kaufman, et al., Coamplification and Coexpression of Human Tissue-Type Plasminogen Activator and Murine Dihydrofolate Reductase Sequences in Chinese Hamster Ovary Cells, *Mol. Cell. Biol.,* 5(7): 1750–1759 (1985).

Kaufman, R. J. High level production of proteins in mammalian cells, in *Genetic Engineering, Principles and Methods,* Vol. 9, J. K. Setlow, editor, Plenum Press, New York (1987).

Kelso, A., Gough, N. M.: Coexpession of granulocyte-macrophage colony-stimulating factor. g-interferon and interleukins-3 and 4 is random in murine alloreactive T lymphocyte clonese. Proc Natl Acad Sci USA 85:9189, 1988

Kitamura, T., Sato, N., Arai, K., Miyajima, A.: Expression cloning of the human IL-3 receptor cDNA reveals a shared beta subunit for the human IL-3 and GM-CSF receptors. Cell 66:1165, 1991

Kondo, M., Takeshita, T., Ishii, N., Nakamura, M., Watanabe, S., Arai, K-I, Sugamura, K.: Sharing of the Interleukin-2 (IL-2) Receptor g Chain Between Receptors for IL-2 and Il-4. Science 262:1874, Dec. 17, 1993.

Kozarides, T. and E. Ziff, *Nature* 336: 646–651, (1988).

Kunkel, T. A. Rapid and efficient site-specific mutagenesis without phenotypic selection. *Proc. Natl. Acad. Sci. USA,* 82: 488–492 (1985).

Laemmli, U. K., Cleavage of structural proteins during assembly of the head of bacteriophage T4, *Nature,* 227:680–685 (1970).

Landshulz, W. H., P. F. Johnson and S. L. Knight, *Science* 240: 1759–1764, (1988).

Lange, B., M. Valtieri, D. Santoli, D. Caracciolo, F. Mavilio, I. Gemperlein, C. Griffin, B. Emanuel, J. Finan, P. Nowell, and G. Rovera. Growth factor requirements of childhood acute leukemia: establishment of GM-CSF-defendent cell lines. *Blood* 70:192 (1987).

Maekawa, T., Metcalf, D., Gearing, D. P.: Enhanced suppression of human myeloid leukemic cell lines by combination of IL-6, LIF, GM-CSF and G-CSF, Int J Cancer 45:353, 1989

Mahler, H. R. and E. H. Cordes, in *Biological Chemistry, p.* 128, New York, Harper and Row (1966).

Maniatis, T., E. F. Fritsch and J. Sambrook, *Molecular Cloning, A Laboratory Manual.* Cold Spring Harbor Laboratory (1982).

Marinus, M. G. Location of DNA methylation genes on the *Escherichia coli* K-12 genetic map. *Molec. Gen. Genet.* 127: 47–55 (1973).

Mayani, H. et al, Cytokine-induced selective expansion and maturation of erythroid versus myeloid progenitors from purified cord blood precursor cells, *Blood, vol.* 81:3252–3258, (1993).

Mazur, E et al, *Blood* 57:277–286, (1981).

McBride, L. J. and Caruthers, M. H. An investigation of several deoxynucleoside phosphoramidites. Tetrahedron Lett., 24, 245–248 (1983).

Messing, J., A multipurpose cloning system based on the single-stranded DNA bacteriophage M13. *Recombinant DNA Technical Bulletin,* NIH Publication No. 79–99, Vol. 2, No. 2, pp. 43–48 (1979).

Metcalf, D., Begley, C. G., Williamson, D., Nice, E. C., DeLamarter, J., Mermod J-J, Thatcher, D., Schmidt, A.: Hemopoietic responses in mice injected with purified recombinant murine GM-CSF. Exp Hematol 15:1, 1987

Metcalf, D.: The molecular control of cell division, differentiation commitment and maturation in haemopoietic cells. Nature 339:27, 1989

Metcalf, D., Nicola, N. A.: Direct proliferative actions of stem cell factor on murine bone marrow cells in vitro. Effects of combinatin with colony-stimulating factors. Proc Natl Acad Sci USA 88:6239, 1991

Murre, C. S. P. S. McCaw and D. Baltimore. *Cell* 56:777–783, (1989).

Murre, C. S. , P. S. McCaw, H. Vassin, M. Caudy, L. Y. Jan, Y. N. Jan, C. V. Cabrera, J. N. Bushkin, S. Hauschka, A. B. Lassar, H. Weintraub and D. Baltimore, *Cell* 58:537–544, (1989).

Neu, H. C. and L. A. Heppel. The release of enzymes from *Escherichia coli* by osmotic shock and during the formation of spheroplasts. *J. Biol. Chem.,* 240: 3685–3692 (1965).

Noguchi, M., Nakamura, Y., Russell, S. M., Ziegler, S. F., Tsang, M., Xiqing, C., Leonard, W. J.: Interleukin-2 Receptor g Chain: A Functional Component of the Interleukin-7 Receptor. Science 262:1877, Dec 17, 1993.

Nordon, P, and Potter, M, A Macrophage-Derived Factor Required by plasmacytomas for Survival and Proliferation in Vitro, *Science* 233:566, (1986).

Obukowicz, M. G., Staten, N. R. and Krivi, G. G., Enhanced Heterologous Gene Expression in Novel rpoH Mutants of *Escherichia coli. Applied and Environmental Microbiology* 58, No. 5, p. 1511–1523 (1992).

Olins, P. O., C. S. Devine, S. H. Rangwala and K. S. Kavka, The T7 phage gene 10 leader RNA, a ribosome-binding site that dramatically enhances the expression of foreign genes in *Escherichia coli, Gene,* 73:227–235 (1988).

Olins, P. O. and S. H. Rangwala, Vector for enhanced translation of foreign genes in *Escherichia coli, Methods in Enzymology,* 185: 115–119 (1990).

Pluznik, D H and Sachs, L. Cloning of normal "mast" cells in tissue culture. *J Cell Comp Physiol* 66:319–324 (1965).

Postmus, et al., Effects of recombinant human interleukin-3 in patients with relapsed small-cell lung cancer treated with chemotherapy: a dose-finding study. *J. Clin. Oncol.,* 10:1131–1140 (1992).

Prober, J. M., G. L. Trainor, R. J. Dam, F. W. Hobbs, C. W. Robertson, R. J. Zagursky, A. J. Cocuzza, M. A. Jensen and K. Baumeister. A system for rapid DNA sequencing with fluorescent chain-terminating dideoxynucleotides. *Science* 238: 336–341 (1987).

Pu, W. T. and K. Struhl, *Nucleic Acids Research* 21:4348–4355, (1993).

Renart J., J. Reiser and G. R. Stark, Transfer of proteins from gels to diazobenzyloxymethyl-paper and detection with anti-sera: a method for studying antibody specificity and antigen structure, *Proc. Natl. Acad. Sci. USA,* 76:3116–3120 (1979).

Russell, S. M., Keegan, A. D., Harada, N., Nakamura, Y., Noguchi, M., Leland, P., Friedmann, M. C., Miyajima, A., Puri, R. K., Paul, W. E., Leonard, W. J.: Interleukin-2 Receptor g Chain: A Functional Component of the Interleukin-4 Receptor. Science 262:1880, Dec. 17, 1993.

Saiki, R. K., Schorf, S., Faloona, F., Mullis, K. B., Horn, G. T., Erlich, H. A. and Arnheim, N., Enzymatic Amplification of β-Globin Genomic Sequences and Restriction Site Analysis for Diagnosis of Sickle Cell Anemia, *Science* , 230: 1350–1354 (1985).

Sambrook, J., et al., *Molecular Cloning, A Laboratory Manual,* 2nd edition, Cold Spring Harbor Laboratory (1989).

Sancar, A., C. Stachelek, W. Konigsberg and W. D. Rupp, Sequences of the recA gene and protein, *Proc. Natl. Acad. Sci.,* 77: 2611–2615 (1980).

Sanger, F., S. Nicklen and A. R. Coulson. DNA sequencing with chain-terminating inhibitors. *Proc. Natl. Acad. Sci. U.S.A.* 74: 5463–5467 (1977).

Santoli, D., Y. Yang, S. C. Clark, B. L. Kreider, D. Caracciolo, and G. Rovera. Synergistic and antagonistic effects of recombinant human interleukin (IL-3), IL-1, granulocyte and macrophage colony-stimulating factors (G-CSF and M-CSF) on the growth of GM-CSF-dependent leukemic cell lines. *J. Immunol.* 139:348 (1987).

Schaller et al., *PROC NATL ACAD SCI USA* 72:737–741, (1975).

Sherr, C. J.: Colony-stimulating factor-1 receptor. Blood 75:1, 1990

Smith, M. In vitro mutagenesis. *Ann. Rev. Genet.,* 19:423–462 (1985).

Soberon, X., L. Covarrubias and F. Bolivar, Construction and characterization of new cloning vehicles. IV. Deletion derivatives of pBR322 and pBR325, *Gene,* 9: 211–223 (1980).

Stader, J. A. and T. J. Silhavy. Engineering *Escherichia coli* to secrete heterologous gene products, *Methods in Enzymology,* 185: 166–87 (1990).

Summers, M. D. and G. E. Smith. A manual of methods for Baculovirus vectors and insect cell culture procedures. *Texas Agricultural Experiment Station Bulletin No.* 1555 (1987).

Takaki, S., Tominage, A., Hitoshi, Y., Mita S., Sonada, E., Yamaguchi, N., Takatsu, K.: Molecular cloning and expression of the murine interleukin-5 receptor. EMBO J 9:4367, 1990

Tapscott, S. J., R. L. Davis, M. J. Thayer, P. F. Cheng, H. Weintraub and A. B. Lassar, *Science* 242:405–411, (1988).

Taylor, J. W., Ott, J. and Eckstein, F. The rapid generation of oligonucleotide-directed mutants at high frequency using phosphorothioate modified DNA. *Nucl. Acids Res.,* 13:8764–8785 (1985).

Treco, D. A., (1989) in *Current protocols in Molecular Biology,* Seidman et al., eds. J Wiley N.Y., unit 2.1.

Valtieri, M., D. Santoli, D. Caracciolo, B. L. Kreider, S. W. Altmann, D. J. Tweardy, I. Gemperlein, F. Mavilio, B. J. Lange and G. Rovera. Establishment and characterization of an undifferentiated human T leukemia cell line which requires granulocyte-macrophage colony stimulating factor for growth. *J. Immunol.* 138:4042 (1987).

Voet, D., W. B. Gatzer, R. A. Cox, P. Doty. Absorption spectra of the common bases. *Biopolymers* 1: 193 (1963).

Weinberg, R. A., De Ciechi, P. A., Obukowicz, M.: A chromosomal expression vector for *Escherichia coli* based on the bacteriophage Mu. Gene 126 (1993) 25–33.

Wells, J. A., Vasser, M., and Powers, D. B. Cassette mutagenesis: an effective method for generation of multiple mutants at defined sites. *Gene,* 34:315–323 (1985).

Wong, Y. Y., R. Seetharam, C. Kotts, R. A. Heeren, B. K. Klein, S. B. Braford, K. J. Mathis, B. F. Bishop, N. R. Siegel, C. E. Smith and W. C. Tacon. Expression of secreted IGF-1 in *Escherichia coli. Gene,* 68: 193–203 (1988).

Yanisch-Perron, C., J. Viera and J. Messing. Improved M13 phage cloning vectors and host strains: nucleotide sequences of the M13mp18 and pUC19 vectors. *Gene* 33: 103–119 (1985).

Yamasaki, K., Taga, T., Hirata, Y., Yawata, H., Kawanishi, Y., Seed, B., Taniguchi, T., Hirano, T., Kishimoto, T.: Cloning and expression of the human interleukin-6 (BSF-2?IFN beta 2) receptor. Science 241:825, 1988

Yarden Y., Kuang, W-J., Yang-Feng, T., Coussens, L., Munemitsu, S., Dull, T. J., Chen, E., Schlesinger, J., Francke, U., Ullrich, A., Human proto-oncogene c-kit: A new cell surface receptor tyrosine kinase for an unidentified ligand. EMBO J 6:3341, 1987

Zoller, M. J. and Smith, M. oligonucleotide-directed mutagenesis using M13-derived vectors: an efficient and general procedure for the production of point mutations in any fragment of DNA. *Nucleic Acid Research,* 10: 6487–6500 (1982).

Zoller, M. J. and Smith, M. oligonucleotide-directed mutagenesis of DNA fragments cloned into M13 vectors. *Methods in Enzymology,* 100:468–500 (1983).

Zoller, M. J. and Smith, M. Oligonucleotide-directed Mutagenesis: A simple method using two oligonucleotide primers and a single-stranded DNA template. *DNA,* 3: 479 (1984).

SEQUENCE LISTING (1) GENERAL INFORMATION:

(iii) NUMBER OF SEQUENCES: 53

(2) INFORMATION FOR SEQ ID NO:1:

(i) SEQUENCE CHARACTERISTICS:
        (A) LENGTH: 133 amino acids
        (B) TYPE: amino acid
        (D) TOPOLOGY: linear (ii) MOLECULE TYPE: peptide (ix) FEATURE:
        (A) NAME/KEY: Modified-site
        (B) LOCATION: 1
        (D) OTHER INFORMATION: /note= "Met- may or may not precede the
             amino acid in position 1"

(ix) FEATURE:
        (A) NAME/KEY: Modified-site
        (B) LOCATION: 17
        (D) OTHER INFORMATION: /note= "Xaa at position 17 is Ser,
             Lys, Gly, Asp, Met, Gln, or Arg"

(ix) FEATURE:
        (A) NAME/KEY: Modified-site
        (B) LOCATION: 18
        (D) OTHER INFORMATION: /note= "Xaa at position 18 is Asn,
             His, Leu, Ile, Phe, Arg, or Gln"

(ix) FEATURE:
        (A) NAME/KEY: Modified-site
        (B) LOCATION: 19
        (D) OTHER INFORMATION: /note= "Xaa at positiion 19 is Met,
             Phe, Ile, Arg, Gly, Ala, or Cys"

(ix) FEATURE:
        (A) NAME/KEY: Modified-site
        (B) LOCATION: 20
        (D) OTHER INFORMATION: /note= "Xaa at position 20 is Ile,
             Cys, Gln, Glu, Arg, Pro, or Ala"

(ix) FEATURE:
        (A) NAME/KEY: Modified-site
        (B) LOCATION: 21
        (D) OTHER INFORMATION: /note= "Xaa at position 21 is Asp,
             Phe, Lys, Arg, Ala, Gly, Glu, Gln, Asn, Thr, Ser,
             or Val"

(ix) FEATURE:
        (A) NAME/KEY: Modified-site
        (B) LOCATION: 22
        (D) OTHER INFORMATION: /note= "Xaa at position 22 is Glu,
             Trp, Pro, Ser, Ala, His, Asp, Asn, Gln, Leu, Val,
             or Gly"

(ix) FEATURE:
        (A) NAME/KEY: Modified-site
        (B) LOCATION: 23
        (D) OTHER INFORMATION: /note= "Xaa at position 23 is Ile,
             Val, Ala, Leu, Gly, Trp, Lys, Phe, Ser, or
             Arg"

(ix) FEATURE:
        (A) NAME/KEY: Modified-site
        (B) LOCATION: 24
        (D) OTHER INFORMATION: /note= "Xaa at position 24 is Ile,
             Gly, Val, Arg, Ser, Phe, or Leu"

(ix) FEATURE:
        (A) NAME/KEY: Modified-site
        (B) LOCATION: 25
        (D) OTHER INFORMATION: /note= "Xaa at position 25 is Thr,
             His, Gly, Gln, Arg, Pro, or Ala"

(ix) FEATURE:
    (A) NAME/KEY: Modified-site
    (B) LOCATION: 26
    (D) OTHER INFORMATION: /note= "Xaa at position 26 is His,
        Thr, Phe, Gly, Arg, Ala, or Trp"

(ix) FEATURE:
    (A) NAME/KEY: Modified-site
    (B) LOCATION: 27
    (D) OTHER INFORMATION: /note= "Xaa at position 27 is Leu,
        Gly, Arg, Thr, Ser, or Ala"

(ix) FEATURE:
    (A) NAME/KEY: Modified-site
    (B) LOCATION: 28
    (D) OTHER INFORMATION: /note= "Xaa at position 28 is Lys,
        Arg, Leu, Gln, Gly, Pro, Val, or Trp"

(ix) FEATURE:
    (A) NAME/KEY: Modified-site
    (B) LOCATION: 29
    (D) OTHER INFORMATION: /note= "Xaa at position 29 is Gln,
        Asn, Leu, Pro, Arg, or Val"

(ix) FEATURE:
    (A) NAME/KEY: Modified-site
    (B) LOCATION: 30
    (D) OTHER INFORMATION: /note= "Xaa at position 30 is Pro,
        His, Thr, Gly, Asp, Gln, Ser, Leu, or Lys"

(ix) FEATURE:
    (A) NAME/KEY: Modified-site
    (B) LOCATION: 31
    (D) OTHER INFORMATION: /note= "Xaa at position 31 is Pro,
        Asp, Gly, Ala, Arg, Leu, or Gln"

(ix) FEATURE:
    (A) NAME/KEY: Modified-site
    (B) LOCATION: 32
    (D) OTHER INFORMATION: /note= "Xaa at position 32 is Leu,
        Val, Arg, Gln, Asn, Gly, Ala, or Glu"

(ix) FEATURE:
    (A) NAME/KEY: Modified-site
    (B) LOCATION: 33
    (D) OTHER INFORMATION: /note= "Xaa at position 33 is Pro,
        Leu, Gln, Ala, Thr, or Glu"

(ix) FEATURE:
    (A) NAME/KEY: Modified-site
    (B) LOCATION: 34
    (D) OTHER INFORMATION: /note= "Xaa at position 34 is Leu,
        Val, Gly, Ser, Lys, Glu, Gln, Thr, Arg, Ala, Phe,
        Ile, or Met"

(ix) FEATURE:
    (A) NAME/KEY: Modified-site
    (B) LOCATION: 35
    (D) OTHER INFORMATION: /note= "Xaa at position 35 is Leu,
        Ala, Gly, Asn, Pro, Gln, or Val"

(ix) FEATURE:
    (A) NAME/KEY: Modified-site
    (B) LOCATION: 36
    (D) OTHER INFORMATION: /note= "Xaa at position 36 is Asp,
        Leu, or Val"

(ix) FEATURE:
    (A) NAME/KEY: Modified-site
    (B) LOCATION: 37
    (D) OTHER INFORMATION: /note= "Xaa at position 37 is Phe,
        Ser, Pro, Trp, or Ile"

(ix) FEATURE:
    (A) NAME/KEY: Modified-site
    (B) LOCATION: 38
    (D) OTHER INFORMATION: /note= "Xaa at position 38 is Asn,
        or Ala"

```
(ix) FEATURE:
    (A) NAME/KEY: Modified-site
    (B) LOCATION: 40
    (D) OTHER INFORMATION: /note= "Xaa at position 40 is Leu,
        Trp, or Arg"

(ix) FEATURE:
    (A) NAME/KEY: Modified-site
    (B) LOCATION: 41
    (D) OTHER INFORMATION: /note= "Xaa at position 41 is Asn,
        Cys, Arg, Leu, His, Met, or Pro"

(ix) FEATURE:
    (A) NAME/KEY: Modified-site
    (B) LOCATION: 42
    (D) OTHER INFORMATION: /note= "Xaa at position 42 is Gly,
        Asp, Ser, Cys, Asn, Lys, Thr, Leu, Val, Glu, Phe, Tyr,
        Ile, Met, or Ala"

(ix) FEATURE:
    (A) NAME/KEY: Modified-site
    (B) LOCATION: 43
    (D) OTHER INFORMATION: /note= "Xaa at position 43 is Glu,
        Asn, Tyr, Leu, Phe, Asp, Ala, Cys, Gln, Arg, Thr, Gly,
        or Ser"

(ix) FEATURE:
    (A) NAME/KEY: Modified-site
    (B) LOCATION: 44
    (D) OTHER INFORMATION: /note= "Xaa at position 44 is Asp,
        Ser, Leu, Arg, Lys, Thr, Met, Trp, Glu, Asn, Gln, Ala,
        or Pro"

(ix) FEATURE:
    (A) NAME/KEY: Modified-site
    (B) LOCATION: 45
    (D) OTHER INFORMATION: /note= "Xaa at position 45 is Gln,
        Pro, Phe, Val, Met, Leu, Thr, Lys, Trp, Asp, Asn, Arg,
        Ser, Ala, Ile, Glu, or His"

(ix) FEATURE:
    (A) NAME/KEY: Modified-site
    (B) LOCATION: 46
    (D) OTHER INFORMATION: /note= "Xaa at position 46 is Asp,
        Phe, Ser, Thr, Cys, Glu, Asn, Gln, Lys, His, Ala, Tyr,
        Ile, Val, or Gly"

(ix) FEATURE:
    (A) NAME/KEY: Modified-site
    (B) LOCATION: 47
    (D) OTHER INFORMATION: /note= "Xaa at position 47 is Ile,
        Gly, Val, Ser, Arg, Pro, or His"

(ix) FEATURE:
    (A) NAME/KEY: Modified-site
    (B) LOCATION: 48
    (D) OTHER INFORMATION: /note= "Xaa at position 48 is Leu,
        Ser, Cys, Arg, Ile, His, Phe, Glu, Lys, Thr, Ala, Met,
        Val, or Asn"

(ix) FEATURE:
    (A) NAME/KEY: Modified-site
    (B) LOCATION: 49
    (D) OTHER INFORMATION: /note= "Xaa at position 49 is Met,
        Arg, Ala, Gly, Pro, Asn, His, or Asp"

(ix) FEATURE:
    (A) NAME/KEY: Modified-site
    (B) LOCATION: 50
    (D) OTHER INFORMATION: /note= "Xaa at position 50 is Glu,
        Leu, Thr, Asp, Tyr, Lys, Asn, Ser, Ala, Ile, Val, His,
        Phe, Met, or Gln"

(ix) FEATURE:
    (A) NAME/KEY: Modified-site
    (B) LOCATION: 51
    (D) OTHER INFORMATION: /note= "Xaa at position 51 is Asn,
        Arg, Met, Pro, Ser, Thr, or His"
```

```
(ix) FEATURE:
    (A) NAME/KEY: Modified-site
    (B) LOCATION: 52
    (D) OTHER INFORMATION: /note= "Xaa at position 52 is Asn,
        His, Arg, Leu, Gly, Ser, or Thr"

(ix) FEATURE:
    (A) NAME/KEY: Modified-site
    (B) LOCATION: 53
    (D) OTHER INFORMATION: /note= "Xaa at position 53 is
        Leu, Thr, Ala, Gly, Glu, Pro, Lys, Ser, or Met"

(ix) FEATURE:
    (A) NAME/KEY: Modified-site
    (B) LOCATION: 54
    (D) OTHER INFORMATION: /note= "Xaa at position 54 is Arg,
        Asp, Ile, Ser, Val, Thr, Gln, Asn, Lys, His, Ala,
        or Leu"

(ix) FEATURE:
    (A) NAME/KEY: Modified-site
    (B) LOCATION: 55
    (D) OTHER INFORMATION: /note= "Xaa at position 55 is Arg,
        Thr, Val, Ser, Leu, or Gly"

(ix) FEATURE:
    (A) NAME/KEY: Modified-site
    (B) LOCATION: 56
    (D) OTHER INFORMATION: /note= "Xaa at position 56 is Pro,
        Gly, Cys, Ser, Gln, Glu, Arg, His, Thr, Ala, Tyr,
        Phe, Leu, Val, or Lys"

(ix) FEATURE:
    (A) NAME/KEY: Modified-site
    (B) LOCATION: 57
    (D) OTHER INFORMATION: /note= "Xaa at position 57 is Asn
        or Gly"

(ix) FEATURE:
    (A) NAME/KEY: Modified-site
    (B) LOCATION: 58
    (D) OTHER INFORMATION: /note= "Xaa at position 58 is Leu,
        Ser, Asp, Arg, Gln, Val, or Cys"

(ix) FEATURE:
    (A) NAME/KEY: Modified-site
    (B) LOCATION: 59
    (D) OTHER INFORMATION: /note= "Xaa at position 59 is Glu,
        Tyr, His, Leu, Pro, or Arg"

(ix) FEATURE:
    (A) NAME/KEY: Modified-site
    (B) LOCATION: 60
    (D) OTHER INFORMATION: /note= "Xaa at position 60 is Ala,
        Ser, Pro, Tyr, Asn, or Thr"

(ix) FEATURE:
    (A) NAME/KEY: Modified-site
    (B) LOCATION: 61
    (D) OTHER INFORMATION: /note= "Xaa at position 61 is Phe,
        Asn, Glu, Pro, Lys, Arg, or Ser"

(ix) FEATURE:
    (A) NAME/KEY: Modified-site
    (B) LOCATION: 62
    (D) OTHER INFORMATION: /note= "Xaa at position 62 is Asn,
        His, Val, Arg, Pro, Thr, Asp, or Ile"

(ix) FEATURE:
    (A) NAME/KEY: Modified-site
    (B) LOCATION: 63
    (D) OTHER INFORMATION: /note= "Xaa at position 63 is Arg,
        Tyr, Trp, Lys, Ser, His, Pro, or Val"

(ix) FEATURE:
    (A) NAME/KEY: Modified-site
    (B) LOCATION: 64
    (D) OTHER INFORMATION: /note= "Xaa at position 64 is Ala,
```

```
                Asn, Pro, Ser, or Lys"

(ix) FEATURE:
    (A) NAME/KEY: Modified-site
    (B) LOCATION: 65
    (D) OTHER INFORMATION: /note= "Xaa at position 65 is Val,
        Thr, Pro, His, Leu, Phe, or Ser"

(ix) FEATURE:
    (A) NAME/KEY: Modified-site
    (B) LOCATION: 66
    (D) OTHER INFORMATION: /note= "Xaa at position 66 is Lys,
        Ile, Arg, Val, Asn, Glu, or Ser"

(ix) FEATURE:
    (A) NAME/KEY: Modified-site
    (B) LOCATION: 67
    (D) OTHER INFORMATION: /note= "Xaa at position 67 is Ser,
        Ala, Phe, Val, Gly, Asn, Ile, Pro, or His"

(ix) FEATURE:
    (A) NAME/KEY: Modified-site
    (B) LOCATION: 68
    (D) OTHER INFORMATION: /note= "Xaa at position 68 is Leu,
        Val, Trp, Ser, Ile, Phe, Thr, or His"

(ix) FEATURE:
    (A) NAME/KEY: Modified-site
    (B) LOCATION: 69
    (D) OTHER INFORMATION: /note= "Xaa at position 69 is Gln,
        Ala, Pro, Thr, Glu, Arg, Trp, Gly, or Leu"

(ix) FEATURE:
    (A) NAME/KEY: Modified-site
    (B) LOCATION: 70
    (D) OTHER INFORMATION: /note= "Xaa at position 70 is Asn,
        Leu, Val, Trp, Pro, or Ala"

(ix) FEATURE:
    (A) NAME/KEY: Modified-site
    (B) LOCATION: 71
    (D) OTHER INFORMATION: /note= "Xaa at position 71 is
        Ala, Met, Leu, Pro, Arg, Glu, Thr, Gln, Trp,
        or Asn"

(ix) FEATURE:
    (A) NAME/KEY: Modified-site
    (B) LOCATION: 72
    (D) OTHER INFORMATION: /note= "Xaa at position 72 is Ser,
        Glu, Met, Ala, His, Asn, Arg, or Asp"

(ix) FEATURE:
    (A) NAME/KEY: Modified-site
    (B) LOCATION: 73
    (D) OTHER INFORMATION: /note= "Xaa at position 73 is Ala,
        Glu, Asp, Leu, Ser, Gly, Thr, or Arg"

(ix) FEATURE:
    (A) NAME/KEY: Modified-site
    (B) LOCATION: 74
    (D) OTHER INFORMATION: /note= "Xaa at position 74 is Ile,
        Met, Thr, Pro, Arg, Gly, or Ala"

(ix) FEATURE:
    (A) NAME/KEY: Modified-site
    (B) LOCATION: 75
    (D) OTHER INFORMATION: /note= "Xaa at position 75 is
        Glu, Lys, Gly, Asp, Pro, Trp, Arg, Ser, Gln,
        or Leu"

(ix) FEATURE:
    (A) NAME/KEY: Modified-site
    (B) LOCATION: 76
    (D) OTHER INFORMATION: /note= "Xaa at position 76 is Ser,
        Val, Ala, Asn, Trp, Glu, Pro, Gly, or Asp"

(ix) FEATURE:
    (A) NAME/KEY: Modified-site
    (B) LOCATION: 77
```

(D) OTHER INFORMATION: /note= "Xaa at position 77 is Ile,
                Ser, Arg, Thr, or Leu"

(ix) FEATURE:
            (A) NAME/KEY: Modified-site
            (B) LOCATION: 78
            (D) OTHER INFORMATION: /note= "Xaa at position 78 is Leu,
                Ala, Ser, Glu, Phe, Gly, or Arg"

(ix) FEATURE:
            (A) NAME/KEY: Modified-site
            (B) LOCATION: 79
            (D) OTHER INFORMATION: /note= "Xaa at position 79 is Lys, Thr,
                Asn, Met, Arg, Ile, Gly, or Asp"

(ix) FEATURE:
            (A) NAME/KEY: Modified-site
            (B) LOCATION: 80
            (D) OTHER INFORMATION: /note= "Xaa at position 80 is Asn,
                Trp, Val, Gly, Thr, Leu, Glu, or Arg"

(ix) FEATURE:
            (A) NAME/KEY: Modified-site
            (B) LOCATION: 81
            (D) OTHER INFORMATION: /note= "Xaa at position 81 is Leu,
                Gln, Gly, Ala, Trp, Arg, Val, or Lys"

(ix) FEATURE:
            (A) NAME/KEY: Modified-site
            (B) LOCATION: 82
            (D) OTHER INFORMATION: /note= "Xaa at position 82 is Leu,
                Gln, Lys, Trp, Arg, Asp, Glu, Asn, His, Thr, Ser, Ala,
                Tyr, Phe, Ile, Met, or Val"

(ix) FEATURE:
            (A) NAME/KEY: Modified-site
            (B) LOCATION: 83
            (D) OTHER INFORMATION: /note= "Xaa at position 83 is Pro,
                Ala, Thr, Trp, Arg, or Met"

(ix) FEATURE:
            (A) NAME/KEY: Modified-site
            (B) LOCATION: 84
            (D) OTHER INFORMATION: /note= "Xaa at position 84 is Cys,
                Glu, Gly, Arg, Met, or Val"

(ix) FEATURE:
            (A) NAME/KEY: Modified-site
            (B) LOCATION: 85
            (D) OTHER INFORMATION: /note= "Xaa at position 85 is Leu,
                Asn, Val, or Gln"

(ix) FEATURE:
            (A) NAME/KEY: Modified-site
            (B) LOCATION: 86
            (D) OTHER INFORMATION: /note= "Xaa at position 86 is Pro,
                Cys, Arg, Ala, or Lys"

(ix) FEATURE:
            (A) NAME/KEY: Modified-site
            (B) LOCATION: 87
            (D) OTHER INFORMATION: /note= "Xaa at position 87 is Leu,
                Ser, Trp, or Gly"

(ix) FEATURE:
            (A) NAME/KEY: Modified-site
            (B) LOCATION: 88
            (D) OTHER INFORMATION: /note= "Xaa at position 88 is Ala,
                Lys, Arg, Val, or Trp"

(ix) FEATURE:
            (A) NAME/KEY: Modified-site
            (B) LOCATION: 89
            (D) OTHER INFORMATION: /note= "Xaa at position 89 is Thr,
                Asp, Cys, Leu, Val, Glu, His, Asn, or Ser"

(ix) FEATURE:
            (A) NAME/KEY: Modified-site
            (B) LOCATION: 90

```
        (D) OTHER INFORMATION: /note= "Xaa at position 90 is Ala,
            Pro, Ser, Thr, Gly, Asp, Ile, or Met"

(ix) FEATURE:
        (A) NAME/KEY: Modified-site
        (B) LOCATION: 91
        (D) OTHER INFORMATION: /note= "Xaa at position 91 is Ala,
            Pro, Ser, Thr, Phe, Leu, Asp, or His"

(ix) FEATURE:
        (A) NAME/KEY: Modified-site
        (B) LOCATION: 92
        (D) OTHER INFORMATION: /note= "Xaa at position 92 is Pro,
            Phe, Arg, Ser, Lys, His, Ala, Gly, Ile, or Leu"

(ix) FEATURE:
        (A) NAME/KEY: Modified-site
        (B) LOCATION: 93
        (D) OTHER INFORMATION: /note= "Xaa at position 93 is Thr,
            Asp, Ser, Asn, Pro, Ala, Leu, or Arg"

(ix) FEATURE:
        (A) NAME/KEY: Modified-site
        (B) LOCATION: 94
        (D) OTHER INFORMATION: /note= "Xaa at position 94 is Arg,
            Ile, Ser, Glu, Leu, Val, Gln, Lys, His, Ala, or Pro"

(ix) FEATURE:
        (A) NAME/KEY: Modified-site
        (B) LOCATION: 95
        (D) OTHER INFORMATION: /note= "Xaa at position 95 is His,
            Gln, Pro, Arg, Val, Leu, Gly, Thr, Asn, Lys, Ser, Ala,
            Trp, Phe, Ile, or Tyr"

(ix) FEATURE:
        (A) NAME/KEY: Modified-site
        (B) LOCATION: 96
        (D) OTHER INFORMATION: /note= "Xaa at position 96 is Pro,
            Lys, Tyr, Gly, Ile, or Thr"

(ix) FEATURE:
        (A) NAME/KEY: Modified-site
        (B) LOCATION: 97
        (D) OTHER INFORMATION: /note= "Xaa at position 97 is Ile,
            Val, Lys, Ala, or Asn"

(ix) FEATURE:
        (A) NAME/KEY: Modified-site
        (B) LOCATION: 98
        (D) OTHER INFORMATION: /note= "Xaa at position 98 is His,
            Ile, Asn, Leu, Asp, Ala, Thr, Glu, Gln, Ser, Phe, Met,
            Val, Lys, Arg, Tyr, or Pro"

(ix) FEATURE:
        (A) NAME/KEY: Modified-site
        (B) LOCATION: 99
        (D) OTHER INFORMATION: /note= "Xaa at position 99 is Ile,
            Leu, Arg, Asp, Val, Pro, Gln, Gly, Ser, Phe,
            or His"

(ix) FEATURE:
        (A) NAME/KEY: Modified-site
        (B) LOCATION: 100
        (D) OTHER INFORMATION: /note= "Xaa at position 100 is
            Lys, Tyr, Leu, His, Arg, Ile, Ser, Gln, or Pro"

(ix) FEATURE:
        (A) NAME/KEY: Modified-site
        (B) LOCATION: 101
        (D) OTHER INFORMATION: /note= "Xaa at position 101 is
            Asp, Pro, Met, Lys, His, Thr, Val, Tyr, Glu, Asn, Ser,
            Ala, Gly, Ile, Leu, or Gln"

(ix) FEATURE:
        (A) NAME/KEY: Modified-site
        (B) LOCATION: 102
        (D) OTHER INFORMATION: /note= "Xaa at position 102 is Gly,
            Leu, Glu, Lys, Ser, Tyr, or Pro"
```

(ix) FEATURE:
    (A) NAME/KEY: Modified-site
    (B) LOCATION: 103
    (D) OTHER INFORMATION: /note= "Xaa at position 103 is Asp,
        or Ser"

(ix) FEATURE:
    (A) NAME/KEY: Modified-site
    (B) LOCATION: 104
    (D) OTHER INFORMATION: /note= "Xaa at position 104 is
        Trp, Val, Cys, Tyr, Thr, Met, Pro, Leu, Gln, Lys, Ala,
        Phe, or Gly"

(ix) FEATURE:
    (A) NAME/KEY: Modified-site
    (B) LOCATION: 105
    (D) OTHER INFORMATION: /note= "Xaa at position 105 is
        Asn, Pro, Ala, Phe, Ser, Trp, Gln, Tyr, Leu, Lys, Ile,
        Asp, or His"

(ix) FEATURE:
    (A) NAME/KEY: Modified-site
    (B) LOCATION: 106
    (D) OTHER INFORMATION: /note= "Xaa at position 106 is Glu,
        Ser, Ala, Lys, Thr, Ile, Gly, or Pro"

(ix) FEATURE:
    (A) NAME/KEY: Modified-site
    (B) LOCATION: 108
    (D) OTHER INFORMATION: /note= "Xaa at position 108 is Arg,
        Lys, Asp, Leu, Thr, Ile, Gln, His, Ser, Ala, or Pro"

(ix) FEATURE:
    (A) NAME/KEY: Modified-site
    (B) LOCATION: 109
    (D) OTHER INFORMATION: /note= "Xaa at position 109 is Arg,
        Thr, Pro, Glu, Tyr, Leu, Ser, or Gly"

(ix) FEATURE:
    (A) NAME/KEY: Modified-site
    (B) LOCATION: 110
    (D) OTHER INFORMATION: /note= "Xaa at position 110 is Lys,
        Ala, Asn, Thr, Leu, Arg, Gln, His, Glu, Ser, Ala,
        or Trp"

(ix) FEATURE:
    (A) NAME/KEY: Modified-site
    (B) LOCATION: 111
    (D) OTHER INFORMATION: /note= "Xaa at position 111 is Leu,
        Ile, Arg, Asp, or Met"

(ix) FEATURE:
    (A) NAME/KEY: Modified-site
    (B) LOCATION: 112
    (D) OTHER INFORMATION: /note= "Xaa at position 112 is Thr,
        Val, Gln, Tyr, Glu, His, Ser, or Phe"

(ix) FEATURE:
    (A) NAME/KEY: Modified-site
    (B) LOCATION: 113
    (D) OTHER INFORMATION: /note= "Xaa at position 113 is Phe,
        Ser, Cys, His, Gly, Trp, Tyr, Asp, Lys, Leu, Ile, Val,
        or Asn"

(ix) FEATURE:
    (A) NAME/KEY: Modified-site
    (B) LOCATION: 114
    (D) OTHER INFORMATION: /note= "Xaa at position 114 is Tyr,
        Cys, His, Ser, Trp, Arg, or Leu"

(ix) FEATURE:
    (A) NAME/KEY: Modified-site
    (B) LOCATION: 115
    (D) OTHER INFORMATION: /note= "Xaa at position 115 is
        Leu, Asn, Val, Pro, Arg, Ala, His, Thr, Trp, or
        Met"

(ix) FEATURE:
    (A) NAME/KEY: Modified-site (B) LOCATION: 116
            (D) OTHER INFORMATION: /note= "Xaa at position 116 is Lys,
                Leu, Pro, Thr, Met, Asp, Val, Glu, Arg, Trp, Ser,
                Asn, His, Ala, Tyr, Phe, Gln, or Ile"

(ix) FEATURE:
            (A) NAME/KEY: Modified-site
            (B) LOCATION: 117
            (D) OTHER INFORMATION: /note= "Xaa at position 117 is Thr,
                Ser, Asn, Ile, Trp, Lys, or Pro"

(ix) FEATURE:
            (A) NAME/KEY: Modified-site
            (B) LOCATION: 118
            (D) OTHER INFORMATION: /note= "Xaa at position 118 is Leu,
                Ser, Pro, Ala, Glu, Cys, Asp, or Tyr"

(ix) FEATURE:
            (A) NAME/KEY: Modified-site
            (B) LOCATION: 119
            (D) OTHER INFORMATION: /note= "Xaa at position 119 is Glu,
                Ser, Lys, Pro, Leu, Thr, Tyr, or Arg"

(ix) FEATURE:
            (A) NAME/KEY: Modified-site
            (B) LOCATION: 120
            (D) OTHER INFORMATION: /note= "Xaa at position 120 is Asn,
                Ala, Pro, Leu, His, Val, or Gln"

(ix) FEATURE:
            (A) NAME/KEY: Modified-site
            (B) LOCATION: 121
            (D) OTHER INFORMATION: /note= "Xaa at position 121 is Ala,
                Ser, Ile, Asn, Pro, Lys, Asp, or Gly"

(ix) FEATURE:
            (A) NAME/KEY: Modified-site
            (B) LOCATION: 122
            (D) OTHER INFORMATION: /note= "Xaa at position 122 is
                Gln, Ser, Met, Trp, Arg, Phe, Pro, His, Ile, Tyr,
                or Cys"

(ix) FEATURE:
            (A) NAME/KEY: Modified-site
            (B) LOCATION: 123
            (D) OTHER INFORMATION: /note= "Xaa at position 123 is Ala,
                Met, Glu, His, Ser, Pro, Tyr, or Leu"

(xi) SEQUENCE DESCRIPTION: SEQ ID NO:1:

Ala Pro Met Thr Gln Thr Thr Ser Leu Lys Thr Ser Trp Val Asn Cys
1               5                   10                  15

Xaa Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Asn Xaa Xaa Xaa Xaa Xaa Xaa Xaa Xaa Xaa
        35                  40                  45

Xaa Xaa Xaa Xaa Xaa Xaa Xaa Xaa Xaa Xaa Xaa Xaa Xaa Xaa Xaa Xaa
    50                  55                  60

Xaa Xaa Xaa Xaa Xaa Xaa Xaa Xaa Xaa Xaa Xaa Xaa Xaa Xaa Xaa Xaa
65                  70                  75                  80

Xaa Xaa Xaa Xaa Xaa Xaa Xaa Xaa Xaa Xaa Xaa Xaa Xaa Xaa Xaa Xaa
            85                  90                  95

Xaa Xaa Xaa Xaa Xaa Xaa Xaa Xaa Phe Xaa Xaa Xaa Xaa Xaa
            100                 105                 110

Xaa Xaa Xaa Xaa Xaa Xaa Xaa Xaa Xaa Xaa Xaa Gln Gln Thr Thr Leu
        115                 120                 125

Ser Leu Ala Ile Phe
        130

(2) INFORMATION FOR SEQ ID NO:2:

```
    (i) SEQUENCE CHARACTERISTICS:
        (A) LENGTH: 133 amino acids
        (B) TYPE: amino acid
        (D) TOPOLOGY: linear (ii) MOLECULE TYPE: peptide (ix) FEATURE:
        (A) NAME/KEY: Modified-site
        (B) LOCATION: 1
        (D) OTHER INFORMATION: /note= "Met- may or may not precede
            the amino acid in position 1"

(ix) FEATURE:
        (A) NAME/KEY: Modified-site
        (B) LOCATION: 17
        (D) OTHER INFORMATION: /note= "Xaa at position 17 is Ser,
            Gly, Asp, Met, or Gln"

(ix) FEATURE:
        (A) NAME/KEY: Modified-site
        (B) LOCATION: 18
        (D) OTHER INFORMATION: /note= "Xaa at position 18 is Asn,
            His, or Ile"

(ix) FEATURE:
        (A) NAME/KEY: Modified-site
        (B) LOCATION: 19
        (D) OTHER INFORMATION: /note= "Xaa at position 19 is Met
            or Ile"

(ix) FEATURE:
        (A) NAME/KEY: Modified-site
        (B) LOCATION: 21
        (D) OTHER INFORMATION: /note="Xaa at position 21 is Asp
            or Glu"

(ix) FEATURE:
        (A) NAME/KEY: Modified-site
        (B) LOCATION: 23
        (D) OTHER INFORMATION: /note= "Xaa at position 23 is Ile,
            Ala, Leu, or Gly"

(ix) FEATURE:
        (A) NAME/KEY: Modified-site
        (B) LOCATION: 24
        (D) OTHER INFORMATION: /note= "Xaa at position 24 is Ile,
            Val, or Leu"

(ix) FEATURE:
        (A) NAME/KEY: Modified-site
        (B) LOCATION: 25
        (D) OTHER INFORMATION: /note= "Xaa at position 25 is Thr,
            His, Gln, or Ala"

(ix) FEATURE:
        (A) NAME/KEY: Modified-site
        (B) LOCATION: 26
        (D) OTHER INFORMATION: /note= "Xaa at position 26 is His
            or Ala"

(ix) FEATURE:
        (A) NAME/KEY: Modified-site
        (B) LOCATION: 29
        (D) OTHER INFORMATION: /note= "Xaa at position 29 is Gln,
            Asn, or Val"

(ix) FEATURE:
        (A) NAME/KEY: Modified-site
        (B) LOCATION: 30
        (D) OTHER INFORMATION: /note= "Xaa at position 30 is Pro,
            Gly, or Gln"

(ix) FEATURE:
        (A) NAME/KEY: Modified-site
        (B) LOCATION: 31
        (D) OTHER INFORMATION: /note= "Xaa at position 31 is Pro,
            Asp, Gly, or Gln"
```

```
(ix) FEATURE:
    (A) NAME/KEY: Modified-site
    (B) LOCATION: 32
    (D) OTHER INFORMATION: /note= "Xaa at position 32 is Leu,
        Arg, Gln, Asn, Gly, Ala, or Glu"

(ix) FEATURE:
    (A) NAME/KEY: Modified-site
    (B) LOCATION: 33
    (D) OTHER INFORMATION: /note= "Xaa at position 33 is Pro
        or Glu"

(ix) FEATURE:
    (A) NAME/KEY: Modified-site
    (B) LOCATION: 34
    (D) OTHER INFORMATION: /note= "Xaa at position 34 is Leu,
        Val, Gly, Ser, Lys, Ala, Arg, Gln, Glu, Ile, Phe,
        Thr, or Met"

(ix) FEATURE:
    (A) NAME/KEY: Modified-site
    (B) LOCATION: 35
    (D) OTHER INFORMATION: /note= "Xaa at position 35 is Leu,
        Ala, Asn, Pro, Gln, or Val"

(ix) FEATURE:
    (A) NAME/KEY: Modified-site
    (B) LOCATION: 37
    (D) OTHER INFORMATION: /note= "Xaa at position 37 is Phe,
        Ser, Pro, or Trp"

(ix) FEATURE:
    (A) NAME/KEY: Modified-site
    (B) LOCATION: 38
    (D) OTHER INFORMATION: /note="Xaa at position 38 is Asn
        or Ala"

(ix) FEATURE:
    (A) NAME/KEY: Modified-site
    (B) LOCATION: 42
    (D) OTHER INFORMATION: /note= "Xaa at position 42 is Gly,
        Asp, Ser, Cys, Ala, Asn, Ile, Leu, Met, Tyr,
        or Arg"

(ix) FEATURE:
    (A) NAME/KEY: Modified-site
    (B) LOCATION: 44
    (D) OTHER INFORMATION: /note="Xaa at position 44 is Asp
        or Glu"

(ix) FEATURE:
    (A) NAME/KEY: Modified-site
    (B) LOCATION: 45
    (D) OTHER INFORMATION: /note= "Xaa at position 45 is Gln,
        Val, Met, Leu, Thr, Ala, Asn, Glu, Ser, or Lys"

(ix) FEATURE:
    (A) NAME/KEY: Modified-site
    (B) LOCATION: 46
    (D) OTHER INFORMATION: /note= "Xaa at position 46 is Asp,
        Phe, Ser, Thr, Ala, Asn, Gln, Glu, His, Ile,
        Lys, Tyr, Val, or Cys"

(ix) FEATURE:
    (A) NAME/KEY: Modified-site
    (B) LOCATION: 50
    (D) OTHER INFORMATION: /note= "Xaa at position 50 is Glu,
        Ala, Asn, Ser, or Asp"

(ix) FEATURE:
    (A) NAME/KEY: Modified-site
    (B) LOCATION: 51
    (D) OTHER INFORMATION: /note= "Xaa at position 51 is Asn,
        Arg, Met, Pro, Ser, Thr, or His"

(ix) FEATURE:
    (A) NAME/KEY: Modified-site
    (B) LOCATION: 54
```

(D) OTHER INFORMATION: /note="Xaa at position 54 is Arg
                    or Ala"

(ix) FEATURE:
                (A) NAME/KEY: Modified-site
                (B) LOCATION: 55
                (D) OTHER INFORMATION: /note= "Xaa at position 55 is Arg,
                    Thr, Val, Leu, or Gly"

(ix) FEATURE:
                (A) NAME/KEY: Modified-site
                (B) LOCATION: 56
                (D) OTHER INFORMATION: /note= "Xaa at position 56 is Pro,
                    Gly, Ser, Gln, Ala, Arg, Asn, Glu, Leu, Thr, Val,
                    or Lys"

(ix) FEATURE:
                (A) NAME/KEY: Modified-site
                (B) LOCATION: 60
                (D) OTHER INFORMATION: /note= "Xaa at position 60 is Ala
                    or Ser"

(ix) FEATURE:
                (A) NAME/KEY: Modified-site
                (B) LOCATION: 62
                (D) OTHER INFORMATION: /note= "Xaa at position 62 is Asn,
                    Pro, Thr, or Ile"

(ix) FEATURE:
                (A) NAME/KEY: Modified-site
                (B) LOCATION: 63
                (D) OTHER INFORMATION: /note= "Xaa at position 63 is Arg
                    or Lys"

(ix) FEATURE:
                (A) NAME/KEY: Modified-site
                (B) LOCATION: 64
                (D) OTHER INFORMATION: /note= "Xaa at position 64 is Ala
                    or Asn"

(ix) FEATURE:
                (A) NAME/KEY: Modified-site
                (B) LOCATION: 65
                (D) OTHER INFORMATION: /note= "Xaa at position 65 is Val
                    or Thr"

(ix) FEATURE:
                (A) NAME/KEY: Modified-site
                (B) LOCATION: 66
                (D) OTHER INFORMATION: /note= "Xaa at position 66 is Lys
                    or Arg"

(ix) FEATURE:
                (A) NAME/KEY: Modified-site
                (B) LOCATION: 67
                (D) OTHER INFORMATION: /note= "Xaa at position 67 is Ser
                    Phe or His"

(ix) FEATURE:
                (A) NAME/KEY: Modified-site
                (B) LOCATION: 68
                (D) OTHER INFORMATION: /note= "Xaa at position 68 is Leu,
                    Ile, Phe, or His"

(ix) FEATURE:
                (A) NAME/KEY: Modified-site
                (B) LOCATION: 69
                (D) OTHER INFORMATION: /note= "Xaa at position 69 is Gln,
                    Ala, Pro, Thr, Glu, Arg, or Gly"

(ix) FEATURE:
                (A) NAME/KEY: Modified-site
                (B) LOCATION: 71
                (D) OTHER INFORMATION: /note= "Xaa at position 71 is Ala,
                    Pro, or Arg"

(ix) FEATURE:
                (A) NAME/KEY: Modified-site
                (B) LOCATION: 72

```
          (D) OTHER INFORMATION: /note= "Xaa at position 72 is Ser,
              Glu, Arg, or Asp"

(ix) FEATURE:
          (A) NAME/KEY: Modified-site
          (B) LOCATION: 73
          (D) OTHER INFORMATION: /note= "Xaa at position 73 is Ala
              or Leu"

(ix) FEATURE:
          (A) NAME/KEY: Modified-site
          (B) LOCATION: 76
          (D) OTHER INFORMATION: /note= "Xaa at position 76 is Ser,
              Val, Ala, Asn, Glu, Pro, or Gly"

(ix) FEATURE:
          (A) NAME/KEY: Modified-site
          (B) LOCATION: 77
          (D) OTHER INFORMATION: /note= "Xaa at position 77 is Ile
              or Leu"

(ix) FEATURE:
          (A) NAME/KEY: Modified-site
          (B) LOCATION: 79
          (D) OTHER INFORMATION: /note= "Xaa at position 79 is
              Lys, Thr, Gly, Asn, Met, Arg, Ile, Gly, or Asp"

(ix) FEATURE:
          (A) NAME/KEY: Modified-site
          (B) LOCATION: 80
          (D) OTHER INFORMATION: /note= "Xaa at position 80 is Asn,
              Gly, Glu, or Arg"

(ix) FEATURE:
          (A) NAME/KEY: Modified-site
          (B) LOCATION: 82
          (D) OTHER INFORMATION: /note= "Xaa at position 82 is Leu,
              Gln, Trp, Arg, Asp, Ala, Asn, Glu, His, Ile,
              Met, Phe, Ser, Thr, Tyr, or Val"

(ix) FEATURE:
          (A) NAME/KEY: Modified-site
          (B) LOCATION: 83
          (D) OTHER INFORMATION: /note= "Xaa at position 83 is Pro
              or Thr"

(ix) FEATURE:
          (A) NAME/KEY: Modified-site
          (B) LOCATION: 85
          (D) OTHER INFORMATION: /note= "Xaa at position 85 is Leu
              or Val"

(ix) FEATURE:
          (A) NAME/KEY: Modified-site
          (B) LOCATION: 87
          (D) OTHER INFORMATION: /note= "Xaa at position 87 is Leu
              or Ser"

(ix) FEATURE:
          (A) NAME/KEY: Modified-site
          (B) LOCATION: 88
          (D) OTHER INFORMATION: /note= "Xaa at position 88 is Ala
              or Trp"

(ix) FEATURE:
          (A) NAME/KEY: Modified-site
          (B) LOCATION: 91
          (D) OTHER INFORMATION: /note= "Xaa at position 91 is Ala
              or Pro"

(ix) FEATURE:
          (A) NAME/KEY: Modified-site
          (B) LOCATION: 93
          (D) OTHER INFORMATION: /note= "Xaa at position 93 is Thr,
              Asp, Ser, Pro, Ala, Leu, or Arg"

(ix) FEATURE:
          (A) NAME/KEY: Modified-site
          (B) LOCATION: 95
```

(D) OTHER INFORMATION: /note= "Xaa at position 95 is His,
                Pro, Arg, Val, Leu, Gly, Asn, Phe, Ser, or Thr"

(ix) FEATURE:
        (A) NAME/KEY: Modified-site
        (B) LOCATION: 96
        (D) OTHER INFORMATION: /note= "Xaa at position 96 is Pro
            or Tyr"

(ix) FEATURE:
        (A) NAME/KEY: Modified-site
        (B) LOCATION: 97
        (D) OTHER INFORMATION: /note= "Xaa at position 97 is Ile
            or Val"

(ix) FEATURE:
        (A) NAME/KEY: Modified-site
        (B) LOCATION: 98
        (D) OTHER INFORMATION: /note= "Xaa at position 98 is His,
            Ile, Asn, Leu, Ala, Thr, Arg, Gln, Lys,
            Met, Ser, Tyr, Val, or Pro"

(ix) FEATURE:
        (A) NAME/KEY: Modified-site
        (B) LOCATION: 99
        (D) OTHER INFORMATION: /note= "Xaa at position 99 is Ile,
            Leu, or Val"

(ix) FEATURE:
        (A) NAME/KEY: Modified-site
        (B) LOCATION: 100
        (D) OTHER INFORMATION: /note= "Xaa at position 100 is Lys,
            Arg, Ile, Gln, Pro, or Ser"

(ix) FEATURE:
        (A) NAME/KEY: Modified-site
        (B) LOCATION: 101
        (D) OTHER INFORMATION: /note= "Xaa at position 101 is Asp,
            Pro, Met, Lys, Thr, His, Asn, Ile, Leu, or Tyr"

(ix) FEATURE:
        (A) NAME/KEY: Modified-site
        (B) LOCATION: 104
        (D) OTHER INFORMATION: /note= "Xaa at position 104 is Trp
            or Leu"

(ix) FEATURE:
        (A) NAME/KEY: Modified-site
        (B) LOCATION: 105
        (D) OTHER INFORMATION: /note= "Xaa at position 105 is
            Asn, Pro, Ala, Ser, Trp, Gln, Tyr, Leu, Lys, Ile,
            Asp, or His"

(ix) FEATURE:
        (A) NAME/KEY: Modified-site
        (B) LOCATION: 106
        (D) OTHER INFORMATION: /note= "Xaa at position 106 is Glu
            or Gly"

(ix) FEATURE:
        (A) NAME/KEY: Modified-site
        (B) LOCATION: 108
        (D) OTHER INFORMATION: /note="Xaa at position 108 is Arg,
            Ala, or Ser"

(ix) FEATURE:
        (A) NAME/KEY: Modified-site
        (B) LOCATION: 109
        (D) OTHER INFORMATION: /note= "Xaa at position 109 is Arg,
            Thr, Glu, Leu, or Ser"

(ix) FEATURE:
        (A) NAME/KEY: Modified-site
        (B) LOCATION: 112
        (D) OTHER INFORMATION: /note= "Xaa at position 112 is Thr,
            Val, or Gln"

(ix) FEATURE:
        (A) NAME/KEY: Modified-site (B) LOCATION: 114
            (D) OTHER INFORMATION: /note= "Xaa at position 114 is Tyr
                or Trp"

(ix) FEATURE:
            (A) NAME/KEY: Modified-site
            (B) LOCATION: 115
            (D) OTHER INFORMATION: /note= "Xaa at position 115 is Leu
                or Ala"

(ix) FEATURE:
            (A) NAME/KEY: Modified-site
            (B) LOCATION: 116
            (D) OTHER INFORMATION: /note= "Xaa at position 116 is Lys,
                Thr, Val, Trp, Ser, Ala, His, Met, Phe, Tyr, or Ile"

(ix) FEATURE:
            (A) NAME/KEY: Modified-site
            (B) LOCATION: 117
            (D) OTHER INFORMATION: /note= "Xaa at position 117 is Thr
                or Ser"

(ix) FEATURE:
            (A) NAME/KEY: Modified-site
            (B) LOCATION: 120
            (D) OTHER INFORMATION: /note= "Xaa at position 120 is Asn,
                Pro, Leu, His, Val, or Gln"

(ix) FEATURE:
            (A) NAME/KEY: Modified-site
            (B) LOCATION: 121
            (D) OTHER INFORMATION: /note= "Xaa at position 121 is Ala,
                Ser, Ile, Asn, Pro, Asp, or Gly"

(ix) FEATURE:
            (A) NAME/KEY: Modified-site
            (B) LOCATION: 122
            (D) OTHER INFORMATION: /note= "Xaa at position 122 is
                Gln, Ser, Met, Trp, Arg, Phe, Pro, His, Ile, Tyr,
                or Cys"

(ix) FEATURE:
            (A) NAME/KEY: Modified-site
            (B) LOCATION: 123
            (D) OTHER INFORMATION: /note= "Xaa at position 123 is Ala,
                Met, Glu, His, Ser, Pro, Tyr, or Leu"

(xi) SEQUENCE DESCRIPTION: SEQ ID NO:2:

Ala Pro Met Thr Gln Thr Thr Ser Leu Lys Thr Ser Trp Val Asn Cys
1               5                   10                  15

Xaa Xaa Xaa Ile Xaa Glu Xaa Xaa Xaa Xaa Leu Lys Xaa Xaa Xaa Xaa
                20                  25                  30

Xaa Xaa Xaa Asp Xaa Xaa Asn Leu Asn Xaa Glu Xaa Xaa Xaa Ile Leu
            35                  40                  45

Met Xaa Xaa Asn Leu Xaa Xaa Xaa Asn Leu Glu Xaa Phe Xaa Xaa Xaa
    50                  55                  60

Xaa Xaa Xaa Xaa Xaa Asn Xaa Xaa Xaa Ile Glu Xaa Xaa Leu Xaa Xaa
65                  70                  75                  80

Leu Xaa Xaa Cys Xaa Pro Xaa Xaa Thr Ala Xaa Pro Xaa Arg Xaa Xaa
                85                  90                  95

Xaa Xaa Xaa Xaa Xaa Gly Asp Xaa Xaa Xaa Phe Xaa Xaa Lys Leu Xaa
                100                 105                 110

Phe Xaa Xaa Xaa Xaa Leu Glu Xaa Xaa Xaa Xaa Gln Gln Thr Thr Leu
    115                 120                 125

Ser Leu Ala Ile Phe
    130

(2) INFORMATION FOR SEQ ID NO:3:

```
    (i) SEQUENCE CHARACTERISTICS:
        (A) LENGTH: 133 amino acids
        (B) TYPE: amino acid
        (D) TOPOLOGY: linear (ii) MOLECULE TYPE: peptide (ix) FEATURE:
        (A) NAME/KEY: Modified-site
        (B) LOCATION: 1
        (D) OTHER INFORMATION: /note= "Met- may or may not precede
            the amino acid in position 1"

(ix) FEATURE:
        (A) NAME/KEY: Modified-site
        (B) LOCATION: 17
        (D) OTHER INFORMATION: /note= "Xaa at position 17 is Ser,
            Gly, Asp, or Gln"

(ix) FEATURE:
        (A) NAME/KEY: Modified-site
        (B) LOCATION: 18
        (D) OTHER INFORMATION: /note= "Xaa at position 18 is Asn,
            His, or Ile"

(ix) FEATURE:
        (A) NAME/KEY: Modified-site
        (B) LOCATION: 23
        (D) OTHER INFORMATION: /note= "Xaa at position 23 is Ile,
            Ala, Leu, or Gly"

(ix) FEATURE:
        (A) NAME/KEY: Modified-site
        (B) LOCATION: 25
        (D) OTHER INFORMATION: /note= "Xaa at position 25 is Thr,
            His, or Gln"

(ix) FEATURE:
        (A) NAME/KEY: Modified-site
        (B) LOCATION: 26
        (D) OTHER INFORMATION: /note= "Xaa at position 26 is His
            or Ala"

(ix) FEATURE:
        (A) NAME/KEY: Modified-site
        (B) LOCATION: 29
        (D) OTHER INFORMATION: /note="Xaa at position 29 is Gln
            or Asn"

(ix) FEATURE:
        (A) NAME/KEY: Modified-site
        (B) LOCATION: 30
        (D) OTHER INFORMATION: /note= "Xaa at position 30 is Pro
            or Gly"

(ix) FEATURE:
        (A) NAME/KEY: Modified-site
        (B) LOCATION: 32
        (D) OTHER INFORMATION: /note= "Xaa at position 32 is Leu,
            Arg, Asn, or Ala"

(ix) FEATURE:
        (A) NAME/KEY: Modified-site
        (B) LOCATION: 34
        (D) OTHER INFORMATION: /note= "Xaa at position 34 is Leu,
            Val, Ser, Ala, Arg, Gln, Glu, Ile, Phe, Thr, or Met"

(ix) FEATURE:
        (A) NAME/KEY: Modified-site
        (B) LOCATION: 35
        (D) OTHER INFORMATION: /note= "Xaa at position 35 is Leu,
            Ala, Asn, or Pro"

(ix) FEATURE:
        (A) NAME/KEY: Modified-site
        (B) LOCATION: 38
        (D) OTHER INFORMATION: /note= "Xaa at position 38 is Asn
            or Ala"
```

-continued

```
(ix) FEATURE:
     (A) NAME/KEY: Modified-site
     (B) LOCATION: 42
     (D) OTHER INFORMATION: /note= "Xaa at position 42 is Gly,
         Asp, Ser, Ala, Asn, Ile, Leu, Met, Tyr, or Arg"

(ix) FEATURE:
     (A) NAME/KEY: Modified-site
     (B) LOCATION: 45
     (D) OTHER INFORMATION: /note= "Xaa at position 45 is Gln,
         Val, Met, Leu, Ala, Asn, Glu, or Lys"

(ix) FEATURE:
     (A) NAME/KEY: Modified-site
     (B) LOCATION: 46
     (D) OTHER INFORMATION: /note= "Xaa at position 46 is Asp,
         Phe, Ser, Gln, Glu, His, Val, or Thr"

(ix) FEATURE:
     (A) NAME/KEY: Modified-site
     (B) LOCATION: 50
     (D) OTHER INFORMATION: /note= "Xaa at position 50 is Glu,
         Asn, Ser, or Asp"

(ix) FEATURE:
     (A) NAME/KEY: Modified-site
     (B) LOCATION: 51
     (D) OTHER INFORMATION: /note= "Xaa at position 51 is Asn,
         Arg, Pro, Thr, or His"

(ix) FEATURE:
     (A) NAME/KEY: Modified-site
     (B) LOCATION: 55
     (D) OTHER INFORMATION: /note= "Xaa at position 55 is Arg,
         Leu, or Gly"

(ix) FEATURE:
     (A) NAME/KEY: Modified-site
     (B) LOCATION: 56
     (D) OTHER INFORMATION: /note= "Xaa at position 56 is Pro,
         Gly, Ser, Ala, Asn, Val, Leu, or Gln"

(ix) FEATURE:
     (A) NAME/KEY: Modified-site
     (B) LOCATION: 62
     (D) OTHER INFORMATION: /note= "Xaa at position 62 is Asn,
         Pro, or Thr"

(ix) FEATURE:
     (A) NAME/KEY: Modified-site
     (B) LOCATION: 64
     (D) OTHER INFORMATION: /note= "Xaa at position 64 is Ala
         or Asn"

(ix) FEATURE:
     (A) NAME/KEY: Modified-site
     (B) LOCATION: 65
     (D) OTHER INFORMATION: /note= "Xaa at position 65 is Val
         or Thr"

(ix) FEATURE:
     (A) NAME/KEY: Modified-site
     (B) LOCATION: 67
     (D) OTHER INFORMATION: /note= "Xaa at position 67 is Ser
         or Phe"

(ix) FEATURE:
     (A) NAME/KEY: Modified-site
     (B) LOCATION: 68
     (D) OTHER INFORMATION: /note= "Xaa at position 68 is Leu
         or Phe"

(ix) FEATURE:
     (A) NAME/KEY: Modified-site
     (B) LOCATION: 69
     (D) OTHER INFORMATION: /note= "Xaa at position 69 is Gln,
         Ala, Glu, or Arg"

(ix) FEATURE:
```

```
        (A) NAME/KEY: Modified-site
        (B) LOCATION: 76
        (D) OTHER INFORMATION: /note= "Xaa at position 76 is Ser,
            Val, Asn, Pro, or Gly"

(ix) FEATURE:
        (A) NAME/KEY: Modified-site
        (B) LOCATION: 77
        (D) OTHER INFORMATION: /note= "Xaa at position 77 is Ile
            or Leu"

(ix) FEATURE:
        (A) NAME/KEY: Modified-site
        (B) LOCATION: 79
        (D) OTHER INFORMATION: /note= "Xaa at position 79 is Lys,
            Asn, Met, Arg, Ile, or Gly"

(ix) FEATURE:
        (A) NAME/KEY: Modified-site
        (B) LOCATION: 80
        (D) OTHER INFORMATION: /note= "Xaa at position 80 is Asn,
            Gly, Glu, or Arg"

(ix) FEATURE:
        (A) NAME/KEY: Modified-site
        (B) LOCATION: 82
        (D) OTHER INFORMATION: /note= "Xaa at position 82 is Leu,
            Gln, Trp, Arg, Asp, Asn, Glu, His, Met, Phe, Ser,
            Thr, Tyr, or Val"

(ix) FEATURE:
        (A) NAME/KEY: Modified-site
        (B) LOCATION: 87
        (D) OTHER INFORMATION: /note= "Xaa at position 87 is Leu
            or Ser"

(ix) FEATURE:
        (A) NAME/KEY: Modified-site
        (B) LOCATION: 88
        (D) OTHER INFORMATION: /note= "Xaa at position 88 is Ala
            or Trp"

(ix) FEATURE:
        (A) NAME/KEY: Modified-site
        (B) LOCATION: 91
        (D) OTHER INFORMATION: /note= "Xaa at position 91 is Ala
            or Pro"

(ix) FEATURE:
        (A) NAME/KEY: Modified-site
        (B) LOCATION: 93
        (D) OTHER INFORMATION: /note= "Xaa at position 93 is Thr,
            Asp, or Ala"

(ix) FEATURE:
        (A) NAME/KEY: Modified-site
        (B) LOCATION: 95
        (D) OTHER INFORMATION: /note= "Xaa at position 95 is His,
            Pro, Arg, Val, Gly, Asn, Ser, or Thr"

(ix) FEATURE:
        (A) NAME/KEY: Modified-site
        (B) LOCATION: 98
        (D) OTHER INFORMATION: /note= "Xaa at position 98 is His,
            Ile, Asn, Ala, Thr, Gln, Glu, Lys, Met, Ser, Tyr,
            Val, or Leu"

(ix) FEATURE:
        (A) NAME/KEY: Modified-site
        (B) LOCATION: 99
        (D) OTHER INFORMATION: /note= "Xaa at position 99 is Ile
            or Leu"

(ix) FEATURE:
        (A) NAME/KEY: Modified-site
        (B) LOCATION: 100
        (D) OTHER INFORMATION: /note= "Xaa at position 100 is Lys
            or Arg"
```

(ix) FEATURE:
            (A) NAME/KEY: Modified-site
            (B) LOCATION: 101
            (D) OTHER INFORMATION: /note= "Xaa at position 101 is Asp,
                Pro, Met, Lys, Thr, His, Asn, Ile, Leu, or Tyr"

(ix) FEATURE:
            (A) NAME/KEY: Modified-site
            (B) LOCATION: 105
            (D) OTHER INFORMATION: /note= "Xaa at position 105 is Asn,
                Pro, Ser, Ile, or Asp"

(ix) FEATURE:
            (A) NAME/KEY: Modified-site
            (B) LOCATION: 108
            (D) OTHER INFORMATION: /note= "Xaa at position 108 is Arg, Ala,
                or Ser"

(ix) FEATURE:
            (A) NAME/KEY: Modified-site
            (B) LOCATION: 109
            (D) OTHER INFORMATION: /note= "Xaa at position 109 is Arg,
                Thr, Glu, Leu, or Ser"

(ix) FEATURE:
            (A) NAME/KEY: Modified-site
            (B) LOCATION: 112
            (D) OTHER INFORMATION: /note= "Xaa at position 112 is Thr
                or Gln"

(ix) FEATURE:
            (A) NAME/KEY: Modified-site
            (B) LOCATION: 116
            (D) OTHER INFORMATION: /note= "Xaa at position 116 is Lys,
                Val, Trp, Ala, His, Phe, Tyr, or Ile"

(ix) FEATURE:
            (A) NAME/KEY: Modified-site
            (B) LOCATION: 117
            (D) OTHER INFORMATION: /note= "Xaa at position 117 is Thr
                or Ser"

(ix) FEATURE:
            (A) NAME/KEY: Modified-site
            (B) LOCATION: 120
            (D) OTHER INFORMATION: /note= "Xaa at position 120 is Asn,
                Pro, Leu, His, Val, or Gln"

(ix) FEATURE:
            (A) NAME/KEY: Modified-site
            (B) LOCATION: 121
            (D) OTHER INFORMATION: /note= "Xaa at position 121 is Ala,
                Ser, Ile, Pro, or Asp"

(ix) FEATURE:
            (A) NAME/KEY: Modified-site
            (B) LOCATION: 122
            (D) OTHER INFORMATION: /note= "Xaa at position 122 is Gln,
                Met, Trp, Phe, Pro, His, Ile, or Tyr"

(ix) FEATURE:
            (A) NAME/KEY: Modified-site
            (B) LOCATION: 123
            (D) OTHER INFORMATION: /note= "Xaa at position 123 is Ala,
                Met, Glu, Ser, or Leu"

(xi) SEQUENCE DESCRIPTION: SEQ ID NO:3:

Ala Pro Met Thr Gln Thr Thr Ser Leu Lys Thr Ser Trp Val Asn Cys
1               5                   10                  15

Xaa Xaa Met Ile Asp Glu Xaa Ile Xaa Xaa Leu Lys Xaa Xaa Pro Xaa
            20                  25                  30

Pro Xaa Xaa Asp Phe Xaa Asn Leu Asn Xaa Glu Asp Xaa Xaa Ile Leu
        35                  40                  45

Met Xaa Xaa Asn Leu Arg Xaa Xaa Asn Leu Glu Ala Phe Xaa Arg Xaa
    50                  55                  60

```
Xaa Lys Xaa Xaa Xaa Asn Ala Ser Ala Ile Glu Xaa Xaa Leu Xaa Xaa
 65                  70                  75                  80

Leu Xaa Pro Cys Leu Pro Xaa Xaa Thr Ala Xaa Pro Xaa Arg Xaa Pro
             85                  90                  95

Ile Xaa Xaa Xaa Xaa Gly Asp Trp Xaa Glu Phe Xaa Xaa Lys Leu Xaa
             100                 105                 110

Phe Tyr Leu Xaa Xaa Leu Glu Xaa Xaa Xaa Xaa Gln Gln Thr Thr Leu
             115                 120                 125

Ser Leu Ala Ile Phe
    130
```

(2) INFORMATION FOR SEQ ID NO:4:

(i) SEQUENCE CHARACTERISTICS:
        (A) LENGTH: 111 amino acids
        (B) TYPE: amino acid
        (D) TOPOLOGY: linear (ii) MOLECULE TYPE: peptide (ix) FEATURE:
        (A) NAME/KEY: Modified-site
        (B) LOCATION: 1
        (D) OTHER INFORMATION: /note= "Met- or Met-Ala- may or may
            not precede the amino acid in position 1"

(ix) FEATURE:
        (A) NAME/KEY: Modified-site
        (B) LOCATION: 3
        (D) OTHER INFORMATION: /note= "Xaa at position 3 is Ser,
            Lys, Gly, Asp, Met, Gln, or Arg"

(ix) FEATURE:
        (A) NAME/KEY: Modified-site
        (B) LOCATION: 4
        (D) OTHER INFORMATION: /note= "Xaa at position 4 is Asn,
            His, Leu, Ile, Phe, Arg, or Gln"

(ix) FEATURE:
        (A) NAME/KEY: Modified-site
        (B) LOCATION: 5
        (D) OTHER INFORMATION: /note= "Xaa at position 5 is Met,
            Phe, Ile, Arg, Gly, Ala, or Cys"

(ix) FEATURE:
        (A) NAME/KEY: Modified-site
        (B) LOCATION: 6
        (D) OTHER INFORMATION: /note= "Xaa at position 6 is Ile,
            Cys, Gln, Glu, Arg, Pro, or Ala"

(ix) FEATURE:
        (A) NAME/KEY: Modified-site
        (B) LOCATION: 7
        (D) OTHER INFORMATION: /note= "Xaa at position 7 is Asp,
            Phe, Lys, Arg, Ala, Gly, Glu, Gln, Asn, Thr, Ser,
            or Val"

(ix) FEATURE:
        (A) NAME/KEY: Modified-site
        (B) LOCATION: 8
        (D) OTHER INFORMATION: /note= "Xaa at position 8 is Glu,
            Trp, Pro, Ser, Ala, His, Asp, Asn, Gln, Leu, Val,
            or Gly"

(ix) FEATURE:
        (A) NAME/KEY: Modified-site
        (B) LOCATION: 9
        (D) OTHER INFORMATION: /note= "Xaa at position 9 is
            Ile, Val, Ala, Leu, Gly, Trp, Lys, Phe, Leu, Ser
            or Arg"

(ix) FEATURE:
        (A) NAME/KEY: Modified-site

```
        (B) LOCATION: 10
        (D) OTHER INFORMATION: /note= "Xaa at position 10 is Ile,
            Gly, Val, Arg, Ser, Phe, or Leu"

(ix) FEATURE:
        (A) NAME/KEY: Modified-site
        (B) LOCATION: 11
        (D) OTHER INFORMATION: /note= "Xaa at position 11 is Thr,
            His, Gly, Gln, Arg, Pro, or Ala"

(ix) FEATURE:
        (A) NAME/KEY: Modified-site
        (B) LOCATION: 12
        (D) OTHER INFORMATION: /note= "Xaa at position 12 is His,
            Thr, Phe, Gly, Arg, Ala, or Trp"

(ix) FEATURE:
        (A) NAME/KEY: Modified-site
        (B) LOCATION: 13
        (D) OTHER INFORMATION: /note= "Xaa at position 13 is Leu,
            Gly, Arg, Thr, Ser, or Ala"

(ix) FEATURE:
        (A) NAME/KEY: Modified-site
        (B) LOCATION: 14
        (D) OTHER INFORMATION: /note= "Xaa at position 14 is Lys,
            Arg, Leu, Gln, Gly, Pro, Val, or Trp"

(ix) FEATURE:
        (A) NAME/KEY: Modified-site
        (B) LOCATION: 15
        (D) OTHER INFORMATION: /note= "Xaa at position 15 is Gln,
            Asn, Leu, Pro, Arg, or Val"

(ix) FEATURE:
        (A) NAME/KEY: Modified-site
        (B) LOCATION: 16
        (D) OTHER INFORMATION: /note= "Xaa at position 16 is Pro,
            His, Thr, Gly, Asp, Gln, Ser, Leu, or Lys"

(ix) FEATURE:
        (A) NAME/KEY: Modified-site
        (B) LOCATION: 17
        (D) OTHER INFORMATION: /note= "Xaa at position 17 is Pro,
            Asp, Gly, Ala, Arg, Leu, or Gln"

(ix) FEATURE:
        (A) NAME/KEY: Modified-site
        (B) LOCATION: 18
        (D) OTHER INFORMATION: /note= "Xaa at position 18 is Leu,
            Val, Arg, Gln, Asn, Gly, Ala, or Glu"

(ix) FEATURE:
        (A) NAME/KEY: Modified-site
        (B) LOCATION: 19
        (D) OTHER INFORMATION: /note= "Xaa at position 19 is Pro,
            Leu, Gln, Ala, Thr, or Glu"

(ix) FEATURE:
        (A) NAME/KEY: Modified-site
        (B) LOCATION: 20
        (D) OTHER INFORMATION: /note= "Xaa at position 20 is Leu,
            Val, Gly, Ser, Lys, Glu, Gln, Thr, Arg, Ala, Phe,
            Ile, or Met"

(ix) FEATURE:
        (A) NAME/KEY: Modified-site
        (B) LOCATION: 21
        (D) OTHER INFORMATION: /note= "Xaa at position 21 is Leu,
            Ala, Gly, Asn, Pro, Gln, or Val"

(ix) FEATURE:
        (A) NAME/KEY: Modified-site
        (B) LOCATION: 22
        (D) OTHER INFORMATION: /note= "Xaa at position 22 is Asp,
            Leu, or Val"

(ix) FEATURE:
        (A) NAME/KEY: Modified-site
```

```
        (B) LOCATION: 23
        (D) OTHER INFORMATION: /note= "Xaa at position 23 is Phe,
            Ser, Pro, Trp, or Ile"

(ix) FEATURE:
        (A) NAME/KEY: Modified-site
        (B) LOCATION: 24
        (D) OTHER INFORMATION: /note= "Xaa at position 24 is Asn
            or Ala"

(ix) FEATURE:
        (A) NAME/KEY: Modified-site
        (B) LOCATION: 26
        (D) OTHER INFORMATION: /note= "Xaa at position 26 is Leu,
            Trp, or Arg"

(ix) FEATURE:
        (A) NAME/KEY: Modified-site
        (B) LOCATION: 27
        (D) OTHER INFORMATION: /note= "Xaa at position 27 is Asn,
            Cys, Arg, Leu, His, Met, or Pro"

(ix) FEATURE:
        (A) NAME/KEY: Modified-site
        (B) LOCATION: 28
        (D) OTHER INFORMATION: /note= "Xaa at position 28 is Gly,
            Asp, Ser, Cys, Ala, Lys, Asn, Thr, Leu, Val, Glu,
            Phe, Tyr, Ile, or Met"

(ix) FEATURE:
        (A) NAME/KEY: Modified-site
        (B) LOCATION: 29
        (D) OTHER INFORMATION: /note= "Xaa at position 29 is Glu,
            Asn, Tyr, Leu, Phe, Asp, Ala, Cys, Gln, Arg, Thr,
            Gly, or Ser"

(ix) FEATURE:
        (A) NAME/KEY: Modified-site
        (B) LOCATION: 30
        (D) OTHER INFORMATION: /note= "Xaa at position 30 is Asp,
            Ser, Leu, Arg, Lys, Thr, Met, Trp, Glu, Asn, Gln,
            Ala, or Pro"

(ix) FEATURE:
        (A) NAME/KEY: Modified-site
        (B) LOCATION: 31
        (D) OTHER INFORMATION: /note= "Xaa at position 31 is Gln,
            Pro, Phe, Val, Met, Leu, Thr, Lys, Asp, Asn, Arg,
            Ser, Ala, Ile, Glu, His, or Trp"

(ix) FEATURE:
        (A) NAME/KEY: Modified-site
        (B) LOCATION: 32
        (D) OTHER INFORMATION: /note= "Xaa at position 32 is Asp,
            Phe, Ser, Thr, Cys, Glu, Asn, Gln, Lys, His, Ala,
            Tyr, Ile, Val, or Gly"

(ix) FEATURE:
        (A) NAME/KEY: Modified-site
        (B) LOCATION: 33
        (D) OTHER INFORMATION: /note= "Xaa at position 33 is Ile,
            Gly, Val, Ser, Arg, Pro, or His"

(ix) FEATURE:
        (A) NAME/KEY: Modified-site
        (B) LOCATION: 34
        (D) OTHER INFORMATION: /note= "Xaa at position 34 is Leu,
            Ser, Cys, Arg, Ile, His, Phe, Glu, Lys, Thr, Ala,
            Met, Val, or Asn"

(ix) FEATURE:
        (A) NAME/KEY: Modified-site
        (B) LOCATION: 35
        (D) OTHER INFORMATION: /note= "Xaa at position 35 is Met,
            Arg, Ala, Gly, Pro, Asn, His, or Asp"

(ix) FEATURE:
        (A) NAME/KEY: Modified-site
        (B) LOCATION: 36
```

```
        (D) OTHER INFORMATION: /note= "Xaa at position 36 is Glu,
            Leu, Thr, Asp, Tyr, Lys, Asn, Ser, Ala, Ile, Val,
            His, Phe, Met, or Gln"

(ix) FEATURE:
        (A) NAME/KEY: Modified-site
        (B) LOCATION: 37
        (D) OTHER INFORMATION: /note= "Xaa at position 37 is Asn,
            Arg, Met, Pro, Ser, Thr, or His"

(ix) FEATURE:
        (A) NAME/KEY: Modified-site
        (B) LOCATION: 38
        (D) OTHER INFORMATION: /note= "Xaa at position 38 is Asn,
            His, Arg, Leu, Gly, Ser, or Thr"

(ix) FEATURE:
        (A) NAME/KEY: Modified-site
        (B) LOCATION: 39
        (D) OTHER INFORMATION: /note= "Xaa at position 39 is
            Leu, Thr, Ala, Gly, Glu, Pro, Lys, Ser, or Met"

(ix) FEATURE:
        (A) NAME/KEY: Modified-site
        (B) LOCATION: 40
        (D) OTHER INFORMATION: /note= "Xaa at position 40 is Arg,
            Asp, Ile, Ser, Val, Thr, Gln, Asn, Lys, His,
            Ala, or Leu"

(ix) FEATURE:
        (A) NAME/KEY: Modified-site
        (B) LOCATION: 41
        (D) OTHER INFORMATION: /note= "Xaa at position 41 is Arg,
            Thr, Val, Ser, Leu, or Gly"

(ix) FEATURE:
        (A) NAME/KEY: Modified-site
        (B) LOCATION: 42
        (D) OTHER INFORMATION: /note= "Xaa at position 42 is Pro,
            Gly, Cys, Ser, Gln, Glu, Arg, His, Thr, Ala, Tyr,
            Phe, Leu, Val, or Lys"

(ix) FEATURE:
        (A) NAME/KEY: Modified-site
        (B) LOCATION: 43
        (D) OTHER INFORMATION: /note= "Xaa at position 43 is Asn
            or Gly"

(ix) FEATURE:
        (A) NAME/KEY: Modified-site
        (B) LOCATION: 44
        (D) OTHER INFORMATION: /note= "Xaa at position 44 is Leu,
            Ser, Asp, Arg, Gln, Val, or Cys"

(ix) FEATURE:
        (A) NAME/KEY: Modified-site
        (B) LOCATION: 45
        (D) OTHER INFORMATION: /note= "Xaa at position 45 is Glu,
            Tyr, His, Leu, Pro, or Arg"

(ix) FEATURE:
        (A) NAME/KEY: Modified-site
        (B) LOCATION: 46
        (D) OTHER INFORMATION: /note= "Xaa at position 46 is Ala,
            Ser, Pro, Tyr, Asn, or Thr"

(ix) FEATURE:
        (A) NAME/KEY: Modified-site
        (B) LOCATION: 47
        (D) OTHER INFORMATION: /note= "Xaa at position 47 is Phe,
            Asn, Glu, Pro, Lys, Arg, or Ser"

(ix) FEATURE:
        (A) NAME/KEY: Modified-site
        (B) LOCATION: 48
        (D) OTHER INFORMATION: /note= "Xaa at position 48 is Asn,
            His, Val, Arg, Pro, Thr, Asp, or Ile"

(ix) FEATURE:
```

-continued (A) NAME/KEY: Modified-site
        (B) LOCATION: 49
        (D) OTHER INFORMATION: /note= "Xaa at position 49 is Arg,
            Tyr, Trp, Lys, Ser, His, Pro, or Val"

(ix) FEATURE:
        (A) NAME/KEY: Modified-site
        (B) LOCATION: 50
        (D) OTHER INFORMATION: /note= "Xaa at position 50 is Ala,
            Asn, Pro, Ser, or Lys"

(ix) FEATURE:
        (A) NAME/KEY: Modified-site
        (B) LOCATION: 51
        (D) OTHER INFORMATION: /note= "Xaa at position 51 is Val,
            Thr, Pro, His, Leu, Phe, or Ser"

(ix) FEATURE:
        (A) NAME/KEY: Modified-site
        (B) LOCATION: 52
        (D) OTHER INFORMATION: /note= "Xaa at position 52 is Lys,
            Ile, Arg, Val, Asn, Glu, or Ser"

(ix) FEATURE:
        (A) NAME/KEY: Modified-site
        (B) LOCATION: 53
        (D) OTHER INFORMATION: /note= "Xaa at position 53 is Ser,
            Ala, Phe, Val, Gly, Asn, Ile, Pro, or His"

(ix) FEATURE:
        (A) NAME/KEY: Modified-site
        (B) LOCATION: 54
        (D) OTHER INFORMATION: /note= "Xaa at position 54 is Leu,
            Val, Trp, Ser, Ile, Phe, Thr, or His"

(ix) FEATURE:
        (A) NAME/KEY: Modified-site
        (B) LOCATION: 55
        (D) OTHER INFORMATION: /note= "Xaa at position 55 is Gln,
            Ala, Pro, Thr, Glu, Arg, Trp, Gly, or Leu"

(ix) FEATURE:
        (A) NAME/KEY: Modified-site
        (B) LOCATION: 56
        (D) OTHER INFORMATION: /note= "Xaa at position 56 is Asn,
            Leu, Val, Trp, Pro, or Ala"

(ix) FEATURE:
        (A) NAME/KEY: Modified-site
        (B) LOCATION: 57
        (D) OTHER INFORMATION: /note= "Xaa at position 57 is Ala,
            Met, Leu, Pro, Arg, Glu, Thr, Gln, Trp, or Asn"

(ix) FEATURE:
        (A) NAME/KEY: Modified-site
        (B) LOCATION: 58
        (D) OTHER INFORMATION: /note= "Xaa at position 58 is Ser,
            Glu, Met, Ala, His, Asn, Arg, or Asp"

(ix) FEATURE:
        (A) NAME/KEY: Modified-site
        (B) LOCATION: 59
        (D) OTHER INFORMATION: /note= "Xaa at position 59 is Ala,
            Glu, Asp, Leu, Ser, Gly, Thr, or Arg"

(ix) FEATURE:
        (A) NAME/KEY: Modified-site
        (B) LOCATION: 60
        (D) OTHER INFORMATION: /note= "Xaa at position 60 is Ile,
            Met, Thr, Pro, Arg, Gly, Ala"

(ix) FEATURE:
        (A) NAME/KEY: Modified-site
        (B) LOCATION: 61
        (D) OTHER INFORMATION: /note= "Xaa at position 61 is
            Glu, Lys, Gly, Asp, Pro, Trp, Arg, Ser, Gln,
            or Leu"

(ix) FEATURE:

```
        (A) NAME/KEY: Modified-site
        (B) LOCATION: 62
        (D) OTHER INFORMATION: /note= "Xaa at position 62 is Ser,
            Val, Ala, Asn, Trp, Glu, Pro, Gly, or Asp"

(ix) FEATURE:
        (A) NAME/KEY: Modified-site
        (B) LOCATION: 63
        (D) OTHER INFORMATION: /note= "Xaa at position 63 is Ile,
            Ser, Arg, Thr, or Leu"

(ix) FEATURE:
        (A) NAME/KEY: Modified-site
        (B) LOCATION: 64
        (D) OTHER INFORMATION: /note= "Xaa at position 64 is Leu,
            Ala, Ser, Glu, Phe, Gly, or Arg"

(ix) FEATURE:
        (A) NAME/KEY: Modified-site
        (B) LOCATION: 65
        (D) OTHER INFORMATION: /note= "Xaa at position 65 is Lys,
            Thr, Gly, Asn, Met, Arg, Ile, or Asp"

(ix) FEATURE:
        (A) NAME/KEY: Modified-site
        (B) LOCATION: 66
        (D) OTHER INFORMATION: /note= "Xaa at position 66 is Asn,
            Trp, Val, Gly, Thr, Leu, Glu, or Arg"

(ix) FEATURE:
        (A) NAME/KEY: Modified-site
        (B) LOCATION: 67
        (D) OTHER INFORMATION: /note= "Xaa at position 67 is Leu,
            Gln, Gly, Ala, Trp, Arg, Val, or Lys"

(ix) FEATURE:
        (A) NAME/KEY: Modified-site
        (B) LOCATION: 68
        (D) OTHER INFORMATION: /note= "Xaa at position 68 is Leu,
            Gln, Lys, Trp, Arg, Asp, Glu, Asn, His, Thr, Ser, Ala,
            Tyr, Phe, Ile, Met, or Val"

(ix) FEATURE:
        (A) NAME/KEY: Modified-site
        (B) LOCATION: 69
        (D) OTHER INFORMATION: /note= "Xaa at position 69 is Pro,
            Ala, Thr, Trp, Arg, or Met"

(ix) FEATURE:
        (A) NAME/KEY: Modified-site
        (B) LOCATION: 70
        (D) OTHER INFORMATION: /note= "Xaa at position 70 is Cys,
            Glu, Gly, Arg, Met, or Val"

(ix) FEATURE:
        (A) NAME/KEY: Modified-site
        (B) LOCATION: 71
        (D) OTHER INFORMATION: /note= "Xaa at position 71 is Leu,
            Asn, Val, or Gln"

(ix) FEATURE:
        (A) NAME/KEY: Modified-site
        (B) LOCATION: 72
        (D) OTHER INFORMATION: /note= "Xaa at position 72 is Pro,
            Cys, Arg, Ala, or Lys"

(ix) FEATURE:
        (A) NAME/KEY: Modified-site
        (B) LOCATION: 73
        (D) OTHER INFORMATION: /note= "Xaa at position 73 is Leu,
            Ser, Trp, or Gly"

(ix) FEATURE:
        (A) NAME/KEY: Modified-site
        (B) LOCATION: 74
        (D) OTHER INFORMATION: /note= "Xaa at position 74 is Ala,
            Lys, Arg, Val, or Trp"

(ix) FEATURE:
```

```
         (A) NAME/KEY: Modified-site
         (B) LOCATION: 75
         (D) OTHER INFORMATION: /note= "Xaa at position 75 is Thr,
             Asp, Cys, Leu, Val, Glu, His, Asn, or Ser"

(ix) FEATURE:
         (A) NAME/KEY: Modified-site
         (B) LOCATION: 76
         (D) OTHER INFORMATION: /note= "Xaa at position 76 is Ala,
             Pro, Ser, Thr, Gly, Asp, Ile, or Met"

(ix) FEATURE:
         (A) NAME/KEY: Modified-site
         (B) LOCATION: 77
         (D) OTHER INFORMATION: /note= "Xaa at position 77 is Ala,
             Pro, Ser, Thr, Phe, Leu, Asp, or His"

(ix) FEATURE:
         (A) NAME/KEY: Modified-site
         (B) LOCATION: 78
         (D) OTHER INFORMATION: /note= "Xaa at position 78 is Pro,
             Phe, Arg, Ser, Lys, His, Ala, Gly, Ile, or Leu"

(ix) FEATURE:
         (A) NAME/KEY: Modified-site
         (B) LOCATION: 79
         (D) OTHER INFORMATION: /note= "Xaa at position 79 is Thr,
             Asp, Ser, Asn, Pro, Ala, Leu, or Arg"

(ix) FEATURE:
         (A) NAME/KEY: Modified-site
         (B) LOCATION: 80
         (D) OTHER INFORMATION: /note= "Xaa at position 80 is Arg,
             Ile, Ser, Glu, Leu, Val, Gln, Lys, His, Ala, or Pro"

(ix) FEATURE:
         (A) NAME/KEY: Modified-site
         (B) LOCATION: 81
         (D) OTHER INFORMATION: /note= "Xaa at position 81 is His,
             Gln, Pro, Arg, Val, Leu, Gly, Thr, Asn, Lys, Ser,
             Ala, Trp, Phe, Ile, or Tyr"

(ix) FEATURE:
         (A) NAME/KEY: Modified-site
         (B) LOCATION: 82
         (D) OTHER INFORMATION: /note= "Xaa at position 82 is Pro,
             Lys, Tyr, Gly, Ile, or Thr"

(ix) FEATURE:
         (A) NAME/KEY: Modified-site
         (B) LOCATION: 83
         (D) OTHER INFORMATION: /note= "Xaa at position 83 is Ile,
             Val, Lys, Ala, or Asn"

(ix) FEATURE:
         (A) NAME/KEY: Modified-site
         (B) LOCATION: 84
         (D) OTHER INFORMATION: /note= "Xaa at position 84 is His,
             Ile, Asn, Leu, Asp, Ala, Thr, Glu, Gln, Ser,
             Phe, Met, Val, Lys, Arg, Tyr, or Pro"

(ix) FEATURE:
         (A) NAME/KEY: Modified-site
         (B) LOCATION: 85
         (D) OTHER INFORMATION: /note= "Xaa at position 85 is
             Ile, Leu, Arg, Asp, Val, Pro, Gln, Gly, Ser,
             Phe, or His"

(ix) FEATURE:
         (A) NAME/KEY: Modified-site
         (B) LOCATION: 86
         (D) OTHER INFORMATION: /note= "Xaa at position 86 is
             Lys, Tyr, Leu, His, Arg, Ile, Ser, Gln, or Pro"

(ix) FEATURE:
         (A) NAME/KEY: Modified-site
         (B) LOCATION: 87
         (D) OTHER INFORMATION: /note= "Xaa at position 87 is
             Asp, Pro, Met, Lys, His, Thr, Val, Tyr, Glu, Asn,
```

Ser, Ala, Gly, Ile, Leu, or Gln"
  (ix) FEATURE:
       (A) NAME/KEY: Modified-site
       (B) LOCATION: 88
       (D) OTHER INFORMATION: /note= "Xaa at position 88 Gly,
            Leu, Glu, Lys, Ser, Tyr, or Pro"

(ix) FEATURE:
       (A) NAME/KEY: Modified-site
       (B) LOCATION: 89
       (D) OTHER INFORMATION: /note= "Xaa at position 89 is Asp
            or Ser"

(ix) FEATURE:
       (A) NAME/KEY: Modified-site
       (B) LOCATION: 90
       (D) OTHER INFORMATION: /note= "Xaa at position 90 is
            Trp, Val, Cys, Tyr, Thr, Met, Pro, Leu, Gln, Lys,
            Ala, Phe, or Gly"

(ix) FEATURE:
       (A) NAME/KEY: Modified-site
       (B) LOCATION: 91
       (D) OTHER INFORMATION: /note= "Xaa at position 91 is
            Asn, Pro, Ala, Phe, Ser, Trp, Gln, Tyr, Leu, Lys,
            Ile, Asp, or His"

(ix) FEATURE:
       (A) NAME/KEY: Modified-site
       (B) LOCATION: 92
       (D) OTHER INFORMATION: /note= "Xaa at position 92 is Glu,
            Ser, Ala, Lys, Thr, Ile, Gly, or Pro"

(ix) FEATURE:
       (A) NAME/KEY: Modified-site
       (B) LOCATION: 94
       (D) OTHER INFORMATION: /note= "Xaa at position 94 is Arg,
            Lys, Asp, Leu, Thr, Ile, Gln, His, Ser, Ala, or Pro"

(ix) FEATURE:
       (A) NAME/KEY: Modified-site
       (B) LOCATION: 95
       (D) OTHER INFORMATION: /note= "Xaa at position 95 is Arg,
            Thr, Pro, Glu, Tyr, Leu, Ser, or Gly"

(ix) FEATURE:
       (A) NAME/KEY: Modified-site
       (B) LOCATION: 96
       (D) OTHER INFORMATION: /note= "Xaa at position 96 is Lys,
            Asn, Thr, Leu, Gln, Arg, His, Glu, Ser, Ala,
            or Trp"

(ix) FEATURE:
       (A) NAME/KEY: Modified-site
       (B) LOCATION: 97
       (D) OTHER INFORMATION: /note= "Xaa at position 97 is Leu,
            Ile, Arg, Asp, or Met"

(ix) FEATURE:
       (A) NAME/KEY: Modified-site
       (B) LOCATION: 98
       (D) OTHER INFORMATION: /note= "Xaa at position 98 is Thr,
            Val, Gln, Tyr, Glu, His, Ser, or Phe"

(ix) FEATURE:
       (A) NAME/KEY: Modified-site
       (B) LOCATION: 99
       (D) OTHER INFORMATION: /note= "Xaa at position 99 is Phe,
            Ser, Cys, His, Gly, Trp, Tyr, Asp, Lys, Leu, Ile,
            Val, or Asn"

(ix) FEATURE:
       (A) NAME/KEY: Modified-site
       (B) LOCATION: 100
       (D) OTHER INFORMATION: /note= "Xaa at position 100 is Tyr,
            Cys, His, Ser, Trp, Arg, or Leu"

(ix) FEATURE:

```
            (A) NAME/KEY: Modified-site
            (B) LOCATION: 101
            (D) OTHER INFORMATION: /note= "Xaa at position 101 is Leu,
                Asn, Val, Pro, Arg, Ala, His, Thr, Trp, or Met"

(ix) FEATURE:
            (A) NAME/KEY: Modified-site
            (B) LOCATION: 102
            (D) OTHER INFORMATION: /note= "Xaa at position 102 is
                Lys, Leu, Pro, Thr, Met, Asp, Val, Glu, Arg, Trp,
                Ser, Asn, His, Ala, Tyr, Phe, Gln, or Ile"

(ix) FEATURE:
            (A) NAME/KEY: Modified-site
            (B) LOCATION: 103
            (D) OTHER INFORMATION: /note= "Xaa at position 103 is Thr,
                Ser, Asn, Ile, Trp, Lys, or Pro"

(ix) FEATURE:
            (A) NAME/KEY: Modified-site
            (B) LOCATION: 104
            (D) OTHER INFORMATION: /note= "Xaa at position 104 is Leu,
                Ser, Pro, Ala, Glu, Cys, Asp, or Tyr"

(ix) FEATURE:
            (A) NAME/KEY: Modified-site
            (B) LOCATION: 105
            (D) OTHER INFORMATION: /note= "Xaa at position 105 is Glu,
                Ser, Lys, Pro, Leu, Thr, Tyr, or Arg"

(ix) FEATURE:
            (A) NAME/KEY: Modified-site
            (B) LOCATION: 106
            (D) OTHER INFORMATION: /note= "Xaa at position 106 is Asn,
                Ala, Pro, Leu, His, Val or Gln"

(ix) FEATURE:
            (A) NAME/KEY: Modified-site
            (B) LOCATION: 107
            (D) OTHER INFORMATION: /note= "Xaa at position 107 is Ala,
                Ser, Ile, Asn, Pro, Lys, Asp, or Gly"

(ix) FEATURE:
            (A) NAME/KEY: Modified-site
            (B) LOCATION: 108
            (D) OTHER INFORMATION: /note= "Xaa at position 108 is
                Gln, Ser, Met, Trp, Arg, Phe, Pro, His, Ile, Tyr,
                or Cys"

(ix) FEATURE:
            (A) NAME/KEY: Modified-site
            (B) LOCATION: 109
            (D) OTHER INFORMATION: /note= "Xaa at position 109 is Ala,
                Met, Glu, His, Ser, Pro, Tyr, or Leu"

(xi) SEQUENCE DESCRIPTION: SEQ ID NO:4:

Asn Cys Xaa Xaa Xaa Xaa Xaa Xaa Xaa Xaa Xaa Xaa Xaa Xaa Xaa
 1               5                  10                  15

Xaa Xaa Xaa Xaa Xaa Xaa Xaa Xaa Asn Xaa Xaa Xaa Xaa Xaa Xaa
             20                  25                  30

Xaa Xaa Xaa Xaa Xaa Xaa Xaa Xaa Xaa Xaa Xaa Xaa Xaa Xaa Xaa
         35                  40                  45

Xaa Xaa Xaa Xaa Xaa Xaa Xaa Xaa Xaa Xaa Xaa Xaa Xaa Xaa Xaa
     50                  55                  60

Xaa Xaa Xaa Xaa Xaa Xaa Xaa Xaa Xaa Xaa Xaa Xaa Xaa Xaa Xaa
65                   70                  75                  80

Xaa Xaa Xaa Xaa Xaa Xaa Xaa Xaa Xaa Xaa Xaa Phe Xaa Xaa Xaa
             85                  90                  95

Xaa Xaa Xaa Xaa Xaa Xaa Xaa Xaa Xaa Xaa Xaa Xaa Xaa Gln Gln
            100                 105                 110
```

```
(2) INFORMATION FOR SEQ ID NO:5:

(i) SEQUENCE CHARACTERISTICS:
         (A) LENGTH: 111 amino acids
         (B) TYPE: amino acid
         (D) TOPOLOGY: linear (ii) MOLECULE TYPE: peptide (ix) FEATURE:
         (A) NAME/KEY: Modified-site
         (B) LOCATION: 1
         (D) OTHER INFORMATION: /note= "Met- or Met-Ala- may or may
             not precede the amino acid in position 1"

(ix) FEATURE:
         (A) NAME/KEY: Modified-site
         (B) LOCATION: 3
         (D) OTHER INFORMATION: /note= "Xaa at position 3 is Ser,
             Gly, Asp, Met, or Gln"

(ix) FEATURE:
         (A) NAME/KEY: Modified-site
         (B) LOCATION: 4
         (D) OTHER INFORMATION: /note= "Xaa at position 4 is Asn,
             His, or Ile"

(ix) FEATURE:
         (A) NAME/KEY: Modified-site
         (B) LOCATION: 5
         (D) OTHER INFORMATION: /note= "Xaa at position 5 is Met
             or Ile"

(ix) FEATURE:
         (A) NAME/KEY: Modified-site
         (B) LOCATION: 7
         (C) OTHER INFORMATION: /note= "Xaa at position 7 is Asp or Glu"

(ix) FEATURE:
         (A) NAME/KEY: Modified-site
         (B) LOCATION: 9
         (D) OTHER INFORMATION: /note= "Xaa at position 9 is Ile,
             Ala, Leu, or Gly"

(ix) FEATURE:
         (A) NAME/KEY: Modified-site
         (B) LOCATION: 10
         (D) OTHER INFORMATION: /note= "Xaa at position 10 is Ile,
             Val, or Leu"

(ix) FEATURE:
         (A) NAME/KEY: Modified-site
         (B) LOCATION: 11
         (D) OTHER INFORMATION: /note= "Xaa at position 11 is Thr,
             His, Gln, or Ala"

(ix) FEATURE:
         (A) NAME/KEY: Modified-site
         (B) LOCATION: 12
         (D) OTHER INFORMATION: /note= "Xaa at position 12 is His
             or Ala"

(ix) FEATURE:
         (A) NAME/KEY: Modified-site
         (B) LOCATION: 15
         (D) OTHER INFORMATION: /note= "Xaa at position 15 is Gln,
             Asn, or Val"

(ix) FEATURE:
         (A) NAME/KEY: Modified-site
         (B) LOCATION: 16
         (D) OTHER INFORMATION: /note= "Xaa at position 16 is Pro,
             Gly, or Gln"

(ix) FEATURE:
         (A) NAME/KEY: Modified-site
         (B) LOCATION: 17
         (D) OTHER INFORMATION: /note= "Xaa at position 17 is Pro,
             Asp, Gly, or Gln"
```

```
(ix) FEATURE:
    (A) NAME/KEY: Modified-site
    (B) LOCATION: 18
    (D) OTHER INFORMATION: /note= "Xaa at position 18 is Leu,
        Arg, Gln, Asn, Gly, Ala, or Glu"

(ix) FEATURE:
    (A) NAME/KEY: Modified-site
    (B) LOCATION: 19
    (D) OTHER INFORMATION: /note= "Xaa at position 19 is Pro
        or Glu"

(ix) FEATURE:
    (A) NAME/KEY: Modified-site
    (B) LOCATION: 20
    (D) OTHER INFORMATION: /note= "Xaa at position 20 is Leu,
        Val, Gly, Ser, Lys, Ala, Arg, Gln, Glu, Ile, Phe,
        Thr, or Met"

(ix) FEATURE:
    (A) NAME/KEY: Modified-site
    (B) LOCATION: 21
    (D) OTHER INFORMATION: /note= "Xaa at position 21 is Leu,
        Ala, Asn, Pro, Gln, or Val"

(ix) FEATURE:
    (A) NAME/KEY: Modified-site
    (B) LOCATION: 23
    (D) OTHER INFORMATION: /note= "Xaa at position 23 is Phe,
        Ser, Pro, or Trp"

(ix) FEATURE:
    (A) NAME/KEY: Modified-site
    (B) LOCATION: 24
    (D) OTHER INFORMATION: /note= "Xaa at position 24 is Asn
        or Ala"

(ix) FEATURE:
    (A) NAME/KEY: Modified-site
    (B) LOCATION: 28
    (D) OTHER INFORMATION: /note= "Xaa at position 28 is Gly,
        Asp, Ser, Cys, Ala, Asn, Ile, Leu, Met, Tyr, or Arg"

(ix) FEATURE:
    (A) NAME/KEY: Modified-site
    (B) LOCATION: 30
    (D) OTHER INFORMATION: /note= "Xaa at position 30 is Asp
        or Glu"

(ix) FEATURE:
    (A) NAME/KEY: Modified-site
    (B) LOCATION: 31
    (D) OTHER INFORMATION: /note= "Xaa at position 31 is Gln,
        Val, Met, Leu, Thr, Ala, Asn, Glu, Ser, or Lys"

(ix) FEATURE:
    (A) NAME/KEY: Modified-site
    (B) LOCATION: 32
    (D) OTHER INFORMATION: /note= "Xaa at position 32 is Asp,
        Phe, Ser, Thr, Ala, Asn, Gln, Glu, His, Ile, Lys,
        Tyr, Val, or Cys"

(ix) FEATURE:
    (A) NAME/KEY: Modified-site
    (B) LOCATION: 36
    (D) OTHER INFORMATION: /note= "Xaa at position 36 is Glu,
        Ala, Asn, Ser, or Asp"

(ix) FEATURE:
    (A) NAME/KEY: Modified-site
    (B) LOCATION: 37
    (D) OTHER INFORMATION: /note= "Xaa at position 37 is Asn,
        Arg, Met, Pro, Ser, Thr, or His"

(ix) FEATURE:
    (A) NAME/KEY: Modified-site
    (B) LOCATION: 40
    (D) OTHER INFORMATION: /note= "Xaa at position 40 is Arg
``` or Ala"

(ix) FEATURE:
    (A) NAME/KEY: Modified-site
    (B) LOCATION: 41
    (D) OTHER INFORMATION: /note= "Xaa at position 41 is Arg,
        Thr, Val, Leu, or Gly"

(ix) FEATURE:
    (A) NAME/KEY: Modified-site
    (B) LOCATION: 42
    (D) OTHER INFORMATION: /note= "Xaa at position 42 is Pro,
        Gly, Ser, Gln, Ala, Arg, Asn, Glu, Leu, Thr, Val,
        or Lys"

(ix) FEATURE:
    (A) NAME/KEY: Modified-site
    (B) LOCATION: 46
    (D) OTHER INFORMATION: /note= "Xaa at position 46 is Ala
        or Ser"

(ix) FEATURE:
    (A) NAME/KEY: Modified-site
    (B) LOCATION: 48
    (D) OTHER INFORMATION: /note= "Xaa at position 48 is Asn,
        Pro, Thr, or Ile"

(ix) FEATURE:
    (A) NAME/KEY: Modified-site
    (B) LOCATION: 49
    (D) OTHER INFORMATION: /note= "Xaa at position 49 is Arg
        or Lys"

(ix) FEATURE:
    (A) NAME/KEY: Modified-site
    (B) LOCATION: 50
    (D) OTHER INFORMATION: /note= "Xaa at position 50 is Ala
        or Asn"

(ix) FEATURE:
    (A) NAME/KEY: Modified-site
    (B) LOCATION: 51
    (D) OTHER INFORMATION: /note= "Xaa at position 51 is Val
        or Thr"

(ix) FEATURE:
    (A) NAME/KEY: Modified-site
    (B) LOCATION: 52
    (D) OTHER INFORMATION: /note= "Xaa at position 52 is Lys
        or Arg"

(ix) FEATURE:
    (A) NAME/KEY: Modified-site
    (B) LOCATION: 53
    (D) OTHER INFORMATION: /note= "Xaa at position 53 is Ser,
        Phe, or His"

(ix) FEATURE:
    (A) NAME/KEY: Modified-site
    (B) LOCATION: 54
    (D) OTHER INFORMATION: /note= "Xaa at position 54 is Leu,
        Ile, Phe, or His"

(ix) FEATURE:
    (A) NAME/KEY: Modified-site
    (B) LOCATION: 55
    (D) OTHER INFORMATION: /note= "Xaa at position 55 is Gln,
        Ala, Pro, Thr, Glu, Arg, or Gly"

(ix) FEATURE:
    (A) NAME/KEY: Modified-site
    (B) LOCATION: 57
    (D) OTHER INFORMATION: /note= "Xaa at position 57 is Ala,
        Pro, or Arg"

(ix) FEATURE:
    (A) NAME/KEY: Modified-site
    (B) LOCATION: 58
    (D) OTHER INFORMATION: /note= "Xaa at position 58 is Ser, Glu, Arg, or Asp"

(ix) FEATURE:
    (A) NAME/KEY: Modified-site
    (B) LOCATION: 59
    (D) OTHER INFORMATION: /note= "Xaa at position 59 is Ala
        or Leu"

(ix) FEATURE:
    (A) NAME/KEY: Modified-site
    (B) LOCATION: 62
    (D) OTHER INFORMATION: /note= "Xaa at position 62 is Ser,
        Val, Ala, Asn, Glu, Pro, or Gly"

(ix) FEATURE:
    (A) NAME/KEY: Modified-site
    (B) LOCATION: 63
    (D) OTHER INFORMATION: /note= "Xaa at position 63 is Ile
        or Leu"

(ix) FEATURE:
    (A) NAME/KEY: Modified-site
    (B) LOCATION: 65
    (D) OTHER INFORMATION: /note= "Xaa at position 65 is Lys,
        Thr, Gly, Asn, Met, Arg, Ile, Gly, or Asp"

(ix) FEATURE:
    (A) NAME/KEY: Modified-site
    (B) LOCATION: 66
    (D) OTHER INFORMATION: /note= "Xaa at position 66 is Asn,
        Gly, Glu, or Arg"

(ix) FEATURE:
    (A) NAME/KEY: Modified-site
    (B) LOCATION: 68
    (D) OTHER INFORMATION: /note= "Xaa at position 68 is Leu,
        Gln, Trp, Arg, Asp, Ala, Asn, Glu, His, Ile, Met,
        Phe, Ser, Thr, Tyr, or Val"

(ix) FEATURE:
    (A) NAME/KEY: Modified-site
    (B) LOCATION: 69
    (D) OTHER INFORMATION: /note= "Xaa at position 69 is Pro
        or Thr"

(ix) FEATURE:
    (A) NAME/KEY: Modified-site
    (B) LOCATION: 71
    (D) OTHER INFORMATION: /note= "Xaa at position 71 is Leu
        or Val"

(ix) FEATURE:
    (A) NAME/KEY: Modified-site
    (B) LOCATION: 73
    (D) OTHER INFORMATION: /note= "Xaa at position 73 is Leu
        or Ser"

(ix) FEATURE:
    (A) NAME/KEY: Modified-site
    (B) LOCATION: 74
    (D) OTHER INFORMATION: /note= "Xaa at position 74 is Ala
        or Trp"

(ix) FEATURE:
    (A) NAME/KEY: Modified-site
    (B) LOCATION: 77
    (D) OTHER INFORMATION: /note= "Xaa at position 77 is Ala
        or Pro"

(ix) FEATURE:
    (A) NAME/KEY: Modified-site
    (B) LOCATION: 79
    (D) OTHER INFORMATION: /note= "Xaa at position 79 is Thr,
        Asp, Ser, Pro, Ala, Leu, or Arg"

(ix) FEATURE:
    (A) NAME/KEY: Modified-site
    (B) LOCATION: 81
    (D) OTHER INFORMATION: /note= "Xaa at position 81 is His, Pro, Arg, Val, Leu, Gly, Asn, Phe, Ser, or Thr"

(ix) FEATURE:
    (A) NAME/KEY: Modified-site
    (B) LOCATION: 82
    (D) OTHER INFORMATION: /note= "Xaa at position 82 is Pro
        or Tyr"

(ix) FEATURE:
    (A) NAME/KEY: Modified-site
    (B) LOCATION: 83
    (D) OTHER INFORMATION: /note= "Xaa at position 83 is Ile
        or Val"

(ix) FEATURE:
    (A) NAME/KEY: Modified-site
    (B) LOCATION: 84
    (D) OTHER INFORMATION: /note= "Xaa at position 84 is His,
        Ile, Asn, Leu, Ala, Thr, Arg, Gln, Lys,
        Met, Ser, Tyr, Val, or Pro"

(ix) FEATURE:
    (A) NAME/KEY: Modified-site
    (B) LOCATION: 85
    (D) OTHER INFORMATION: /note= "Xaa at position 85 is Ile,
        Leu, or Val"

(ix) FEATURE:
    (A) NAME/KEY: Modified-site
    (B) LOCATION: 86
    (D) OTHER INFORMATION: /note= "Xaa at position 86 is Lys,
        Arg, Ile, Gln, Pro, or Ser"

(ix) FEATURE:
    (A) NAME/KEY: Modified-site
    (B) LOCATION: 87
    (D) OTHER INFORMATION: /note= "Xaa at position 87 is Asp,
        Pro, Met, Lys, His, Thr, Asn, Ile, Leu, or Tyr"

(ix) FEATURE:
    (A) NAME/KEY: Modified-site
    (B) LOCATION: 90
    (D) OTHER INFORMATION: /note= "Xaa at position 90 is Trp
        or Leu"

(ix) FEATURE:
    (A) NAME/KEY: Modified-site
    (B) LOCATION: 91
    (D) OTHER INFORMATION: /note="Xaa at position 91 is Asn,
        Pro, Ala, Ser, Trp, Gln, Tyr, Leu, Lys, Ile, Asp,
        or His"

(ix) FEATURE:
    (A) NAME/KEY: Modified-site
    (B) LOCATION: 92
    (D) OTHER INFORMATION: /note= "Xaa at position 92 is Glu
        or Gly"

(ix) FEATURE:
    (A) NAME/KEY: Modified-site
    (B) LOCATION: 94
    (C) OTHER INFORMATION: /note= "Xaa at position 94 is Arg,
        Ala, or Ser"

(ix) FEATURE:
    (A) NAME/KEY: Modified-site
    (B) LOCATION: 95
    (D) OTHER INFORMATION: /note= "Xaa at position 95 is Arg,
        Thr, Glu, Leu, or Ser"

(ix) FEATURE:
    (A) NAME/KEY: Modified-site
    (B) LOCATION: 98
    (D) OTHER INFORMATION: /note= "Xaa at position 98 is Thr,
        Val, or Gln"

(ix) FEATURE:
    (A) NAME/KEY: Modified-site
    (B) LOCATION: 100

(D) OTHER INFORMATION: /note= "Xaa at position 100 is Tyr or Trp"

(ix) FEATURE:
  (A) NAME/KEY: Modified-site
  (B) LOCATION: 101
  (D) OTHER INFORMATION: /note= "Xaa at position 101 is Leu or Ala"

(ix) FEATURE:
  (A) NAME/KEY: Modified-site
  (B) LOCATION: 102
  (D) OTHER INFORMATION: /note= "Xaa at position 102 is Lys, Thr, Val, Trp, Ser, Ala, His, Met, Phe, Tyr, or Ile"

(ix) FEATURE:
  (A) NAME/KEY: Modified-site
  (B) LOCATION: 103
  (D) OTHER INFORMATION: /note= "Xaa at position 103 is Thr or Ser"

(ix) FEATURE:
  (A) NAME/KEY: Modified-site
  (B) LOCATION: 106
  (D) OTHER INFORMATION: /note= "Xaa at position 106 is Asn, Pro, Leu, His, Val, or Gln"

(ix) FEATURE:
  (A) NAME/KEY: Modified-site
  (B) LOCATION: 107
  (D) OTHER INFORMATION: /note= "Xaa at position 107 is Ala, Ser, Ile, Asn, Pro, Asp, or Gly"

(ix) FEATURE:
  (A) NAME/KEY: Modified-site
  (B) LOCATION: 108
  (D) OTHER INFORMATION: /note= "Xaa at position 108 is Gln, Ser, Met, Trp, Arg, Phe, Pro, His, Ile, Tyr, or Cys"

(ix) FEATURE:
  (A) NAME/KEY: Modified-site
  (B) LOCATION: 109
  (D) OTHER INFORMATION: /note= "Xaa at position 109 is Ala, Met, Glu, His, Ser, Pro, Tyr, or Leu"

(xi) SEQUENCE DESCRIPTION: SEQ ID NO:5:

```
Asn Cys Xaa Xaa Xaa Ile Xaa Glu Xaa Xaa Xaa Xaa Leu Lys Xaa Xaa
1               5                  10                  15

Xaa Xaa Xaa Xaa Xaa Asp Xaa Xaa Asn Leu Asn Xaa Glu Xaa Xaa Xaa
            20                  25                  30

Ile Leu Met Xaa Xaa Asn Leu Xaa Xaa Xaa Asn Leu Glu Xaa Phe Xaa
            35                  40                  45

Xaa Xaa Xaa Xaa Xaa Xaa Xaa Asn Xaa Xaa Xaa Ile Glu Xaa Xaa Leu
    50                  55                  60

Xaa Xaa Leu Xaa Xaa Cys Xaa Pro Xaa Xaa Thr Ala Xaa Pro Xaa Arg
65                  70                  75                  80

Xaa Xaa Xaa Xaa Xaa Xaa Xaa Gly Asp Xaa Xaa Xaa Phe Xaa Xaa Lys
            85                  90                  95

Leu Xaa Phe Xaa Xaa Xaa Xaa Leu Glu Xaa Xaa Xaa Xaa Gln Gln
            100                 105                 110
```

(2) INFORMATION FOR SEQ ID NO:6:

(i) SEQUENCE CHARACTERISTICS:
    (A) LENGTH: 111 amino acids
    (B) TYPE: amino acid
    (D) TOPOLOGY: linear (ii) MOLECULE TYPE: peptide (ix) FEATURE:

(A) NAME/KEY: Modified-site
        (B) LOCATION: 1
        (D) OTHER INFORMATION: /note= "Met- or Met-Ala- may or may
            not precede the amino acid in position 1"

(ix) FEATURE:
        (A) NAME/KEY: Modified-site
        (B) LOCATION: 3
        (D) OTHER INFORMATION: /note= "Xaa at position 3 is Ser,
            Gly, Asp, or Gln"

(ix) FEATURE:
        (A) NAME/KEY: Modified-site
        (B) LOCATION: 4
        (D) OTHER INFORMATION: /note= "Xaa at position 4 is Asn,
            His, or Ile"

(ix) FEATURE:
        (A) NAME/KEY: Modified-site
        (B) LOCATION: 9
        (D) OTHER INFORMATION: /note= "Xaa at position 9 is Ile,
            Ala, Leu, or Gly"

(ix) FEATURE:
        (A) NAME/KEY: Modified-site
        (B) LOCATION: 11
        (D) OTHER INFORMATION: /note= "Xaa at position 11 is Thr,
            His, or Gln"

(ix) FEATURE:
        (A) NAME/KEY: Modified-site
        (B) LOCATION: 12
        (D) OTHER INFORMATION: /note= "Xaa at position 12 is His
            or Ala"

(ix) FEATURE:
        (A) NAME/KEY: Modified-site
        (B) LOCATION: 15
        (D) OTHER INFORMATION: /note= "Xaa at position 15 is Gln
            or Asn"

(ix) FEATURE:
        (A) NAME/KEY: Modified-site
        (B) LOCATION: 16
        (D) OTHER INFORMATION: /note= "Xaa at position 16 is Pro
            or Gly"

(ix) FEATURE:
        (A) NAME/KEY: Modified-site
        (B) LOCATION: 18
        (D) OTHER INFORMATION: /note= "Xaa at position 18 is Leu,
            Arg, Asn, or Ala"

(ix) FEATURE:
        (A) NAME/KEY: Modified-site
        (B) LOCATION: 20
        (D) OTHER INFORMATION: /note= "Xaa at position 20 is Leu,
            Val, Ser, Ala, Arg, Gln, Glu, Ile, Phe, Thr, or Met"

(ix) FEATURE:
        (A) NAME/KEY: Modified-site
        (B) LOCATION: 21
        (D) OTHER INFORMATION: /note= "Xaa at position 21 is Leu,
            Ala, Asn, or Pro"

(ix) FEATURE:
        (A) NAME/KEY: Modified-site
        (B) LOCATION: 24
        (D) OTHER INFORMATION: /note= "Xaa at position 24 is Asn
            or Ala"

(ix) FEATURE:
        (A) NAME/KEY: Modified-site
        (B) LOCATION: 28
        (D) OTHER INFORMATION: /note= "Xaa at position 28 is Gly,
            Asp, Ser, Ala, Asn, Ile, Leu, Met, Tyr, or Arg"

(ix) FEATURE:
        (A) NAME/KEY: Modified-site

```
         (B) LOCATION: 31
         (D) OTHER INFORMATION: /note= "Xaa at position 31 is Gln,
             Val, Met, Leu, Ala, Asn, Glu, or Lys"

(ix) FEATURE:
         (A) NAME/KEY: Modified-site
         (B) LOCATION: 32
         (D) OTHER INFORMATION: /note= "Xaa at position 32 is Asp,
             Phe, Ser, Ala, Gln, Glu, His, Val, or Thr"

(ix) FEATURE:
         (A) NAME/KEY: Modified-site
         (B) LOCATION: 36
         (D) OTHER INFORMATION: /note= "Xaa at position 36 is Glu,
             Asn, Ser, or Asp"

(ix) FEATURE:
         (A) NAME/KEY: Modified-site
         (B) LOCATION: 37
         (D) OTHER INFORMATION: /note= "Xaa at position 37 is Asn,
             Arg, Pro, Thr, or His"

(ix) FEATURE:
         (A) NAME/KEY: Modified-site
         (B) LOCATION: 41
         (D) OTHER INFORMATION: /note= "Xaa at position 41 is Arg,
             Leu, or Gly"

(ix) FEATURE:
         (A) NAME/KEY: Modified-site
         (B) LOCATION: 42
         (D) OTHER INFORMATION: /note= "Xaa at position 42 is Pro,
             Gly, Ser, Ala, Asn, Val, Leu, or Gln"

(ix) FEATURE:
         (A) NAME/KEY: Modified-site
         (B) LOCATION: 48
         (D) OTHER INFORMATION: /note= "Xaa at position 48 is Asn,
             Pro, or Thr"

(ix) FEATURE:
         (A) NAME/KEY: Modified-site
         (B) LOCATION: 50
         (D) OTHER INFORMATION: /note= "Xaa at position 50 is Ala
             or Asn"

(ix) FEATURE:
         (A) NAME/KEY: Modified-site
         (B) LOCATION: 51
         (D) OTHER INFORMATION: /note= "Xaa at position 51 is Val
             or Thr"

(ix) FEATURE:
         (A) NAME/KEY: Modified-site
         (B) LOCATION: 53
         (D) OTHER INFORMATION: /note= "Xaa at position 53 is Ser
             or Phe"

(ix) FEATURE:
         (A) NAME/KEY: Modified-site
         (B) LOCATION: 54
         (D) OTHER INFORMATION: /note= "Xaa at position 54 is Leu
             or Phe"

(ix) FEATURE:
         (A) NAME/KEY: Modified-site
         (B) LOCATION: 55
         (D) OTHER INFORMATION: /note= "Xaa at position 55 is Gln,
             Ala, Glu, or Arg"

(ix) FEATURE:
         (A) NAME/KEY: Modified-site
         (B) LOCATION: 62
         (D) OTHER INFORMATION: /note= "Xaa at position 62 is Ser,
             Val, Asn, Pro, or Gly"

(ix) FEATURE:
         (A) NAME/KEY: Modified-site
         (B) LOCATION: 63
```

(D) OTHER INFORMATION: /note= "Xaa at position 63 is Ile
                    or Leu"

(ix) FEATURE:
                (A) NAME/KEY: Modified-site
                (B) LOCATION: 65
                (D) OTHER INFORMATION: /note= "Xaa at position 65 is Lys,
                    Asn, Met, Arg, Ile, or Gly"

(ix) FEATURE:
                (A) NAME/KEY: Modified-site
                (B) LOCATION: 66
                (D) OTHER INFORMATION: /note= "Xaa at position 66 is Asn,
                    Gly, Glu, or Arg"

(ix) FEATURE:
                (A) NAME/KEY: Modified-site
                (B) LOCATION: 68
                (D) OTHER INFORMATION: /note= "Xaa at position 68 is Leu,
                    Gln, Trp, Arg, Asp, Asn, Glu, His, Met, Phe, Ser,
                    Thr, Tyr, or Val"

(ix) FEATURE:
                (A) NAME/KEY: Modified-site
                (B) LOCATION: 73
                (D) OTHER INFORMATION: /note= "Xaa at position 73 is Leu
                    or Ser"

(ix) FEATURE:
                (A) NAME/KEY: Modified-site
                (B) LOCATION: 74
                (D) OTHER INFORMATION: /note= "Xaa at position 74 is Ala
                    or Trp"

(ix) FEATURE:
                (A) NAME/KEY: Modified-site
                (B) LOCATION: 77
                (D) OTHER INFORMATION: /note= "Xaa at position 77 is Ala
                    or Pro"

(ix) FEATURE:
                (A) NAME/KEY: Modified-site
                (B) LOCATION: 79
                (D) OTHER INFORMATION: /note= "Xaa at position 79 is Thr,
                    Asp, or Ala"

(ix) FEATURE:
                (A) NAME/KEY: Modified-site
                (B) LOCATION: 81
                (D) OTHER INFORMATION: /note= "Xaa at position 81 is His,
                    Pro, Arg, Val, Gly, Asn, Ser, or Thr"

(ix) FEATURE:
                (A) NAME/KEY: Modified-site
                (B) LOCATION: 84
                (D) OTHER INFORMATION: /note= "Xaa at position 84 is His,
                    Ile, Asn, Leu, Ala, Thr, Arg, Gln, Glu, Lys, Met,
                    Ser, Tyr, Val, or Leu"

(ix) FEATURE:
                (A) NAME/KEY: Modified-site
                (B) LOCATION: 85
                (D) OTHER INFORMATION: /note= "Xaa at position 85 is Ile
                    or Leu"

(ix) FEATURE:
                (A) NAME/KEY: Modified-site
                (B) LOCATION: 86
                (D) OTHER INFORMATION: /note= "Xaa at position 86 is Lys
                    or Arg"

(ix) FEATURE:
                (A) NAME/KEY: Modified-site
                (B) LOCATION: 87
                (D) OTHER INFORMATION: /note= "Xaa at position 87 is Asp,
                    Pro, Met, Lys, His, Pro, Asn, Ile, Leu, or Tyr"

(ix) FEATURE:
                (A) NAME/KEY: Modified-site

```
          (B) LOCATION: 91
          (D) OTHER INFORMATION: /note= "Xaa at position 91 is Asn,
              Pro, Ser, Ile, or Asp"

(ix) FEATURE:
          (A) NAME/KEY: Modified-site
          (B) LOCATION: 94
          (D) OTHER INFORMATION: /note="Xaa at position 94 is Arg,
              Ala, or Ser"

(ix) FEATURE:
          (A) NAME/KEY: Modified-site
          (B) LOCATION: 95
          (D) OTHER INFORMATION: /note= "Xaa at position 95 is Arg,
              Thr, Glu, Leu, or Ser"

(ix) FEATURE:
          (A) NAME/KEY: Modified-site
          (B) LOCATION: 98
          (D) OTHER INFORMATION: /note= "Xaa at position 98 is Thr
              or Gln"

(ix) FEATURE:
          (A) NAME/KEY: Modified-site
          (B) LOCATION: 102
          (D) OTHER INFORMATION: /note= "Xaa at position 102 is Lys,
              Val, Trp, or Ile"

(ix) FEATURE:
          (A) NAME/KEY: Modified-site
          (B) LOCATION: 103
          (D) OTHER INFORMATION: /note= "Xaa at position 103 is Thr,
              Ala, His, Phe, Tyr, or Ser"

(ix) FEATURE:
          (A) NAME/KEY: Modified-site
          (B) LOCATION: 106
          (D) OTHER INFORMATION: /note= "Xaa at position 106 is Asn,
              Pro, Leu, His, Val, or Gln"

(ix) FEATURE:
          (A) NAME/KEY: Modified-site
          (B) LOCATION: 107
          (D) OTHER INFORMATION: /note= "Xaa at position 107 is Ala,
              Ser, Ile, Pro, or Asp"

(ix) FEATURE:
          (A) NAME/KEY: Modified-site
          (B) LOCATION: 108
          (D) OTHER INFORMATION: /note= "Xaa at position 108 is Gln,
              Met, Trp, Phe, Pro, His, Ile, or Tyr"

(ix) FEATURE:
          (A) NAME/KEY: Modified-site
          (B) LOCATION: 109
          (D) OTHER INFORMATION: /note= "Xaa at position 109 is Ala,
              Met, Glu, Ser, or Leu"

(xi) SEQUENCE DESCRIPTION: SEQ ID NO:6:

Asn Cys Xaa Xaa Met Ile Asp Glu Xaa Ile Xaa Xaa Leu Lys Xaa Xaa
 1               5                  10                  15

Pro Xaa Pro Xaa Xaa Asp Phe Xaa Asn Leu Asn Xaa Glu Asp Xaa Xaa
                20                  25                  30

Ile Leu Met Xaa Xaa Asn Leu Arg Xaa Xaa Asn Leu Glu Ala Phe Xaa
             35                  40                  45

Arg Xaa Xaa Lys Xaa Xaa Xaa Asn Ala Ser Ala Ile Glu Xaa Xaa Leu
 50                  55                  60

Xaa Xaa Leu Xaa Pro Cys Leu Pro Xaa Xaa Thr Ala Xaa Pro Xaa Arg
 65                  70                  75                  80

Xaa Pro Ile Xaa Xaa Xaa Xaa Gly Asp Trp Xaa Glu Phe Xaa Xaa Lys
                 85                  90                  95

Leu Xaa Phe Tyr Leu Xaa Xaa Leu Glu Xaa Xaa Xaa Xaa Gln Gln
```

-continued

```
                100                 105                 110
```

(2) INFORMATION FOR SEQ ID NO:7:

(i) SEQUENCE CHARACTERISTICS:
        (A) LENGTH: 133 amino acids
        (B) TYPE: amino acid
        (D) TOPOLOGY: linear (ii) MOLECULE TYPE: peptide (ix) FEATURE:
        (A) NAME/KEY: Modified-site
        (B) LOCATION: 1
        (D) OTHER INFORMATION: /note= "Met- may or may not precede
            the amino acid in position 1"

(ix) FEATURE:
        (A) NAME/KEY: Modified-site
        (B) LOCATION: 18
        (D) OTHER INFORMATION: /note= "Xaa at position 18 is Asn
            or Ile"

(ix) FEATURE:
        (A) NAME/KEY: Modified-site
        (B) LOCATION: 19
        (D) OTHER INFORMATION: /note= "Xaa at position 19 is Met,
            Ala, or Ile"

(ix) FEATURE:
        (A) NAME/KEY: Modified-site
        (B) LOCATION: 20
        (D) OTHER INFORMATION: /note= "Xaa at position 20 is Ile,
            Pro, or Leu"

(ix) FEATURE:
        (A) NAME/KEY: Modified-site
        (B) LOCATION: 23
        (D) OTHER INFORMATION: /note= "Xaa at position 23 is Ile,
            Ala, or Leu"

(ix) FEATURE:
        (A) NAME/KEY: Modified-site
        (B) LOCATION: 25
        (D) OTHER INFORMATION: /note= "Xaa at position 25 is Thr
            or His"

(ix) FEATURE:
        (A) NAME/KEY: Modified-site
        (B) LOCATION: 29
        (D) OTHER INFORMATION: /note= "Xaa at position 29 is Gln,
            Arg, Val, or Ile"

(ix) FEATURE:
        (A) NAME/KEY: Modified-site
        (B) LOCATION: 32
        (D) OTHER INFORMATION: /note= "Xaa at position 32 is Leu,
            Ala, Asn, or Arg"

(ix) FEATURE:
        (A) NAME/KEY: Modified-site
        (B) LOCATION: 34
        (D) OTHER INFORMATION: /note= "Xaa at position 34 is Leu
            or Ser"

(ix) FEATURE:
        (A) NAME/KEY: Modified-site
        (B) LOCATION: 37
        (D) OTHER INFORMATION: /note= "Xaa at position 37 is Phe,
            Pro, or Ser"

(ix) FEATURE:
        (A) NAME/KEY: Modified-site
        (B) LOCATION:; 38
        (D) OTHER INFORMATION: /note= "Xaa at position 38 is Asn
            or Ala"

(ix) FEATURE:

```
          (A) NAME/KEY: Modified-site
          (B) LOCATION: 42
          (D) OTHER INFORMATION: /note= "Xaa at position 42 is Gly,
              Ala, Ser, Asp, or Asn"

(ix) FEATURE:
          (A) NAME/KEY: Modified-site
          (B) LOCATION: 45
          (D) OTHER INFORMATION: /note= "Xaa at position 45 is Gln,
              Val, or Met"

(ix) FEATURE:
          (A) NAME/KEY: Modified-site
          (B) LOCATION: 46
          (D) OTHER INFORMATION: /note= "Xaa at position 46 is Asp
              or Ser"

(ix) FEATURE:
          (A) NAME/KEY: Modified-site
          (B) LOCATION: 49
          (D) OTHER INFORMATION: /note= "Xaa at position 49 is Met,
              Ile, Leu, or Asp"

(ix) FEATURE:
          (A) NAME/KEY: Modified-site
          (B) LOCATION: 50
          (D) OTHER INFORMATION: /note= "Xaa at position 50 is Glu
              or Asp"

(ix) FEATURE:
          (A) NAME/KEY: Modified-site
          (B) LOCATION: 51
          (D) OTHER INFORMATION: /note= "Xaa at position 51 is Asn,
              Arg, or Ser"

(ix) FEATURE:
          (A) NAME/KEY: Modified-site
          (B) LOCATION: 55
          (D) OTHER INFORMATION: /note= "Xaa at position 55 is Arg,
              Leu, or Thr"

(ix) FEATURE:
          (A) NAME/KEY: Modified-site
          (B) LOCATION: 56
          (D) OTHER INFORMATION: /note= "Xaa at position 56 is Pro
              or Ser"

(ix) FEATURE:
          (A) NAME/KEY: Modified-site
          (B) LOCATION: 59
          (D) OTHER INFORMATION: /note= "Xaa at position 59 is Glu
              or Leu"

(ix) FEATURE:
          (A) NAME/KEY: Modified-site
          (B) LOCATION: 60
          (D) OTHER INFORMATION: /note= "Xaa at position 60 is Ala
              or Ser"

(ix) FEATURE:
          (A) NAME/KEY: Modified-site
          (B) LOCATION: 62
          (D) OTHER INFORMATION: /note= "Xaa at position 62 is Asn
              Val, or Pro"

(ix) FEATURE:
          (A) NAME/KEY: Modified-site
          (B) LOCATION: 63
          (D) OTHER INFORMATION: /note= "Xaa at position 63 is Arg
              or His"

(ix) FEATURE:
          (A) NAME/KEY: Modified-site
          (B) LOCATION: 65
          (D) OTHER INFORMATION: /note= "Xaa at position 65 is Val
              or Ser"

(ix) FEATURE:
          (A) NAME/KEY: Modified-site
```

```
          (B) LOCATION: 67
          (D) OTHER INFORMATION: /note= "Xaa at position 67 is Ser,
              Asn, His, or Gln"

(ix) FEATURE:
          (A) NAME/KEY: Modified-site
          (B) LOCATION: 69
          (D) OTHER INFORMATION: /note= "Xaa at position 69 is Gln
              or Glu"

(ix) FEATURE:
          (A) NAME/KEY: Modified-site
          (B) LOCATION: 73
          (D) OTHER INFORMATION: /note= "Xaa at position 73 is Ala
              or Gly"

(ix) FEATURE:
          (A) NAME/KEY: Modified-site
          (B) LOCATION: 76
          (D) OTHER INFORMATION: /note= "Xaa at position 76 is Ser,
              Ala, or Pro"

(ix) FEATURE:
          (A) NAME/KEY: Modified-site
          (B) LOCATION: 79
          (D) OTHER INFORMATION: /note= "Xaa at position 79 is Lys,
              Arg, or Ser"

(ix) FEATURE:
          (A) NAME/KEY: Modified-site
          (B) LOCATION: 82
          (D) OTHER INFORMATION: /note= "Xaa at position 82 is Leu,
              Glu, Val, or Trp"

(ix) FEATURE:
          (A) NAME/KEY: Modified-site
          (B) LOCATION: 85
          (D) OTHER INFORMATION: /note= "Xaa at position 85 is Leu
              or Val"

(ix) FEATURE:
          (A) NAME/KEY: Modified-site
          (B) LOCATION: 87
          (D) OTHER INFORMATION: /note= "Xaa at position 87 is Leu,
              Ser, or Tyr"

(ix) FEATURE:
          (A) NAME/KEY: Modified-site
          (B) LOCATION: 88
          (D) OTHER INFORMATION: /note= "Xaa at position 88 is Ala
              or Trp"

(ix) FEATURE:
          (A) NAME/KEY: Modified-site
          (B) LOCATION: 91
          (D) OTHER INFORMATION: /note= "Xaa at position 91 is Ala
              or Pro"

(ix) FEATURE:
          (A) NAME/KEY: Modified-site
          (B) LOCATION: 93
          (D) OTHER INFORMATION: /note= "Xaa at position 93 is Pro
              or Ser"

(ix) FEATURE:
          (A) NAME/KEY: Modified-site
          (B) LOCATION: 95
          (D) OTHER INFORMATION: /note= "Xaa at position 95 is His
              or Thr"

(ix) FEATURE:
          (A) NAME/KEY: Modified-site
          (B) LOCATION: 98
          (D) OTHER INFORMATION: /note= "Xaa at position 98 is His,
              Ile, or Thr"

(ix) FEATURE:
          (A) NAME/KEY: Modified-site
          (B) LOCATION: 100
```

(D) OTHER INFORMATION: /note= "Xaa at position 100 is Lys
                  or Arg"

(ix) FEATURE:
              (A) NAME/KEY: Modified-site
              (B) LOCATION: 101
              (D) OTHER INFORMATION: /note= "Xaa at position 101 is Asp,
                  Ala, or Met"

(ix) FEATURE:
              (A) NAME/KEY: Modified-site
              (B) LOCATION: 105
              (D) OTHER INFORMATION: /note= "Xaa at position 105 is Asn
                  or Glu"

(ix) FEATURE:
              (A) NAME/KEY: Modified-site
              (B) LOCATION: 109
              (D) OTHER INFORMATION: /note= "Xaa at position 109 is Arg,
                  Glu, or Leu"

(ix) FEATURE:
              (A) NAME/KEY: Modified-site
              (B) LOCATION: 112
              (D) OTHER INFORMATION: /note= "Xaa at position 112 is Thr
                  or Gln"

(ix) FEATURE:
              (A) NAME/KEY: Modified-site
              (B) LOCATION: 116
              (D) OTHER INFORMATION: /note= "Xaa at position 116 is Lys,
                  Val, Trp, or Ser"

(ix) FEATURE:
              (A) NAME/KEY: Modified-site
              (B) LOCATION: 117
              (D) OTHER INFORMATION: /note= "Xaa at position 117 is Thr
                  or Ser"

(ix) FEATURE:
              (A) NAME/KEY: Modified-site
              (B) LOCATION: 120
              (D) OTHER INFORMATION: /note= "Xaa at position 120 is Asn,
                  Gln, or His"

(ix) FEATURE:
              (A) NAME/KEY: Modified-site
              (B) LOCATION: 123
              (D) OTHER INFORMATION: /note= "Xaa at position 123 is Ala
                  or Glu"

(xi) SEQUENCE DESCRIPTION: SEQ ID NO:7:

Ala Pro Met Thr Gln Thr Thr Ser Leu Lys Thr Ser Trp Val Asn Cys
 1               5                  10                  15

Ser Xaa Xaa Xaa Asp Glu Xaa Ile Xaa His Leu Lys Xaa Pro Pro Xaa
                20                  25                  30

Pro Xaa Leu Asp Xaa Xaa Asn Leu Asn Xaa Glu Asp Xaa Xaa Ile Leu
            35                  40                  45

Xaa Xaa Xaa Asn Leu Arg Xaa Xaa Asn Leu Xaa Xaa Phe Xaa Xaa Ala
50                  55                  60

Xaa Lys Xaa Leu Xaa Asn Ala Ser Xaa Ile Glu Xaa Ile Leu Xaa Asn
65                  70                  75                  80

Leu Xaa Pro Cys Xaa Pro Xaa Xaa Thr Ala Xaa Pro Xaa Arg Xaa Pro
            85                  90                  95

Ile Xaa Ile Xaa Xaa Gly Asp Trp Xaa Glu Phe Arg Xaa Lys Leu Xaa
            100                 105                 110

Phe Tyr Leu Xaa Xaa Leu Glu Xaa Ala Gln Xaa Gln Gln Thr Thr Leu
            115                 120                 125

Ser Leu Ala Ile Phe
130

-continued (2) INFORMATION FOR SEQ ID NO:8:

(i) SEQUENCE CHARACTERISTICS:
        (A) LENGTH: 111 amino acids
        (B) TYPE: amino acid
        (D) TOPOLOGY: linear (ii) MOLECULE TYPE: peptide (ix) FEATURE:
        (A) NAME/KEY: Modified-site
        (B) LOCATION: 1
        (D) OTHER INFORMATION: /note= "Met- or Met-Ala may or may
            not precede the amino acid in position 1"

(ix) FEATURE:
        (A) NAME/KEY: Modified-site
        (B) LOCATION: 4
        (D) OTHER INFORMATION: /note= "Xaa at position 4 is Asn or
            Ile"

(ix) FEATURE:
        (A) NAME/KEY: Modified-site
        (B) LOCATION: 5
        (D) OTHER INFORMATION: /note= "Xaa at position 5 is Met,
            Ala, or Ile"

(ix) FEATURE:
        (A) NAME/KEY: Modified-site
        (B) LOCATION: 6
        (D) OTHER INFORMATION: /note= "Xaa at position 6 is Ile,
            Pro, or Leu"

(ix) FEATURE:
        (A) NAME/KEY: Modified-site
        (B) LOCATION: 9
        (D) OTHER INFORMATION: /note= "Xaa at position 9 is Ile,
            Ala, or Leu"

(ix) FEATURE:
        (A) NAME/KEY: Modified-site
        (B) LOCATION: 11
        (D) OTHER INFORMATION: /note= "Xaa at position 11 is Thr
            or His"

(ix) FEATURE:
        (A) NAME/KEY: Modified-site
        (B) LOCATION: 15
        (D) OTHER INFORMATION: /note= "Xaa at position 15 is Gln,
            Arg, Val, or Ile"

(ix) FEATURE:
        (A) NAME/KEY: Modified-site
        (B) LOCATION: 18
        (D) OTHER INFORMATION: /note= "Xaa at position 18 is Leu,
            Ala, Asn, or Arg"

(ix) FEATURE:
        (A) NAME/KEY: Modified-site
        (B) LOCATION: 20
        (D) OTHER INFORMATION: /note= "Xaa at position 20 is Leu
            or Ser"

(ix) FEATURE:
        (A) NAME/KEY: Modified-site
        (B) LOCATION: 23
        (D) OTHER INFORMATION: /note= "Xaa at position 23 is Phe,
            Pro, or Ser"

(ix) FEATURE:
        (A) NAME/KEY: Modified-site
        (B) LOCATION: 24
        (D) OTHER INFORMATION: /note= "Xaa at position 24 is Asn
            or Ala"

(ix) FEATURE:
        (A) NAME/KEY: Modified-site

-continued

```
          (B) LOCATION: 28
          (D) OTHER INFORMATION: /note= "Xaa at position 28 is Gly,
              Ala, Ser, Asp, or Asn"

(ix) FEATURE:
          (A) NAME/KEY: Modified-site
          (B) LOCATION: 31
          (D) OTHER INFORMATION: /note= "Xaa at position 31 is Gln,
              Val, or Met"

(ix) FEATURE:
          (A) NAME/KEY: Modified-site
          (B) LOCATION: 32
          (D) OTHER INFORMATION: /note= "Xaa at position 32 is Asp
              or Ser"

(ix) FEATURE:
          (A) NAME/KEY: Modified-site
          (B) LOCATION: 35
          (D) OTHER INFORMATION: /note= "Xaa at position 35 is Met,
              Ile, or Asp"

(ix) FEATURE:
          (A) NAME/KEY: Modified-site
          (B) LOCATION: 36
          (D) OTHER INFORMATION: /note= "Xaa at position 36 is Glu
              or Asp"

(ix) FEATURE:
          (A) NAME/KEY: Modified-site
          (B) LOCATION: 37
          (D) OTHER INFORMATION: /note= "Xaa at position 37 is Asn,
              Arg, or Ser"

(ix) FEATURE:
          (A) NAME/KEY: Modified-site
          (B) LOCATION: 41
          (D) OTHER INFORMATION: /note= "Xaa at position 41 is Arg,
              Leu, or Thr"

(ix) FEATURE:
          (A) NAME/KEY: Modified-site
          (B) LOCATION: 42
          (D) OTHER INFORMATION: /note= "Xaa at position 42 is Pro
              or Ser"

(ix) FEATURE:
          (A) NAME/KEY: Modified-site
          (B) LOCATION: 45
          (D) OTHER INFORMATION: /note= "Xaa at position 45 is Glu
              or Leu"

(ix) FEATURE:
          (A) NAME/KEY: Modified-site
          (B) LOCATION: 46
          (D) OTHER INFORMATION: /note= "Xaa at position 46 is Ala
              or Ser"

(ix) FEATURE:
          (A) NAME/KEY: Modified-site
          (B) LOCATION: 48
          (D) OTHER INFORMATION: /note= "Xaa at position 48 is Asn,
              Val, or Pro"

(ix) FEATURE:
          (A) NAME/KEY: Modified-site
          (B) LOCATION: 49
          (D) OTHER INFORMATION: /note= "Xaa at position 49 is Arg
              or His"

(ix) FEATURE:
          (A) NAME/KEY: Modified-site
          (B) LOCATION: 51
          (D) OTHER INFORMATION: /note= "Xaa at position 51 is Val
              or Ser"

(ix) FEATURE:
          (A) NAME/KEY: Modified-site
          (B) LOCATION: 53
```

```
        (D) OTHER INFORMATION: /note= "Xaa at position 53 is Ser,
            Asn, His, or Gln"

(ix) FEATURE:
        (A) NAME/KEY: Modified-site
        (B) LOCATION: 55
        (D) OTHER INFORMATION: /note= "Xaa at position 55 is Gln
            or Glu"

(ix) FEATURE:
        (A) NAME/KEY: Modified-site
        (B) LOCATION: 59
        (D) OTHER INFORMATION: /note= "Xaa at position 59 is Ala
            or Gly"

(ix) FEATURE:
        (A) NAME/KEY: Modified-site
        (B) LOCATION: 62
        (D) OTHER INFORMATION: /note= "Xaa at position 62 is Ser,
            Ala, or Pro"

(ix) FEATURE:
        (A) NAME/KEY: Modified-site
        (B) LOCATION: 65
        (D) OTHER INFORMATION: /note= "Xaa at position 65 is Lys,
            Arg, or Ser"

(ix) FEATURE:
        (A) NAME/KEY: Modified-site
        (B) LOCATION: 67
        (D) OTHER INFORMATION: /note= "Xaa at position 67 is Leu,
            Glu, or Val"

(ix) FEATURE:
        (A) NAME/KEY: Modified-site
        (B) LOCATION: 68
        (D) OTHER INFORMATION: /note= "Xaa at position 68 is Leu,
            Glu, Val, or Trp"

(ix) FEATURE:
        (A) NAME/KEY: Modified-site
        (B) LOCATION: 71
        (D) OTHER INFORMATION: /note= "Xaa at position 71 is Leu
            or Val"

(ix) FEATURE:
        (A) NAME/KEY: Modified-site
        (B) LOCATION: 73
        (D) OTHER INFORMATION: /note= "Xaa at position 73 is Leu,
            Ser, or Tyr"

(ix) FEATURE:
        (A) NAME/KEY: Modified-site
        (B) LOCATION: 74
        (D) OTHER INFORMATION: /note= "Xaa at position 74 is Ala
            or Trp"

(ix) FEATURE:
        (A) NAME/KEY: Modified-site
        (B) LOCATION: 77
        (D) OTHER INFORMATION: /note= "Xaa at position 77 is Ala
            or Pro"

(ix) FEATURE:
        (A) NAME/KEY: Modified-site
        (B) LOCATION: 79
        (D) OTHER INFORMATION: /note= "Xaa at position 79 is Pro
            or Ser"

(ix) FEATURE:
        (A) NAME/KEY: Modified-site
        (B) LOCATION: 81
        (D) OTHER INFORMATION: /note= "Xaa at position 81 is His
            or Thr"

(ix) FEATURE:
        (A) NAME/KEY: Modified-site
        (B) LOCATION: 84
        (D) OTHER INFORMATION: /note= "Xaa at position 84 is His,
```

Ile, or Thr"

(ix) FEATURE:
  (A) NAME/KEY: Modified-site
  (B) LOCATION: 86
  (D) OTHER INFORMATION: /note= "Xaa at position 86 is Lys
      or Arg"

(ix) FEATURE:
  (A) NAME/KEY: Modified-site
  (B) LOCATION: 87
  (D) OTHER INFORMATION: /note= "Xaa at position 87 is Asp,
      Ala, or Met"

(ix) FEATURE:
  (A) NAME/KEY: Modified-site
  (B) LOCATION: 91
  (D) OTHER INFORMATION: /note= "Xaa at position 91 is Asn
      or Glu"

(ix) FEATURE:
  (A) NAME/KEY: Modified-site
  (B) LOCATION: 95
  (D) OTHER INFORMATION: /note= "Xaa at position 95 is Arg,
      Glu, or Leu"

(ix) FEATURE:
  (A) NAME/KEY: Modified-site
  (B) LOCATION: 98
  (D) OTHER INFORMATION: /note= "Xaa at position 98 is Thr
      or Gln"

(ix) FEATURE:
  (A) NAME/KEY: Modified-site
  (B) LOCATION: 102
  (D) OTHER INFORMATION: /note= "Xaa at position 102 is Lys,
      Val, Trp, or Ser"

(ix) FEATURE:
  (A) NAME/KEY: Modified-site
  (B) LOCATION: 103
  (D) OTHER INFORMATION: /note= "Xaa at position 103 is Thr
      or Ser"

(ix) FEATURE:
  (A) NAME/KEY: Modified-site
  (B) LOCATION: 106
  (D) OTHER INFORMATION: /note= "Xaa at position 106 is Asn,
      Gln, or His"

(ix) FEATURE:
  (A) NAME/KEY: Modified-site
  (B) LOCATION: 109
  (D) OTHER INFORMATION: /note= "Xaa at position 109 is Ala
      or Glu"

(xi) SEQUENCE DESCRIPTION: SEQ ID NO:8:

Asn Cys Ser Xaa Xaa Xaa Asp Glu Xaa Ile Xaa His Leu Lys Xaa Pro
1               5                   10                  15

Pro Xaa Pro Xaa Leu Asp Xaa Xaa Asn Leu Asn Xaa Glu Asp Xaa Xaa
            20                  25                  30

Ile Leu Xaa Xaa Xaa Asn Leu Arg Xaa Xaa Asn Leu Xaa Xaa Phe Xaa
            35                  40                  45

Xaa Ala Xaa Lys Xaa Leu Xaa Asn Ala Ser Xaa Ile Glu Xaa Ile Leu
    50                  55                  60

Xaa Asn Xaa Xaa Pro Cys Xaa Pro Xaa Xaa Thr Ala Xaa Pro Xaa Arg
65                  70                  75                  80

Xaa Pro Ile Xaa Ile Xaa Xaa Gly Asp Trp Xaa Glu Phe Arg Xaa Lys
                85                  90                  95

Leu Xaa Phe Tyr Leu Xaa Xaa Leu Glu Xaa Ala Gln Xaa Gln Gln
            100                 105                 110

(2) INFORMATION FOR SEQ ID NO:9:

(i) SEQUENCE CHARACTERISTICS:
        (A) LENGTH: 111 amino acids
        (B) TYPE: amino acid
        (D) TOPOLOGY: linear (ii) MOLECULE TYPE: peptide (xi) SEQUENCE DESCRIPTION: SEQ ID NO:9:

```
Asn Cys Ser Ile Met Ile Asp Glu Ile Ile His His Leu Lys Arg Pro
1               5                   10                  15

Pro Ala Pro Leu Leu Asp Pro Asn Asn Leu Asn Ala Glu Asp Val Asp
            20                  25                  30

Ile Leu Met Glu Asn Asn Leu Arg Arg Pro Asn Leu Glu Ala Phe Asn
        35                  40                  45

Arg Ala Val Lys Ser Leu Gln Asn Ala Ser Ala Ile Glu Ser Ile Leu
    50                  55                  60

Lys Asn Leu Leu Pro Cys Leu Pro Leu Ala Thr Ala Ala Pro Thr Arg
65                  70                  75                  80

His Pro Ile His Ile Lys Asp Gly Asp Trp Asn Glu Phe Arg Arg Lys
                85                  90                  95

Leu Thr Phe Tyr Leu Lys Thr Leu Glu Asn Ala Gln Ala Gln Gln
                100                 105                 110
```

(2) INFORMATION FOR SEQ ID NO:10:

(i) SEQUENCE CHARACTERISTICS:
        (A) LENGTH: 111 amino acids
        (B) TYPE: amino acid
        (D) TOPOLOGY: linear (ii) MOLECULE TYPE: peptide (xi) SEQUENCE DESCRIPTION: SEQ ID NO:10:

```
Asn Cys Ser Ile Met Ile Asp Glu Ile Ile His His Leu Lys Arg Pro
1               5                   10                  15

Pro Asn Pro Leu Leu Asp Pro Asn Asn Leu Asn Ser Glu Asp Met Asp
            20                  25                  30

Ile Leu Met Glu Asn Asn Leu Arg Arg Pro Asn Leu Glu Ala Phe Asn
        35                  40                  45

Arg Ala Val Lys Ser Leu Gln Asn Ala Ser Ala Ile Glu Ser Ile Leu
    50                  55                  60

Lys Asn Leu Leu Pro Cys Leu Pro Leu Ala Thr Ala Ala Pro Thr Arg
65                  70                  75                  80

His Pro Ile His Ile Lys Asp Gly Asp Trp Asn Glu Phe Arg Arg Lys
                85                  90                  95

Leu Thr Phe Tyr Leu Lys Thr Leu Glu Asn Ala Gln Ala Gln Gln
                100                 105                 110
```

(2) INFORMATION FOR SEQ ID NO:11:

(i) SEQUENCE CHARACTERISTICS:
        (A) LENGTH: 111 amino acids
        (B) TYPE: amino acid
        (D) TOPOLOGY: linear (ii) MOLECULE TYPE: peptide (xi) SEQUENCE DESCRIPTION: SEQ ID NO:11:

Asn Cys Ser Ile Met Ile Asp Glu Ile Ile His His Leu Lys Val Pro

```
1               5                    10                   15
Pro Ala Pro Leu Leu Asp Ser Asn Asn Leu Asn Ser Glu Asp Met Asp
                20                  25                  30

Ile Leu Met Glu Asn Asn Leu Arg Arg Pro Asn Leu Glu Ala Phe Asn
            35                  40                  45

Arg Ala Val Lys Ser Leu Gln Asn Ala Ser Ala Ile Glu Ser Ile Leu
        50                  55                  60

Lys Asn Leu Leu Pro Cys Leu Pro Leu Ala Thr Ala Ala Pro Thr Arg
65                  70                  75                  80

His Pro Ile His Ile Lys Asp Gly Asp Trp Asn Glu Phe Arg Arg Lys
                85                  90                  95

Leu Thr Phe Tyr Leu Lys Thr Leu Glu Asn Ala Gln Ala Gln Gln
            100                 105                 110
```

(2) INFORMATION FOR SEQ ID NO:12:

(i) SEQUENCE CHARACTERISTICS:
        (A) LENGTH: 111 amino acids
        (B) TYPE: amino acid
        (D) TOPOLOGY: linear (ii) MOLECULE TYPE: peptide (xi) SEQUENCE DESCRIPTION: SEQ ID NO:12:

```
Asn Cys Ser Asn Met Ile Asp Glu Ile Ile Thr His Leu Lys Gln Pro
1               5                   10                  15

Pro Leu Pro Leu Leu Asp Phe Asn Asn Leu Asn Gly Glu Asp Gln Asp
                20                  25                  30

Ile Leu Met Glu Arg Asn Leu Arg Leu Pro Asn Leu Leu Ala Phe Val
            35                  40                  45

Arg Ala Val Lys Asn Leu Glu Asn Ala Ser Ala Ile Glu Ser Ile Leu
        50                  55                  60

Lys Asn Leu Leu Pro Cys Leu Pro Leu Ala Thr Ala Ala Pro Thr Arg
65                  70                  75                  80

His Pro Ile His Ile Lys Asp Gly Asp Trp Asn Glu Phe Arg Arg Lys
                85                  90                  95

Leu Thr Phe Tyr Leu Lys Thr Leu Glu Asn Ala Gln Ala Gln Gln
            100                 105                 110
```

(2) INFORMATION FOR SEQ ID NO:13:

(i) SEQUENCE CHARACTERISTICS:
        (A) LENGTH: 111 amino acids
        (B) TYPE: amino acid
        (D) TOPOLOGY: linear (ii) MOLECULE TYPE: peptide (xi) SEQUENCE DESCRIPTION: SEQ ID NO:13:

```
Asn Cys Ser Asn Met Ile Asp Glu Ile Ile Thr His Leu Lys Gln Pro
1               5                   10                  15

Pro Leu Pro Leu Leu Asp Phe Asn Asn Leu Asn Gly Glu Asp Gln Asp
                20                  25                  30

Ile Leu Met Glu Arg Asn Leu Arg Leu Pro Asn Leu Glu Ser Phe Val
            35                  40                  45

Arg Ala Val Lys Asn Leu Glu Asn Ala Ser Ala Ile Glu Ser Ile Leu
        50                  55                  60

Lys Asn Leu Leu Pro Cys Leu Pro Leu Ala Thr Ala Ala Pro Thr Arg
65                  70                  75                  80
```

```
His Pro Ile His Ile Lys Asp Gly Asp Trp Asn Glu Phe Arg Arg Lys
                85                  90                  95

Leu Thr Phe Tyr Leu Lys Thr Leu Glu Asn Ala Gln Ala Gln Gln
                100                 105                 110

(2) INFORMATION FOR SEQ ID NO:14:

(i) SEQUENCE CHARACTERISTICS:
        (A) LENGTH: 111 amino acids
        (B) TYPE: amino acid
        (D) TOPOLOGY: linear (ii) MOLECULE TYPE: peptide (xi) SEQUENCE DESCRIPTION: SEQ ID NO:14:

Asn Cys Ser Asn Met Ile Asp Glu Ile Ile Thr His Leu Lys Gln Pro
1               5                   10                  15

Pro Leu Pro Leu Leu Asp Phe Asn Asn Leu Asn Gly Glu Asp Gln Asp
                20                  25                  30

Ile Leu Met Glu Arg Asn Leu Arg Thr Pro Asn Leu Leu Ala Phe Val
                35                  40                  45

Arg Ala Val Lys His Leu Glu Asn Ala Ser Ala Ile Glu Ser Ile Leu
50                  55                  60

Lys Asn Leu Leu Pro Cys Leu Pro Leu Ala Thr Ala Ala Pro Thr Arg
65                  70                  75                  80

His Pro Ile His Ile Lys Asp Gly Asp Trp Asn Glu Phe Arg Arg Lys
                85                  90                  95

Leu Thr Phe Tyr Leu Lys Thr Leu Glu Asn Ala Gln Ala Gln Gln
                100                 105                 110

(2) INFORMATION FOR SEQ ID NO:15:

(i) SEQUENCE CHARACTERISTICS:
        (A) LENGTH: 111 amino acids
        (B) TYPE: amino acid
        (D) TOPOLOGY: linear (ii) MOLECULE TYPE: peptide (xi) SEQUENCE DESCRIPTION: SEQ ID NO:15:

Asn Cys Ser Asn Met Ile Asp Glu Ile Ile Thr His Leu Lys Gln Pro
1               5                   10                  15

Pro Leu Pro Leu Leu Asp Phe Asn Asn Leu Asn Gly Glu Asp Gln Asp
                20                  25                  30

Ile Leu Met Glu Asn Asn Leu Arg Arg Pro Asn Leu Glu Ala Phe Asn
                35                  40                  45

Arg Ala Val Lys Ser Leu Gln Asn Ala Ser Gly Ile Glu Ala Ile Leu
50                  55                  60

Arg Asn Leu Gln Pro Cys Leu Pro Ser Ala Thr Ala Ala Pro Ser Arg
65                  70                  75                  80

His Pro Ile Ile Ile Lys Ala Gly Asp Trp Gln Glu Phe Arg Arg Lys
                85                  90                  95

Leu Thr Phe Tyr Leu Lys Thr Leu Glu Asn Ala Gln Ala Gln Gln
                100                 105                 110

(2) INFORMATION FOR SEQ ID NO:16:

(i) SEQUENCE CHARACTERISTICS:
        (A) LENGTH: 111 amino acids
        (B) TYPE: amino acid
```

(D) TOPOLOGY: linear (ii) MOLECULE TYPE: peptide (xi) SEQUENCE DESCRIPTION: SEQ ID NO:16:

Asn Cys Ser Asn Met Ile Asp Glu Ile Ile Thr His Leu Lys Gln Pro
1               5                   10                  15

Pro Leu Pro Leu Leu Asp Phe Asn Asn Leu Asn Gly Glu Asp Gln Asp
            20                  25                  30

Ile Leu Met Glu Asn Asn Leu Arg Arg Pro Asn Leu Glu Ala Phe Asn
        35                  40                  45

Arg Ala Val Lys Ser Leu Gln Asn Ala Ser Gly Ile Glu Ala Ile Leu
50                  55                  60

Arg Asn Leu Val Pro Cys Leu Pro Ser Ala Thr Ala Ala Pro Ser Arg
65                  70                  75                  80

His Pro Ile Thr Ile Lys Ala Gly Asp Trp Gln Glu Phe Arg Arg Lys
                85                  90                  95

Leu Thr Phe Tyr Leu Lys Thr Leu Glu Asn Ala Gln Ala Gln Gln
            100                 105                 110

(2) INFORMATION FOR SEQ ID NO:17:

(i) SEQUENCE CHARACTERISTICS:
         (A) LENGTH: 111 amino acids
         (B) TYPE: amino acid
         (D) TOPOLOGY: linear (ii) MOLECULE TYPE: peptide (xi) SEQUENCE DESCRIPTION: SEQ ID NO:17:

Asn Cys Ser Asn Met Ile Asp Glu Ile Ile Thr His Leu Lys Gln Pro
1               5                   10                  15

Pro Leu Pro Leu Leu Asp Phe Asn Asn Leu Asn Gly Glu Asp Gln Asp
            20                  25                  30

Ile Leu Met Glu Asn Asn Leu Arg Arg Pro Asn Leu Glu Ala Phe Asn
        35                  40                  45

Arg Ala Val Lys Ser Leu Gln Asn Ala Ser Ala Ile Glu Ser Ile Leu
50                  55                  60

Lys Asn Leu Leu Pro Cys Leu Pro Leu Ala Thr Ala Ala Pro Thr Arg
65                  70                  75                  80

His Pro Ile His Ile Lys Asp Gly Asp Trp Asn Glu Phe Arg Glu Lys
                85                  90                  95

Leu Thr Phe Tyr Leu Val Thr Leu Glu Gln Ala Gln Glu Gln Gln
            100                 105                 110

(2) INFORMATION FOR SEQ ID NO:18:

(i) SEQUENCE CHARACTERISTICS:
         (A) LENGTH: 111 amino acids
         (B) TYPE: amino acid
         (D) TOPOLOGY: linear (ii) MOLECULE TYPE: peptide (xi) SEQUENCE DESCRIPTION: SEQ ID NO:18:

Asn Cys Ser Asn Met Ile Asp Glu Ile Ile Thr His Leu Lys Gln Pro
1               5                   10                  15

Pro Leu Pro Leu Leu Asp Phe Asn Asn Leu Asn Gly Glu Asp Gln Asp
            20                  25                  30

Ile Leu Met Glu Asn Asn Leu Arg Arg Pro Asn Leu Glu Ala Phe Asn

```
             35                  40                  45
Arg Ala Val Lys Ser Leu Gln Asn Ala Ser Ala Ile Glu Ser Ile Leu
 50                  55                  60

Lys Asn Leu Leu Pro Cys Leu Pro Leu Ala Thr Ala Ala Pro Thr Arg
 65                  70                  75                  80

His Pro Ile His Ile Lys Asp Gly Asp Trp Asn Glu Phe Arg Glu Lys
                 85                  90                  95

Leu Thr Phe Tyr Leu Val Ser Leu Glu His Ala Gln Glu Gln Gln
                100                 105                 110
```

(2) INFORMATION FOR SEQ ID NO:19:

(i) SEQUENCE CHARACTERISTICS:
        (A) LENGTH: 111 amino acids
        (B) TYPE: amino acid
        (D) TOPOLOGY: linear (ii) MOLECULE TYPE: peptide (xi) SEQUENCE DESCRIPTION: SEQ ID NO:19:

```
Asn Cys Ser Asn Met Ile Asp Glu Ile Ile Thr His Leu Lys Gln Pro
 1               5                  10                  15

Pro Leu Pro Leu Leu Asp Phe Asn Asn Leu Asn Gly Glu Asp Gln Asp
                 20                  25                  30

Ile Leu Met Glu Asn Asn Leu Arg Arg Pro Asn Leu Glu Ala Phe Asn
                 35                  40                  45

Arg Ala Val Lys Ser Leu Gln Asn Ala Ser Gly Ile Glu Ala Ile Leu
 50                  55                  60

Arg Asn Leu Gln Pro Cys Leu Pro Ser Ala Thr Ala Ala Pro Ser Arg
 65                  70                  75                  80

His Pro Ile Ile Ile Lys Ala Gly Asp Trp Gln Glu Phe Arg Glu Lys
                 85                  90                  95

Leu Thr Phe Tyr Leu Val Thr Leu Glu Gln Ala Gln Glu Gln Gln
                100                 105                 110
```

(2) INFORMATION FOR SEQ ID NO:20:

(i) SEQUENCE CHARACTERISTICS:
        (A) LENGTH: 111 amino acids
        (B) TYPE: amino acid
        (D) TOPOLOGY: linear (ii) MOLECULE TYPE: peptide (xi) SEQUENCE DESCRIPTION: SEQ ID NO:20:

```
Asn Cys Ser Asn Met Ile Asp Glu Ile Ile Thr His Leu Lys Gln Pro
 1               5                  10                  15

Pro Leu Pro Leu Leu Asp Phe Asn Asn Leu Asn Gly Glu Asp Gln Asp
                 20                  25                  30

Ile Leu Met Glu Asn Asn Leu Arg Arg Pro Asn Leu Glu Ala Phe Asn
                 35                  40                  45

Arg Ala Val Lys Ser Leu Gln Asn Ala Ser Gly Ile Glu Ala Ile Leu
 50                  55                  60

Arg Asn Leu Val Pro Cys Leu Pro Ser Ala Thr Ala Ala Pro Ser Arg
 65                  70                  75                  80

His Pro Ile Thr Ile Lys Ala Gly Asp Trp Gln Glu Phe Arg Glu Lys
                 85                  90                  95

Leu Thr Phe Tyr Leu Val Thr Leu Glu Gln Ala Gln Glu Gln Gln
                100                 105                 110
```

(2) INFORMATION FOR SEQ ID NO:21:

(i) SEQUENCE CHARACTERISTICS:
        (A) LENGTH: 111 amino acids
        (B) TYPE: amino acid
        (D) TOPOLOGY: linear (ii) MOLECULE TYPE: peptide (xi) SEQUENCE DESCRIPTION: SEQ ID NO:21:

```
Asn Cys Ser Asn Met Ile Asp Glu Ile Ile Thr His Leu Lys Gln Pro
1               5                   10                  15

Pro Leu Pro Leu Leu Asp Phe Asn Asn Leu Asn Gly Glu Asp Gln Asp
            20                  25                  30

Ile Leu Met Glu Asn Asn Leu Arg Arg Pro Asn Leu Glu Ala Phe Asn
            35                  40                  45

Arg Ala Val Lys Ser Leu Gln Asn Ala Ser Gly Ile Glu Ala Ile Leu
        50                  55                  60

Arg Asn Leu Val Pro Cys Leu Pro Ser Ala Thr Ala Ala Pro Ser Arg
65                  70                  75                  80

His Pro Ile Thr Ile Lys Ala Gly Asp Trp Gln Glu Phe Arg Glu Lys
                85                  90                  95

Leu Thr Phe Tyr Leu Val Ser Leu Glu His Ala Gln Glu Gln Gln
                100                 105                 110
```

(2) INFORMATION FOR SEQ ID NO:22:

(i) SEQUENCE CHARACTERISTICS:
        (A) LENGTH: 111 amino acids
        (B) TYPE: amino acid
        (D) TOPOLOGY: linear (ii) MOLECULE TYPE: peptide (xi) SEQUENCE DESCRIPTION: SEQ ID NO:22:

```
Asn Cys Ser Ile Met Ile Asp Glu Ile Ile His His Leu Lys Arg Pro
1               5                   10                  15

Pro Ala Pro Leu Leu Asp Pro Asn Asn Leu Asn Ala Glu Asp Val Asp
            20                  25                  30

Ile Leu Met Glu Arg Asn Leu Arg Leu Pro Asn Leu Glu Ser Phe Val
            35                  40                  45

Arg Ala Val Lys Asn Leu Glu Asn Ala Ser Ala Ile Glu Ser Ile Leu
        50                  55                  60

Lys Asn Leu Leu Pro Cys Leu Pro Leu Ala Thr Ala Ala Pro Thr Arg
65                  70                  75                  80

His Pro Ile His Ile Lys Asp Gly Asp Trp Asn Glu Phe Arg Arg Lys
                85                  90                  95

Leu Thr Phe Tyr Leu Lys Thr Leu Glu Asn Ala Gln Ala Gln Gln
                100                 105                 110
```

(2) INFORMATION FOR SEQ ID NO:23:

(i) SEQUENCE CHARACTERISTICS:
        (A) LENGTH: 111 amino acids
        (B) TYPE: amino acid
        (D) TOPOLOGY: linear (ii) MOLECULE TYPE: peptide (xi) SEQUENCE DESCRIPTION: SEQ ID NO:23:

```
Asn Cys Ser Ile Met Ile Asp Glu Ile Ile His His Leu Lys Arg Pro
 1               5                  10                  15

Pro Asn Pro Leu Leu Asp Pro Asn Asn Leu Asn Ser Glu Asp Met Asp
                20                  25                  30

Ile Leu Met Glu Arg Asn Leu Arg Thr Pro Asn Leu Leu Ala Phe Val
            35                  40                  45

Arg Ala Val Lys His Leu Glu Asn Ala Ser Ala Ile Glu Ser Ile Leu
        50                  55                  60

Lys Asn Leu Leu Pro Cys Leu Pro Leu Ala Thr Ala Ala Pro Thr Arg
 65                  70                  75                  80

His Pro Ile His Ile Lys Asp Gly Asp Trp Asn Glu Phe Arg Arg Lys
                85                  90                  95

Leu Thr Phe Tyr Leu Lys Thr Leu Glu Asn Ala Gln Ala Gln Gln
                100                 105                 110

(2) INFORMATION FOR SEQ ID NO:24:

(i) SEQUENCE CHARACTERISTICS:
        (A) LENGTH: 111 amino acids
        (B) TYPE: amino acid
        (D) TOPOLOGY: linear (ii) MOLECULE TYPE: peptide (xi) SEQUENCE DESCRIPTION: SEQ ID NO:24:

Asn Cys Ser Ile Met Ile Asp Glu Ile Ile His His Leu Lys Val Pro
 1               5                  10                  15

Pro Ala Pro Leu Leu Asp Ser Asn Asn Leu Asn Ser Glu Asp Met Asp
                20                  25                  30

Ile Leu Met Glu Arg Asn Leu Arg Leu Pro Asn Leu Leu Ala Phe Val
            35                  40                  45

Arg Ala Val Lys Asn Leu Glu Asn Ala Ser Ala Ile Glu Ser Ile Leu
        50                  55                  60

Lys Asn Leu Leu Pro Cys Leu Pro Leu Ala Thr Ala Ala Pro Thr Arg
 65                  70                  75                  80

His Pro Ile His Ile Lys Asp Gly Asp Trp Asn Glu Phe Arg Arg Lys
                85                  90                  95

Leu Thr Phe Tyr Leu Lys Thr Leu Glu Asn Ala Gln Ala Gln Gln
                100                 105                 110

(2) INFORMATION FOR SEQ ID NO:25:

(i) SEQUENCE CHARACTERISTICS:
        (A) LENGTH: 113 amino acids
        (B) TYPE: amino acid
        (D) TOPOLOGY: linear (ii) MOLECULE TYPE: peptide (xi) SEQUENCE DESCRIPTION: SEQ ID NO:25:

Met Ala Asn Cys Ser Asn Met Ile Asp Glu Ile Ile Thr His Leu Lys
 1               5                  10                  15

Gln Pro Pro Leu Pro Leu Leu Asp Phe Asn Asn Leu Asn Gly Glu Asp
                20                  25                  30

Gln Asp Ile Leu Met Glu Asn Asn Leu Arg Arg Pro Asn Leu Glu Ala
            35                  40                  45

Phe Asn Arg Ala Val Lys Ser Leu Gln Asn Ala Ser Gly Ile Glu Ala
        50                  55                  60

Ile Leu Arg Asn Leu Gln Pro Cys Leu Pro Ser Ala Thr Ala Ala Pro
```

```
                65                  70                  75                  80
Ser Arg His Pro Ile Ile Lys Ala Gly Asp Trp Gln Glu Phe Arg
                    85                  90                  95

Glu Lys Leu Thr Phe Tyr Leu Val Thr Leu Glu Gln Ala Gln Glu Gln
                    100                 105                 110

Gln
```

(2) INFORMATION FOR SEQ ID NO:26:

(i) SEQUENCE CHARACTERISTICS:
        (A) LENGTH: 113 amino acids
        (B) TYPE: amino acid
        (D) TOPOLOGY: linear (ii) MOLECULE TYPE: peptide (xi) SEQUENCE DESCRIPTION: SEQ ID NO:26:

```
Met Ala Asn Cys Ser Asn Met Ile Asp Glu Ile Ile Thr His Leu Lys
1               5                   10                  15

Gln Pro Pro Leu Pro Leu Leu Asp Phe Asn Asn Leu Asn Gly Glu Asp
                20                  25                  30

Gln Asp Ile Leu Met Glu Asn Asn Leu Arg Arg Pro Asn Leu Glu Ala
                35                  40                  45

Phe Asn Arg Ala Val Lys Ser Leu Gln Asn Ala Ser Gly Ile Glu Ala
            50                  55                  60

Ile Leu Arg Asn Leu Val Pro Cys Leu Pro Ser Ala Thr Ala Ala Pro
65                  70                  75                  80

Ser Arg His Pro Ile Thr Ile Lys Ala Gly Asp Trp Gln Glu Phe Arg
                    85                  90                  95

Glu Lys Leu Thr Phe Tyr Leu Val Thr Leu Glu Gln Ala Gln Glu Gln
                    100                 105                 110

Gln
```

(2) INFORMATION FOR SEQ ID NO:27:

(i) SEQUENCE CHARACTERISTICS:
        (A) LENGTH: 113 amino acids
        (B) TYPE: amino acid
        (D) TOPOLOGY: linear (ii) MOLECULE TYPE: peptide (xi) SEQUENCE DESCRIPTION: SEQ ID NO:27:

```
Met Ala Asn Cys Ser Asn Met Ile Asp Glu Ile Ile Thr His Leu Lys
1               5                   10                  15

Gln Pro Pro Leu Pro Leu Leu Asp Phe Asn Asn Leu Asn Gly Glu Asp
                20                  25                  30

Gln Asp Ile Leu Met Glu Asn Asn Leu Arg Arg Pro Asn Leu Glu Ala
                35                  40                  45

Phe Asn Arg Ala Val Lys Ser Leu Gln Asn Ala Ser Gly Ile Glu Ala
            50                  55                  60

Ile Leu Arg Asn Leu Val Pro Cys Leu Pro Ser Ala Thr Ala Ala Pro
65                  70                  75                  80

Ser Arg His Pro Ile Thr Ile Lys Ala Gly Asp Trp Gln Glu Phe Arg
                    85                  90                  95

Glu Lys Leu Thr Phe Tyr Leu Val Ser Leu Glu His Ala Gln Glu Gln
                    100                 105                 110

Gln
```

(2) INFORMATION FOR SEQ ID NO:28:

(i) SEQUENCE CHARACTERISTICS:
        (A) LENGTH: 113 amino acids
        (B) TYPE: amino acid
        (D) TOPOLOGY: linear (ii) MOLECULE TYPE: peptide (xi) SEQUENCE DESCRIPTION: SEQ ID NO:28:

```
Met Ala Asn Cys Ser Ile Met Ile Asp Glu Ile Ile His His Leu Lys
1               5                  10                  15

Arg Pro Pro Ala Pro Leu Leu Asp Pro Asn Asn Leu Asn Ala Glu Asp
            20                  25                  30

Val Asp Ile Leu Met Glu Arg Asn Leu Arg Leu Pro Asn Leu Glu Ser
        35                  40                  45

Phe Val Arg Ala Val Lys Asn Leu Glu Asn Ala Ser Ala Ile Glu Ser
    50                  55                  60

Ile Leu Lys Asn Leu Leu Pro Cys Leu Pro Leu Ala Thr Ala Ala Pro
65                  70                  75                  80

Thr Arg His Pro Ile His Ile Lys Asp Gly Asp Trp Asn Glu Phe Arg
                85                  90                  95

Arg Lys Leu Thr Phe Tyr Leu Lys Thr Leu Glu Asn Ala Gln Ala Gln
            100                 105                 110

Gln
```

(2) INFORMATION FOR SEQ ID NO:29:

(i) SEQUENCE CHARACTERISTICS:
        (A) LENGTH: 113 amino acids
        (B) TYPE: amino acid
        (D) TOPOLOGY: linear (ii) MOLECULE TYPE: peptide (xi) SEQUENCE DESCRIPTION: SEQ ID NO:29:

```
Met Ala Asn Cys Ser Ile Met Ile Asp Glu Ile Ile His His Leu Lys
1               5                  10                  15

Arg Pro Pro Asn Pro Leu Leu Asp Pro Asn Asn Leu Asn Ser Glu Asp
            20                  25                  30

Met Asp Ile Leu Met Glu Arg Asn Leu Arg Thr Pro Asn Leu Leu Ala
        35                  40                  45

Phe Val Arg Ala Val Lys His Leu Glu Asn Ala Ser Ala Ile Glu Ser
    50                  55                  60

Ile Leu Lys Asn Leu Leu Pro Cys Leu Pro Leu Ala Thr Ala Ala Pro
65                  70                  75                  80

Thr Arg His Pro Ile His Ile Lys Asp Gly Asp Trp Asn Glu Phe Arg
                85                  90                  95

Arg Lys Leu Thr Phe Tyr Leu Lys Thr Leu Glu Asn Ala Gln Ala Gln
            100                 105                 110

Gln
```

(2) INFORMATION FOR SEQ ID NO:30:

(i) SEQUENCE CHARACTERISTICS:
        (A) LENGTH: 113 amino acids
        (B) TYPE: amino acid
        (D) TOPOLOGY: linear (ii) MOLECULE TYPE: peptide (xi) SEQUENCE DESCRIPTION: SEQ ID NO:30:

Met Ala Asn Cys Ser Ile Met Ile Asp Glu Ile Ile His His Leu Lys
1               5                   10                  15

Val Pro Pro Ala Pro Leu Leu Asp Ser Asn Asn Leu Asn Ser Glu Asp
                20                  25                  30

Met Asp Ile Leu Met Glu Arg Asn Leu Arg Leu Pro Asn Leu Leu Ala
            35                  40                  45

Phe Val Arg Ala Val Lys Asn Leu Glu Asn Ala Ser Ala Ile Glu Ser
        50                  55                  60

Ile Leu Lys Asn Leu Leu Pro Cys Leu Pro Leu Ala Thr Ala Ala Pro
65                  70                  75                  80

Thr Arg His Pro Ile His Ile Lys Asp Gly Asp Trp Asn Glu Phe Arg
                85                  90                  95

Arg Lys Leu Thr Phe Tyr Leu Lys Thr Leu Glu Asn Ala Gln Ala Gln
                100                 105                 110

Gln (2) INFORMATION FOR SEQ ID NO:31:

(i) SEQUENCE CHARACTERISTICS:
            (A) LENGTH: 113 amino acids
            (B) TYPE: amino acid
            (D) TOPOLOGY: linear (ii) MOLECULE TYPE: peptide (xi) SEQUENCE DESCRIPTION: SEQ ID NO:31:

Met Ala Asn Cys Ser Ile Met Ile Asp Glu Ile Ile His His Leu Lys
1               5                   10                  15

Arg Pro Pro Ala Pro Leu Leu Asp Pro Asn Asn Leu Asn Ala Glu Asp
                20                  25                  30

Val Asp Ile Leu Met Glu Arg Asn Leu Arg Leu Pro Asn Leu Glu Ser
            35                  40                  45

Phe Val Arg Ala Val Lys Asn Leu Glu Asn Ala Ser Gly Ile Glu Ala
        50                  55                  60

Ile Leu Arg Asn Leu Gln Pro Cys Leu Pro Ser Ala Thr Ala Ala Pro
65                  70                  75                  80

Ser Arg His Pro Ile Ile Ile Lys Ala Gly Asp Trp Gln Glu Phe Arg
                85                  90                  95

Glu Lys Leu Thr Phe Tyr Leu Val Thr Leu Glu Gln Ala Gln Glu Gln
                100                 105                 110

Gln (2) INFORMATION FOR SEQ ID NO:32:

(i) SEQUENCE CHARACTERISTICS:
            (A) LENGTH: 113 amino acids
            (B) TYPE: amino acid
            (D) TOPOLOGY: linear (ii) MOLECULE TYPE: peptide (xi) SEQUENCE DESCRIPTION: SEQ ID NO:32:

Met Ala Asn Cys Ser Ile Met Ile Asp Glu Ile Ile His His Leu Lys
1               5                   10                  15

Arg Pro Pro Asn Pro Leu Leu Asp Pro Asn Asn Leu Asn Ser Glu Asp
                20                  25                  30

```
Met Asp Ile Leu Met Glu Arg Asn Leu Arg Thr Pro Asn Leu Leu Ala
        35                  40                  45

Phe Val Arg Ala Val Lys His Leu Glu Asn Ala Ser Gly Ile Glu Ala
    50                  55                  60

Ile Leu Arg Asn Leu Gln Pro Cys Leu Pro Ser Ala Thr Ala Ala Pro
65                  70                  75                  80

Ser Arg His Pro Ile Ile Ile Lys Ala Gly Asp Trp Gln Glu Phe Arg
                85                  90                  95

Glu Lys Leu Thr Phe Tyr Leu Val Thr Leu Glu Gln Ala Gln Glu Gln
            100                 105                 110

Gln
```

(2) INFORMATION FOR SEQ ID NO:33:

(i) SEQUENCE CHARACTERISTICS:
        (A) LENGTH: 113 amino acids
        (B) TYPE: amino acid
        (D) TOPOLOGY: linear (ii) MOLECULE TYPE: peptide (xi) SEQUENCE DESCRIPTION: SEQ ID NO:33:

```
Met Ala Asn Cys Ser Ile Met Ile Asp Glu Ile Ile His His Leu Lys
1               5                   10                  15

Val Pro Pro Ala Pro Leu Leu Asp Ser Asn Asn Leu Asn Ser Glu Asp
            20                  25                  30

Met Asp Ile Leu Met Glu Arg Asn Leu Arg Leu Pro Asn Leu Leu Ala
        35                  40                  45

Phe Val Arg Ala Val Lys Asn Leu Glu Asn Ala Ser Gly Ile Glu Ala
    50                  55                  60

Ile Leu Arg Asn Leu Gln Pro Cys Leu Pro Ser Ala Thr Ala Ala Pro
65                  70                  75                  80

Ser Arg His Pro Ile Ile Ile Lys Ala Gly Asp Trp Gln Glu Phe Arg
                85                  90                  95

Glu Lys Leu Thr Phe Tyr Leu Val Thr Leu Glu Gln Ala Gln Glu Gln
            100                 105                 110

Gln
```

(2) INFORMATION FOR SEQ ID NO:34:

(i) SEQUENCE CHARACTERISTICS:
        (A) LENGTH: 113 amino acids
        (B) TYPE: amino acid
        (D) TOPOLOGY: linear (ii) MOLECULE TYPE: peptide (xi) SEQUENCE DESCRIPTION: SEQ ID NO:34:

```
Met Ala Asn Cys Ser Ile Met Ile Asp Glu Ile Ile His His Leu Lys
1               5                   10                  15

Arg Pro Pro Ala Pro Leu Leu Asp Pro Asn Asn Leu Asn Ala Glu Asp
            20                  25                  30

Val Asp Ile Leu Met Glu Arg Asn Leu Arg Leu Pro Asn Leu Glu Ser
        35                  40                  45

Phe Val Arg Ala Val Lys Asn Leu Glu Asn Ala Ser Gly Ile Glu Ala
    50                  55                  60

Ile Leu Arg Asn Leu Val Pro Cys Leu Pro Ser Ala Thr Ala Ala Pro
65                  70                  75                  80
```

```
Ser Arg His Pro Ile Thr Ile Lys Ala Gly Asp Trp Gln Glu Phe Arg
            85                  90                  95

Glu Lys Leu Thr Phe Tyr Leu Val Thr Leu Glu Gln Ala Gln Glu Gln
            100                 105                 110

Gln
```

(2) INFORMATION FOR SEQ ID NO:35:

(i) SEQUENCE CHARACTERISTICS:
        (A) LENGTH: 113 amino acids
        (B) TYPE: amino acid
        (D) TOPOLOGY: linear (ii) MOLECULE TYPE: peptide (xi) SEQUENCE DESCRIPTION: SEQ ID NO:35:

```
Met Ala Asn Cys Ser Ile Met Ile Asp Glu Ile Ile His His Leu Lys
1               5                   10                  15

Val Pro Pro Ala Pro Leu Leu Asp Ser Asn Asn Leu Asn Ser Glu Asp
            20                  25                  30

Met Asp Ile Leu Met Glu Arg Asn Leu Arg Leu Pro Asn Leu Leu Ala
            35                  40                  45

Phe Val Arg Ala Val Lys Asn Leu Glu Asn Ala Ser Gly Ile Glu Ala
        50                  55                  60

Ile Leu Arg Asn Leu Val Pro Cys Leu Pro Ser Ala Thr Ala Ala Pro
65                  70                  75                  80

Ser Arg His Pro Ile Thr Ile Lys Ala Gly Asp Trp Gln Glu Phe Arg
            85                  90                  95

Glu Lys Leu Thr Phe Tyr Leu Val Thr Leu Glu Gln Ala Gln Glu Gln
            100                 105                 110

Gln
```

(2) INFORMATION FOR SEQ ID NO:36:

(i) SEQUENCE CHARACTERISTICS:
        (A) LENGTH: 113 amino acids
        (B) TYPE: amino acid
        (D) TOPOLOGY: linear (ii) MOLECULE TYPE: peptide (xi) SEQUENCE DESCRIPTION: SEQ ID NO:36:

```
Met Ala Asn Cys Ser Ile Met Ile Asp Glu Ile Ile His His Leu Lys
1               5                   10                  15

Arg Pro Pro Asn Pro Leu Leu Asp Pro Asn Asn Leu Asn Ser Glu Asp
            20                  25                  30

Met Asp Ile Leu Met Glu Arg Asn Leu Arg Thr Pro Asn Leu Leu Ala
            35                  40                  45

Phe Val Arg Ala Val Lys His Leu Glu Asn Ala Ser Gly Ile Glu Ala
        50                  55                  60

Ile Leu Arg Asn Leu Val Pro Cys Leu Pro Ser Ala Thr Ala Ala Pro
65                  70                  75                  80

Ser Arg His Pro Ile Thr Ile Lys Ala Gly Asp Trp Gln Glu Phe Arg
            85                  90                  95

Glu Lys Leu Thr Phe Tyr Leu Val Ser Leu Glu His Ala Gln Glu Gln
            100                 105                 110

Gln
```

(2) INFORMATION FOR SEQ ID NO:37:

(i) SEQUENCE CHARACTERISTICS:
        (A) LENGTH: 113 amino acids
        (B) TYPE: amino acid
        (D) TOPOLOGY: linear (ii) MOLECULE TYPE: peptide (xi) SEQUENCE DESCRIPTION: SEQ ID NO:37:

```
Met Ala Asn Cys Ser Ile Met Ile Asp Glu Ile Ile His His Leu Lys
1               5                   10                  15

Val Pro Pro Ala Pro Leu Leu Asp Ser Asn Asn Leu Asn Ser Glu Asp
                20                  25                  30

Met Asp Ile Leu Met Glu Arg Asn Leu Arg Leu Pro Asn Leu Leu Ala
            35                  40                  45

Phe Val Arg Ala Val Lys Asn Leu Glu Asn Ala Ser Gly Ile Glu Ala
        50                  55                  60

Ile Leu Arg Asn Leu Val Pro Cys Leu Pro Ser Ala Thr Ala Ala Pro
65                  70                  75                  80

Ser Arg His Pro Ile Thr Ile Lys Ala Gly Asp Trp Gln Glu Phe Arg
                85                  90                  95

Glu Lys Leu Thr Phe Tyr Leu Val Ser Leu Glu His Ala Gln Glu Gln
                100                 105                 110

Gln
```

(2) INFORMATION FOR SEQ ID NO:38:

(i) SEQUENCE CHARACTERISTICS:
        (A) LENGTH: 113 amino acids
        (B) TYPE: amino acid
        (D) TOPOLOGY: linear (ii) MOLECULE TYPE: peptide (xi) SEQUENCE DESCRIPTION: SEQ ID NO:38:

```
Met Ala Asn Cys Ser Ile Met Ile Asp Glu Ile Ile His His Leu Lys
1               5                   10                  15

Arg Pro Pro Asn Pro Leu Leu Asp Pro Asn Asn Leu Asn Ser Glu Asp
                20                  25                  30

Met Asp Ile Leu Met Glu Arg Asn Leu Arg Thr Pro Asn Leu Leu Ala
            35                  40                  45

Phe Val Arg Ala Val Lys His Leu Glu Asn Ala Ser Gly Ile Glu Ala
        50                  55                  60

Ile Leu Arg Asn Leu Val Pro Cys Leu Pro Ser Ala Thr Ala Ala Pro
65                  70                  75                  80

Ser Arg His Pro Ile Thr Ile Lys Ala Gly Asp Trp Gln Glu Phe Arg
                85                  90                  95

Glu Lys Leu Thr Phe Tyr Leu Val Thr Leu Glu Gln Ala Gln Glu Gln
                100                 105                 110

Gln
```

(2) INFORMATION FOR SEQ ID NO:39:

(i) SEQUENCE CHARACTERISTICS:
        (A) LENGTH: 113 amino acids
        (B) TYPE: amino acid
        (D) TOPOLOGY: linear (ii) MOLECULE TYPE: peptide (xi) SEQUENCE DESCRIPTION: SEQ ID NO:39:

Met Ala Asn Cys Ser Ile Met Ile Asp Glu Ile Ile His His Leu Lys
1               5                   10                  15

Arg Pro Pro Ala Pro Leu Leu Asp Pro Asn Asn Leu Asn Ala Glu Asp
                20                  25                  30

Val Asp Ile Leu Met Glu Arg Asn Leu Arg Leu Pro Asn Leu Glu Ser
            35                  40                  45

Phe Val Arg Ala Val Lys Asn Leu Glu Asn Ala Ser Gly Ile Glu Ala
        50                  55                  60

Ile Leu Arg Asn Leu Val Pro Cys Leu Pro Ser Ala Thr Ala Ala Pro
65                  70                  75                  80

Ser Arg His Pro Ile Thr Ile Lys Ala Gly Asp Trp Gln Glu Phe Arg
                85                  90                  95

Glu Lys Leu Thr Phe Tyr Leu Val Ser Leu Glu His Ala Gln Glu Gln
                100                 105                 110

Gln (2) INFORMATION FOR SEQ ID NO:40:

(i) SEQUENCE CHARACTERISTICS:
        (A) LENGTH: 113 amino acids
        (B) TYPE: amino acid
        (D) TOPOLOGY: linear (ii) MOLECULE TYPE: peptide (xi) SEQUENCE DESCRIPTION: SEQ ID NO:40:

Met Ala Asn Cys Ser Ile Met Ile Asp Glu Ile Ile His His Leu Lys
1               5                   10                  15

Arg Pro Pro Ala Pro Leu Leu Asp Pro Asn Asn Leu Asn Ala Glu Asp
                20                  25                  30

Val Asp Ile Leu Met Asp Arg Asn Leu Arg Leu Ser Asn Leu Glu Ser
            35                  40                  45

Phe Val Arg Ala Val Lys Asn Leu Glu Asn Ala Ser Gly Ile Glu Ala
        50                  55                  60

Ile Leu Arg Asn Leu Gln Pro Cys Leu Pro Ser Ala Thr Ala Ala Pro
65                  70                  75                  80

Ser Arg His Pro Ile Ile Ile Lys Ala Gly Asp Trp Gln Glu Phe Arg
                85                  90                  95

Glu Lys Leu Thr Phe Tyr Leu Val Thr Leu Glu Gln Ala Gln Glu Gln
                100                 105                 110

Gln (2) INFORMATION FOR SEQ ID NO:41:

(i) SEQUENCE CHARACTERISTICS:
        (A) LENGTH: 113 amino acids
        (B) TYPE: amino acid
        (D) TOPOLOGY: linear (ii) MOLECULE TYPE: peptide (xi) SEQUENCE DESCRIPTION: SEQ ID NO:41:

Met Ala Asn Cys Ser Ile Met Ile Asp Glu Ala Ile His His Leu Lys
1               5                   10                  15

Arg Pro Pro Ala Pro Ser Leu Asp Pro Asn Asn Leu Asn Asp Glu Asp
                20                  25                  30

```
Met Ser Ile Leu Met Glu Arg Asn Leu Arg Leu Pro Asn Leu Glu Ser
        35                  40                  45

Phe Val Arg Ala Val Lys Asn Leu Glu Asn Ala Ser Gly Ile Glu Ala
    50                  55                  60

Ile Leu Arg Asn Leu Gln Pro Cys Leu Pro Ser Ala Thr Ala Ala Pro
65                  70                  75                  80

Ser Arg His Pro Ile Ile Ile Lys Ala Gly Asp Trp Gln Glu Phe Arg
                85                  90                  95

Glu Lys Leu Thr Phe Tyr Leu Val Thr Leu Glu Gln Ala Gln Glu Gln
            100                 105                 110

Gln (2) INFORMATION FOR SEQ ID NO:42:

(i) SEQUENCE CHARACTERISTICS:
        (A) LENGTH: 113 amino acids
        (B) TYPE: amino acid
        (D) TOPOLOGY: linear (ii) MOLECULE TYPE: peptide (xi) SEQUENCE DESCRIPTION: SEQ ID NO:42:

Met Ala Asn Cys Ser Ile Met Ile Asp Glu Ile Ile His His Leu Lys
1               5                   10                  15

Arg Pro Pro Ala Pro Leu Leu Asp Pro Asn Asn Leu Asn Asp Glu Asp
                20                  25                  30

Met Ser Ile Leu Met Glu Arg Asn Leu Arg Leu Pro Asn Leu Glu Ser
        35                  40                  45

Phe Val Arg Ala Val Lys Asn Leu Glu Asn Ala Ser Gly Ile Glu Ala
    50                  55                  60

Ile Leu Arg Asn Leu Gln Pro Cys Leu Pro Ser Ala Thr Ala Ala Pro
65                  70                  75                  80

Ser Arg His Pro Ile Ile Ile Lys Ala Gly Asp Trp Gln Glu Phe Arg
                85                  90                  95

Glu Lys Leu Thr Phe Tyr Leu Val Thr Leu Glu Gln Ala Gln Glu Gln
            100                 105                 110

Gln (2) INFORMATION FOR SEQ ID NO:43:

(i) SEQUENCE CHARACTERISTICS:
        (A) LENGTH: 113 amino acids
        (B) TYPE: amino acid
        (D) TOPOLOGY: linear (ii) MOLECULE TYPE: peptide (xi) SEQUENCE DESCRIPTION: SEQ ID NO:43:

Met Ala Asn Cys Ser Ile Met Ile Asp Glu Ile Ile His His Leu Lys
1               5                   10                  15

Arg Pro Pro Ala Pro Leu Leu Asp Pro Asn Asn Leu Asn Ala Glu Asp
                20                  25                  30

Val Asp Ile Leu Met Asp Arg Asn Leu Arg Leu Pro Asn Leu Glu Ser
        35                  40                  45

Phe Val Arg Ala Val Lys Asn Leu Glu Asn Ala Ser Gly Ile Glu Ala
    50                  55                  60

Ile Leu Arg Asn Leu Gln Pro Cys Leu Pro Ser Ala Thr Ala Ala Pro
65                  70                  75                  80
```

```
Ser Arg His Pro Ile Ile Ile Lys Ala Gly Asp Trp Gln Glu Phe Arg
                85                  90                  95

Glu Lys Leu Thr Phe Tyr Leu Val Thr Leu Glu Gln Ala Gln Glu Gln
            100                 105                 110

Gln
```

(2) INFORMATION FOR SEQ ID NO:44:

(i) SEQUENCE CHARACTERISTICS:
        (A) LENGTH: 113 amino acids
        (B) TYPE: amino acid
        (D) TOPOLOGY: linear (ii) MOLECULE TYPE: peptide (xi) SEQUENCE DESCRIPTION: SEQ ID NO:44:

```
Met Ala Asn Cys Ser Ile Met Ile Asp Glu Ile Ile His His Leu Lys
1               5                   10                  15

Arg Pro Pro Ala Pro Leu Leu Asp Pro Asn Asn Leu Asn Asp Glu Asp
                20                  25                  30

Val Ser Ile Leu Met Glu Arg Asn Leu Arg Leu Pro Asn Leu Glu Ser
            35                  40                  45

Phe Val Arg Ala Val Lys Asn Leu Glu Asn Ala Ser Gly Ile Glu Ala
        50                  55                  60

Ile Leu Arg Asn Leu Gln Pro Cys Leu Pro Ser Ala Thr Ala Ala Pro
65                  70                  75                  80

Ser Arg His Pro Ile Ile Ile Lys Ala Gly Asp Trp Gln Glu Phe Arg
                85                  90                  95

Glu Lys Leu Thr Phe Tyr Leu Val Thr Leu Glu Gln Ala Gln Glu Gln
            100                 105                 110

Gln
```

(2) INFORMATION FOR SEQ ID NO:45:

(i) SEQUENCE CHARACTERISTICS:
        (A) LENGTH: 113 amino acids
        (B) TYPE: amino acid
        (D) TOPOLOGY: linear (ii) MOLECULE TYPE: peptide (xi) SEQUENCE DESCRIPTION: SEQ ID NO:45:

```
Met Ala Asn Cys Ser Ile Met Ile Asp Glu Ile Ile His His Leu Lys
1               5                   10                  15

Arg Pro Pro Ala Pro Leu Leu Asp Pro Asn Asn Leu Asn Asp Glu Asp
                20                  25                  30

Met Ser Ile Leu Met Glu Arg Asn Leu Arg Leu Pro Asn Leu Glu Ser
            35                  40                  45

Phe Val Arg Ala Val Lys Asn Leu Glu Asn Ala Ser Gly Ile Glu Ala
        50                  55                  60

Ile Leu Arg Asn Leu Gln Pro Cys Leu Pro Ser Ala Thr Ala Ala Pro
65                  70                  75                  80

Ser Arg His Pro Ile Ile Ile Lys Ala Gly Asp Trp Gln Glu Phe Arg
                85                  90                  95

Glu Lys Leu Thr Phe Tyr Leu Val Thr Leu Glu Gln Ala Gln Glu Gln
            100                 105                 110

Gln
```

(2) INFORMATION FOR SEQ ID NO:46:

(i) SEQUENCE CHARACTERISTICS:
        (A) LENGTH: 125 amino acids
        (B) TYPE: amino acid
        (D) TOPOLOGY: linear (ii) MOLECULE TYPE: peptide (xi) SEQUENCE DESCRIPTION: SEQ ID NO:46:

```
Met Ala Tyr Pro Glu Thr Asp Tyr Lys Asp Asp Asp Lys Asn Cys
 1               5                  10                  15

Ser Ile Met Ile Asp Glu Ile Ile His His Leu Lys Arg Pro Pro Ala
             20                  25                  30

Pro Leu Leu Asp Pro Asn Asn Leu Asn Ala Glu Asp Val Asp Ile Leu
             35                  40                  45

Met Glu Arg Asn Leu Arg Leu Pro Asn Leu Glu Ser Phe Val Arg Ala
     50                  55                  60

Val Lys Asn Leu Glu Asn Ala Ser Gly Ile Glu Ala Ile Leu Arg Asn
 65                  70                  75                  80

Leu Gln Pro Cys Leu Pro Ser Ala Thr Ala Ala Pro Ser Arg His Pro
                 85                  90                  95

Ile Ile Ile Lys Ala Gly Asp Trp Gln Glu Phe Arg Glu Lys Leu Thr
                100                 105                 110

Phe Tyr Leu Val Thr Leu Glu Gln Ala Gln Glu Gln Gln
        115                 120                 125
```

(2) INFORMATION FOR SEQ ID NO:47:

(i) SEQUENCE CHARACTERISTICS:
        (A) LENGTH: 125 amino acids
        (B) TYPE: amino acid
        (D) TOPOLOGY: linear (ii) MOLECULE TYPE: peptide (xi) SEQUENCE DESCRIPTION: SEQ ID NO:47:

```
Met Ala Tyr Pro Glu Thr Asp Tyr Lys Asp Asp Asp Lys Asn Cys
 1               5                  10                  15

Ser Ile Met Ile Asp Glu Ile Ile His His Leu Lys Arg Pro Pro Asn
             20                  25                  30

Pro Leu Leu Asp Pro Asn Asn Leu Asn Ser Glu Asp Met Asp Ile Leu
             35                  40                  45

Met Glu Arg Asn Leu Arg Thr Pro Asn Leu Leu Ala Phe Val Arg Ala
     50                  55                  60

Val Lys His Leu Glu Asn Ala Ser Gly Ile Glu Ala Ile Leu Arg Asn
 65                  70                  75                  80

Leu Gln Pro Cys Leu Pro Ser Ala Thr Ala Ala Pro Ser Arg His Pro
                 85                  90                  95

Ile Ile Ile Lys Ala Gly Asp Trp Gln Glu Phe Arg Glu Lys Leu Thr
                100                 105                 110

Phe Tyr Leu Val Thr Leu Glu Gln Ala Gln Glu Gln Gln
        115                 120                 125
```

(2) INFORMATION FOR SEQ ID NO:48:

(i) SEQUENCE CHARACTERISTICS:
        (A) LENGTH: 113 amino acids
        (B) TYPE: amino acid
        (D) TOPOLOGY: linear (ii) MOLECULE TYPE: peptide (xi) SEQUENCE DESCRIPTION: SEQ ID NO:48:

Met Ala Asn Cys Ser Ile Met Ile Asp Glu Leu Ile His His Leu Lys
1               5                   10                  15

Ile Pro Pro Asn Pro Ser Leu Asp Ser Ala Asn Leu Asn Ser Glu Asp
                20                  25                  30

Val Ser Ile Leu Met Glu Arg Asn Leu Arg Thr Pro Asn Leu Leu Ala
            35                  40                  45

Phe Val Arg Ala Val Lys His Leu Glu Asn Ala Ser Gly Ile Glu Ala
        50                  55                  60

Ile Leu Arg Asn Leu Gln Pro Cys Leu Pro Ser Ala Thr Ala Ala Pro
65                  70                  75                  80

Ser Arg His Pro Ile Ile Ile Lys Ala Gly Asp Trp Gln Glu Phe Arg
                85                  90                  95

Glu Lys Leu Thr Phe Tyr Leu Val Thr Leu Glu Gln Ala Gln Glu Gln
                100                 105                 110

Gln (2) INFORMATION FOR SEQ ID NO:49:

(i) SEQUENCE CHARACTERISTICS:
        (A) LENGTH: 134 amino acids
        (B) TYPE: amino acid
        (D) TOPOLOGY: linear (ii) MOLECULE TYPE: peptide (xi) SEQUENCE DESCRIPTION: SEQ ID NO:49:

Met Ala Pro Met Thr Gln Thr Thr Ser Leu Lys Thr Ser Trp Val Asn
1               5                   10                  15

Cys Ser Asn Met Ile Asp Glu Ile Ile Thr His Leu Lys Gln Pro Pro
                20                  25                  30

Leu Pro Leu Leu Asp Phe Asn Asn Leu Asn Gly Glu Asp Gln Asp Ile
            35                  40                  45

Leu Met Glu Asn Asn Leu Arg Arg Pro Asn Leu Glu Ala Phe Asn Arg
        50                  55                  60

Ala Val Lys Ser Leu Gln Asn Ala Ser Ala Ile Glu Ser Ile Leu Lys
65                  70                  75                  80

Asn Leu Leu Pro Cys Leu Pro Leu Ala Thr Ala Ala Pro Thr Arg His
                85                  90                  95

Pro Ile His Ile Lys Asp Gly Asp Trp Asn Glu Phe Arg Arg Lys Leu
                100                 105                 110

Thr Phe Tyr Leu Lys Thr Leu Glu Asn Ala Gln Ala Gln Gln Thr Thr
            115                 120                 125

Leu Ser Leu Ala Ile Phe
    130

(2) INFORMATION FOR SEQ ID NO:50:

(i) SEQUENCE CHARACTERISTICS:
        (A) LENGTH: 36 amino acids
        (B) TYPE: amino acid
        (D) TOPOLOGY: linear (ii) MOLECULE TYPE: peptide (xi) SEQUENCE DESCRIPTION: SEQ ID NO:50:

Gly Gly Gly Ser Gly Gly Gly Ser Gly Gly Gly Ser Glu Gly Gly Gly

```
                1               5              10              15
Ser Glu Gly Gly Gly Ser Glu Gly Gly Gly Ser Glu Gly Gly Gly Ser
                               20              25              30

Gly Gly Gly Ser
            35
```

(2) INFORMATION FOR SEQ ID NO:51:

(i) SEQUENCE CHARACTERISTICS:
        (A) LENGTH: 24 amino acids
        (B) TYPE: amino acid
        (D) TOPOLOGY: linear (ii) MOLECULE TYPE: peptide (xi) SEQUENCE DESCRIPTION: SEQ ID NO:51:

```
Ile Ser Glu Pro Ser Gly Pro Ile Ser Thr Ile Asn Pro Ser Pro Pro
1               5                  10                  15

Ser Lys Glu Ser His Lys Ser Pro
                20
```

(2) INFORMATION FOR SEQ ID NO:52:

(i) SEQUENCE CHARACTERISTICS:
        (A) LENGTH: 28 amino acids
        (B) TYPE: amino acid
        (D) TOPOLOGY: linear (ii) MOLECULE TYPE: peptide (xi) SEQUENCE DESCRIPTION: SEQ ID NO:52:

```
Ile Glu Gly Arg Ile Ser Glu Pro Ser Gly Pro Ile Ser Thr Ile Asn
1               5                  10                  15

Pro Ser Pro Pro Ser Lys Glu Ser His Lys Ser Pro
                20                  25
```

(2) INFORMATION FOR SEQ ID NO:53:

(i) SEQUENCE CHARACTERISTICS:
        (A) LENGTH: 408 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:53:

```
ATGGCTCCAA TGACTCAGAC TACTTCTCTT AAGACTTCTT GGGTTAACTG CTCTAACATG      60

ATCGATGAAA TTATAACACA CTTAAAGCAG CCACCTTTGC CTTTGCTGGA CTTCAACAAC     120

CTCAATGGGG AAGACCAAGA CATTCTGATG GAAAATAACC TTCGAAGGCC AAACCTGGAG     180

GCATTCAACA GGGCTGTCAA GAGTTTACAG AATGCATCAG CAATTGAGAG CATTCTTAAA     240

AATCTCCTGC CATGTCTGCC CCTGGCCACG GCCGCACCCA CGCGACATCC AATCCATATC     300

AAGGACGGTG ACTGGAATGA ATTCCGTCGT AAACTGACCT TCTATCTGAA AACCTTGGAG     360

AACGCGCAGG CTCAACAGAC CACTCTGTCG CTAGCGATCT TTTAATAA                  408
```

What is claimed is:

1. A fusion protein comprising a sequence of the formula selected from the group consisting of:

$R_1$-L-$R_2$, $R_2$-L-$R_1$, $R_1$-$R_2$, $R_2$-L-$R_1$, Met-Ala-$R_1$-L-$R_2$, Met-Ala-$R_2$-L-$R_1$, Met-Ala-$R_1$-$R_2$, Met-Ala-$R_2$-$R_1$, Met-$R_1$-L-$R_2$, Met-$R_2$-L-$R_1$, Met-$R_1$-$R_2$, Met-$R_2$-$R_1$, Ala-$R_1$-L-$R_2$, Ala-$R_2$-L-$R_1$, Ala-$R_1$-$R_2$ and Ala-$R_2$-$R_1$;

wherein $R_1$ is a mutant human interleukin-3 polypeptide comprising a modified hIL-3 amino acid sequence of SEQ ID NO:1;

wherein

Xaa at position 17 is Ser, Lys, Gly, Asp, Met, Gln or Arg;
Xaa at position 18 is Asn, His, Leu, Ile, Phe, Arg or Gln;
Xaa at position 19 is Met, Phe, Ile, Arg, Gly, Ala or Cys;
Xaa at position 20 is Ile, Cys, Gln, Glu, Arg, Pro or Ala;
Xaa at position 21 is Asp, Phe, Lys, Arg, Ala, Gly, Glu, Gln, Asn, Thr, Ser or Val;
Xaa at position 22 is Glu, Trp, Pro, Ser, Ala, His, Asp, Asn, Gin, Leu, Val or Gly;
Xaa at position 23 is Ile, Val, Ala, Leu, Gly, Trp, Lys, Phe, Ser or Arg;
Xaa at position 24 is Ile, Gly, Val, Arg, Ser, Phe or Leu;
Xaa at position 25 is Thr, His, Gly, Gln, Arg, Pro or Ala;
Xaa at position 26 is His, Thr, Phe, Gly, Arg, Ala or Trp;
Xaa at position 27 is Leu, Gly, Arg, Thr, Ser or Ala;
Xaa at position 28 is Lys, Arg, Leu, Gln, Gly, Pro, Val or Trp;
Xaa at position 29 is Gln, Asn, Leu, Pro, Arg or Val;
Xaa at position 30 is Pro, His, Thr, Gly, Asp, Gln, Ser, Leu or Lys;
Xaa at position 31 is Pro, Asp, Gly, Ala, Arg, Leu or Gln;
Xaa at position 32 is Leu, Val, Arg, Gln, Asn, Gly, Ala or Glu;
Xaa at position 33 is Pro, Leu, Gln, Ala, Thr or Glu;
Xaa at position 34 is Leu, Val, Gly, Ser, Lys, Glu, Gln, Thr, Arg, Ala, Phe, Ile or Met;
Xaa at position 35 is Leu, Ala, Gly, Asn, Pro, Gln or Val;
Xaa at position 36 is Asp, Leu or Val;
Xaa at position 37 is Phe, Ser, Pro, Trp or Ile;
Xaa at position 38 is Asn or Ala;
Xaa at position 40 is Leu, Trp or Arg;
Xaa at position 41 is Asn, Cys, Arg, Leu, His, Met or Pro;
Xaa at position 42 is Gly, Asp, Ser, Cys, Asn, Lys, Thr, Leu, Val, Glu, Phe, Tyr, Ile, Met or Ala;
Xaa at position 43 is Glu, Asn, Tyr, Leu, Phe, Asp, Ala, Cys, Gln, Arg, Thr, Gly or Ser;
Xaa at position 44 is Asp, Ser, Leu, Arg, Lys, Thr, Met, Trp, Glu, Asn, Gln, Ala or Pro;
Xaa at position 45 is Gln, Pro, Phe, Val, Met, Leu, Thr, Lys, Trp, Asp, Asn, Arg, Ser, Ala, Ile, Glu or His;
Xaa at position 46 is Asp, Phe, Ser, Thr, Cys, Glu, Asn, Gln, Lys, His, Ala, Tyr, Ile, Val or Gly;
Xaa at position 47 is Ile, Gly, Val, Ser, Arg, Pro or His;
Xaa at position 48 is Leu, Ser, Cys, Arg, Ile, His, Phe, Glu, Lys, Thr, Ala, Met, Val or Asn;
Xaa at position 49 is Met, Arg, Ala, Gly, Pro, Asn, His or Asp;
Xaa at position 50 is Glu, Leu, Thr, Asp, Tyr, Lys, Asn, Ser, Ala, Ile, Val, His, Phe, Met or Gln;
Xaa at position 51 is Asn, Arg, Met, Pro, Ser, Thr or His;
Xaa at position 52 is Asn, His, Arg, Leu, Gly, Ser or Thr;
Xaa at position 53 is Leu, Thr, Ala, Gly, Glu, Pro, Lys, Ser or Met;
Xaa at position 54 is Arg, Asp, Ile, Ser, Val, Thr, Gln, Asn, Lys, His, Ala or Leu;
Xaa at position 55 is Arg, Thr, Val, Ser, Leu or Gly;
Xaa at position 56 is Pro, Gly, Cys, Ser, Gln, Glu, Arg, His, Thr, Ala, Tyr, Phe, Leu, Val or Lys;
Xaa at position 57 is Asn or Gly;
Xaa at position 58 is Leu, Ser, Asp, Arg, Gln, Val or Cys;
Xaa at position 59 is Glu Tyr, His, Leu, Pro or Arg;
Xaa at position 60 is Ala, Ser, Pro, Tyr, Asn or Thr;
Xaa at position 61 is Phe, Asn, Glu, Pro, Lys, Arg or Ser;
Xaa at position 62 is Asn, His, Val, Arg, Pro, Thr, Asp or Ile;
Xaa at position 63 is Arg, Tyr, Trp, Ser, Pro or Val;
Xaa at position 64 is Ala, Asn, Pro, Ser or Lys;
Xaa at position 65 is Val, Thr, Pro, His, Leu, Phe or Ser;
Xaa at position 66 is Lys, Ile, Arg, Val, Asn, Glu or Ser;
Xaa at position 67 is Ser, Ala, Phe, Val, Gly, Asn, Ile, Pro or His;
Xaa at position 68 is Leu, Val, Trp, Ser, Ile, Phe, Thr or His;
Xaa at position 69 is Gln, Ala, Pro, Thr, Glu, Arg, Trp, Gly or Leu;
Xaa at position 70 is Asn, Leu, Val, Trp, Pro or Ala;
Xaa at position 71 is Ala, Met, Leu, Pro, Arg, Glu, Thr, Gln, Trp or Asn;
Xaa at position 72 is Ser, Glu, Met, Ala, His, Asn, Arg or Asp;
Xaa at position 73 is Ala, Glu, Asp, Leu, Ser, Gly, Thr or Arg;
Xaa at position 74 is Ile, Met, Thr, Pro, Arg, Gly, Ala;
Xaa at position 75 is Glu, Lys, Gly, Asp, Pro, Trp, Arg, Ser, Gln or Leu;
Xaa at position 76 is Ser, Val, Ala, Asn, Trp, Glu, Pro, Gly or Asp;
Xaa at position 77 is Ile, Ser, Arg, Thr or Leu;
Xaa at position 78 is Leu, Ala, Ser, Glu, Phe, Gly or Arg;
Xaa at position 79 is Lys, Thr, Asn, Met, Arg, Ile, Gly or Asp;
Xaa at position 80 is Asn, Trp, Val, Gly, Thr, Leu, Glu or Arg;
Xaa at position 81 is Leu, Gln, Gly, Ala, Trp, Arg, Val or Lys;
Xaa at position 82 is Leu, Gln, Lys, Trp, Arg, Asp, Glu, Asn, His, Thr, Ser, Ala, Tyr, Phe, Ile, Met or Val;
Xaa at position 83 is Pro, Ala, Thr, Trp, Arg or Met;
Xaa at position 84 is Cys, Glu, Gly, Arg, Met or Val;
Xaa at position 85 is Leu, Asn, Val or Gln;
Xaa at position 86 is Pro, Cys, Arg, Ala or Lys;
Xaa at position 87 is Leu, Ser, Trp or Gly;
Xaa at position 88 is Ala, Lys, Arg, Val or Trp;
Xaa at position 89 is Thr, Asp, Cys, Leu, Val, Glu, His, Asn or Ser;
Xaa at position 90 is Ala, Pro, Ser, Thr, Gly, Asp, Ile or Met;
Xaa at position 91 is Ala, Pro, Ser, Thr, Phe, Leu, Asp or His;
Xaa at position 92 is Pro, Phe, Arg, Ser, Lys, His, Ala, Gly, Ile or Leu;
Xaa at position 93 is Thr, Asp, Ser, Asn, Pro, Ala, Leu or Arg;
Xaa at position 94 is Arg, Ile, Ser, Glu, Leu, Val, Gln, Lys, His, Ala or Pro;
Xaa at position 95 is His, Gln, Pro, Val, Leu, Gly, Thr, Asn, Ser, Ala, Trp, Phe, Ile or Tyr;
Xaa at position 96 is Pro, Lys, Tyr, Gly, Ile or Thr;
Xaa at position 97 is Ile, Val, Lys, Ala or Asn;
Xaa at position 98 is His, Ile, Asn, Leu, Asp, Ala, Thr, Glu, Gln, Ser, Phe, Met, Val, Lys, Arg, Tyr or Pro;
Xaa at position 99 is Ile, Leu, Arg, Asp, Val, Pro, Gln, Gly, Ser, Phe or His;
Xaa at position 100 is Lys, Tyr, Leu, His, Arg, Ile, Ser, Gln or Pro;
Xaa at position 101 is Asp;
Xaa at position 102 is Gly, Leu, Glu, Lys, Ser, Tyr or Pro;
Xaa at position 103 is Asp or Ser;
Xaa at position 104 is Trp, Val, Cys, Tyr, Thr, Met, Pro, Leu, Gln, Lys, Ala, Phe or Gly;
Xaa at position 105 is Asn, Pro, Ala, Phe, Ser, Trp, Gln, Tyr, Leu, Lys, Ile, Asp or His;
Xaa at position 106 is Glu, Ser, Ala, Lys, Thr, Ile, Gly or Pro;
Xaa at position 108 is Arg, Lys, Asp, Leu, Thr, Ile, Gln, His, Ser, Ala or Pro;
Xaa at position 109 is Arg, Thr, Pro, Glu, Tyr, Leu, Ser or Gly;
Xaa at position 110 is Lys, Ala, Asn, Thr, Leu, Arg, Gln, His, Glu, Ser or Trp;
Xaa at position 111 is Leu, Ile, Arg, Asp or Met;

Xaa at position 112 is Thr, Val, Gln, Tyr, Glu, or Phe;
Xaa at position 113 is Phe, Ser, Cys, His, Gly, Trp, Tyr, Asp, Lys, Leu, Ile, Val or Asn;
Xaa at position 114 is Tyr, Cys, His, Ser, Trp, Arg or Leu;
Xaa at position 115 is Leu, Asn, Val, Pro, Arg, Ala, His, Thr, Trp or Met;
Xaa at position 116 is Lys;
Xaa at position 117 is Thr, Ser, Asn, Ile, Trp, Lys or Pro;
Xaa at position 118 is Leu, Ser, Pro, Ala, Glu, Cys, Asp or Tyr;
Xaa at position 119 is Glu, Ser, Lys, Pro, Leu, Thr, Tyr or Arg;
Xaa at position 120 is Asn, Ala, Pro, Leu, His, Val or Gln;
Xaa at position 121 is Ala, Ser, Ile, Asn, Pro, Lys or Asp;
Xaa at position 122 is Gln, Ser, Met, Trp, Arg, Phe, Pro, His, Ile, Tyr or Cys;
Xaa at position 123 is Ala, Met, Glu, His, Ser, Pro, Tyr or Leu;

wherein from 1 to 14 amino acids are optionally deleted from the N-terminus and/or from 1 to 15 amino acids are optionally deleted from the C-terminus; wherein from 4 to about 44 of the amino acids designated by Xaa are different from the corresponding amino acids of native (1–133) human interleukin-3;

and wherein a polypeptide having only the sequence of said mutant human interleukin-3 polypeptide $R_1$ has at least three times greater activity than native human interleukin-3, Xaa at position 12 is His, Thr, Phe, Gly, Arg, Ala or Trp;
Xaa at position 13 is Leu, Gly, Arg, Thr, Ser or Ala;
Xaa at position 14 is Lys, Arg, Leu, Gln, Gly, Pro, Val or Trp;
Xaa at position 15 is Gln, Asn, Leu, Pro, Arg or Val;
Xaa at position 16 is Pro, His, Thr, Gly, Asp, Gln, Ser, Leu or Lys;
Xaa at position 17 is Pro, Asp, Gly, Ala, Arg, Leu or Gln;
Xaa at position 18 is Leu, Val, Arg, Gln, Asn, Gly, Ala or Glu;
Xaa at position 19 is Pro, Leu, Gln, Ala, Thr or Glu;
Xaa at position 20 is Leu, Val, Gly, Ser, Lys, Glu, Gln, Thr, Arg, Ala, Phe, Ile or Met;
Xaa at position 21 is Leu, Ala, Gly, Asn, Pro, Gln or Val;
Xaa at position 22 is Asp, Leu or Val;
Xaa at position 23 is Phe, Ser, Pro, Trp or Ile;
Xaa at position 24 is Asn or Ala;
Xaa at position 26 is Leu, Trp or Arg;
Xaa at position 27 is Asn, Cys, Arg, Leu, His, Met, Pro;
Xaa at position 28 is Gly, Asp, Ser, Cys, Ala, Lys, Asn, Thr, Leu, Val, Glu, Phe, Tyr, Ile or Met;
Xaa at position 29 is Glu, Asn, Tyr, Leu, Phe, Asp, Ala, Cys, Gln, Arg, Thr, Gly or Ser;
Xaa at position 30 is Asp, Ser, Leu, Arg, Lys, Thr, Met, Trp, Glu, Asn, Gln, Ala or Pro;
Xaa at position 31 is Gln, Pro, Phe, Val, Met, Leu, Thr, Lys, Asp, Asn, Arg, Ser, Ala, Ile, Glu, His or Trp;
Xaa at position 32 is Asp, Phe, Ser, Thr, Cys, Glu, Asn, Gln, Lys, His, Ala, Tyr, Ile, Val or Gly;
Xaa at position 33 is Ile, Gly, Val, Ser, Arg, Pro or His;
Xaa at position 34 is Leu, Ser, Cys, Arg, Ile, His, Phe, Glu, Lys, Thr, Ala, Met, Val or Asn;
Xaa at position 35 is Met, Arg, Ala, Gly, Pro, Asn, His or Asp;
Xaa at position 36 is Glu, Leu, Thr, Asp, Tyr, Lys, Asn, Ser, Ala, Ile, Val, His, Phe, Met or Gln;
Xaa at position 37 is Asn, Arg, Met, Pro, Ser, Thr or His;
Xaa at position 38 is Asn, His, Arg, Leu, Gly, Ser or Thr;
Xaa at position 39 is Leu, Thr, Ala, Gly, Glu, Pro, Lys, Ser or Met;
Xaa at position 40 is Arg, Asp, Ile, Ser, Val, Thr, Gln, Asn, Lys, His, Ala or Leu;
Xaa at position 41 is Arg, Thr, Val, Ser, Leu or Gly;
Xaa at position 42 is Pro, Gly, Cys, Ser, Gln, Glu, Arg, His, Thr, Ala, Tyr, Phe, Leu, Val or Lys;
Xaa at position 43 is Asn or Gly;
Xaa at position 44 is Leu, Ser, Asp, Arg, Gln, Val or Cys;
Xaa at position 45 is Glu Tyr, His, Leu, Pro or Arg;
Xaa at position 46 is Ala, Ser, Pro, Tyr, Asn or Thr;
Xaa at position 47 is Phe, Asn, Glu, Pro, Lys, Arg or Ser;
Xaa at position 48 is Asn, His, Val, Arg, Pro, Thr, Asp or Ile;
Xaa at position 49 is Arg, Tyr, Trp, Ser, Pro or Val;
Xaa at position 50 is Ala, Asn, Pro, Ser or Lys;
Xaa at position 51 is Val, Thr, Pro, His, Leu, Phe or Ser;
Xaa at position 52 is Lys, Ile, Arg, Val, Asn, Glu or Ser;
Xaa at position 53 is Ser, Ala, Phe, Val, Gly, Asn, Ile, Pro or His;
Xaa at position 54 is Leu, Val, Trp, Ser, Ile, Phe, Thr or His;
Xaa at position 55 is Gln, Ala, Pro, Thr, Glu, Arg, Trp, Gly or Leu;
Xaa at position 56 is Asn, Leu, Val, Trp, Pro or Ala;
Xaa at position 57 is Ala, Met, Leu, Pro, Arg, Glu, Thr, Gln, Trp or Asn;
Xaa at position 58 is Ser, Glu, Met, Ala, His, Asn, Arg or Asp;
Xaa at position 59 is Ala, Glu, Asp, Leu, Ser, Gly, Thr or Arg;
Xaa at position 60 is Ile, Met, Thr, Pro, Arg, Gly, Ala;
Xaa at position 61 is Glu, Lys, Gly, Asp, Pro, Trp, Arg, Ser, Gln or Leu;
Xaa at position 62 is Ser, Val, Ala, Asn, Trp, Glu, Pro, Gly or Asp;
Xaa at position 63 is Ile, Ser, Arg, Thr or Leu;
Xaa at position 64 is Leu, Ala, Ser, Glu, Phe, Gly or Arg;
Xaa at position 65 is Lys, Thr, Gly, Asn, Met, Arg, Ile or Asp;
Xaa at position 66 is Asn, Trp, Val, Gly, Thr, Leu, Glu or Arg;
Xaa at position 67 is Leu, Gln, Gly, Ala, Trp, Arg, Val or Lys;
Xaa at position 68 is Leu, Gln, Lys, Trp, Arg, Asp, Glu, Asn, His, Thr, Ser, Ala, Tyr, Phe, Ile, Met or Val;
Xaa at position 69 is Pro, Ala, Thr, Trp, Arg or Met;
Xaa at position 70 is Cys, Glu, Gly, Arg, Met or Val;
Xaa at position 71 is Leu, Asn, Val or Gln;
Xaa at position 72 is Pro, Cys, Arg, Ala or Lys;
Xaa at position 73 is Leu, Ser, Trp or Gly;
Xaa at position 74 is Ala, Lys, Arg, Val or Trp;
Xaa at position 75 is Thr, Asp, Cys, Leu, Val, Glu, His, Asn or Ser;
Xaa at position 76 is Ala, Pro, Ser, Thr, Gly, Asp, Ile or Met;
Xaa at position 77 is Ala, Pro, Ser, Thr, Phe, Leu, Asp or His;
Xaa at position 78 is Pro, Phe, Arg, Ser, Lys, His, Ala, Gly, Ile or Leu;
Xaa at position 79 is Thr, Asp, Ser, Asn, Pro, Ala, Leu or Arg;
Xaa at position 80 is Arg, Ile, Ser, Glu, Leu, Val, Gln, Lys, His, Ala or Pro;
Xaa at position 81 is His, Gln, Pro, Val, Leu, Gly, Thr, Asn, Ser, Ala, Trp, Phe, Ile or Tyr;
Xaa at position 82 is Pro, Lys, Tyr, Gly, Ile or Thr;
Xaa at position 83 is Ile, Val, Lys, Ala or Asn;
Xaa at position 84 is His, Ile, Asn, Leu, Asp, Ala, Thr, Glu, Gln, Ser, Phe, Met, Val, Lys, Arg, Tyr or Pro;
Xaa at position 85 is Ile, Leu, Arg, Asp, Val, Pro, Gln, Gly, Ser, Phe or His;
Xaa at position 86 is Lys, Tyr, Leu, His, Arg, Ile, Ser, Gln or Pro;
Xaa at position 87 is Asp;
Xaa at position 88 is Gly, Leu, Glu, Lys, Ser, Tyr or Pro;
Xaa at position 89 is Asp or Ser;
Xaa at position 90 is Trp, Val, Cys, Tyr, Thr, Met, Pro, Leu, Gln, Lys, Ala, Phe or Gly;
Xaa at position 91 is Asn, Pro, Ala, Phe, Ser, Trp, Gln, Tyr, Leu, Lys, Ile, Asp or His;
Xaa at position 92 is Glu, Ser, Ala, Lys, Thr, Ile, Gly, or Pro;
Xaa at position 94 is Arg, Lys, Asp, Leu, Thr, Ile, Gln, His, Ser, Ala or Pro;
Xaa at position 95 is Arg, Thr, Pro, Glu, Tyr, Leu, Ser, or Gly;
Xaa at position 96 is Lys, Asn, Thr, Leu, Gln, Arg, His, Glu, Ser, Ala or Trp;
Xaa at position 97 is Leu, Ile, Arg, Asp or Met;
Xaa at position 98 is Thr, Val, Gln, Tyr, Glu, or Phe;
Xaa at position 99 is Phe, Ser, Cys, His, Gly, Trp, Tyr, Asp, Lys, Leu, Ile, Val or Asn;
Xaa at position 100 is Tyr, Cys, His, Ser, Trp, Arg or Leu;
Xaa at position 101 is Leu, Asn, Val, Pro, Arg, Ala, His, Thr, Trp or Met;
Xaa at position 102 is Lys;
Xaa at position 103 is Thr, Ser, Asn, Ile, Trp, Lys or Pro;
Xaa at position 104 is Leu, Ser, Pro, Ala, Glu, Cys, Asp, or Tyr;
Xaa at position 105 is Glu, Ser, Lys, Pro, Leu, Thr, Tyr, or Arg;
Xaa at position 106 is Asn, Ala, Pro, Leu, His, Val or Gln;
Xaa at position 107 is Ala, Ser, Ile, Asn, Pro, Lys or Asp;

Xaa at position 108 is Gln, Ser, Met, Trp, Arg, Phe, Pro, His, Ile, Tyr or Cys;
Xaa at position 109 is Ala, Met, Glu, His, Ser, Pro, Tyr, or Leu;
wherein from 4 to about 44 of the amino acids designated by Xaa are different from the corresponding native amino acids of (1–133) human interleukin-3; and a polypeptide having only the sequence of said mutant (15–125) human interleukin-3 polypeptide $R_1$ has at least three times greater activity than native human interleukin-3, in at least one assay selected from the group consisting of: AML cell proliferation, TF-1 cell proliferation and Methylcellulose assay;
$R_2$ is $R_1$ or a factor selected from the group consisting of a colony stimulating factor, a cytokine, a lymphokine, an interleukin, and a hematopoietic growth factor; and
L is a linker capable of linking $R_1$ to $R_2$.

5. The fusion protein of claim 4 wherein said factor is selected from the group consisting of: GM-CSF, CSF-1, G-CSF, G-CSF $Ser^{17}$, M-CSF, erythropoietin (EPO), IL-1, IL-4, IL-2, IL-5, IL-6, IL-7, IL-8, IL-9, IL-10, IL-11, IL-12, IL-13, LIF, human growth hormone, B-cell growth factor, B-cell differentiation factor, eosinophil differentiation factor and stem cell factor (SCF).

6. The fusion protein of claim 4 wherein $R_1$ is a mutant human (15–125) interleukin-3 polypeptide comprising a modified hIL-3 amino acid sequence of SEQ ID NO:6;

wherein

Xaa at position 3 is Ser, Gly, Asp or Gln;
Xaa at position 4 is Asn, His or Ile;
Xaa at position 9 is Ile, Ala, Leu or Gly;
Xaa at position 11 is Thr, His or Gln;
Xaa at position 12 is His or Ala;
Xaa at position 15 is Gln or Asn;
Xaa at position 16 is Pro or Gly;
Xaa at position 18 is Leu, Arg, Asn or Ala;
Xaa at position 20 is Leu, Val, Ser, Ala, Arg, Gln, Glu, Ile, Phe, Thr or Met;
Xaa at position 21 is Leu, Ala, Asn or Pro;
Xaa at position 24 is Asn or Ala;
Xaa at position 28 is Gly, Asp, Ser, Ala, Asn, Ile, Leu, Met, Tyr or Arg;
Xaa at position 31 is Gln, Val, Met, Leu, Ala, Asn, Glu or Lys;
Xaa at position 32 is Asp, Phe, Ser, Ala, Gln, Glu, His, Val or Thr;
Xaa at position 36 is Glu, Asn, Ser or Asp;
Xaa at position 37 is Asn, Arg, Pro, Thr or His;
Xaa at position 41 is Arg, Leu or Gly;
Xaa at position 42 is Pro, Gly, Ser, Ala, Asn, Val, Leu or Gln;
Xaa at position 48 is Asn, Pro or Thr;
Xaa at position 50 is Ala or Asn;
Xaa at position 51 is Val or Thr;
Xaa at position 53 is Ser or Phe;
Xaa at position 54 is Leu or Phe;
Xaa at position 55 is. Gln, Ala, Glu or Arg;
Xaa at position 62 is Ser, Val, Asn, Pro or Gly;
Xaa at position 63 is Ile or Leu;
Xaa at position 65 is Lys, Asn, Met, Arg, Ile or Gly;
Xaa at position 66 is Asn, Gly, Glu or Arg;
Xaa at position 68 is Leu, Gln, Trp, Arg, Asp, Asn, Glu, His, Met, Phe, Ser, Thr, Tyr or Val;
Xaa at position 73 is Leu or Ser;
Xaa at position 74 is Ala or Trp;
Xaa at position 77 is Ala or Pro;
Xaa at position 79 is Thr, Asp or Ala;
Xaa at position 81 is His, Pro, Val, Gly, Asn, Ser or Thr;
Xaa at position 84 is His, Ile, Asn, Ala, Thr, Arg, Gln, Glu, Lys, Met, Ser, Tyr, Val or Leu;
Xaa at position 85 is Ile or Leu;
Xaa at position 86 is Lys or Arg;
Xaa at position 87 is Asp;
Xaa at position 91 is Asn, Pro, Ser, Ile or Asp;
Xaa at position 94 is Arg, Ala or Ser;
Xaa at position 95 is Arg, Thr, Glu, Leu or Ser;
Xaa at position 98 is Thr or Gln;
Xaa at position 102 is Lys;
Xaa at position 106 is Asn, Pro, Leu, His, Val or Gln;
Xaa at position 107 is Ala, Ser, Ile, Pro or Asp;
Xaa at position 108 is Gln, Met, Trp, Phe, Pro, His, Ile, or Tyr;
Xaa at position 109 is Ala, Met, Glu, Ser or Leu;

wherein from 4 to about 26 of the amino acids designated by Xaa are different from the corresponding amino acids of native (1–133)human interleukin-3; and wherein a polypeptide having only the sequence of said mutant (15–125) human interleukin-3 polypeptide $R_1$ has at least three times greater activity than native human interleukin-3, in at least one assay selected from the group consisting of: AML cell proliferation, TF-1 cell proliferation and Methylcellulose assay.

7. A fusion protein comprising a sequence of the formula selected from the group consisting of:

$R_1$-L-$R_2$, $R_2$-L-$R_1$, $R_1$-$R_2$, $R_2$-L-$R_1$, Met-Ala-$R_1$-L-$R_2$, Met-Ala-$R_2$-L-$R_1$, Met-Ala-$R_1$-$R_2$, Met-Ala-$R_2$-$R_1$, Met-$R_1$-L-$R_2$, Met-$R_2$-L-$R_1$, Met-$R_1$-$R_2$, Met-$R_2$-$R_1$, Ala-$R_1$-L-$R_2$, Ala-$R_2$-L-$R_1$, Ala-$R_1$-$R_2$ and Ala-$R_2$-$R_1$;

wherein $R_1$ is a mutant (15–125) human interleukin-3 polypeptide comprising a modified hIL-3 amino acid sequence of SEQ ID NO:8;

wherein

Xaa at position 4 is Asn or Ile;
Xaa at position 5 is Met, Ala or Ile:
Xaa at position 6 is Ile, Pro or Leu;
Xaa at position 9 is Ile, Ala or Leu;
Xaa at position 11 is Thr or His;
Xaa at position 15 is Gln, Arg, Val or Ile;
Xaa at position 18 is Leu, Ala, Asn or Arg;
Xaa at position 20 is Leu or Ser;
Xaa at position 23 is Phe, Pro or Ser;
Xaa at position 24 is Asn or Ala;
Xaa at position 28 is Gly, Ala, Ser, Asp or Asn;
Xaa at position 31 is Gln, Val or Met;
Xaa at position 32 is Asp or Ser;
Xaa at position 35 is Met, Ile or Asp;
Xaa at position 36 is Glu or Asp;
Xaa at position 37 is Asn, Arg or Ser;
Xaa at position 41 is Arg, Leu or Thr;
Xaa at position 42 is Pro or Ser;
Xaa at position 45 is Glu or Leu;
Xaa at position 46 is Ala or Ser;
Xaa at position 48 is Asn, Val or Pro;
Xaa at position 49 is Arg or His;
Xaa at position 51 is Val or Ser;
Xaa at position 53 is Ser, Asn, His or Gln;
Xaa at position 55 is Gln or Glu;
Xaa at position 59 is Ala or Gly;
Xaa at position 62 is Ser, Ala or Pro;
Xaa at position 65 is Lys, Arg or Ser;
Xaa at position 67 is Leu, Glu or Val;
Xaa at position 68 is Leu, Glu, Val or Trp;
Xaa at position 71 is Leu or Val;
Xaa at position 73 is Leu, Ser or Tyr;
Xaa at position 74 is Ala or Trp;

Xaa at position 77 is Ala or Pro;
Xaa at position 79 is Pro or Ser;
Xaa at position 81 is His or Thr;
Xaa at position 84 is His, Ile or Thr;
Xaa at position 86 is Lys or Arg;
Xaa at position 87 is Asp;
Xaa at position 91 is Asn or Glu;
Xaa at position 95 is Arg, Glu, Leu;
Xaa at position 98 Thr or Gln;
Xaa at position 102 is Lys;
Xaa at position 103 is Thr or Ser;
Xaa at position 106 is Asn, Gln or His;
Xaa at position 109 is Ala or Glu;
  wherein from four to about forty-four of the amino acids designated by Xaa are different from the corresponding amino acids of native (15–125)human interleukin-3; and wherein a polypeptide having only the sequence of said mutant (15–125) human interleukin-3 polypeptide $R_1$ has at least three times greater activity than native human interleukin-3, in at least one assay selected from the group consisting of: AML cell proliferation, TF-1 cell proliferation and Methylcellulose assay;

$R_2$ is $R_1$ or a factor selected from the group consisting of a colony stimulating factor, a cytokine, a lymphokine, an interleukin, and a hematopoietic growth factor; and L is a linker capable of linking $R_1$ to $R_2$.

8. A fusion protein comprising a sequence of the formula selected from the group consisting of:

$R_1$-L-$R_2$, $R_2$-L-$R_1$, $R_1$-$R_2$, $R_2$-L-$R_1$, Met-Ala-$R_1$-L-$R_2$, Met-Ala-$R_2$-L-$R_1$, Met-Ala-$R_1$-$R_2$, Met-Ala-$R_2$-$R_1$, Met-$R_1$-L-$R_2$, Met-$R_2$-L-$R_1$, Met-$R_1$-$R_2$, Met-$R_2$-$R_1$, Ala-$R_1$-L-$R_2$, Ala-$R_2$-L-$R_1$, Ala-$R_1$-$R_2$ and Ala-$R_2$-$R_1$;

wherein $R_1$ is a mutant human (15–125) interleukin-3 polypeptide comprising a modified hIL-3 amino acid sequence of SEQ ID NO 4; wherein Xaa at position 42 is Gly, Asp, Ser, Ile, Leu, Met, Tyr or Ala;
Xaa at position 45 is Gln, Val, Met or Asn;
Xaa at position 46 is Asp, Ser, Gln, His or Val;
Xaa at position 50 is Glu or Asp;
Xaa at position 51 is Asn, Pro or Thr;
Xaa at position 62 is Asn or Pro;
Xaa at position 76 is Ser or Pro;
Xaa at position 82 is Leu, Trp, Asp, Asn Glu, His, Phe, Ser or Tyr;
Xaa at position 95 is His, Arg, Thr, Asn or Ser;
Xaa at position 98 is His, Ile, Leu, Ala, Gln, Lys, Met, Ser, Tyr or Val;
Xaa at position 100 is Lys or Arg;
Xaa at position 105 is Asn or Pro;
Xaa at position 108 is Arg, Ala or Ser;
Xaa at position 121 is Ala or Ile;
Xaa at position 122 is Gln or Ile; and
Xaa at position 123 is Ala, Met or Glu;

wherein from 4 to about 44 of the amino acids designated by Xaa are different from the corresponding native amino acids of (1–133) human interleukin-3; and a polypeptide having only the sequence of said mutant (15–125) human interleukin-3 polypeptide $R_1$ has at least three times greater activity than native human interleukin-3, in at least one assay selected from the group consisting of: AML cell proliferation, TF-1 cell proliferation and Methylcellulose assay;

$R_2$ is $R_1$ or a factor selected from the group consisting of a colony stimulating factor, a cytokine, a lymphokine, an interleukin, and a hematopoietic growth factor; and L is a linker capable of linking $R_1$ to $R_2$.

9. A fusion protein comprising a sequence of the formula selected from the group consisting of:

$R_1$-L-$R_2$, $R_2$-L-$R_1$, $R_1$-$R_2$, $R_2$-L-$R_1$, Met-Ala-$R_1$-L-$R_2$, Met-Ala-$R_2$-L-$R_1$, Met-Ala-$R_1$-$R_2$, Met-Ala-$R_2$-$R_1$, Met-$R_1$-L-$R_2$, Met-$R_2$-L-$R_1$, Met-$R_1$-$R_2$, Met-$R_2$-$R_1$, Ala-$R_1$-L-$R_2$, Ala-$R_2$-L-$R_1$, Ala-$R_1$-$R_2$ and Ala-$R_2$-$R_1$;

wherein $R_1$ is a mutant human (15–125) interleukin-3 polypeptide comprising a modified hIL-3 amino acid sequence selected from the group consisting of:

(18I, 25H, 29R, 32A, 37P, 42A, 45V, 51R, 55L, 60S, 62V, 67N, 69E, 73G, 76A, 79R, 82Q, 87S, 93S, 98I, 101A, 105Q, 109E, 116V, 120Q and 123E)-(15–125)hIL-3, residues 3–113 of SEQ ID NO:31;

(18I, 25H, 29R, 32N, 37P, 42S, 45M, 51R, 55T, 59L, 62V, 67H, 69E, 73G, 76A, 79R, 82Q, 87S, 93S, 98I, 101A, 105Q, 109E, 116V, 120Q and 123E)-(15–125)hIL-3, residues 3–113 of SEQ ID NO:32;

(18I, 25H, 29V, 32A, 37S, 42S, 45M, 51R, 55L, 59L, 62V, 67N, 69E, 73G, 76A, 79R, 82Q, 87S, 93S, 98I, 101A, 105Q, 109E, 116V, 120Q and 123E)-(15–125)hIL-3, residues 3–113 of SEQ ID NO:33;

(18I, 25H, 29R, 32A, 37P, 42A, 45V, 51R, 55L, 60S, 62V, 67N, 69E, 73G, 76A, 79R, 82V, 87S, 93S, 98T, 101A, 105Q, 109E, 116V, 120Q and 123E)-(15–125)hIL-3, residues 3–113 of SEQ ID NO:34;

(18I, 25H, 29V, 32A, 37S, 42S, 45M, 51R, 55L, 59L, 62V, 67N, 69E, 73G, 76A, 79R, 82V, 87S, 93S, 98T, 101A, 105Q, 109E, 116V, 120Q and 123E)-(15–125)hIL-3, residues 3–113 of SEQ ID NO:35;

(18I, 25H, 29R, 32N, 37P, 42S, 45M, 51R, 55T, 59L, 62V, 67H, 69E, 73G, 76A, 79R, 82V, 87S, 93S, 98T, 101A, 105Q, 109E, 116V, 117S, 120H and 123E)-(15–125)hIL-3, residues 3–113 of SEQ ID NO:36;

(18I, 25H, 29V, 32A, 37S, 42S, 45M, 51R, 55L, 59L, 62V, 67N, 69E, 73G, 76A, 79R, 82V, 87S, 93S, 98T, 101A, 105Q, 109E, 116V, 117S, 120H and 123E)-(15–125)hIL-3, residues 3–113 of SEQ ID NO:37;

(18I, 25H, 29R, 32N, 37P, 42S, 45M, 51R, 55T, 59L, 62V, 67H, 69E, 73G, 76A, 79R, 82V, 87S, 93S, 98T, 101A, 105Q, 109E, 116V, 120Q and 123E)-(15–125)hIL-3, residues 3–113 of SEQ ID NO:38;

(18I, 25H, 29R, 32A, 37P, 42A, 45V, 51R, 55L, 60S, 62V, 67N, 69E, 73G, 76A, 79R, 82V, 87S, 93S, 98T, 101A, 105Q, 109E, 116V, 117S, 120H and 123E)-(15–125)hIL-3, residues 3–113 of SEQ ID NO:39;

(18I, 25H, 29R, 32A, 37P, 42A, 45V, 50D, 51R, 55L, 56S, 60S, 62V, 67N, 69E, 73G, 76A, 79R, 82Q, 87S, 93S, 98I, 101A, 105Q, 109E, 116V, 120Q and 123E)-(15–125)hIL-3, residues 3–113 of SEQ ID NO:40;

(18I, 23A, 25H, 29R, 32A, 34S, 37P, 42D, 45M, 46S, 51R, 55L, 60S, 62V, 67N, 69E, 73G, 76A, 79R, 82Q, 87S, 93S, 98I, 101A, 105Q, 109E, 116V, 120Q and 123E)-(15–125) hIL-3, residues 3–113 of SEQ ID NO:41;

(18I, 25H, 29R, 32A, 37P, 42D, 45M, 46S, 51R, 55L, 60S, 62V, 67N, 69E, 73G, 76A, 79R, 82Q, 87S, 93S, 98I, 101A, 105Q, 109E, 116V, 120Q and 123E)-(15–125)hIL-3, residues 3–113 of SEQ ID NO:42;

(18I, 25H, 29R, 32A, 37P, 42A, 45V, 50D, 51R, 55L, 60S, 62V, 67N, 69E, 73G, 76A, 79R, 82Q, 87S, 93S, 98I, 101A, 105Q, 109E, 116V, 120Q and 123E)-(15–125)hIL-3, residues 3–113 of SEQ ID NO:43;

(18I, 25H, 29R, 32A, 37P, 42D, 45V, 46S, 50D, 51R, 55L, 60S, 62V, 67N, 69E, 73G, 76A, 79R, 82Q, 87S, 93S, 98I, 101A, 105Q, 109E, 116V, 120Q and 123E)-(15–125)hIL-3, residues 3–113 of SEQ ID NO:44;

(18I, 25H, 29R, 32A, 37P, 42D, 45M, 46S, 50D, 51R, 55L, 60S, 62V, 67N, 69E, 73G, 76A, 79R, 82Q, 87S, 93S, 98I, 101A, 105Q, 109E, 116V, 120Q and 123E)-(15–125)hIL-3, residues 3–113 of SEQ ID NO:45;

R$_2$ is R$_1$ or a factor selected from the group consisting of a colony stimulating factor, a cytokine, a lymphokine, an interleukin, and a hematopoietic growth factor; and L is a linker capable of linking R$_1$ to R$_2$.

10. The fusion protein of claim 9 wherein R$_1$ is a mutant human (15–125) interleukin-3 polypeptide comprising a modified hIL-3 amino acid sequence selected from the group consisting of:

(18I, 25H, 29R, 32A, 37P, 42A, 45V, 51R, 55L, 60S, 62V, 67N, 69E, 73G, 76A, 79R, 82Q, 87S, 93S, 98I, 101A, 105Q, 109E, 116V, 120Q and 123E)-(15–125)hIL-3, residues 3–113 of SEQ ID NO:31;

(18I, 25H, 29R, 32N, 37P, 42S, 45M, 51R, 55T, 59L, 62V, 67H, 69E, 73G, 76A, 79R, 82Q, 87S, 93S, 98I, 101A, 105Q, 109E, 116V, 120Q and 123E)-(15–125)hIL-3, residues 3–113 of SEQ ID NO:32; and (18I, 25H, 29V, 32A, 37S, 42S, 45M, 51R, 55L, 59L, 62V, 67N, 69E, 73G, 76A, 79R, 82Q, 87S, 93S, 98I, 101A, 105Q, 109E, 116V, 120Q and 123E)-(15–125)hIL-3, residues 3–113 of SEQ ID NO:33;

R$_2$ is G-CSF Ser$^{17}$; and

L is a linker capable of linking R$_1$ to R$_2$.

11. The fusion protein of claim 1, 2, 3, 4, 5, 6, 7, 8 or 9 wherein said factor is selected from the group consisting of G-CSF, G-CSF Ser$^{17}$ and GM-CSF.

12. The fusion protein of claim 1, 2, 3, 4, 5, 6, 7, or 8 wherein a polypeptide having only the sequence of said human interleukin-3 polypeptide R$_1$ has at least five times greater activity than native human interleukin-3.

13. The fusion protein of claim 1, 2, 3, 4, 5, 6, 7, or 8 wherein a polypeptide having only the sequence of said human interleukin-3 polypeptide R$_1$ has at least ten times greater activity than native human interleukin-3.

14. The fusion protein of claim 1, 2, 3, 4, 5, 6, 7, or 8 wherein a polypeptide having only the sequence of said human interleukin-3 polypeptide R$_1$ has at least five times greater activity than native human interleukin-3.

15. The fusion protein of claim 1, 2, 3, 4, 5, 6, 7, or 8 wherein a polypeptide having only the sequence of said human interleukin-3 polypeptide R$_1$ has at least ten times greater activity than native human interleukin-3.

16. A fusion protein consisting of a sequence of the formula selected from the group consisting of:

R$_1$-L-R$_2$, R$_2$-L-R$_1$, R$_1$-R$_2$, R$_2$-L-R$_1$, Met-Ala-R$_1$-L-R$_2$, Met-Ala-R$_2$-L-R$_1$, Met-Ala-R$_1$-R$_2$, Met-Ala-R$_2$-R$_1$, Met-R$_1$-L-R$_2$, Met-R$_2$-L-R$_1$, Met-R$_1$-R$_2$, Met-R$_2$-R$_1$, Ala-R$_1$-L-R$_2$, Ala-R$_2$-L-R$_1$, Ala-R$_1$-R$_2$ and Ala-R$_2$-R$_1$;

wherein R$_1$ is a mutant human interleukin-3 polypeptide consisting of a modified hIL-3 amino acid sequence of SEQ ID NO:1;

wherein

Xaa at position 17 is Ser, Lys, Gly, Asp, Met, Gln or Arg;
Xaa at position 18 is Asn, His, Leu, Ile, Phe, Arg or Gln;
Xaa at position 19 is Met, Phe, Ile, Arg, Gly, Ala or Cys;
Xaa at position 20 is Ile, Cys, Gln, Glu, Arg, Pro or Ala;
Xaa at position 21 is Asp, Phe, Lys, Arg, Ala, Gly, Glu, Gln, Asn, Thr, Ser or Val;
Xaa at position 22 is Glu, Trp, Pro, Ser, Ala, His, Asp, Asn, Gln, Leu, Val or Gly;
Xaa at position 23 is Ile, Val, Ala, Leu, Gly, Trp, Lys, Phe, Ser or Arg;
Xaa at position 24 is Ile, Gly, Val, Arg, Ser, Phe or Leu;
Xaa at position 25 is Thr, His, Gly, Gln, Arg, Pro or Ala;
Xaa at position 26 is His, Thr, Phe, Gly, Arg, Ala or Trp;
Xaa at position 27 is Leu, Gly, Arg, Thr, Ser or Ala;
Xaa at position 28 is Lys, Arg, Leu, Gln, Gly, Pro, Val or Trp;
Xaa at position 29 is Gln, Asn, Leu, Pro, Arg or Val;
Xaa at position 30 is Pro, His, Thr, Gly, Asp, Gln, Ser, Leu or Lys;
Xaa at position 31 is Pro, Asp, Gly, Ala, Arg, Leu or Gln;
Xaa at position 32 is Leu, Val, Arg, Gln, Asn, Gly, Ala or Glu;
Xaa at position 33 is Pro, Leu, Gln, Ala, Thr or Glu;
Xaa at position 34 is Leu, Val, Gly, Ser, Lys, Glu, Gln, Thr, Arg, Ala, Phe, Ile or Met;
Xaa at position 35 is Leu, Ala, Gly, Asn, Pro, Gln or Val;
Xaa at position 36 is Asp, Leu or Val;
Xaa at position 37 is Phe, Ser, Pro, Trp or Ile;
Xaa at position 38 is Asn or Ala;
Xaa at position 40 is Leu, Trp or Arg;
Xaa at position 41 is Asn, Cys, Arg, Leu, His, Met or Pro;
Xaa at position 42 is Gly, Asp, Ser, Cys, Asn, Lys, Thr, Leu, Val, Glu, Phe, Tyr, Ile, Met or Ala;
Xaa at position 43 is Glu, Asn, Tyr, Leu, Phe, Asp, Ala, Cys, Gln, Arg, Thr, Gly or Ser;
Xaa at position 44 is Asp, Ser, Leu, Arg, Lys, Thr, Met, Trp, Glu, Asn, Gln, Ala or Pro;
Xaa at position 45 is Gln, Pro, Phe, Val, Met, Leu, Thr, Lys, Trp, Asp, Asn, Arg, Ser, Ala, Ile, Glu or His;
Xaa at position 46 is Asp, Phe, Ser, Thr, Cys, Glu, Asn, Gln, Lys, His, Ala, Tyr, Ile, Val or Gly;
Xaa at position 47 is Ile, Gly, Val, Ser, Arg, Pro or His;
Xaa at position 48 is Leu, Ser, Cys, Arg, Ile, His, Phe, Glu, Lys, Thr, Ala, Met, Val or Asn;
Xaa at position 49 is Met, Arg, Ala, Gly, Pro, Asn, His or Asp;
Xaa at position 50 is Glu, Leu, Thr, Asp, Tyr, Lys, Asn, Ser, Ala, Ile, Val, His, Phe, Met or Gln;
Xaa at position 51 is Asn, Arg, Met, Pro, Ser, Thr or His;
Xaa at position 52 is Asn, His, Arg, Leu, Gly, Ser or Thr;
Xaa at position 53 is Leu, Thr, Ala, Gly, Glu, Pro, Lys, Ser or Met;
Xaa at position 54 is Arg, Asp, Ile, Ser, Val, Thr, Gln, Asn, Lys, His, Ala or Leu;
Xaa at position 55 is Arg, Thr, Val, Ser, Leu or Gly;
Xaa at position 56 is Pro, Gly, Cys, Ser, Gln, Glu, Arg, His, Thr, Ala, Tyr, Phe, Leu, Val or Lys;
Xaa at position 57 is Asn or Gly;
Xaa at position 58 is Leu, Ser, Asp, Arg, Gln, Val or Cys;
Xaa at position 59 is Glu Tyr, His, Leu, Pro or Arg;
Xaa at position 60 is Ala, Ser, Pro, Tyr, Asn or Thr;
Xaa at position 61 is Phe, Asn, Glu, Pro, Lys, Arg or Ser;
Xaa at position 62 is Asn, His, Val, Arg, Pro, Thr, Asp or Ile;
Xaa at position 63 is Arg, Tyr, Trp, Ser, Pro or Val;
Xaa at position 64 is Ala, Asn, Pro, Ser or Lys;
Xaa at position 65 is Val, Thr, Pro, His, Leu, Phe or Ser;
Xaa at position 66 is Lys, Ile, Arg, Val, Asn, Glu or Ser;
Xaa at position 67 is Ser, Ala, Phe, Val, Gly, Asn, Ile, Pro or His;
Xaa at position 68 is Leu, Val, Trp, Ser, Ile, Phe, Thr or His;
Xaa at position 69 is Gln, Ala, Pro, Thr, Glu, Arg, Trp, Gly or Leu;
Xaa at position 70 is Asn, Leu, Val, Trp, Pro or Ala;
Xaa at position 71 is Ala, Met, Leu, Pro, Arg, Glu, Thr, Gln, Trp or Asn;
Xaa at position 72 is Ser, Glu, Met, Ala, His, Asn, Arg or Asp;
Xaa at position 73 is Ala, Glu, Asp, Leu, Ser, Gly, Thr or Arg;
Xaa at position 74 is Ile, Met, Thr, Pro, Arg, Gly, Ala;
Xaa at position 75 is Glu, Lys, Gly, Asp, Pro, Trp, Arg, Ser, Gln or Leu;

Xaa at position 76 is Ser, Val, Ala, Asn, Trp, Glu, Pro, Gly or Asp;
Xaa at position 77 is Ile, Ser, Arg, Thr or Leu;
Xaa at position 78 is Leu, Ala, Ser, Glu, Phe, Gly or Arg;
Xaa at position 79 is Lys, Thr, Asn, Met, Arg, Ile, Gly or Asp;
Xaa at position 80 is Asn, Trp, Val, Gly, Thr, Leu, Glu or Arg;
Xaa at position 81 is Leu, Gln, Gly, Ala, Trp, Arg, Val or Lys;
Xaa at position 82 is Leu, Gln, Lys, Trp, Arg, Asp, Glu, Asn, His, Thr, Ser, Ala, Tyr, Phe, Ile, Met or Val;
Xaa at position 83 is Pro, Ala, Thr, Trp, Arg or Met;
Xaa at position 84 is Cys, Glu, Gly, Arg, Met or Val;
Xaa at position 85 is Leu, Asn, Val or Gln;
Xaa at position 86 is Pro, Cys, Arg, Ala or Lys;
Xaa at position 87 is Leu, Ser, Trp or Gly;
Xaa at position 88 is Ala, Lys, Arg, Val or Trp;
Xaa at position 89 is Thr, Asp, Cys, Leu, Val, Glu, His, Asn or Ser;
Xaa at position 90 is Ala, Pro, Ser, Thr, Gly, Asp, Ile or Met;
Xaa at position 91 is Ala, Pro, Ser, Thr, Phe, Leu, Asp or His;
Xaa at position 92 is Pro, Phe, Arg, Ser, Lys, His, Ala, Gly, Ile or Leu;
Xaa at position 93 is Thr, Asp, Ser, Asn, Pro, Ala, Leu or Arg;
Xaa at position 94 is Arg, Ile, Ser, Glu, Leu, Val, Gln, Lys, His, Ala or Pro;
Xaa at position 95 is His, Gln, Pro, Val, Leu, Gly, Thr, Asn, Ser, Ala, Trp, Phe, Ile or Tyr;
Xaa at position 96 is Pro, Lys, Tyr, Gly, Ile or Thr;
Xaa at position 97 is Ile, Val, Lys, Ala or Asn;
Xaa at position 98 is His, Ile, Asn, Leu, Asp, Ala, Thr, Glu, Gln, Ser, Phe, Met, Val, Lys, Arg, Tyr or Pro;
Xaa at position 99 is Ile, Leu, Arg, Asp, Val, Pro, Gln, Gly, Ser, Phe or His;
Xaa at position 100 is Lys, Tyr, Leu, His, Arg, Ile, Ser, Gln or Pro;
Xaa at position 101 is Asp;
Xaa at position 102 is Gly, Leu, Glu, Lys, Ser, Tyr or Pro;
Xaa at position 103 is Asp or Ser;
Xaa at position 104 is Trp, Val, Cys, Tyr, Thr, Met, Pro, Leu, Gln, Lys, Ala, Phe or Gly;
Xaa at position 105 is Asn, Pro, Ala, Phe, Ser, Trp, Gln, Tyr, Leu, Lys, Ile, Asp or His;
Xaa at position 106 is Glu, Ser, Ala, Lys, Thr, Ile, Gly or Pro;
Xaa at position 108 is Arg, Lys, Asp, Leu, Thr, Ile, Gln, His, Ser, Ala or Pro;
Xaa at position 109 is Arg, Thr, Pro, Glu, Tyr, Leu, Ser or Gly;
Xaa at position 110 is Lys, Ala, Asn, Thr, Leu, Arg, Gln, His, Glu, Ser or Trp;
Xaa at position 111 is Leu, Ile, Arg, Asp or Met;
Xaa at position 112 is Thr, Val, Gln, Tyr, Glu, or Phe;
Xaa at position 113 is Phe, Ser, Cys, His, Gly, Trp, Tyr, Asp, Lys, Leu, Ile, Val or Asn;
Xaa at position 114 is Tyr, Cys, His, Ser, Trp, Arg or Leu;
Xaa at position 115 is Leu, Asn, Val, Pro, Arg, Ala, His, Thr, Trp or Met;
Xaa at position 116 is Lys;
Xaa at position 117 is Thr, Ser, Asn, Ile, Trp, Lys or Pro;
Xaa at position 118 is Leu, Ser, Pro, Ala, Glu, Cys, Asp or Tyr;
Xaa at position 119 is Glu, Ser, Lys, Pro, Leu, Thr, Tyr or Arg;
Xaa at position 120 is Asn, Ala, Pro, Leu, His, Val or Gin;
Xaa at position 121 is Ala, Ser, Ile, Asn, Pro, Lys or Asp;
Xaa at position 122 is Gln, Ser, Met, Trp, Arg, Phe, Pro, His, Ile, Tyr or Cys;

Xaa at position 123 is Ala, Met, Glu, His, Ser, Pro, Tyr or Leu;
  wherein from 1 to 14 amino acids are optionally deleted from the N-terminus and/or from 1 to 15 amino acids are optionally deleted from the C-terminus; wherein from 4 to about 44 of the amino acids designated by Xaa are different from the corresponding amino acids of native (1–133) human interleukin-3; and wherein a polypeptide having only the sequence of said mutant human interleukin-3 polypeptide $R_1$ has at least three times greater activity than native human interleukin-3, in at least one assay selected from the group consisting of: AML cell proliferation, TF-1 cell proliferation and Methylcellulose assay;

$R_2$ is $R_1$ or a factor selected from the group consisting of a colony stimulating factor, a cytokine, a lymphokine, an interleukin, and a hematopoietic growth factor; and L is a linker capable of linking $R_1$ to $R_2$.

17. The fusion protein of claim 16 wherein said factor is selected from the group consisting of: GM-CSF, CSF-1, G-CSF, G-CSF $Ser^{17}$, M-CSF, erythropoietin (EPO), IL-1, IL-4, IL-2, IL-3, IL-5, IL-6, IL-7, IL-8, IL-9, IL-10, IL-11, IL-12, IL-13, LIF, human growth hormone, B-cell growth factor, B-cell differentiation factor, eosinophil differentiation factor and stem cell factor (SCF).

18. A fusion protein consisting of a sequence of the formula selected from the group consisting of:

$R_1$-L-$R_2$, $R_2$-L-$R_1$, $R_1$-$R_2$, $R_2$-L-$R_1$, Met-Ala-$R_1$-L-$R_2$, Met-Ala-$R_2$-L-$R_1$, Met-Ala-$R_1$-$R_2$, Met-Ala-$R_2$-$R_1$, Met-$R_1$-L-$R_2$, Met-$R_2$-L-$R_1$, Met-$R_1$-$R_2$, Met-$R_2$-$R_1$, Ala-$R_1$-L-$R_2$, Ala-$R_2$-L-$R_1$, Ala-$R_1$-$R_2$ and Ala-$R_2$-$R_1$;

wherein $R_1$ is a mutant human (15–125) interleukin-3 polypeptide consisting of a modified hIL-3 amino acid sequence of SEQ ID NO:4;

wherein

Xaa at position 3 is Ser, Lys, Gly, Asp, Met, Gln or Arg;
Xaa at position 4 is Asn, His, Leu, Ile, Phe, Arg or Gln;
Xaa at position 5 is Met, Phe, Ile, Arg, Gly, Ala or Cys;
Xaa at position 6 is Ile, Cys, Gln, Glu, Arg, Pro or Ala;
Xaa at position 7 is Asp, Phe, Lys, Arg, Ala, Gly, Glu, Gln, Asn, Thr, Ser or Val;
Xaa at position 8 is Glu, Trp, Pro, Ser, Ala, His, Asp, Asn, Gln, Leu, Val or Gly;
Xaa at position 9 is Ile, Val, Ala, Leu, Gly, Trp, Lys, Phe, Ser, or Arg;
Xaa at position 10 is Ile, Gly, Val, Arg, Ser, Phe or Leu;
Xaa at position 11 is Thr, His, Gly, Gln, Arg, Pro or Ala;
Xaa at position 12 is His, Thr, Phe, Gly, Arg, Ala or Trp;
Xaa at position 13 is Leu, Gly, Arg, Thr, Ser or Ala;
Xaa at position 14 is Lys, Arg, Leu, Gln, Gly, Pro, Val or Trp;
Xaa at position 15 is Gln, Asn, Leu, Pro, Arg or Val;
Xaa at position 16 is Pro, His, Thr, Gly, Asp, Gln, Ser, Leu or Lys;
Xaa at position 17 is Pro, Asp, Gly, Ala, Arg, Leu or Gln;
Xaa at position 18 is Leu, Val, Arg, Gln, Asn, Gly, Ala or Glu;
Xaa at position 19 is Pro, Leu, Gln, Ala, Thr or Glu;
Xaa at position 20 is Leu, Val, Gly, Ser, Lys, Glu, Gln, Thr, Arg, Ala, Phe, Ile or Met;
Xaa at position 21 is Leu, Ala, Gly, Asn, Pro, Gln or Val;
Xaa at position 22 is Asp, Leu or Val;
Xaa at position 23 is Phe, Ser, Pro, Trp or Ile;
Xaa at position 24 is Asn or Ala;
Xaa at position 26 is Leu, Trp or Arg;
Xaa at position 27 is Asn, Cys, Arg, Leu, His, Met, Pro;
Xaa at position 28 is Gly, Asp, Ser, Cys, Ala, Lys, Asn, Thr, Leu, Val, Glu, Phe, Tyr, Ile or Met;

Xaa at position 29 is Glu, Asn, Tyr, Leu, Phe, Asp, Ala, Cys, Gln, Arg, Thr, Gly or Ser;
Xaa at position 30 is Asp, Ser, Leu, Arg, Lys, Thr, Met, Trp, Glu, Asn, Gln, Ala or Pro;
Xaa at position 31 is Gln, Pro, Phe, Val, Met, Leu, Thr, Lys, Asp, Asn, Arg, Ser, Ala, Ile, Glu, His or Trp;
Xaa at position 32 is Asp, Phe, Ser, Thr, Cys, Glu, Asn, Gln, Lys, His, Ala, Tyr, Ile, Val or Gly;
Xaa at position 33 is Ile, Gly, Val, Ser, Arg, Pro or His;
Xaa at position 34 is Leu, Ser, Cys, Arg, Ile, His, Phe, Glu, Lys, Thr, Ala, Met, Val or Asn;
Xaa at position 35 is Met, Arg, Ala, Gly, Pro, Asn, His or Asp;
Xaa at position 36 is Glu, Leu, Thr, Asp, Tyr, Lys, Asn, Ser, Ala, Ile, Val, His, Phe, Met or Gln;
Xaa at position 37 is Asn, Arg, Met, Pro, Ser, Thr or His;
Xaa at position 38 is Asn, His, Arg, Leu, Gly, Ser or Thr;
Xaa at position 39 is Leu, Thr, Ala, Gly, Glu, Pro, Lys, Ser or Met;
Xaa at position 40 is Arg, Asp, Ile, Ser, Val, Thr, Gln, Asn, Lys, His, Ala or Leu;
Xaa at position 41 is Arg, Thr, Val, Ser, Leu or Gly;
Xaa at position 42 is Pro, Gly, Cys, Ser, Gln, Glu, Arg, His, Thr, Ala, Tyr, Phe, Leu, Val or Lys;
Xaa at position 43 is Asn or Gly;
Xaa at position 44 is Leu, Ser, Asp, Arg, Gln, Val or Cys;
Xaa at position 45 is Glu Tyr, His, Leu, Pro or Arg;
Xaa at position 46 is Ala, Ser, Pro, Tyr, Asn or Thr;
Xaa at position 47 is Phe, Asn, Glu, Pro, Lys, Arg or Ser;
Xaa at position 48 is Asn, His, Val, Arg, Pro, Thr, Asp or Ile;
Xaa at position 49 is Arg, Tyr, Trp, Ser, Pro or Val;
Xaa at position 50 is Ala, Asn, Pro, Ser or Lys;
Xaa at position 51 is Val, Thr, Pro, His, Leu, Phe or Ser;
Xaa at position 52 is Lys, Ile, Arg, Val, Asn, Glu or Ser;
Xaa at position 53 is Ser, Ala, Phe, Val, Gly, Asn, Ile, Pro or His;
Xaa at position 54 is Leu, Val, Trp, Ser, Ile, Phe, Thr or His;
Xaa at position 55 is Gln, Ala, Pro, Thr, Glu, Arg, Trp, Gly or Leu;
Xaa at position 56 is Asn, Leu, Val, Trp, Pro or Ala;
Xaa at position 57 is Ala, Met, Leu, Pro, Arg, Glu, Thr, Gln, Trp or Asn;
Xaa at position 58 is Ser, Glu, Met, Ala, His, Asn, Arg or Asp;
Xaa at position 59 is Ala, Glu, Asp, Leu, Ser, Gly, Thr or Arg;
Xaa at position 60 is Ile, Met, Thr, Pro, Arg, Gly, Ala;
Xaa at position 61 is Glu, Lys, Gly, Asp, Pro, Trp, Arg, Ser, Gln or Leu;
Xaa at position 62 is Ser, Val, Ala, Asn, Trp, Glu, Pro, Gly or Asp;
Xaa at position 63 is Ile, Ser, Arg, Thr or Leu;
Xaa at position 64 is Leu, Ala, Ser, Glu, Phe, Gly or Arg;
Xaa at position 65 is Lys, Thr, Gly, Asn, Met, Arg, Ile or Asp;
Xaa at position 66 is Asn, Trp, Val, Gly, Thr, Leu, Glu or Arg;
Xaa at position 67 is Leu, Gln, Gly, Ala, Trp, Arg, Val or Lys;
Xaa at position 68 is Leu, Gln, Lys, Trp, Arg, Asp, Glu, Asn, His, Thr, Ser, Ala, Tyr, Phe, Ile, Met or Val;
Xaa at position 69 is Pro, Ala, Thr, Trp, Arg or Met;
Xaa at position 70 is Cys, Glu, Gly, Arg, Met or Val;
Xaa at position 71 is Leu, Asn, Val or Gln;
Xaa at position 72 is Pro, Cys, Arg, Ala or Lys;
Xaa at position 73 is Leu, Ser, Trp or Gly;
Xaa at position 74 is Ala, Lys, Arg, Val or Trp;
Xaa at position 75 is Thr, Asp, Cys, Leu, Val, Glu, His, Asn or Ser;
Xaa at position 76 is Ala, Pro, Ser, Thr, Gly, Asp, Ile or Met;
Xaa at position 77 is Ala, Pro, Ser, Thr, Phe, Leu, Asp or His;
Xaa at position 78 is Pro, Phe, Arg, Ser, Lys, His, Ala, Gly, Ile or Leu;
Xaa at position 79 is Thr, Asp, Ser, Asn, Pro, Ala, Leu or Arg;
Xaa at position 80 is Arg, Ile, Ser, Glu, Leu, Val, Gln, Lys, His, Ala or Pro;
Xaa at position 81 is His, Gln, Pro, Val, Leu, Gly, Thr, Asn, Ser, Ala, Trp, Phe, Ile or Tyr;
Xaa at position 82 is Pro, Lys, Tyr, Gly, Ile or Thr;
Xaa at position 83 is Ile, Val, Lys, Ala or Asn;
Xaa at position 84 is His, Ile, Asn, Leu, Asp, Ala, Thr, Glu, Gln, Ser, Phe, Met, Val, Lys, Arg, Tyr or Pro;
Xaa at position 85 is Ile, Leu, Arg, Asp, Val, Pro, Gln, Gly, Ser, Phe or His;
Xaa at position 86 is Lys, Tyr, Leu, His, Arg, Ile, Ser, Gln or Pro;
Xaa at position 87 is Asp;
Xaa at position 88 is Gly, Leu, Glu, Lys, Ser, Tyr or Pro;
Xaa at position 89 is Asp or Ser;
Xaa at position 90 is Trp, Val, Cys, Tyr, Thr, Met, Pro, Leu, Gln, Lys, Ala, Phe or Gly;
Xaa at position 91 is Asn, Pro, Ala, Phe, Ser, Trp, Gln, Tyr, Leu, Lys, Ile, Asp or His;
Xaa at position 92 is Glu, Ser, Ala, Lys, Thr, Ile, Gly, or Pro;
Xaa at position 94 is Arg, Lys, Asp, Leu, Thr, Ile, Gln, His, Ser, Ala or Pro;
Xaa at position 95 is Arg, Thr, Pro, Glu, Tyr, Leu, Ser, or Gly;
Xaa at position 96 is Lys, Asn, Thr, Leu, Gln, Arg, His, Glu, Ser, Ala or Trp;
Xaa at position 97 is Leu, Ile, Arg, Asp or Met;
Xaa at position 98 is Thr, Val, Gln, Tyr, Glu, or Phe;
Xaa at position 99 is Phe, Ser, Cys, His, Gly, Trp, Tyr, Asp, Lys, Leu, Ile, Val or Asn;
Xaa at position 100 is Tyr, Cys, His, Ser, Trp, Arg or Leu;
Xaa at position 101 is Leu, Asn, Val, Pro, Arg, Ala, His, Thr, Trp or Met;
Xaa at position 102 is Lys;
Xaa at position 103 is Thr, Ser, Asn, Ile, Trp, Lys or Pro;
Xaa at position 104 is Leu, Ser, Pro, Ala, Glu, Cys, Asp, or Tyr;
Xaa at position 105 is Glu, Ser, Lys, Pro, Leu, Thr, Tyr, or Arg;
Xaa at position 106 is Asn, Ala, Pro, Leu, His, Val or Gln;
Xaa at position 107 is Ala, Ser, Ile, Asn, Pro, Lys or Asp;
Xaa at position 108 is Gln, Ser, Met, Trp, Arg, Phe, Pro, His, Ile, Tyr or Cys;
Xaa at position 109 is Ala, Met, Glu, His, Ser, Pro, Tyr, or Leu;

wherein from 4 to about 44 of the amino acids designated by Xaa are different from the corresponding native amino acids of (1–133) human interleukin-3; and wherein a polypeptide having only the sequence of said mutant (15–125) human interleukin-3 polypeptide $R_1$ has at least three times greater activity than native human interleukin-3, in at least one assay selected from the group consisting of: AML cell proliferation, TF-1 cell proliferation and Methylcellulose assay;

$R_2$ is $R_1$ or a factor selected from the group consisting of a colony stimulating factor, a cytokine, a lymphokine, an interleukin, and a hematopoietic growth factor; and L is a linker capable of linking $R_1$ to $R_2$.

19. The fusion protein of claim 18 wherein said factor is selected from the group consisting of: GM-CSF, CSF-1, G-CSF, G-CSF $Ser^{17}$, M-CSF, erythropoietin (EPO), IL-1, IL-4, IL-2, IL-5, IL-6, IL-7, IL-8, IL-9, IL-10, IL-11, IL-12, IL-13, LIF, human growth hormone, B-cell growth factor, B-cell differentiation factor, eosinophil differentiation factor and stem cell factor (SCF).

20. A fusion protein consisting of a sequence of the formula selected from the group consisting of:

$R_1$-L-$R_2$, $R_2$-L-$R_1$, $R_1$-$R_2$, $R_2$-L-$R_1$, Met-Ala-$R_1$-L-$R_2$, Met-Ala-$R_2$-L-$R_1$, Met-Ala-$R_1$-$R_2$, Met-Ala-$R_2$-$R_1$, Met-$R_1$-L-$R_2$, Met-$R_2$-L-$R_1$, Met-$R_1$-$R_2$, Met-$R_2$-$R_1$, Ala-$R_1$-L-$R_2$, Ala-$R_2$-L-$R_1$, Ala-$R_1$-$R_2$ and Ala-$R_2$-$R_1$;

wherein $R_1$ is a mutant (15–125) human interleukin-3 polypeptide consisting of a modified hIL-3 amino acid sequence of SEQ ID NO:8;

wherein

Xaa at position 4 is Asn or Ile;
Xaa at position 5 is Met, Ala or Ile:
Xaa at position 6 is Ile, Pro or Leu;
Xaa at position 9 is Ile, Ala or Leu;
Xaa at position 11 is Thr or His;
Xaa at position 15 is Gln, Arg, Val or Ile;
Xaa at position 18 is Leu, Ala, Asn or Arg;
Xaa at position 20 is Leu or Ser;
Xaa at position 23 is Phe, Pro or Ser;
Xaa at position 24 is Asn or Ala;
Xaa at position 28 is Gly, Ala, Ser, Asp or Asn;
Xaa at position 31 is Gln, Val or Met;
Xaa at position 32 is Asp or Ser;
Xaa at position 35 is Met, Ile or Asp;
Xaa at position 36 is Glu or Asp;
Xaa at position 37 is Asn, Arg or Ser;
Xaa at position 41 is Arg, Leu or Thr;
Xaa at position 42 is Pro or Ser;
Xaa at position 45 is Glu or Leu;
Xaa at position 46 is Ala or Ser;
Xaa at position 48 is Asn, Val or Pro;
Xaa at position 49 is Arg or His;
Xaa at position 51 is Val or Ser;
Xaa at position 53 is Ser, Asn, His or Gln;
Xaa at position 55 is Gln or Glu;
Xaa at position 59 is Ala or Gly;
Xaa at position 62 is Ser, Ala or Pro;
Xaa at position 65 is Lys, Arg or Ser;
Xaa at position 67 is Leu, Glu or Val;
Xaa at position 68 is Leu, Glu, Val or Trp;
Xaa at position 71 is Leu or Val;
Xaa at position 73 is Leu, Ser or Tyr;
Xaa at position 74 is Ala or Trp;
Xaa at position 77 is Ala or Pro;
Xaa at position 79 is Pro or Ser;
Xaa at position 81 is His or Thr;
Xaa at position 84 is His, Ile or Thr;
Xaa at position 86 is Lys or Arg;
Xaa at position 87 is Asp;
Xaa at position 91 is Asn or Glu;
Xaa at position 95 is Arg, Glu, Leu;
Xaa at position 98 Thr or Gln;
Xaa at position 102 is Lys;
Xaa at position 103 is Thr or Ser;
Xaa at position 106 is Asn, Gln or His;
Xaa at position 109 is Ala or Glu;

wherein from four to about forty-four of the amino acids designated by Xaa are different from the corresponding amino acids of native (15–125)human interleukin-3; and wherein a polypeptide having only the sequence of said mutant (15–125) human interleukin-3 polypeptide $R_1$ has at least three times greater activity than native human interleukin-3, in at least one assay selected from the group consisting of: AML cell proliferation, TF-1 cell proliferation and Methylcellulose assay;

$R_2$ is $R_1$ or a factor selected from the group consisting of a colony stimulating factor, a cytokine, a lymphokine, an interleukin, and a hematopoietic growth factor; and L is a linker capable of linking $R_1$ to $R_2$.

21. A fusion protein consisting of a sequence of the formula selected from the group consisting of:

$R_1$-L-$R_2$, $R_2$-L-$R_1$, $R_1$-$R_2$, $R_2$-L-$R_1$, Met-Ala-$R_1$-L-$R_2$, Met-Ala-$R_2$-L-$R_1$, Met-Ala-$R_1$-$R_2$, Met-Ala-$R_2$-$R_1$, Met-$R_1$-L-$R_2$, Met-$R_2$-L-$R_1$, Met-$R_1$-$R_2$, Met-$R_2$-$R_1$, Ala-$R_1$-L-$R_2$, Ala-$R_2$-L-$R_1$, Ala-$R_1$-$R_2$ and Ala-$R_2$-$R_1$;

wherein $R_1$ is a mutant human (15–125) interleukin-3 polypeptide consisting of a modified hIL-3 amino acid sequence of SEQ ID NO 4; wherein Xaa at position 42 is Gly, Asp, Ser, Ile, Leu, Met, Tyr or Ala;
Xaa at position 45 is Gln, Val, Met or Asn;
Xaa at position 46 is Asp, Ser, Gln, His or Val;
Xaa at position 50 is Glu or Asp;
Xaa at position 51 is Asn, Pro or Thr;
Xaa at position 62 is Asn or Pro;
Xaa at position 76 is Ser or Pro;
Xaa at position 82 is Leu, Trp, Asp, Asn Glu, His, Phe, Ser or Tyr;
Xaa at position 95 is His, Arg, Thr, Asn or Ser;
Xaa at position 98 is His, Ile, Leu, Ala, Gln, Lys, Met, Ser, Tyr or Val;
Xaa at position 100 is Lys or Arg;
Xaa at position 101 is Asp;
Xaa at position 105 is Asn or Pro;
Xaa at position 108 is Arg, Ala or Ser;
Xaa at position 116 is Lys;
Xaa at position 122 is Gln or Ile; and
Xaa at position 123 is Ala, Met or Glu;

wherein from 4 to about 44 of the amino acids designated by Xaa are different from the corresponding amino acids of native (1–133) human interleukin-3; and wherein a polypeptide having only the sequence of said mutant human interleukin-3 polypeptide $R_1$ has at least three times greater activity than native human interleukin-3, in at least one assay selected from the group consisting of: AML cell proliferation, TF-1 cell proliferation and Methylcellulose assay;

$R_2$ is $R_1$ or a factor selected from the group consisting of a colony stimulating factor, a cytokine, a lymphokine, an interleukin, and a hematopoietic growth factor; and L is a linker capable of linking $R_1$ to $R_2$.

22. A fusion protein consisting of a sequence of the formula selected from the group consisting of:

$R_1$-L-$R_2$, $R_2$-L-$R_1$, $R_1$-$R_2$, $R_2$-L-$R_1$, Met-Ala-$R_1$-L-$R_2$, Met-Ala-$R_2$-L-$R_1$, Met-Ala-$R_1$-$R_2$, Met-Ala-$R_2$-$R_1$, Met-$R_1$-L-$R_2$, Met-$R_2$-L-$R_1$, Met-$R_1$-$R_2$, Met-$R_2$-$R_1$, Ala-$R_1$-L-$R_2$, Ala-$R_2$-L-$R_1$, Ala-$R_1$-$R_2$ and Ala-$R_2$-$R_1$;

wherein $R_1$ is a mutant human (15–125) interleukin-3 polypeptide consisting of a modified hIL-3 amino acid sequence selected from the group consisting of:

(18I, 25H, 29R, 32A, 37P, 42A, 45V, 51R, 55L, 60S, 62V, 67N, 69E, 73G, 76A, 79R, 82Q, 87S, 93S, 98I, 101A, 105Q, 109E, 116V, 120Q and 123E)-(15–125)hIL-3, residues 3–113 of SEQ ID NO:31;

(18I, 25H, 29R, 32N, 37P, 42S, 45M, 51R, 55T, 59L, 62V, 67H, 69E, 73G, 76A, 79R, 82Q, 87S, 93S, 98I, 101A, 105Q, 109E, 116V, 120Q and 123E)-(15–125)hIL-3, residues 3–113 of SEQ ID NO:32;

(18I, 25H, 29V, 32A, 37S, 42S, 45M, 51R, 55L, 59L, 62V, 67N, 69E, 73G, 76A, 79R, 82Q, 87S, 93S, 98I, 101A, 105Q, 109E, 116V, 120Q and 123E)-(15–125)hIL-3, residues 3–113 of SEQ ID NO:33;
(18I, 25H, 29R, 32A, 37P, 42A, 45V, 51R, 55L, 60S, 62V, 67N, 69E, 73G, 76A, 79R, 82V, 87S, 93S, 98T, 101A, 105Q, 109E, 116V, 120Q and 123E)-(15–125)hIL-3, residues 3–113 of SEQ ID NO:34;
(18I, 25H, 29V, 32A, 37S, 42S, 45M, 51R, 55L, 59L, 62V, 67N, 69E, 73G, 76A, 79R, 82V, 87S, 93S, 98T, 101A, 105Q, 109E, 116V, 120Q and 123E)-(15–125)hIL-3, residues 3–113 of SEQ ID NO:35;
(18I, 25H, 29R, 32N, 37P, 42S, 45M, 51R, 55T, 59L, 62V, 67H, 69E, 73G, 76A, 79R, 82V, 87S, 93S, 98T, 101A, 105Q, 109E, 116V, 117S, 120H and 123E)-(15–125)hIL-3, residues 3–113 of SEQ ID NO:36;
(18I, 25H, 29V, 32A, 37S, 42S, 45M, 51R, 55L, 59L, 62V, 67N, 69E, 73G, 76A, 79R, 82V, 87S, 93S, 98T, 101A, 105Q, 109E, 116V, 117S, 120H and 123E)-(15–125)hIL-3, residues 3–113 of SEQ ID NO:37;
(18I, 25H, 29R, 32N, 37P, 42S, 45M, 51R, 55T, 59L, 62V, 67H, 69E, 73G, 76A, 79R, 82V, 87S, 93S, 98T, 101A, 105Q, 109E, 116V, 120Q and 123E)-(15–125)hIL-3, residues 3–113 of SEQ ID NO:38;
(18I, 25H, 29R, 32A, 37P, 42A, 45V, 51R, 55L, 60S, 62V, 67N, 69E, 73G, 76A, 79R, 82V, 87S, 93S, 98T, 101A, 105Q, 109E, 116V, 117S, 120H and 123E)-(15–125)hIL-3, residues 3–113 of SEQ ID NO:39;
(18I, 25H, 29R, 32A, 37P, 42A, 45V, 50D, 51R, 55L, 56S, 60S, 62V, 67N, 69E, 73G, 76A, 79R, 82Q, 87S, 93S, 98I, 101A, 105Q, 109E, 116V, 120Q and 123E)-(15–125)hIL-3, residues 3–113 of SEQ ID NO:40;
(18I, 23A, 25H, 29R, 32A, 34S, 37P, 42D, 45M, 46S, 51R, 55L, 60S, 62V, 67N, 69E, 73G, 76A, 79R, 82Q, 87S, 93S, 98I, 101A, 105Q, 109E, 116V, 120Q and 123E)-(15–125)hIL-3, residues 3–113 of SEQ ID NO:41;
(18I, 25H, 29R, 32A, 37P, 42D, 45M, 46S, 51R, 55L, 60S, 62V, 67N, 69E, 73G, 76A, 79R, 82Q, 87S, 93S, 98I, 101A, 105Q, 109E, 116V, 120Q and 123E)-(15–125)hIL-3, residues 3–113 of SEQ ID NO:42;
(18I, 25H, 29R, 32A, 37P, 42A, 45V, 50D, 51R, 55L, 60S, 62V, 67N, 69E, 73G, 76A, 79R, 82Q, 87S, 93S, 98I, 101A, 105Q, 109E, 116V, 120Q and 123E)-(15–125)hIL-3, residues 3–113 of SEQ ID NO:43;
(18I, 25H, 29R, 32A, 37P, 42D, 45V, 46S, 50D, 51R, 55L, 60S, 62V, 67N, 69E, 73G, 76A, 79R, 82Q, 87S, 93S, 98I, 101A, 105Q, 109E, 116V, 120Q and 123E)-(15–125)hIL-3, residues 3–113 of SEQ ID NO:44;
(18I, 25H, 29R, 32A, 37P, 42D, 45M, 46S, 50D, 51R, 55L, 60S, 62V, 67N, 69E, 73G, 76A, 79R, 82Q, 87S, 93S, 98I, 101A, 105Q, 109E, 116V, 120Q and 123E)-(15–125) hIL-3, residues 3–113 of SEQ ID NO:45;

$R_2$ is $R_1$ or a factor selected from the group consisting of a colony stimulating factor, a cytokine, a lymphokine, an interleukin, and a hematopoietic growth factor; and L is a linker capable of linking $R_1$ to $R_2$.

23. The fusion protein of claim 22 wherein said factor is selected from the group consisting of: GM-CSF, CSF-1, G-CSF, G-CSF Ser[17], M-CSF, erythropoietin (EPO), IL-1, IL-4, IL-2, IL-5, IL-6, IL-7, IL-8, IL-9, IL-10, IL-11, IL-12, IL-13, LIF, human growth hormone, B-cell growth factor, B-cell differentiation factor, eosinophil differentiation factor and stem cell factor (SCF).

24. The fusion protein of claim 22 wherein said factor is G-CSF Ser[17].

25. The fusion protein of claim 16, 17, 18, 19, 20, or 21 wherein a polypeptide having only the sequence of said human interleukin-3 polypeptide $R_1$ has at least five times greater activity than native human interleukin-3.

26. The fusion protein of claim 16, 17, 18, 19, 20, or 21 wherein a polypeptide having only the sequence of said human interleukin-3 polypeptide $R_1$ has at least ten times greater activity than native human interleukin-3.

27. A nucleic acid molecule encoding the fusion protein of claim 1.
28. A nucleic acid molecule encoding the fusion protein of claim 2.
29. A nucleic acid molecule encoding the fusion protein of claim 3.
30. A nucleic acid molecule encoding the fusion protein of claim 4.
31. A nucleic acid molecule encoding the fusion protein of claim 5.
32. A nucleic acid molecule encoding the fusion protein of claim 6.
33. A nucleic acid molecule encoding the fusion protein of claim 7.
34. A nucleic acid molecule encoding the fusion protein of claim 8.
35. A nucleic acid molecule encoding the fusion protein of claim 9.
36. A nucleic acid molecule encoding the fusion protein of claim 10.
37. A nucleic acid molecule encoding the fusion protein of claim 11.
38. A nucleic acid molecule encoding the fusion protein of claim 12.
39. A nucleic acid molecule encoding the fusion protein of claim 13.
40. A nucleic acid molecule encoding the fusion protein of claim 14.
41. A nucleic acid molecule encoding the fusion protein of claim 15.
42. A nucleic acid molecule encoding the fusion protein of claim 16.
43. A nucleic acid molecule encoding the fusion protein of claim 17.
44. A nucleic acid molecule encoding the fusion protein of claim 18.
45. A nucleic acid molecule encoding the fusion protein of claim 19.
46. A nucleic acid molecule encoding the fusion protein of claim 20.
47. A nucleic acid molecule encoding the fusion protein of claim 21.
48. A nucleic acid molecule encoding the fusion protein of claim 22.
49. A nucleic acid molecule encoding the fusion protein of claim 23.
50. A nucleic acid molecule encoding the fusion protein of claim 24.
51. A nucleic acid molecule encoding the fusion protein of claim 25.
52. A nucleic acid molecule encoding the fusion protein of claim 26.
53. A method of producing a fusion protein comprising: growing under suitable nutrient conditions, a host cell transformed or transfected with a replicable vector comprising said nucleic acid molecule of claim 27, 28, 29, 30, 31, 32, 33, 34, 35 or 36 in a manner allowing expression of said fusion protein and recovering said fusion protein.
54. A method of producing a fusion protein comprising: growing under suitable nutrient conditions, a host cell transformed or transfected with a replicable vector comprising said nucleic acid molecule of claim 37 in a manner allowing expression of said fusion protein and recovering said fusion protein.

55. A method of producing a fusion protein comprising:

growing under suitable nutrient conditions, a host cell transformed or transfected with a replicable vector comprising said nucleic acid molecule of claim 38 in a manner allowing expression of said fusion protein and recovering said fusion protein.

56. A method of producing a fusion protein comprising:

growing under suitable nutrient conditions, a host cell transformed or transfected with a replicable vector comprising said nucleic acid molecule of claim 39 in a manner allowing expression of said fusion protein and recovering said fusion protein.

57. A method of producing a polypeptide comprising:

growing under suitable nutrient conditions, a host cell transformed or transfected with a replicable vector comprising said nucleic acid molecule of claim 40, in a manner allowing expression of said polypeptide and recovering said polypeptide.

58. A method of producing a polypeptide comprising:

growing under suitable nutrient conditions, a host cell transformed or transfected with a replicable vector comprising said nucleic acid molecule of claim 41, in a manner allowing expression of said polypeptide and recovering said polypeptide.

59. A method of producing a fusion protein comprising:

growing under suitable nutrient conditions, a host cell transformed or transfected with a replicable vector comprising said nucleic acid molecule of claim 42, 43, 44, 45, 46, 47, 48, 49, or 50, in a manner allowing expression of said fusion protein and recovering said fusion protein.

60. A method of producing a fusion protein comprising:

growing under suitable nutrient conditions, a host cell transformed or transfected with a replicable vector comprising said nucleic acid molecule of claim 51, in a manner allowing expression of said fusion protein and recovering said fusion protein.

61. A method of producing a polypeptide comprising:

growing under suitable nutrient conditions, a host cell transformed or transfected with a replicable vector comprising said nucleic acid molecule of claim 52, in a manner allowing expression of said polypeptide and recovering said polypeptide.

62. A pharmaceutical composition comprising the fusion protein of claim 1, 2, 3, 4, 5, 6, 7, 8, 9, or 10 and a pharmaceutically acceptable carrier.

63. A pharmaceutical composition comprising the fusion protein of claim 11 and a pharmaceutically acceptable carrier.

64. A pharmaceutical composition comprising the fusion protein of claim 12 and a pharmaceutically acceptable carrier.

65. A pharmaceutical composition comprising the fusion protein of claim 13 and a pharmaceutically acceptable carrier.

66. A pharmaceutical composition comprising the fusion protein of claim 14 and a pharmaceutically acceptable carrier.

67. A pharmaceutical composition comprising the fusion protein of claim 15 and a pharmaceutically acceptable carrier.

68. A pharmaceutical composition comprising the fusion protein of claim 16, 17, 18, 19, 20, 21, 22, 23 or 24 and a pharmaceutically acceptable carrier.

69. A pharmaceutical composition comprising the fusion protein of claim 25 and a pharmaceutically acceptable carrier.

70. A pharmaceutical composition comprising the fusion protein of claim 26 and a pharmaceutically acceptable carrier.

* * * * *